(12) United States Patent
Barbosa et al.

(10) Patent No.: US 12,329,857 B2
(45) Date of Patent: Jun. 17, 2025

(54) SYSTEMS AND METHODS FOR MANUFACTURING LIPID NANOPARTICLES AND LIPOSOMES

(71) Applicant: ACUITAS THERAPEUTICS, INC., Vancouver (CA)

(72) Inventors: Christopher J. Barbosa, Coquitlam (CA); Kody Moleschi, Delta (CA); David Cretney, Vancouver (CA)

(73) Assignee: Acuitas Therapeutics, Inc., Vancouver (CA)

( * ) Notice: Subject to any disclaimer, the term of this patent is extended or adjusted under 35 U.S.C. 154(b) by 710 days.

(21) Appl. No.: 17/277,691

(22) PCT Filed: Sep. 20, 2019

(86) PCT No.: PCT/US2019/052105
§ 371 (c)(1),
(2) Date: Mar. 18, 2021

(87) PCT Pub. No.: WO2020/061426
PCT Pub. Date: Mar. 26, 2020

(65) Prior Publication Data
US 2022/0273567 A1    Sep. 1, 2022

Related U.S. Application Data

(60) Provisional application No. 62/734,837, filed on Sep. 21, 2018.

(51) Int. Cl.
*A61K 9/1272* (2025.01)
*A61K 9/51* (2006.01)
(Continued)

(52) U.S. Cl.
CPC .......... *A61K 9/1272* (2013.01); *A61K 9/5146* (2013.01); *A61K 31/7105* (2013.01);
(Continued)

(58) Field of Classification Search
CPC ...... B01F 35/834; A61K 9/127; A61K 9/1272
See application file for complete search history.

(56) References Cited

U.S. PATENT DOCUMENTS

| | | | |
|---|---|---|---|
| 2,856,420 A | 10/1958 | Crawford, Jr. | |
| 3,340,299 A | 9/1967 | Weintraub et al. | |

(Continued)

FOREIGN PATENT DOCUMENTS

| | | |
|---|---|---|
| CN | 102604115 A | 7/2012 |
| CN | 104876831 A | 9/2015 |

(Continued)

OTHER PUBLICATIONS

U.S. Appl. No. 17/496,530, filed Oct. 7, 2021.
(Continued)

*Primary Examiner* — Marc C Howell
*Assistant Examiner* — Patrick M McCarty
(74) *Attorney, Agent, or Firm* — Seed IP Law Group LLP

(57) ABSTRACT

Systems including specific arrangements of pumps, valves, and conduits, such as for mixing precursors to lipid nanoparticles to form the lipid nanoparticles, are provided. Methods of using such systems to manufacture the lipid nanoparticles are also provided.

24 Claims, 5 Drawing Sheets

(51) Int. Cl.
*A61K 31/7105* (2006.01)
*B01F 23/45* (2022.01)
*B01F 25/23* (2022.01)
*B01F 35/71* (2022.01)
*B01F 35/83* (2022.01)

(52) U.S. Cl.
CPC .............. *B01F 23/45* (2022.01); *B01F 25/23* (2022.01); *B01F 35/71805* (2022.01); *B01F 35/834* (2022.01)

(56) References Cited

U.S. PATENT DOCUMENTS

| | | |
|---|---|---|
| 3,729,564 A | 4/1973 | Chang et al. |
| 3,931,430 A | 1/1976 | Tada et al. |
| 3,951,581 A | 4/1976 | Nakayama et al. |
| 4,121,898 A | 10/1978 | Kirschnek et al. |
| 4,639,468 A | 1/1987 | Roncucci et al. |
| 4,897,355 A | 1/1990 | Eppstein et al. |
| 4,946,787 A | 8/1990 | Eppstein et al. |
| 5,049,386 A | 9/1991 | Eppstein et al. |
| 5,176,996 A | 1/1993 | Hogan et al. |
| 5,389,221 A * | 2/1995 | Jorgenson .............. G01N 30/38 204/603 |
| 5,420,032 A | 5/1995 | Marshall et al. |
| 5,422,251 A | 6/1995 | Fresco |
| 5,705,385 A | 1/1998 | Bally et al. |
| 5,756,785 A | 5/1998 | O'Lenick, Jr. |
| 5,789,538 A | 8/1998 | Rebar et al. |
| 5,919,743 A | 7/1999 | O'Lenick, Jr. |
| 5,925,523 A | 7/1999 | Dove et al. |
| 5,965,542 A | 10/1999 | Wasan et al. |
| 5,976,567 A | 11/1999 | Wheeler et al. |
| 5,981,501 A | 11/1999 | Wheeler et al. |
| 6,007,988 A | 12/1999 | Choo et al. |
| 6,008,336 A | 12/1999 | Hanson et al. |
| 6,013,453 A | 1/2000 | Choo et al. |
| 6,013,813 A | 1/2000 | O'Lenick, Jr. |
| 6,034,137 A | 3/2000 | Belloni et al. |
| 6,077,509 A | 6/2000 | Weiner et al. |
| 6,107,286 A | 8/2000 | Byk et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,300,321 B1 | 10/2001 | Scherman et al. |
| 6,333,433 B1 | 12/2001 | Banerjee et al. |
| 6,410,248 B1 | 6/2002 | Greisman et al. |
| 6,410,328 B1 | 6/2002 | Maclachlan et al. |
| 6,443,610 B1 * | 9/2002 | Shechter ................ B01F 25/23 366/173.1 |
| 6,453,242 B1 | 9/2002 | Eisenberg et al. |
| 6,458,381 B1 | 10/2002 | Sourovoi et al. |
| 6,479,626 B1 | 11/2002 | Kim et al. |
| 6,503,717 B2 | 1/2003 | Case et al. |
| 6,534,018 B1 * | 3/2003 | Baker ................ B01F 35/8311 425/5 |
| 6,534,261 B1 | 3/2003 | Cox, III et al. |
| 6,534,484 B1 | 3/2003 | Wheeler et al. |
| 6,586,410 B1 | 7/2003 | Wheeler et al. |
| 6,599,692 B1 | 7/2003 | Case et al. |
| 6,607,882 B1 | 8/2003 | Cox, III et al. |
| 6,620,794 B1 | 9/2003 | O'Lenick, Jr. et al. |
| 6,689,558 B2 | 2/2004 | Case |
| 6,723,551 B2 | 4/2004 | Kotin et al. |
| 6,794,136 B1 | 9/2004 | Eisenberg et al. |
| 6,815,432 B2 | 11/2004 | Wheeler et al. |
| 6,824,978 B1 | 11/2004 | Cox, III et al. |
| 6,833,252 B1 | 12/2004 | Dujon et al. |
| 6,858,224 B2 | 2/2005 | Wheeler et al. |
| 6,903,185 B2 | 6/2005 | Kim et al. |
| 6,933,113 B2 | 8/2005 | Case et al. |
| 6,979,539 B2 | 12/2005 | Cox, III et al. |
| 6,986,902 B1 | 1/2006 | Chen et al. |
| 6,989,264 B2 | 1/2006 | Atkinson et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,112,337 B2 | 9/2006 | Huang et al. |
| 7,153,949 B2 | 12/2006 | Kim et al. |
| 7,163,824 B2 | 1/2007 | Cox, III et al. |
| 7,217,509 B2 | 5/2007 | Wolffe et al. |
| 7,253,273 B2 | 8/2007 | Collingwood |
| 7,262,054 B2 | 8/2007 | Jamieson et al. |
| 7,271,002 B2 | 9/2007 | Kotin et al. |
| 7,361,635 B2 | 4/2008 | Miller et al. |
| 7,404,969 B2 | 7/2008 | Chen et al. |
| 7,419,817 B2 | 9/2008 | Chiorini et al. |
| 7,470,781 B2 | 12/2008 | Crouzet et al. |
| 7,745,651 B2 | 6/2010 | Heyes et al. |
| 7,785,792 B2 | 8/2010 | Wolffe et al. |
| 7,799,565 B2 | 9/2010 | MacLachlan et al. |
| 7,803,397 B2 | 9/2010 | Heyes et al. |
| 7,811,602 B2 | 10/2010 | Cullis et al. |
| 7,888,121 B2 | 2/2011 | Urnov et al. |
| 7,893,302 B2 | 2/2011 | Chen et al. |
| 7,901,708 B2 | 3/2011 | MacLachlan et al. |
| 7,914,796 B2 | 3/2011 | Miller et al. |
| 7,923,542 B2 | 4/2011 | Wolffe et al. |
| 7,938,295 B2 * | 5/2011 | Wootton ............... B29B 7/7668 222/145.5 |
| 7,951,925 B2 | 5/2011 | Ando et al. |
| 7,972,854 B2 | 7/2011 | Miller et al. |
| 7,982,027 B2 | 7/2011 | MacLachlan et al. |
| 8,034,376 B2 | 10/2011 | Manoharan et al. |
| 8,034,598 B2 | 10/2011 | Miller |
| 8,071,370 B2 | 12/2011 | Wolffe et al. |
| 8,110,379 B2 | 2/2012 | DeKelver et al. |
| 8,153,773 B2 | 4/2012 | Jemielity et al. |
| 8,158,601 B2 | 4/2012 | Chen et al. |
| 8,206,747 B2 | 6/2012 | Zale et al. |
| 8,278,036 B2 | 10/2012 | Kariko et al. |
| 8,283,333 B2 | 10/2012 | Yaworski et al. |
| 8,293,276 B2 | 10/2012 | Troiano et al. |
| 8,318,208 B1 | 11/2012 | Zale et al. |
| 8,318,211 B2 | 11/2012 | Zale et al. |
| 8,329,070 B2 | 12/2012 | MacLachlan et al. |
| 8,409,861 B2 | 4/2013 | Guschin et al. |
| 8,466,122 B2 | 6/2013 | Heyes et al. |
| 8,563,314 B2 | 10/2013 | Gregory et al. |
| 8,569,256 B2 | 10/2013 | Heyes et al. |
| 8,575,123 B2 | 11/2013 | Manoharan et al. |
| 8,586,526 B2 | 11/2013 | Gregory et al. |
| 8,597,912 B2 | 12/2013 | Collingwood et al. |
| 8,623,618 B2 | 1/2014 | Doyon et al. |
| 8,642,076 B2 | 2/2014 | Manoharan et al. |
| 8,691,750 B2 | 4/2014 | Constien et al. |
| 8,697,359 B1 | 4/2014 | Zhang |
| 8,703,489 B2 | 4/2014 | Wang |
| 8,722,082 B2 | 5/2014 | Manoharan et al. |
| 8,748,089 B2 | 6/2014 | Kariko et al. |
| 8,754,062 B2 | 6/2014 | De Fougerolles et al. |
| 8,771,985 B2 | 7/2014 | Cui et al. |
| 8,772,453 B2 | 7/2014 | Paschon et al. |
| 8,802,644 B2 | 8/2014 | Chen et al. |
| 8,822,668 B2 | 9/2014 | Yaworski et al. |
| 8,835,108 B2 | 9/2014 | Kariko et al. |
| 8,945,868 B2 | 2/2015 | Collingwood et al. |
| 8,956,828 B2 | 2/2015 | Bonini et al. |
| 8,962,281 B2 | 2/2015 | Doyon et al. |
| 9,005,973 B2 | 4/2015 | Cost et al. |
| 9,012,498 B2 | 4/2015 | Manoharan et al. |
| 9,045,763 B2 | 6/2015 | DeKelver et al. |
| 9,139,554 B2 | 9/2015 | Hope et al. |
| 9,150,847 B2 | 10/2015 | Rebar |
| 9,200,266 B2 | 12/2015 | Wang |
| 9,234,016 B2 | 1/2016 | Gregory et al. |
| 9,255,250 B2 | 2/2016 | Gregory et al. |
| 9,352,042 B2 | 5/2016 | Heyes et al. |
| 9,394,545 B2 | 7/2016 | Miller |
| 9,458,205 B2 | 10/2016 | Gregory et al. |
| 9,604,908 B2 | 3/2017 | Stanton et al. |

(56) References Cited

U.S. PATENT DOCUMENTS

| | | |
|---|---|---|
| 9,682,922 B2 | 6/2017 | Manoharan et al. |
| 9,693,958 B2 | 7/2017 | Zhu |
| 9,737,619 B2 | 8/2017 | Ansell et al. |
| 9,738,593 B2 | 8/2017 | Ansell et al. |
| 9,750,824 B2 | 9/2017 | Kariko et al. |
| 9,795,566 B2 | 10/2017 | Oya et al. |
| 10,106,490 B2 | 10/2018 | Du |
| 10,144,725 B2 | 12/2018 | Brown |
| 10,166,298 B2 | 1/2019 | Ansell et al. |
| 10,221,127 B2 | 3/2019 | Du et al. |
| 10,682,374 B2 | 6/2020 | Dong et al. |
| 10,723,692 B2 | 7/2020 | Ansell et al. |
| 11,040,112 B2 | 6/2021 | Ansell et al. |
| 11,168,051 B2 | 11/2021 | Du et al. |
| 11,357,856 B2 | 6/2022 | Ansell et al. |
| 11,453,639 B2 | 9/2022 | Du |
| 11,524,932 B2 | 12/2022 | Du |
| 11,542,225 B2 | 1/2023 | Du |
| 11,634,379 B2 | 4/2023 | Ansell et al. |
| 11,639,329 B2 | 5/2023 | Du |
| 11,648,324 B2 | 5/2023 | Nowruzi et al. |
| 11,712,481 B2 | 8/2023 | Hope et al. |
| 11,820,728 B2 | 11/2023 | Du et al. |
| 11,976,019 B2 | 5/2024 | Gatenyo et al. |
| 12,065,396 B2 | 8/2024 | Du |
| 12,129,223 B2 | 10/2024 | Du et al. |
| 2003/0031704 A1 | 2/2003 | Huang et al. |
| 2003/0153081 A1 | 8/2003 | Tagawa et al. |
| 2003/0232410 A1 | 12/2003 | Liljedahl et al. |
| 2004/0002092 A1 | 1/2004 | Arnould et al. |
| 2004/0142025 A1 | 7/2004 | MacLachlan et al. |
| 2004/0142474 A1 | 7/2004 | Mahato et al. |
| 2005/0026157 A1 | 2/2005 | Baltimore et al. |
| 2005/0064474 A1 | 3/2005 | Urnov et al. |
| 2005/0064595 A1 | 3/2005 | MacLachlan et al. |
| 2005/0208489 A1 | 9/2005 | Carroll et al. |
| 2005/0222064 A1 | 10/2005 | Vargeese et al. |
| 2005/0250723 A1 | 11/2005 | Hoerr et al. |
| 2005/0267061 A1 | 12/2005 | Martin |
| 2006/0063231 A1 | 3/2006 | Li et al. |
| 2006/0078552 A1 | 4/2006 | Arnould et al. |
| 2006/0083780 A1 | 4/2006 | Heyes et al. |
| 2006/0100177 A1 | 5/2006 | Nishimura et al. |
| 2006/0153836 A1 | 7/2006 | Bailly et al. |
| 2006/0188490 A1 | 8/2006 | Hoerr et al. |
| 2006/0188987 A1 | 8/2006 | Guschin et al. |
| 2006/0206949 A1 | 9/2006 | Arnould et al. |
| 2006/0240554 A1 | 10/2006 | Chen et al. |
| 2007/0042031 A1 | 2/2007 | MacLachlan et al. |
| 2007/0117128 A1 | 5/2007 | Smith et al. |
| 2007/0218528 A1 | 9/2007 | Miller |
| 2008/0020058 A1 | 1/2008 | Chen et al. |
| 2008/0025944 A1 | 1/2008 | Hoerr et al. |
| 2008/0131962 A1 | 6/2008 | Miller |
| 2008/0159996 A1 | 7/2008 | Ando et al. |
| 2009/0068164 A1 | 3/2009 | Segal et al. |
| 2009/0086558 A1 | 4/2009 | Do |
| 2009/0136465 A1 | 5/2009 | Merenick et al. |
| 2009/0209037 A1 | 8/2009 | Tagawa et al. |
| 2009/0247608 A1 | 10/2009 | Manoharan et al. |
| 2009/0263407 A1 | 10/2009 | Dande et al. |
| 2009/0285881 A1 | 11/2009 | Dande et al. |
| 2009/0305346 A1 | 12/2009 | Miller |
| 2009/0324584 A1 | 12/2009 | Hoerr et al. |
| 2010/0036115 A1 | 2/2010 | Beigelman et al. |
| 2010/0068285 A1 | 3/2010 | Zale et al. |
| 2010/0068286 A1 | 3/2010 | Troiano et al. |
| 2010/0069426 A1 | 3/2010 | Zale et al. |
| 2010/0087337 A1 | 4/2010 | Dewitt |
| 2010/0104645 A1 | 4/2010 | Ali et al. |
| 2010/0104655 A1 | 4/2010 | Zale et al. |
| 2010/0189729 A1 | 7/2010 | Hoerr et al. |
| 2010/0203076 A1 | 8/2010 | Fotin-Mleczek et al. |
| 2010/0218264 A1 | 8/2010 | Cui et al. |
| 2010/0285112 A1 | 11/2010 | Novobrantseva et al. |
| 2010/0291156 A1 | 11/2010 | Barner et al. |
| 2010/0305196 A1 | 12/2010 | Probst et al. |
| 2010/0324120 A1 | 12/2010 | Chen et al. |
| 2011/0045473 A1 | 2/2011 | De Fougerolles et al. |
| 2011/0091525 A1 | 4/2011 | Heyes et al. |
| 2011/0097720 A1 | 4/2011 | Ciufolini et al. |
| 2011/0145940 A1 | 6/2011 | Voytas et al. |
| 2011/0200582 A1 | 8/2011 | Baryza et al. |
| 2011/0201055 A1 | 8/2011 | Doyon et al. |
| 2011/0250225 A1 | 10/2011 | Fotin-Mleczek et al. |
| 2011/0256175 A1 | 10/2011 | Hope et al. |
| 2011/0262491 A1 | 10/2011 | Keegan et al. |
| 2011/0262527 A1 | 10/2011 | Heyes et al. |
| 2011/0265198 A1 | 10/2011 | Gregory et al. |
| 2011/0274759 A1 | 11/2011 | Troiano et al. |
| 2011/0294717 A1 | 12/2011 | Ali et al. |
| 2011/0300205 A1 | 12/2011 | Geall et al. |
| 2011/0301073 A1 | 12/2011 | Gregory et al. |
| 2011/0305770 A1 | 12/2011 | Zhao et al. |
| 2011/0311582 A1 | 12/2011 | Manoharan et al. |
| 2011/0311583 A1 | 12/2011 | Manoharan et al. |
| 2012/0004293 A1 | 1/2012 | Zale et al. |
| 2012/0017290 A1 | 1/2012 | Cui et al. |
| 2012/0021043 A1 | 1/2012 | Kramps et al. |
| 2012/0027796 A1 | 2/2012 | Manoharan et al. |
| 2012/0027803 A1 | 2/2012 | Manoharan et al. |
| 2012/0040398 A1 | 2/2012 | Miller |
| 2012/0046478 A1 | 2/2012 | Manoharan et al. |
| 2012/0058144 A1 | 3/2012 | Manoharan et al. |
| 2012/0058188 A1 | 3/2012 | Manoharan et al. |
| 2012/0060230 A1 | 3/2012 | Collingwood et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0172411 A1 | 7/2012 | Heyes et al. |
| 2012/0177724 A1 | 7/2012 | Irvine et al. |
| 2012/0178702 A1 | 7/2012 | Huang et al. |
| 2012/0183602 A1 | 7/2012 | Chen et al. |
| 2012/0195936 A1 | 8/2012 | Rudolph et al. |
| 2012/0202871 A1 | 8/2012 | Heyes et al. |
| 2012/0207845 A1 | 8/2012 | Sung et al. |
| 2012/0225434 A1 | 9/2012 | Ciufolini et al. |
| 2012/0244207 A1 | 9/2012 | Fitzgerald et al. |
| 2012/0251618 A1 | 10/2012 | Schrum et al. |
| 2012/0264810 A1 | 10/2012 | Lin et al. |
| 2012/0276209 A1 | 11/2012 | Cullis et al. |
| 2012/0288541 A1 | 11/2012 | Zale et al. |
| 2012/0295832 A1 | 11/2012 | Constien et al. |
| 2013/0017223 A1 | 1/2013 | Hope et al. |
| 2013/0022649 A1 | 1/2013 | Yaworski et al. |
| 2013/0064894 A1 | 3/2013 | Martin et al. |
| 2013/0108685 A1 | 5/2013 | Kuboyama et al. |
| 2013/0122104 A1 | 5/2013 | Yaworski et al. |
| 2013/0122591 A1 | 5/2013 | Cost et al. |
| 2013/0123338 A1 | 5/2013 | Heyes et al. |
| 2013/0129754 A1 | 5/2013 | Thess et al. |
| 2013/0129811 A1 | 5/2013 | Kuboyama et al. |
| 2013/0137104 A1 | 5/2013 | Cost et al. |
| 2013/0164400 A1* | 6/2013 | Knopov .......... B01J 13/04 425/5 |
| 2013/0177690 A1 | 7/2013 | Regar |
| 2013/0177983 A1 | 7/2013 | Rebar |
| 2013/0196373 A1 | 8/2013 | Gregory et al. |
| 2013/0259879 A1 | 10/2013 | Baumhof et al. |
| 2013/0261172 A1 | 10/2013 | Kariko et al. |
| 2013/0266640 A1 | 10/2013 | de Fougerolles et al. |
| 2013/0280283 A1 | 10/2013 | Lorenz et al. |
| 2013/0280305 A1 | 10/2013 | Kuboyama et al. |
| 2013/0295043 A1 | 11/2013 | Kallen et al. |
| 2013/0323269 A1 | 12/2013 | Manoharan et al. |
| 2013/0336998 A1 | 12/2013 | Kallen et al. |
| 2013/0338210 A1 | 12/2013 | Manoharan et al. |
| 2014/0017212 A1 | 1/2014 | Rebar et al. |
| 2014/0044772 A1 | 2/2014 | MacLachlan et al. |
| 2014/0087036 A1* | 3/2014 | Organ .......... G01N 1/44 426/241 |
| 2014/0120622 A1 | 5/2014 | Gregory et al. |
| 2014/0121393 A1 | 5/2014 | Manoharan et al. |
| 2014/0134260 A1 | 5/2014 | Heyes et al. |

(56) References Cited

U.S. PATENT DOCUMENTS

| | | |
|---|---|---|
| 2014/0179761 A1 | 6/2014 | Manoharan et al. |
| 2014/0256785 A1 | 9/2014 | Manoharan et al. |
| 2014/0294937 A1 | 10/2014 | MacLachlan et al. |
| 2014/0295449 A1 | 10/2014 | Ciufolini et al. |
| 2014/0308304 A1 | 10/2014 | Manoharan et al. |
| 2014/0323548 A1 | 10/2014 | Budzik et al. |
| 2015/0037326 A1 | 2/2015 | Butler-Ransohoff et al. |
| 2015/0050302 A1 | 2/2015 | Thess |
| 2015/0056705 A1 | 2/2015 | Conway et al. |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0159172 A1 | 6/2015 | Miller et al. |
| 2015/0165006 A1 | 6/2015 | Thess et al. |
| 2015/0184195 A1 | 7/2015 | Thess et al. |
| 2015/0203446 A1 | 7/2015 | Manoharan et al. |
| 2015/0218554 A1 | 8/2015 | Thess |
| 2015/0306249 A1 | 10/2015 | Baumhof et al. |
| 2015/0335708 A1 | 11/2015 | Kwak et al. |
| 2016/0009637 A1 | 1/2016 | Manoharan et al. |
| 2016/0024474 A1 | 1/2016 | Cost et al. |
| 2016/0095924 A1 | 4/2016 | Hope et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0235864 A1 | 8/2016 | Schlake et al. |
| 2016/0243255 A1* | 8/2016 | Nechev .................. B01F 35/92 |
| 2016/0304883 A1 | 10/2016 | Grund et al. |
| 2016/0326548 A1 | 11/2016 | Cost |
| 2016/0361411 A1 | 12/2016 | Gindy et al. |
| 2017/0027803 A1 | 2/2017 | Agrawal et al. |
| 2017/0029847 A1 | 2/2017 | Thess |
| 2017/0100682 A1* | 4/2017 | Wikfors ................. G01N 30/34 |
| 2017/0173080 A1 | 6/2017 | Lee et al. |
| 2017/0211075 A1 | 7/2017 | Lee et al. |
| 2017/0248502 A1* | 8/2017 | Organ .................... B01L 3/0293 |
| 2017/0252430 A1 | 9/2017 | Fotin-Mleczek et al. |
| 2017/0266292 A1 | 9/2017 | Luo et al. |
| 2017/0326225 A1 | 11/2017 | Rauch et al. |
| 2018/0043320 A1* | 2/2018 | Ramsay ............... B01J 19/0093 |
| 2018/0044687 A1 | 2/2018 | Thess et al. |
| 2018/0064827 A1 | 3/2018 | Conway et al. |
| 2018/0087072 A1 | 3/2018 | Miller et al. |
| 2018/0088091 A1* | 3/2018 | Cormier ................. G01N 30/32 |
| 2018/0125952 A1 | 5/2018 | Fotin-Mleczek et al. |
| 2018/0126003 A1 | 5/2018 | Hoerr |
| 2018/0148727 A1 | 5/2018 | Grund et al. |
| 2018/0185516 A1 | 7/2018 | Ansell et al. |
| 2018/0195954 A1* | 7/2018 | Strande ............. G01N 33/5306 |
| 2018/0214537 A1 | 8/2018 | Mutzke et al. |
| 2018/0237786 A1 | 8/2018 | Schlake et al. |
| 2018/0296663 A1 | 10/2018 | Hipp et al. |
| 2018/0303925 A1 | 10/2018 | Weissman et al. |
| 2018/0312545 A1 | 11/2018 | Baumhof et al. |
| 2019/0022247 A1 | 1/2019 | Ansell et al. |
| 2019/0024096 A1 | 1/2019 | Schmid et al. |
| 2019/0160164 A1 | 5/2019 | Rauch et al. |
| 2019/0274968 A1 | 9/2019 | Weissman et al. |
| 2020/0046838 A1 | 2/2020 | Ansell et al. |
| 2020/0121809 A1 | 4/2020 | Hope et al. |
| 2020/0163878 A1 | 5/2020 | Baumhof et al. |
| 2020/0172472 A1 | 6/2020 | Du |
| 2020/0283372 A1 | 9/2020 | Du |
| 2021/0008552 A1* | 1/2021 | Regan ................ G01N 35/1095 |
| 2021/0107861 A1 | 4/2021 | Ansell et al. |
| 2021/0122702 A1 | 4/2021 | Du |
| 2021/0122703 A1 | 4/2021 | Du |
| 2021/0128488 A1 | 5/2021 | Du |
| 2021/0251898 A1 | 8/2021 | Baumhof et al. |
| 2021/0395188 A1 | 12/2021 | Ansell |
| 2022/0040285 A1 | 2/2022 | Weissman et al. |
| 2022/0072155 A1 | 3/2022 | Ansell et al. |
| 2022/0081392 A1 | 3/2022 | Du et al. |
| 2022/0106257 A1 | 4/2022 | Gatenyo et al. |
| 2022/0226461 A1 | 7/2022 | Weissman et al. |
| 2023/0123534 A1 | 4/2023 | Du |
| 2023/0372537 A1 | 11/2023 | Hope et al. |
| 2024/0075163 A1 | 3/2024 | Ansell et al. |
| 2024/0122854 A1 | 4/2024 | Du et al. |
| 2024/0270679 A1 | 8/2024 | Du et al. |
| 2024/0308952 A1 | 9/2024 | Du |

FOREIGN PATENT DOCUMENTS

| | | |
|---|---|---|
| EP | 1 083 232 B1 | 2/2005 |
| GB | 1 277 947 A | 6/1972 |
| GB | 2 338 237 A | 12/1999 |
| JP | H05-331118 A | 12/1993 |
| JP | H10-3643 A | 1/1998 |
| JP | 2001-338416 A | 12/2001 |
| JP | 4681425 B2 | 5/2011 |
| WO | 87/07183 A1 | 12/1987 |
| WO | 95/19431 A1 | 7/1995 |
| WO | 96/06166 A1 | 2/1996 |
| WO | 97/03939 A1 | 2/1997 |
| WO | 98/16599 A1 | 4/1998 |
| WO | 98/37186 A1 | 8/1998 |
| WO | 98/53057 A1 | 11/1998 |
| WO | 98/53058 A1 | 11/1998 |
| WO | 98/53059 A1 | 11/1998 |
| WO | 98/53060 A1 | 11/1998 |
| WO | 98/54311 A1 | 12/1998 |
| WO | 99/05094 A1 | 2/1999 |
| WO | 99/33493 A1 | 7/1999 |
| WO | 00/27878 A1 | 5/2000 |
| WO | 00/30444 A1 | 6/2000 |
| WO | 01/07548 A1 | 2/2001 |
| WO | 01/48233 A1 | 7/2001 |
| WO | 01/60970 A2 | 8/2001 |
| WO | 01/88197 A2 | 11/2001 |
| WO | 02/016536 A1 | 2/2002 |
| WO | 02/099084 A2 | 12/2002 |
| WO | 03/016496 A2 | 2/2003 |
| WO | 03/053409 A1 | 7/2003 |
| WO | 2005/060934 A1 | 7/2005 |
| WO | 2006/138380 A2 | 12/2006 |
| WO | 2007/014275 A2 | 2/2007 |
| WO | 2007/024708 A2 | 3/2007 |
| WO | 2008/103276 A2 | 8/2008 |
| WO | 2008/121949 A1 | 10/2008 |
| WO | 2009/086558 A1 | 7/2009 |
| WO | 2009/127060 A1 | 10/2009 |
| WO | 2009/132131 A1 | 10/2009 |
| WO | 2010/005721 A2 | 1/2010 |
| WO | 2010/005723 A2 | 1/2010 |
| WO | 2010/005725 A2 | 1/2010 |
| WO | 2010/005726 A2 | 1/2010 |
| WO | 2010/005740 A2 | 1/2010 |
| WO | 2010/021865 A1 | 2/2010 |
| WO | 2010/030763 A2 | 3/2010 |
| WO | 2010/042877 A1 | 4/2010 |
| WO | 2010/048536 A2 | 4/2010 |
| WO | 2010/054384 A1 | 5/2010 |
| WO | 2010/054401 A1 | 5/2010 |
| WO | 2010/054405 A1 | 5/2010 |
| WO | 2010/054406 A1 | 5/2010 |
| WO | 2010/057150 A1 | 5/2010 |
| WO | 2010/062322 A2 | 6/2010 |
| WO | 2010/079430 A1 | 7/2010 |
| WO | 2010/080724 A1 | 7/2010 |
| WO | 2010/088537 A2 | 8/2010 |
| WO | 2010/129709 A1 | 11/2010 |
| WO | 2011/022460 A1 | 2/2011 |
| WO | 2011/043913 A2 | 4/2011 |
| WO | 2011/075656 A1 | 6/2011 |
| WO | 2011/076807 A2 | 6/2011 |
| WO | 2011/084513 A2 | 7/2011 |
| WO | 2011/084521 A2 | 7/2011 |
| WO | 2011/090965 A1 | 7/2011 |
| WO | 2011/094198 A1 | 8/2011 |

(56) References Cited

FOREIGN PATENT DOCUMENTS

| | | |
|---|---|---|
| WO | 2011/127255 A1 | 10/2011 |
| WO | 2011/141703 A1 | 11/2011 |
| WO | 2011/141705 A1 | 11/2011 |
| WO | 2011/143230 A1 | 11/2011 |
| WO | 2011/149733 A2 | 12/2011 |
| WO | 2011/153120 A1 | 12/2011 |
| WO | 2012/000104 A1 | 1/2012 |
| WO | 2012/006378 A1 | 1/2012 |
| WO | 2012/006380 A2 | 1/2012 |
| WO | 2012/016184 A2 | 2/2012 |
| WO | 2012/019630 A1 | 2/2012 |
| WO | 2012/030901 A1 | 3/2012 |
| WO | 2012/031043 A1 | 3/2012 |
| WO | 2012/031046 A2 | 3/2012 |
| WO | 2012/040184 A2 | 3/2012 |
| WO | 2012/044638 A1 | 4/2012 |
| WO | 2012/054365 A2 | 4/2012 |
| WO | 2012/054923 A2 | 4/2012 |
| WO | 2012/061259 A2 | 5/2012 |
| WO | 2012/068176 A1 | 5/2012 |
| WO | 2013/014073 A1 | 1/2013 |
| WO | 2013/016058 A1 | 1/2013 |
| WO | 2013/044008 A2 | 3/2013 |
| WO | 2013/059496 A1 | 4/2013 |
| WO | 2013/086322 A1 | 6/2013 |
| WO | 2013/086354 A1 | 6/2013 |
| WO | 2013/086373 A1 | 6/2013 |
| WO | 2013/143555 A1 | 10/2013 |
| WO | 2014/008334 A1 | 1/2014 |
| WO | 2014/028487 A1 | 2/2014 |
| WO | 2014/089239 A1 | 6/2014 |
| WO | 2014/153163 A1 | 9/2014 |
| WO | 2014/160243 A1 | 10/2014 |
| WO | 2014/160284 A1 | 10/2014 |
| WO | 2015/074085 A1 | 5/2015 |
| WO | 2015/123576 A2 | 8/2015 |
| WO | 2015/130584 A2 | 9/2015 |
| WO | 2015/164674 A1 | 10/2015 |
| WO | 2015/177752 A1 | 11/2015 |
| WO | 2016/010840 A1 | 1/2016 |
| WO | 2016/014794 A1 | 1/2016 |
| WO | 2016/183298 A1 | 11/2016 |
| WO | 2017/004143 A1 | 1/2017 |
| WO | 2017/021546 A1 | 2/2017 |
| WO | 2017/048770 A1 | 3/2017 |
| WO | 2017/049245 A2 | 3/2017 |
| WO | 2017/074526 A1 | 5/2017 |
| WO | 2017/075531 A1 | 5/2017 |
| WO | 2017/112865 A1 | 6/2017 |
| WO | 2017/117528 A1 | 7/2017 |
| WO | 2017/140905 A1 | 8/2017 |
| WO | 2017/173054 A1 | 10/2017 |
| WO | 2017/182634 A1 | 10/2017 |
| WO | 2017/194454 A1 | 11/2017 |
| WO | 2017/201332 A1 | 11/2017 |
| WO | 2016/176330 A1 | 3/2018 |
| WO | 2018/078053 A1 | 5/2018 |
| WO | 2018/081638 A1 | 5/2018 |
| WO | 2018/191657 A1 | 10/2018 |
| WO | 2018/191719 A1 | 10/2018 |
| WO | 2018/200943 A1 | 11/2018 |
| WO | 2019/089828 A1 | 5/2019 |
| WO | 2021/030701 A1 | 2/2021 |

OTHER PUBLICATIONS

U.S. Appl. No. 17/634,516, filed Feb. 10, 2022.
Akinc et al., "A combinatorial library of lipid-like materials for delivery of RNAi therapeutics," Nature Biotechnology 26(5):561-569, May 2008.
Akinc et al., "Targeted delivery of RNAi therapeutics with endogenous and exogenous ligand-based mechanisms," *Mol. Ther.* 18(7):1357-1364, 2010.
Alabi et al., "Multiparametric approach for the evaluation of lipid nanoparticles for siRNA delivery," PNAS 110(32):12881-12886, Aug. 6, 2013.
Alexidis et al., "Novel 1,4 Substituted Piperidine Derivatives. Synthesis and Correlation of Antioxidant Activity with Structure and Lipophilicity," J. Pharm. Pharmacol. 47:131-137, 1995.
Anderson et al., "Incorporation of pseudouridine into mRNA enhances translation by diminishing PKR activation," *Nucleic Acids Res.* 38(17):5884-5892, 2010.
Anderson et al., "Nucleoside modifications in RNA limit activation of 2'-5'-oligoadenylate synthetase and increase resistance to cleavage by RNase L.," *Nucleic Acids Research* 39(21):9329-9338, 2011.
Ansell et al., "Application of Oligo-(14-amino-3,6,9,12-tetraoxatetradecanoic acid) Lipid Conjugates as Steric Barrier Molecules in Liposomal Formulations," *Bioconjugate Chem.* 10:653-666, 1999.
Basha et al., "Influence of cationic lipid composition on gene silencing properties of lipid nanoparticle formulations of siRNA in antigen-presenting cells," *Mol. Ther.* 19(12):2186-2200, 2011.
Belliveau et al., "Microfluidic Synthesis of Highly Potent Limit-size Lipid Nanoparticles for In Vivo Delivery of siRNA," *Mol. Ther. Nucleic Acids* 1:e37, 2012 (9 pages).
Bhattacharya et al., "Synthesis, Thermotropic Behavior, and Permeability Properties of Vesicular Membranes Composed of Cationic Mixed-Chain Surfactants," *Langmuir* 11:4748-4757, 1995.
Brito et al., "A Cationic Nanoemulsion for the Delivery of Next-generation RNA Vaccines," *Molecular Therapy* 22(12):2118-2129, 2014.
Cattanach et al., "Studies in the Indole Series. Part IV. Tetrahydro-1H-pyrido[4,3-b]-indoles as Serotonin Antagonists," *J. Chem Soc.* (C):1235-1243, 1968.
Chen et al., "Influence of particle size on the in vivo potency of lipid nanoparticle formulations of siRNA," *Journal of Controlled Release* 235:236-244, 2016.
Chen et al., "Rapid Discovery of Potent siRNA-Containing Lipid Nanoparticles Enabled by Controlled Microfluidic Formulation," *J. Am. Chem. Soc.* 134:6948-6951, 2012.
Chevalier et al., "Design, Activity, and Structure of a Highly Specific Artificial Endonuclease," *Molecular Cell* 10:895-905, 2002.
Choo et al., "Advances in Zinc Finger Engineering," *Current Opinion in Structural Biology* 10:411-416, 2000.
Cook et al., "Synthesis and Characterization of cis-Dioxomolybdenum(VI) Complexes with Sterically Bulky Tripodal Tetradentate Ligands," *Inorganica Chimica Acta* 144:81-87, 1988.
Durbin et al., "RNAs Containing Modified Nucleotides Fail to Trigger RIG-I Conformational Changes for Innate Immune Signaling," *mBio* 7(5):e00833-16, 2016 (11 pages).
Ernsting et al., "Factors controlling the pharmacokinetics, biodistribution and intratumoral penetration of nanoparticles," *Journal of Controlled Release* 172:782-794, 2013.
Fagerlund et al., "The Cpf1 CRISPR-Cas Protein Expands Genome-Editing Tools," *Genom Bio* 16:251, 2015 (3 pages).
Falcone et al., "Both the 5' Untranslated Region and the Sequences Surrounding the Start Site Contribute to Efficient Initiation of Translation In Vitro," *Molecular and Cellular Biology* 11(5):2656-2664, 1991.
Frisch et al. "A New Triantennary Galactose-Targeted PEGylated Gene Carrier, Characterization of Its Complex with DNA, and Transfection of Hepatoma Cells," *Bioconjugate Chem.* 15: 754-764, 2004.
Gronquist et al., "Synthesis of Unsaturated Polyazamacrolides from the Ladybird Beetle Subcoccinella vigintiquatuorpunctata," *J. Org. Chem.* 66:1075-1081, 2001.
Haft et al., "A Guild of 45 CRISPR-Associated (Cas) Protein Families and Multiple CRISPR/Cas Subtypes Exist in Prokaryotic Genomes," *PLoS Computational Biology* 1(6):e60, 2005.
Han et al., "Synthesis and Properties of Di-Chain Esterquat Surfactants," *J. Surfact Deterg.* 18: 91-95, 2015.
Hancock et al., "Monoalkylaminopropanols and Butanols and their Esters," *J. Am. Chem. Soc.* 66(10):1738-1747, 1944.
Hekele et al., "Rapidly produced SAM® vaccine against H7N9 influenza is immunogenic in mice," *Emerging Microbes and Infections* 2:e52, 2013 (7 pages).

(56) References Cited

OTHER PUBLICATIONS

Heuer et al., "Repeat Domain Diversity of avrBs3-Like Genes in Ralstonia Solancearum Strains and Association with Host Preferences in the Field," *Applied and Environmental Microbiology* 73(13):4379-4384, 2007.

Higashi et al., "Novel lipidated sorbitol-based molecular transporters for non-viral gene delivery," *Journal of Controlled Release* 136:140-147, 2009.

Jasin, "Genetic Manipulation of Genomes with Rare-Cutting Endonucleases," *Trends Genet* 12:224-228, 1996.

Jayaraman et al., "Maximizing the Potency of siRNA Lipid Nanoparticles for Hepatic Gene Silencing In Vivo," *Angew. Chem. Int. Ed.* 51(34):8529-8533, XP055063645, 2012.

Karikó et al., "Incorporation of Pseudouridine into mRNA Yields Superior Nonimmunogenic Vector With Increased Translational Capacity and Biological Stability," *Mol. Ther.* 16(11):1833-1840, 2008.

Karikó et al., "Increased Erythropoiesis in Mice Injected with Submicrogram Quantities of Pseudouridine-containing mRNA Encoding Erythropoietin," *Mol. Ther.* 20(5):948-953, 2012.

Karikó et al., "Suppression of RNA Recognition by Toll-like Receptors: The Impact of Nucleoside Modification and the Evolutionary Origin of RNA," *Immunity* 23:165-175, 2005.

Kay et al., "A Bacterial Effector Acts as a Plant Transcription Factor and Induces a Cell Size Regulator," *Science* 318:648-651, 2007.

Kim et al., "Hybrid restriction enzymes: zinc finger fusions to Fok I cleavage domain," *PNAS USA* 93(3):1156-1160, 1996.

Kim et al., "Highly Efficient RNA-Guided Genome Editing in Human Cells via Delivery of Purified Cas9 Ribonucleoproteins," *Genome Research* 24(6):1012-1019, 2014.

Kim et al., "Synthesis of Novel Poly(amido ethylenimine) (PAMEIM) Dendrimer and Its Self-assembly with Plasmid DNA," *Bull. Korean Chem. Soc.* 27(11):1894-1896, 2006.

Lee et al., "Lipid nanoparticle siRNA systems for silencing the androgen receptor in human prostate cancer in vivo," *Int. J. Cancer* 131(5):E781-E790, 2012.

Leroueil et al., "Wide Varieties of Cationic Nanoparticles Induce Defects in Supported Lipid Bilayers," *Nano Letters* 8(2):420-424, 2008.

Leung et al., "Lipid Nanoparticles Containing siRNA Synthesized by Microfluidic Mixing Exhibit an Electron-Dense Nanostructured Core," *J. Phys. Chem. C. Nanomater. Interfaces* 116(34):18440-18450, 2012.

Leung et al., "Microfluidic Mixing: A General Method for Encapsulating Macromolecules in Lipid Nanoparticle Systems," *J. Phys. Chem. B* 119:8698-8706, 2015.

Li et al., "ATRP in Waterborne Miniemulsion via a Simultaneous Reverse and Normal Initiation Process," *Macromolecules* 37(6):2106-2112, 2004.

Mahon et al., "A combinatorial approach to determine functional group effects on lipidoid-mediated siRNA delivery," *Bioconjug Chem.* 21(8):1448-1454, 2010. (17 pages).

Maier et al., "Biodegradable lipids enabling rapidly eliminated lipid nanoparticles for systemic delivery of RNAi therapeutics," *Mol. Ther.* 21(8):1570-1578, 2013.

Makarova et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," *Biology Direct* 1:7, 2006.

Marchi-Artzner et al., "Adhesion of Arg-Gly-Asp (RGD) Peptide Vesicles onto an Integrin Surface: Visualization of the Segregation of RGD Ligands into the Adhesion Plaques by Fluorescence," *Langmuir* 19:835-841, 2003.

Masuda et al., "Envelope-type lipid nanoparticles incorporating a short PEG-lipid conjugate for improved control of intracellular trafficking and transgene transcription," *Biomaterials* 30:4806-4814, 2009.

Mui et al., "Influence of Polyethylene Glycol Lipid Desorption Rates on Pharmacokinetics and Pharmacodynamics of siRNA Lipid Nanoparticles," *Mol. Ther. Nucleic Acids* 2:e139, 2013 (8 pages).

Nguyen et al., "Lipid-derived nanoparticles for immunostimulatory RNA adjuvant delivery", Proceedings of the National Academy of Sciences 109(14):E797-E803, 2012.

Nishida, "Disk-shaped magnetic recording medium," Caplus Database, Accession No. 2001:881906, 2001 (1 page).

Pabo et al., "Design and Selection of Novel $Cys_2$-$His_2$ Zinc Finger Proteins," *Ann. Rev. Biochem.* 70:313-340, 2001.

Pardi et al., "Expression kinetics of nucleoside-modified mRNA delivered in lipid nanoparticles to mice by various routes," *Journal of Controlled Release* 217:345-351, 2015.

Patani et al., "Bioisosterism: A Rational Approach in Drug Design," *Chem. Rev.* 96(8):3147-3176, 1996.

Petsch et al., "Protective efficacy of in vitro synthesized, specific mRNA vaccines against influenza A virus infection," *Nature Biotechnology* 30(12):1210-1216, 2012 (9 pages).

Perler et al., "Protein splicing elements: inteins and exteins a definition of terms and recommended nomenclature," *Nucleic Acids Research* 22:1125-1127, 1994.

Rajesh et al., "Dramatic Influence of the Orientation of Linker between Hydrophilic and Hydrophobic Lipid Moiety in Liposomal Gene Delivery," *Journal of the American Chemical Society* 129(37):11408-11420, 2007.

Russell et al., "The Stability of Human β-Globin mRNA is Dependent on Structural Determinants Positioned Within Its 3' Untranslated Region," *Blood* 87:5314-5323, 1996.

Schar et al., "Long Chain Linear Fatty Alcohols from ZIEGLER-Synthesis, their Mixtures, Derivatives and Use," IP.com Prior Art Database Technical Disclosure, Jan. 17, 2011, 39 pages.

Schnee et al., "An mRNA Vaccine Encoding Rabies Virus Glycoprotein Induces Protection against Lethal Infection in Mice and Correlates of Protection in Adult and Newborn Pigs," *PLoS Negl. Trop. Dis.* 10(6):e0004746, 2016 (20 pages).

Semple et al., "Interactions of liposomes and lipid-based carrier systems with blood proteins: Relation to clearance behaviour in vivo," *Advanced Drug Delivery Reviews* 32:3-17, 1998.

Semple et al., "Rational design of cationic lipids for siRNA delivery," *Nature Biotechnology* 28(2):172-176, 2010. (26 pages).

Szebeni et al., "Activation of complement by therapeutic liposomes and other lipid excipient-based therapeutic products: Prediction and prevention," *Advanced Drug Delivery Reviews* 63:1020-1030, 2011.

Szebeni et al., "Complement activation as a bioequivalence issue relevant to the development of generic liposomes and other nanoparticulate drugs," *Biochemical and Biophysical Research Communications* 468:490-497, 2015.

Szebeni, "Complement activation-related pseudoallergy: A stress reaction in blood triggered by nanomedicines and biologicals," *Molecular Immunology* 61:163-173, 2014.

Szolcsányi et al., "Short racemic syntheses of calvine and epicalvine," *Tetrahedron Letters* 49:1357-1360, 2008.

Tam et al., "Advances in Lipid Nanoparticles for siRNA Delivery," *Pharmaceutics* 5:498-507, 2013.

Tam et al., "Small molecule ligands for enhanced intracellular delivery of lipid nanoparticle formulations of siRNA," *Nanomedicine* 9(5):665-674, 2013.

Tekmira Pharmaceuticals Corp, Form 20-F, EDGAR Online, filed Mar. 27, 2013, 298 pages.

Tekmira, "Tekmira and Alnylam Restructure Relationship and Settle All Litigation," Tekmira Pharmaceuticals Corporation, Nov. 12, 2012, 3 pages.

Torrecilla et al., "Lipid Nanoparticles as Carriers for RNAi against Viral Infections: Current Status and Future Perspectives," BioMed Research International 2014:Article ID 161794, 17 pages.

Van Doren et al., "Structure-Property Relationships in D-Glucitol Derivatives with Two Geminal Hydrocarbon Chains," J. Mater. Chem. 5(12):2153-2160, 1995.

Vanderah et al., "Oligo(ethylene oxide) Self-Assembled Monolayers with Self-Limiting Packing Densities for the Inhibition of Nonspecific Protein Adsorption," *Langmuir* 25(9):5026-5030, 2009.

Vogel et al., "A Bacterial Seek-and-Destroy System for Foreign DNA," *Science* 344(6187):972-73, 2014.

Wang et al., "Composite Nanoparticles for Gene Delivery," *Adv. Genet.* 88:111-137, 2014.

(56) References Cited

OTHER PUBLICATIONS

Whitehead et al., "Synergistic Silencing: Combinations of Lipid-like Materials for Efficacious siRNA Delivery," *Molecular Therapy* 19(9):1688-1694, 2011.
Xue et al., "Lipid-Based Nanocarriers for RNA Delivery," *Current Pharmaceutical Design* 21:3140-3147, 2015.
Yoshimura et al., "Solution Properties of Tadpole-type Cationic Amphiphilic Dendrimers Consisting of an Alkyl Chain, a Quaternary Ammonium, and a Poly(amidoamine) Dendron," Journal of Oleo Science 62(4):213-221, 2013.
Zhang et al., "Biodegradable Amino-Ester Nanomaterials for Cas9 mRNA Delivery in Vitro and in Vivo," *ACS Appl. Mater. Interfaces* 9(30):25481-25487, 2017. (15 pages).
Zhang et al., "Lipid-modified spermine derivatives and liposome prepared with said derivatives," Caplus Database, Accession No. 2015:1437089, 2015. (2 pages).
U.S. Appl. No. 18/295,63, filed Apr. 4, 2023.
U.S. Appl. No. 18/421,751, filed Jan. 24, 2024.
U.S. Appl. No. 18/480,964, filed Oct. 4, 2023.
U.S. Appl. No. 18/612,888, filed Mar. 21, 2024.
U.S. Appl. No. 18/639,750, filed Apr. 18, 2024.
U.S. Appl. No. 18/655,061, filed May 3, 2024.
U.S. Appl. No. 18/661,116, filed May 10, 2024.
U.S. Appl. No. 18/720,478, filed Jun. 14, 2024.
U.S. Appl. No. 18/720,483, filed Jun. 14, 2024.
U.S. Appl. No. 18/744,241, filed Jun. 14, 2024.
U.S. Appl. No. 18/744,246, filed Jun. 14, 2024.
U.S. Appl. No. 18/744,413, filed Jun. 14, 2024.
U.S. Appl. No. 18/767,373, filed Jul. 9, 2024.
U.S. Appl. No. 18/886,871, filed Sep. 16, 2024.
U.S. Appl. No. 18/902,591, filed Sep. 30, 2024.

\* cited by examiner

SYSTEMS AND METHODS FOR MANUFACTURING LIPID NANOPARTICLES AND LIPOSOMES

BACKGROUND

Technical Field

Embodiments of the present disclosure generally relate to lipid nanoparticles (LNPs) and methods and systems for their manufacture.

Description of the Related Art

The manufacturing process for lipid nanoparticles/liposomes is highly specialized, in part because control of the particle size is considered important and such control is not trivial. Early systems involve preparations of large particles using relatively slow and/or uncontrolled mixing processes. These particles were then reduced in size by means such as extrusion through membranes with well-defined pore sizes. Such systems have been implemented on commercial scales although they can suffer from issues with clogging of the extrusion membranes.

Other systems are based on relatively more rapid mixing of aqueous and organic components such that the particles are formed at the target size. These systems can be based on a slow addition of one component to the other component under rapid mixing conditions. Such systems have the inherent drawback that the composition of the mixture continually changes during addition of one component to the other, and as such the formed particles may also vary from the first part of the addition to the end.

Another approach involves continuous addition of both components in a fixed proportion, e.g., in-line mixing. In this approach, the formation of the particles occurs under a constant condition throughout the batch. Such systems generally require some kind of mixing chamber/assembly (e.g., T-mixer or microfluidic device) to bring the component streams together in a fixed manner and allow the output to be continually delivered to a receptacle. An inherent drawback with such devices is the ability to properly prime the system to ensure component proportions and mixing conditions (e.g., flow rates, pressures, etc.) within the chamber/device. The practical reality is that significant material is discarded at the beginning of a manufacturing run while the pumps and mixing assembly are primed with component solutions and reach target flow rates while the mixing assembly equilibrates to a steady state with respect to flows and pressures, and other parameters.

Accordingly, there remains a need for improved systems and method for manufacturing lipid nanoparticles (LNPs) and liposomes. The present disclosure provides these and related advantages.

BRIEF SUMMARY

The present disclosure is directed to systems and methods for manufacturing lipid nanoparticles and liposomes.

Accordingly, one embodiment provides a system, comprising a first reservoir, the first reservoir containing an organic lipid stock solution, a first pump having a first pump inlet and a first pump outlet, the first pump inlet fluidically coupled to the first reservoir, a second reservoir, the second reservoir containing an aqueous nucleic acid stock solution, a second pump having a second pump inlet and a second pump outlet, the second pump inlet fluidically coupled to the second reservoir, a valve having a first valve inlet port fluidically coupled to the first pump outlet, a second valve inlet port fluidically coupled to the second pump outlet, a first valve outlet port, and a second valve outlet port, and a mixing assembly having a first mixing assembly inlet fluidically coupled to the first valve outlet port, a second mixing assembly inlet fluidically coupled to the second valve outlet port, and a mixing assembly outlet, wherein the first mixing assembly inlet is fluidically coupled to the mixing assembly outlet and the second mixing assembly inlet is fluidically coupled to the mixing assembly outlet, wherein the valve has a first operating position in which the first valve inlet port is fluidically coupled to the first valve outlet port and the second valve inlet port is fluidically coupled to the second valve outlet port and a second operating position in which the first valve inlet port is not fluidically coupled to the first valve outlet port and the second valve inlet port is not fluidically coupled to the second valve outlet port.

Another embodiment provides a method for manufacturing lipid nanoparticles, the method comprising providing the system as described in any one of the embodiments described herein.

Accordingly, one embodiment provides a method of manufacturing lipid nanoparticles, comprising providing an organic lipid stock solution within a first reservoir, providing an aqueous nucleic acid stock solution within a second reservoir, pumping the organic lipid stock solution from the first reservoir to a first valve inlet port of a valve, pumping the aqueous nucleic acid stock solution from the second reservoir to a second valve inlet port of the valve, flowing the organic lipid stock solution and the aqueous nucleic acid stock through the valve and operating the valve in a second operating position in which the first valve inlet port is not fluidically connected to a first mixing assembly inlet of a mixing assembly and the second valve inlet port is not fluidically connected to a second mixing assembly inlet of the mixing assembly in the second operating position, and switching the valve to a first operating position and flowing the organic lipid stock solution through the valve to the first mixing assembly inlet of a mixing assembly and flowing the aqueous nucleic acid stock solution through the valve to the second mixing assembly inlet of the mixing assembly thereby mixing the organic lipid stock solution and the aqueous nucleic acid stock solution within the mixing assembly to create a first mixture and flowing the first mixture out of the mixing assembly through a mixing assembly outlet.

These and other aspects of embodiments of the disclosure will be apparent upon reference to the following detailed description.

BRIEF DESCRIPTION OF THE SEVERAL VIEWS OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
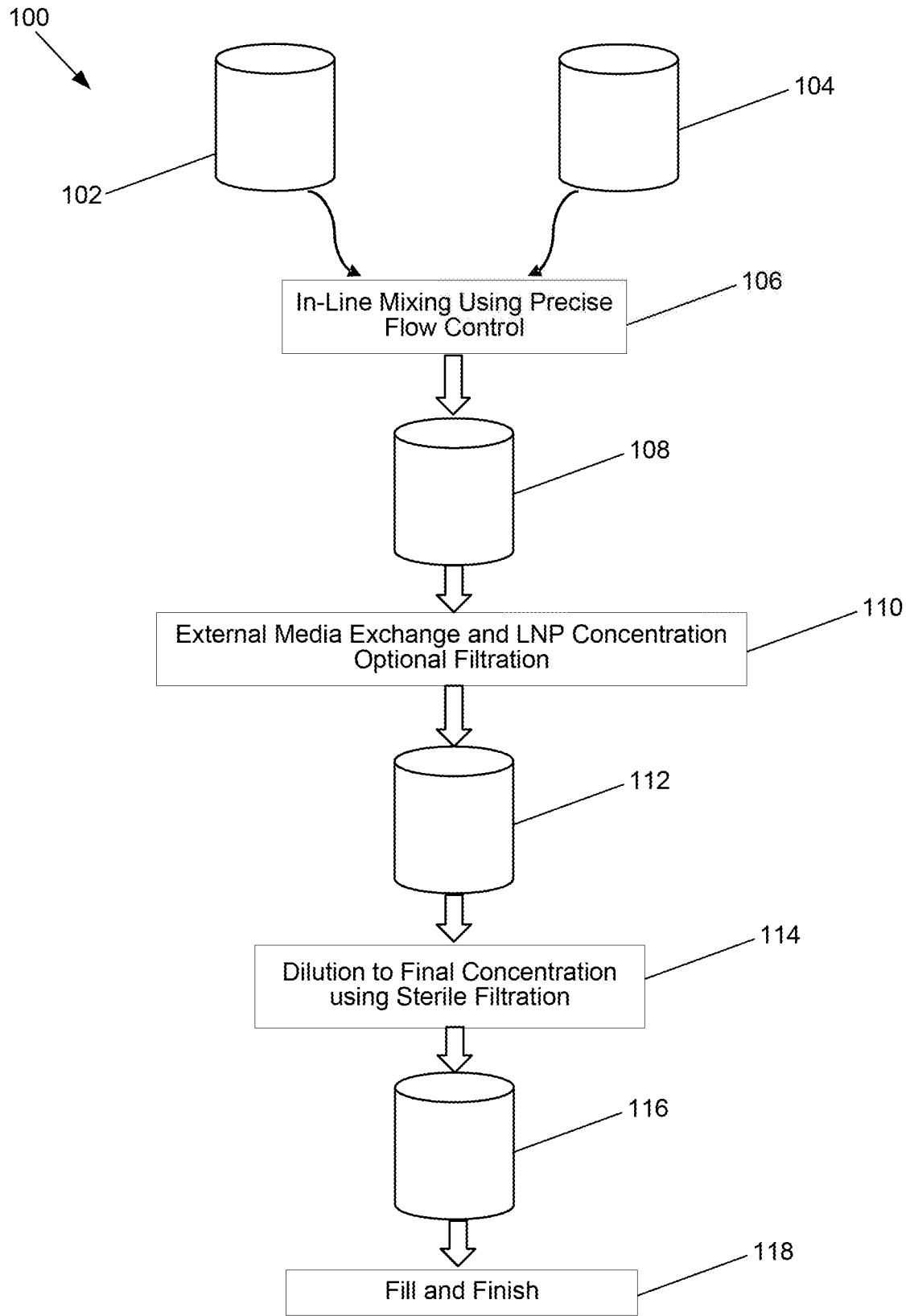
FIG. 1 illustrates a method of manufacturing lipid nanoparticles.

The current disclosure provides a solution to the issues associated with initiation of an in-line mixing process for manufacture of lipid nanoparticles/liposomes. Significant material and time is lost during the initiation of manufacturing (i.e., while priming, equilibrating, stabilizing flow rates, etc. in a conventional manner). These issues are addressed by introduction of a multiport switching valve into a system between the pumps and a mixing device (e.g., a T-mixer) that allows priming of the pumps and associated fluid lines (i.e., while the system is in a priming mode) with safe return of the respective stock solutions before moving to a mixing mode. In this way, the mixing system is primed and ready without loss of any stock solution until it can be effectively and instantaneously switched to the mixing mode in a manner such that the component solutions are immediately introduced to the mixing device at the target proportions and mixing conditions. The switch from priming mode to mixing mode drastically reduces the amount of material and time lost to conventional priming/equilibrating processes.

In the following description, certain specific details are set forth in order to provide a thorough understanding of various embodiments of the disclosure. However, one skilled in the art will understand that the disclosure may be practiced without these details.

The lipid nanoparticles of embodiments of the present disclosure may be used for a variety of purposes, including the delivery of encapsulated or associated (e.g., complexed) therapeutic agents such as nucleic acids to cells, both in vitro and in vivo. As described herein, lipid nanoparticles manufactured according to embodiments of the present disclosure are particularly useful for the delivery of nucleic acids, including, e.g., mRNA, antisense oligonucleotide, plasmid DNA, microRNA (miRNA), miRNA inhibitors (antagomirs/antimirs), messenger-RNA-interfering complementary RNA (micRNA), DNA, closed end DNA, multivalent RNA, dicer substrate RNA, complementary DNA (cDNA), small interfering RNA (siRNA), etc.

Nucleic acids for use with embodiments of this disclosure may be prepared according to the techniques known in the art and as described herein. The nucleic acids for use with embodiments of this disclosure are not particularly limited. For mRNA, methodology for preparation and purification are known in the art (e.g., enzymatic synthesis or in vitro transcription; see, e.g., Linpinsel, J. L and Conn, G. L., General protocols for preparation of plasmid DNA template and Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012; Losick, R., 1972, In vitro transcription, Ann Rev Biochem v.41 409-46; Kamakaka, R. T. and Kraus, W. L. 2001. In Vitro Transcription. Current Protocols in Cell Biology. 2:11.6:11.6.1-11.6.17; Beckert, B. And Masquida, B., (2010) Synthesis of RNA by In Vitro Transcription in RNA in Methods in Molecular Biology v. 703 (Neilson, H. Ed), New York, N.Y. Humana Press, 2010; Brunelle, J. L. and Green, R., 2013, Chapter Five—In vitro transcription from plasmid or PCR-amplified DNA, Methods in Enzymology v. 530, 101-114; all of which are incorporated herein by reference). In vitro transcription can be performed using a variety of commercially available kits including, but not limited to RiboMax Large Scale RNA Production System (Promega), MegaScript Transcription kits (Life Technologies) as well as with commercially available reagents including RNA polymerases and rNTPs.

Techniques for the isolation of the mRNA transcripts are also well known in the art. Procedures include phenol/chloroform extraction or precipitation with either alcohol (e.g., ethanol, isopropanol) in the presence of monovalent cations or lithium chloride. Additional, non-limiting examples of purification procedures which can be used include size exclusion chromatography (Lukavsky, P. J. and Puglisi, J. D., 2004, Large-scale preparation and purification of polyacrylamide-free RNA oligonucleotides, RNA v.10, 889-893), silica-based affinity chromatography and polyacrylamide gel electrophoresis (Bowman, J. C., Azizi, B., Lenz, T. K., Ray, P., and Williams, L. D. in RNA in vitro transcription and RNA purification by denaturing PAGE in Recombinant and in vitro RNA syntheses Methods v. 941 Conn G. L. (ed), New York, N.Y. Humana Press, 2012). Purification can be performed using a variety of commercially available kits including, but not limited to SV Total Isolation System (Promega) and In Vitro Transcription Cleanup and Concentration Kit (Norgen Biotek).

Additionally, a significant variety of modifications have been described in the art which are used to alter specific properties of in vitro transcribed mRNA, and improve its utility. These include, but are not limited to modifications to the 5' and 3' termini of the mRNA. Multiple distinct cap structures and techniques can be used to generate a 5'-cap of in vitro transcribed synthetic mRNA, for example, an Anti-Reverse Cap Analog (ARCA) cap or enzymatic capping post-transcriptionally. Numerous synthetic 5'-cap analogs have been developed and are known in the art to enhance mRNA stability and translatability (see, e.g., Grudzien-Nogalska, E., Kowalska, J., Su, W., Kuhn, A. N., Slepenkov, S. V., Darynkiewicz, E., Sahin, U., Jemielity, J., and Rhoads, R. E., Synthetic mRNAs with superior translation and stability properties in Synthetic Messenger RNA and Cell Metabolism Modulation in Methods in Molecular Biology v.969 (Rabinovich, P. H. Ed), 2013).

On the 3'-terminus, a long chain of adenine nucleotides (poly-A tail) is normally added to mRNA molecules during RNA processing. Poly(A) tailing of in vitro transcribed mRNA can be achieved using various approaches including, but not limited to, cloning of a poly(T) tract into a DNA template or by post-transcriptional addition using Poly(A) polymerase. 5'-capping and 3'-poly(A) tailing can be performed using a variety of commercially available kits including, but not limited to Poly(A) Polymerase Tailing kit (EpiCenter), mMESSAGE mMACHINE T7 Ultra kit and Poly(A) Tailing kit (Life Technologies) as well as with commercially available reagents, various ARCA caps, Poly (A) polymerase, etc.

In addition to 5' cap and 3' poly adenylation, other modifications of the in vitro transcripts have been reported to provide benefits as related to efficiency of translation and stability. The introduction of modified nucleosides into in vitro transcribed mRNA can be used to prevent recognition and activation of RNA sensors, thus mitigating this undesired immunostimulatory activity and enhancing translation capacity (see, e.g., Kariko, K. And Weissman, D. 2007, Naturally occurring nucleoside modifications suppress the immunostimulatory activity of RNA: implication for therapeutic RNA development, Curr Opin Drug Discov Devel, v.10 523-532; Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v.969 (Rabinovich, P. H. Ed), 2013); Kariko, K., Muramatsu, H., Welsh, F. A., Ludwig, J., Kato, H., Akira, S., Weissman, D., 2008, Incorporation of Pseudouridine Into mRNA Yields Superior Nonimmunogenic Vector With Increased Translational Capacity and Biological Stability, Mol Ther v.16, 1833-1840; U.S. Pub. No. 2012/0251618).

Other components of mRNA which can be modified to provide benefit in terms of translatability and stability include the 5' and 3' untranslated regions (UTR). (see, e.g., Pardi, N., Muramatsu, H., Weissman, D., Kariko, K., In vitro transcription of long RNA containing modified nucleosides in Synthetic Messenger RNA and Cell Metabolism Modulation in Methods in Molecular Biology v.969 (Rabinovich, P. H. Ed), 2013).

In addition to mRNA, other nucleic acid payloads may be used for this disclosure. For oligonucleotides, methods of preparation include but are not limited to chemical synthesis and enzymatic, chemical cleavage of a longer precursor, in vitro transcription as described above, etc. Methods of synthesizing DNA and RNA nucleotides are widely used and well known in the art (see, e.g., Gait, M. J. (ed.) Oligonucleotide synthesis: a practical approach, Oxford [Oxfordshire], Washington, D.C.: TRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

For plasmid DNA, preparation for use with embodiments of this disclosure commonly utilizes but is not limited to expansion and isolation of the plasmid DNA in vitro in a liquid culture of bacteria containing the plasmid of interest. The presence of a gene in the plasmid of interest that encodes resistance to a particular antibiotic (penicillin, kanamycin, etc.) allows those bacteria containing the plasmid of interest to selectively grow in antibiotic-containing cultures. Methods of isolating plasmid DNA are widely used and well known in the art (see, e.g., Heilig, J., Elbing, K. L. and Brent, R (2001) Large-Scale Preparation of Plasmid DNA. Current Protocols in Molecular Biology. 41:II:1.7: 1.7.1-1.7.16; Rozkov, A., Larsson, B., Gillström, S., Bjornestedt, R. and Schmidt, S. R. (2008), Large-scale production of endotoxin-free plasmids for transient expression in mammalian cell culture. Biotechnol. Bioeng., 99: 557-566; and U.S. Pat. No. 6,197,553 B1). Plasmid isolation can be performed using a variety of commercially available kits including, but not limited to Plasmid Plus (Qiagen), GenJET plasmid MaxiPrep (Thermo) and PureYield MaxiPrep (Promega) kits as well as with commercially available reagents.

As used herein, the following terms have the meanings ascribed to them unless specified otherwise.

Unless the context requires otherwise, throughout the present specification and claims, the word "comprise" and variations thereof, such as, "comprises" and "comprising" are to be construed in an open and inclusive sense, that is, as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs. As used in the specification and claims, the singular form "a", "an" and "the" include plural references unless the context clearly dictates otherwise.

The term "nucleic acid" as used herein refers to a polymer containing at least two deoxyribonucleotides or ribonucleotides in either single- or double-stranded form and includes DNA, RNA, and hybrids thereof. DNA may be in the form of antisense molecules, plasmid DNA, closed end DNA, cDNA, PCR products, or vectors. RNA may be in the form of small hairpin RNA (shRNA), messenger RNA (mRNA), antisense RNA, miRNA, micRNA, multivalent RNA, dicer substrate RNA or viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, single nucleotide polymorphisms, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are generally characterized by being poorly soluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "steroid" is a compound comprising the following carbon skeleton:

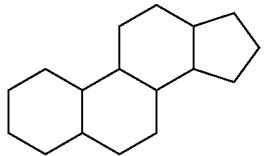

Non-limiting examples of steroids include cholesterol, and the like.

A "cationic lipid" refers to a lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of the lipid nanoparticle under different pH conditions. This charge state can influence plasma protein absorption, blood clearance and tissue distribution (Semple, S. C., et al., Adv. Drug Deliv Rev 32:3-17 (1998)) as well as the ability to form non-bilayer structures (Hafez, I. M., et al., Gene Ther 8:1188-1196 (2001)) critical to the intracellular delivery of nucleic acids.

An "anionic lipid" refers to a lipid capable of being negatively charged. Exemplary anionic lipids include one or more phosphate group(s) which bear a negative charge, for example at physiological pHs. In some embodiments, the anionic lipid does not include a serine moiety, including phosphatidylserine lipids.

"Phosphatidylglycerol lipid" refers to a lipid with a structure that generally comprises a glycerol 3-phosphate backbone which is attached to saturated or unsaturated fatty acids via and ester linkage. Exemplary phosphatidylglycerol lipids have the following structure:

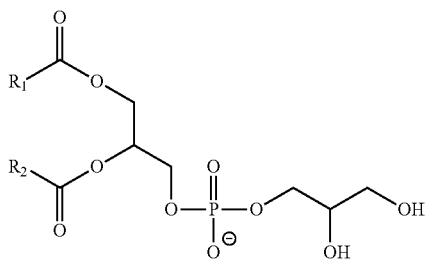

wherein $R_1$ and $R_2$ are each independently a branched or straight, saturated or unsaturated carbon chain (e.g., alkyl, alkenyl, alkynyl).

The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-DMG) and the like.

The term "neutral lipid" refers to any of a number of lipid species that exist either in an uncharged or neutral zwitterionic form at a selected pH. At physiological pH, such lipids include, but are not limited to, phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. Neutral lipids may be synthetic or naturally derived.

The term "charged lipid" refers to any of a number of lipid species that exist in either a positively charged or negatively charged form independent of the pH within a useful physiological range, e.g., pH~3 to pH~9. Charged lipids may be synthetic or naturally derived. Examples of charged lipids include phosphatidylserines, phosphatidic acids, phosphatidylglycerols, phosphatidylinositols, sterol hemisuccinates, dialkyl trimethylammonium-propanes, (e.g., DOTAP, DOTMA), dialkyl dimethylaminopropanes, ethyl phosphocholines, dimethylaminoethane carbamoyl sterols (e.g., DC-Chol).

The term "lipid nanoparticle" or "liposome" (which are used interchangeably) refer to particles having at least one dimension on the order of nanometers (e.g., 1-1,000 nm) which include a cationic lipid or lipids. In some embodiments, lipid nanoparticles are included in a formulation that can be used to deliver an active agent or therapeutic agent, such as a nucleic acid (e.g., mRNA) to a target site of interest (e.g., cell, tissue, organ, tumor, and the like). In some embodiments, the lipid nanoparticles of the disclosure comprise a nucleic acid. Such lipid nanoparticles typically comprise a cationic lipid and one or more excipient selected from neutral lipids, charged lipids (anionic or cationic lipids), steroids and polymer conjugated lipids. In some embodiments, the active agent or therapeutic agent, such as a nucleic acid, may be encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells, e.g., an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, nucleic acids, when present in the lipid nanoparticles, are resistant in aqueous solution to degradation with a nuclease.

Lipids and their method of preparation are disclosed in, e.g., U.S. Pat. Nos. 8,569,256, 5,965,542 and U.S. Patent Publication Nos. 2016/0199485, 2016/0009637, 2015/0273068, 2015/0265708, 2015/0203446, 2015/0005363, 2014/0308304, 2014/0200257, 2013/086373, 2013/0338210, 2013/0323269, 2013/0245107, 2013/0195920, 2013/0123338, 2013/0022649, 2013/0017223, 2012/0295832, 2012/0183581, 2012/0172411, 2012/0027803, 2012/0058188, 2011/0311583, 2011/0311582, 2011/0262527, 2011/0216622, 2011/0117125, 2011/0091525, 2011/0076335, 2011/0060032, 2010/0130588, 2007/0042031, 2006/0240093, 2006/0083780, 2006/0008910, 2005/0175682, 2005/017054, 2005/0118253, 2005/0064595, 2004/0142025, 2007/0042031, 1999/009076 and PCT Pub. Nos. WO 99/39741, WO 2017/117528, WO 2017/004143, WO 2017/075531, WO 2015/199952, WO 2014/008334, WO 2013/086373, WO 2013/086322, WO 2013/016058, WO 2013/086373, WO2011/141705, and WO 2001/07548, the full disclosures of which are herein incorporated by reference in their entirety for all purposes. LNPs are prepared according to the methods and using the systems disclosed herein.

Other exemplary lipids and their manufacture are described in the art, for example in U.S. Patent Application Publication No. U.S. 2012/0276209, 2015/0376115, 2016/0376224, 2018/0000735, U.S. Pat. Nos. 9,415,109; 9,579,338 Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, European Patent Nos. 2558074 and 1937213 each of which are incorporated by reference in their entirety.

As used herein, "lipid encapsulated" refers to a lipid nanoparticle that provides an active agent or therapeutic agent, such as a nucleic acid (e.g., mRNA), with full encapsulation, partial encapsulation, or both. In an embodiment, the nucleic acid (e.g., mRNA) is fully encapsulated in the lipid nanoparticle.

As used herein, the term "aqueous solution" refers to a composition comprising water.

"Amino acid" refers to naturally-occurring and non-naturally occurring amino acids. An amino acid lipid can be made from a genetically encoded amino acid, a naturally occurring non-genetically encoded amino acid, or a synthetic amino acid. Examples of amino acids include Ala, Arg, Asn, Asp, Cys, Gln, Glu, Gly, His, Ile, Leu, Lys, Met, Phe, Pro, Ser, Thr, Trp, Tyr, and Val. Examples of amino acids also include azetidine, 2-aminooctadecanoic acid, 2-aminoadipic acid, 3-aminoadipic acid, 2,3-diaminopropionic acid, 2-aminobutyric acid, 4-aminobutyric acid, 2,3-diaminobutyric acid, 2,4-diaminobutyric acid, 2-aminoisobutyric acid, 4-aminoisobutyric acid, 2-aminopimelic acid, 2,2'-diaminopimelic acid, 6-aminohexanoic acid, 6-aminocaproic acid, 2-aminoheptanoic acid, desmosine, ornithine, citrulline, N-methylisoleucine, norleucine, tert-leucine, phenylglycine, t-butylglycine, N-methylglycine, sacrosine, N-ethylglycine, cyclohexylglycine, 4-oxo-cyclo-hexylglycine, N-ethylasparagine, cyclohexylalanine, t-butylalanine, naphthylalanine, pyridylalanine, 3-chloroalanine, 3-benzothienylalanine, 4-halophenylalanine, 4-chlorophenylalanine, 2-fluorophenylalanine, 3-fluorophenylalanine, 4-fluorophenylalanine, penicillamine, 2-thienylalanine, methionine, methionine sulfoxide, homoarginine, norarginine, nor-norarginine, N-acetyllysine, 4-aminophenylalanine, N-methylvaline, homocysteine, homoserine, hydroxylysine, allo-hydroxylysine, 3-hydroxyproline, 4-hydroxyproline, isodesmosine, allo-isoleucine, 6-N-methyllysine, norvaline, 0-allyl-serine, 0-allyl-threonine, alpha-aminohexanoic acid, alpha-aminovaleric acid, pyroglutamic acid, and derivatives thereof "Amino acid" includes alpha- and beta-amino acids. Examples of amino acid residues can be found in Fasman, CRC Practical Handbook of Biochemistry and Molecular Biology, CRC Press, Inc. (1989).

"Alkyl" refers to a straight or branched hydrocarbon chain radical consisting solely of carbon and hydrogen atoms, which is saturated or unsaturated (i.e., contains one or more double (alkenyl) and/or triple bonds (alkynyl)), having, for example, from one to twenty-four carbon atoms ($C_1$-$C_{24}$ alkyl), four to twenty carbon atoms ($C_4$-$C_{20}$ alkyl), six to sixteen carbon atoms ($C_6$-$C_{16}$ alkyl), six to nine carbon atoms ($C_6$-$C_9$ alkyl), one to fifteen carbon atoms ($C_1$-$C_{15}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n propyl, 1 methylethyl(iso propyl), n butyl, n pentyl, 1,1-dimethylethyl(t butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double (alkenylene) and/or triple bonds (alkynylene)), and having, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

The term "alkenyl" refers to an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkoxy" refers to an alkyl, cycloalkyl, alkenyl, or alkynyl group covalently bonded to an oxygen atom.

"Alkanoyloxy" refers to —O—C(=O)-alkyl groups.

"Alkylamino" refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The terms "acyl," "carbonyl," and "alkanoyl" refer to any alkyl, alkenyl, or alkynyl wherein the carbon at the point of attachment is substituted with an oxo group, as defined below. The following are non-limiting examples of acyl, carbonyl or alkanoyl groups: —C(=O)alkyl, —C(=O)alkenyl, and —C(=O)alkynyl.

"Aryl" refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

"Carboxyl" refers to a functional group of the formula —C(=O)OH.

"Cyano" refers to a functional group of the formula —CN.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1] heptanyl, and the like. Unless otherwise stated specifically in the specification, a cycloalkyl group may be optionally substituted.

"Cycloalkylene" is a divalent cycloalkyl group. Unless otherwise stated specifically in the specification, a cycloalkylene group may be optionally substituted.

The term "diacylglycerol" or "DAG" includes a compound having 2 fatty acyl chains, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl (C12), myristoyl (C14), palmitoyl (C16), stearoyl (C18), and icosoyl (C20). In preferred embodiments, the fatty acid acyl chains of one compound are the same, i.e., both myristoyl (i.e., dimyristoyl), both stearoyl (i.e., distearoyl), etc.

The term "heterocycle" or "heterocyclyl" refers to an aromatic or nonaromatic ring system of from five to twenty-two atoms, wherein from 1 to 4 of the ring atoms are heteroatoms selected from oxygen, nitrogen, and sulfur. Thus, a heterocycle may be a heteroaryl or a dihydro or tetrathydro version thereof. Heterocycles include, but are not limited to, pyrrolidine, tetryhydrofuran, thiolane, azetidine, oxetane, thietane, diazetidine, dioxetane, dithietane, piperidine, tetrahydrofuran, pyran, tetrahydropyran, thiacyclohexane, tetrahydrothiophene, pyridine, pyrimidine and the like.

"Heteroaryl" refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The terms "alkylamine" and "dialkylamine" refer to —NH(alkyl) and —N(alkyl)$_2$ radicals respectively.

The term "alkylphosphate" refers to —O—P(Q')(Q")-O—R, wherein Q' and Q" are each independently O, S, N(R)$_2$, optionally substituted alkyl or alkoxy; and R is optionally substituted alkyl, ω-aminoalkyl or ω-(substituted)aminoalkyl.

The term "alkylphosphorothioate" refers to an alkylphosphate wherein at least one of Q' or Q" is S.

The term "alkylphosphonate" refers to an alkylphosphate wherein at least one of Q' or Q" is alkyl.

"Hydroxyalkyl" refers to an —O-alkyl radical.

The term "alkylheterocycle" refers to an alkyl where at least one methylene has been replaced by a heterocycle.

The term "ω-aminoalkyl" refers to -alkyl-NH$_2$ radical. And the term "ω-(substituted)aminoalkyl refers to an ω-aminoalkyl wherein at least one of the H on N has been replaced with alkyl.

The term "ω-phosphoalkyl" refers to -alkyl-O—P(Q')(Q")-O—R, wherein Q' and Q" are each independently O or S and R optionally substituted alkyl.

The term "ω-thiophosphoalkyl" refers to ω-phosphoalkyl wherein at least one of Q' or Q" is S.

The term "substituted" used herein means any of the above groups (e.g., alkyl, alkylene, cycloalkyl or cycloalkylene) wherein at least one hydrogen atom is replaced by a bond to a non-hydrogen atom such as, but not limited to: a halogen atom such as F, Cl, Br, or I; oxo groups (=O); hydroxyl groups (—OH); $C_1$-$C_{12}$ alkyl groups; cycloalkyl groups; —(C=O)OR'; —O(C=O)R'; —C(=O)R; —OR'; —S(O)$_x$R'; —S—SR'; —C(=O)SR'; —SC(=O)R'; —NR'R'; —NR'C(=O)R'; —C(=O)NR'R'; —NR'C(=O)NR'R'; —OC(=O)NR'R'; —NR'C(=O)OR'; —NR'S(O)$_x$NR'R'; —NR'S(O)$_x$R'; and —S(O)$_x$NR'R', wherein: R' is, at each occurrence, independently H, $C_1$-$C_{15}$ alkyl or cycloalkyl, and x is 0, 1 or 2. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is an oxo group. In other embodiments, the substituent is a hydroxyl group. In other embodiments, the substituent is an alkoxy group (—OR'). In other embodiments, the substituent is a carboxyl group. In other embodiments, the substituent is an amine group (—NR'R').

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Prodrug" is meant to indicate a compound, such as a therapeutic agent, that may be converted under physiological conditions or by solvolysis to a biologically active compound of the disclosure. Thus, the term "prodrug" refers to a metabolic precursor of a compound of the disclosure that is pharmaceutically acceptable. A prodrug may be inactive when administered to a subject in need thereof, but is converted in vivo to an active compound of the disclosure. Prodrugs are typically rapidly transformed in vivo to yield the parent compound of the disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the disclosure in vivo when such prodrug is administered to a mammalian subject. Prodrugs (e.g., a prodrug of a therapeutic agent) may be prepared by modifying functional groups present in the compound of the disclosure in such a way that the modifications are cleaved, either in routine manipulation or in vivo, to the parent compound of the disclosure. Prodrugs include compounds wherein a hydroxy, amino or mercapto group is bonded to any group such that, when the prodrug is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the therapeutic agents of the disclosure and the like.

Embodiments of the disclosure disclosed herein are also meant to encompass all pharmaceutically acceptable lipid nanoparticles and components thereof (e.g., cationic lipid, therapeutic agent, etc.) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{17}$O, $^{18}$O, $^{31}$P, $^{32}$P, $^{35}$S, $^{18}$F, $^{36}$Cl, $^{123}$I and $^{125}$I, respectively. These radiolabeled LNPs could be useful to help determine or measure the effectiveness of the compounds, by characterizing, for example, the site or mode of action, or binding affinity to pharmacologically important site of action. Certain isotopically-labelled LNPs, for example, those incorporating a radioactive isotope, are useful in drug and/or substrate tissue distribution studies. The radioactive isotopes tritium, i.e., $^3$H, and carbon-14, that is, $^{14}$C, are particularly useful for this purpose in view of their ease of incorporation and ready means of detection.

Substitution with heavier isotopes such as deuterium, that is, $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula I, II, III, IV or V can generally be prepared by conventional techniques known to those skilled in the art or by processes analogous to those described in the Examples as set out below using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydramine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of an LNP of the disclosure and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the disclosure which, when administered to a mammal, preferably a human, is sufficient to effect treatment in the mammal, preferably a human. The amount of a lipid nanoparticle of the disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:
  (i) preventing the disease or condition from occurring in a mammal, in particular, when such mammal is predisposed to the condition but has not yet been diagnosed as having it;
  (ii) inhibiting the disease or condition, i.e., arresting its development;
  (iii) relieving the disease or condition, i.e., causing regression of the disease or condition; or
  (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Diluent" refers to a solvent used to dilute a solution comprising lipid nanoparticles. That is, when the diluent is added to a solution including lipid nanoparticles, the concentration of the lipid nanoparticles is lowered as a result of the added solvent. A diluent may be an aqueous solution (including buffered solutions), an organic solution (e.g., ethanol), or a combination thereof.

"Organic lipid stock solution" refers to a solution comprising an organic solvent (e.g., an organic alcohol such as ethanol) and one or more lipids (e.g., cationic lipids, neutral lipids, a polymer conjugated lipid) or mixtures thereof. In some embodiments, the organic lipid stock solution is contained in a first reservoir and is mixed with an aqueous nucleic acid stock solution, thereby forming a lipid nanoparticle comprising a nucleic acid or oligomer thereof.

"Aqueous nucleic acid stock solution" refers to a solution comprising water (e.g., Water For Injection or "WFI") and a nucleic acid or oligomer thereof. In some embodiments, the aqueous nucleic acid stock solution is contained in a second reservoir and is mixed with an organic lipid stock solution, thereby forming a lipid nanoparticle comprising the nucleic acid or oligomer thereof. In some embodiments, the aqueous nucleic acid stock solution comprises additional buffering agents (e.g., citrate, citric acid). The pH of the aqueous nucleic acid stock solution may also vary and is not particularly limited in that respect.

Lipid Nanoparticle Manufacture System

In certain embodiments, the present disclosure provides lipid nanoparticles and systems and methods for their manufacture.

FIG. 1 illustrates a method of manufacturing lipid nanoparticles 100. As illustrated in FIG. 1, the method 100 may include, at 102, providing a first reservoir with an organic lipid stock solution, and at 104, providing a second reservoir with an aqueous nucleic acid stock solution. In some implementations, during operation and performance of the method 100 illustrated in FIG. 1, the method 100 may include verifying mRNA and Lipid concentration and proportions within the first and second reservoirs 102 and 104. As also illustrated in FIG. 1, the method 100 may also include, at 106, in-line mixing of the organic lipid stock solution and the aqueous nucleic acid stock solution using precise flow control of the two stock solutions to form a dilute intermediate product at 108. In some implementations, during operation and performance of the method 100 illustrated in FIG. 1, the method 100 may include verifying the size of nanoparticles within the dilute intermediate product and verifying mRNA and Lipid concentration and proportions within the dilute intermediate product at 108.

As also illustrated in FIG. 1, the method 100 may also include, at 110, an external media exchange and concentration of the nanoparticles, as well as filtration of the dilute intermediate product at 108, to produce a concentrated intermediate product at 112. In some implementations, during operation and performance of the method 100 illustrated in FIG. 1, the method 100 may include performing an assay of mRNA and Lipid concentration of the concentrated intermediate product, and determining size(s) and levels of polydispersity and/or encapsulation of the nanoparticles within the concentrated intermediate product at 112. As also illustrated in FIG. 1, the method 100 may also include, at 114, dilution of the concentrated intermediate product at 112, such as by using a sterile filtration, to produce a final bulk product at 116. As also illustrated in FIG. 1, the method 100 may also include, at 118, fill and finish and/or freeze and thaw operations to complete the process. In some implementations, during operation and performance of the method 100 illustrated in FIG. 1, the method 100 may include determining mRNA content and verifying size and levels of encapsulation of the nanoparticles at the end of the method 100, such as after any freeze and thaw operations.

Figure 2:
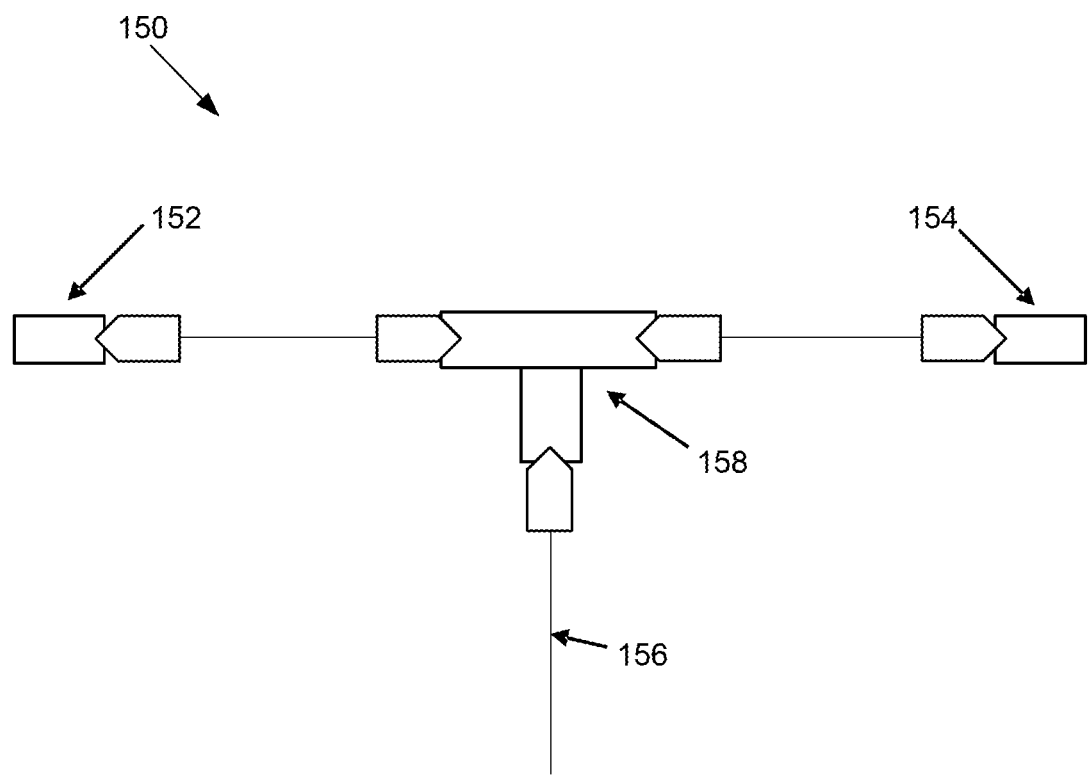
FIG. 2 illustrates a mixing assembly for use in the method of FIG. 1.

FIG. 2 illustrates a mixing assembly 150 that can be used in the method 100. For example, the mixing assembly 150 may be used for in-line mixing of the organic lipid stock solution and the aqueous nucleic acid stock solution using precise flow control of the two stock solutions to form a dilute intermediate product. As illustrated in FIG. 2, the mixing assembly 150 includes a first mixing assembly inlet 152 that has a valve fitting for fluidically coupling the inlet 152 to a valve, as described further elsewhere herein. The mixing assembly 150 also includes a second mixing assembly inlet 154 that has a valve fitting for fluidically coupling the inlet 154 to the valve. The mixing assembly 150 also includes a mixing assembly outlet 156. The mixing assembly 150 also includes a main body portion 158 that houses a mixing chamber and internal conduits that fluidically couple the first mixing assembly inlet 152, the second mixing assembly inlet 154, and the mixing assembly outlet 156 to the mixing chamber, and to one another via the mixing chamber.

Thus, in operation, the organic lipid stock solution can flow into the mixing assembly 150 through the first mixing assembly inlet 152, the aqueous nucleic acid stock solution can flow into the mixing assembly 150 through the second mixing assembly inlet 154, the two stock solutions can mix within the mixing chamber housed within the main body 158 of the mixing assembly 150, and the mixture can flow out of the mixing chamber and the mixing assembly 150 through the mixing assembly outlet 156. The first mixing assembly inlet 152 can have a first inside diameter, the second mixing assembly inlet 154 can have a second inside diameter, and the mixing assembly outlet 156 can have a third inside diameter.

In some implementations, the first, second, and/or third inside diameters may be the same as one another. In other implementations, however, the first, second, and/or third inside diameters may be different than one another. For example, in some specific implementations, the first inside diameter is half of, or approximately half of, the second inside diameter, and/or the second inside diameter is half of, or approximately half of, the third inside diameter. In other specific implementations, the first inside diameter is half of, or approximately half of, the second inside diameter, and/or the second inside diameter is the same as, or approximately the same as, the third inside diameter. In some implementations, the first, second, and third inside diameters may be small enough to maintain laminar flow of the stock solutions through the first mixing assembly inlet 152, and through the second mixing assembly inlet 154. In some implementations the flow rates may be high enough to induce turbulent flow of the stock solutions through the first mixing assembly inlet 152, and through the second mixing assembly inlet 154. In some implementations the flows meet and are rapidly mixed within the mixing chamber.

In some specific implementations, the first inside diameter is 0.01 inches, or approximately 0.01 inches, the second inside diameter is 0.02 inches, or approximately 0.02 inches, and/or the third inside diameter is 0.04 inches, or approximately 0.04 inches. In other specific implementations, the first inside diameter is 0.02 inches, or approximately 0.02 inches, the second inside diameter is 0.04 inches, or approximately 0.04 inches, and/or the third inside diameter is 0.04 inches, or approximately 0.04 inches.

In some implementations, the mixing assembly 150 is a commercially-available, off the shelf mixing assembly, such as a PEEK Tee mixing assembly with 0.02 inch diameter through holes that fluidically couple the mixing assembly inlets 152, 154, mixing assembly outlet 156, and internal mixing chamber to one another. In other implementations, any suitable alternative mixing device, assembly, or system may be used in place of such specific products, or the mixing assembly 150 described herein.

Figure 3:
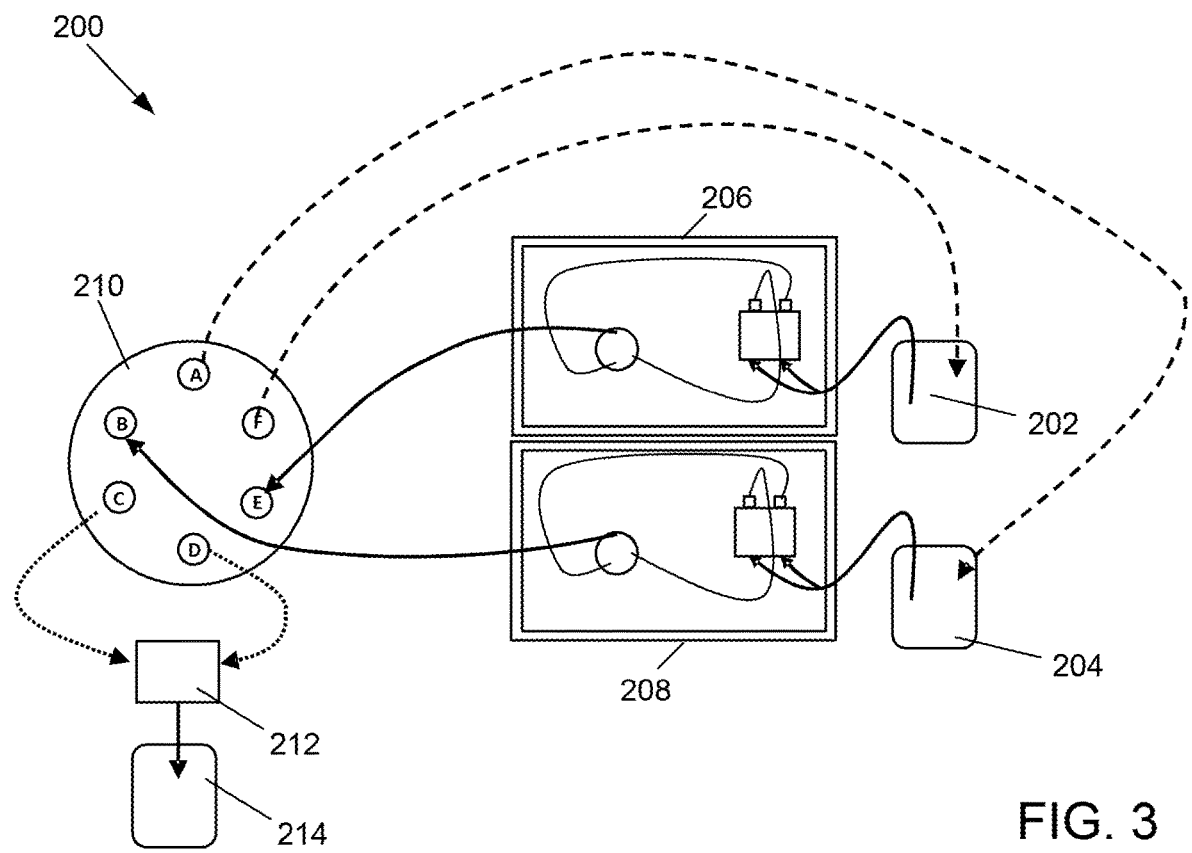
FIG. 3 illustrates an arrangement of pumps and valves for use in the method of FIG. 1.

FIG. 3 illustrates a system 200 for mixing two stock solutions, such as for use in the method 100. As illustrated in FIG. 3, the system 200 includes a first reservoir 202 for holding a first one of the stock solutions, which may be an organic lipid stock solution, as well as a second reservoir 204 for holding a second one of the stock solutions, which may be an aqueous nucleic acid stock solution. In some implementations, the first and second reservoirs 202 and 204 are commercially-available, off the shelf reservoirs, and can be made of polyethylene terephthalate copolyester (PETG), polypropylene, or polycarbonate. In some implementations, the first and second reservoirs 202 and 204 are commercially available reservoirs, for example, the first and second reservoirs can be bags comprising polyethylene (e.g., St. Gobain bioprocess bags). The system 200 also includes a first pump 206 that is fluidically coupled to the first reservoir 202 and a second pump 208 that is fluidically coupled to the second reservoir 204. For example, an inlet of the first pump 206 may be fluidically coupled to an outlet of the first reservoir 202 and an inlet of the second pump 208 may be fluidically coupled to an outlet of the second reservoir 204. In some implementations, the first pump 206 is a commercially-available, off the shelf pump, and can be a Knauer Azura 2.1—250 mL/min pump. In some implementations, the second pump 208 is a commercially-available, off the shelf pump, and can be a Knauer Azura 2.1—500 mL/min pump. In some implementations, the first pump 206 can be a a Knauer Azura 2.1—500 mL/min pump and the second pump 208 can be a Knauer Azura 2.1—1000 mL/min pump. In other implementations, however, the first and second pumps 206, 208 may be any other suitable pumps, including any suitable peristaltic pumps, syringe pumps, centrifugal pumps, diaphragm pumps, membrane pumps, any HPLC (high-performance liquid chromatography) or UHPLC (ultra-high-performance liquid chromatography)-type positive displacement piston pumps, and/or quaternary diaphragm pumps, for example, pumps available under the brand name QUATTROFLOW.

As also illustrated in FIG. 3, the system 200 includes a 6-port, 2-position valve 210 that is fluidically coupled to the first and second pumps 206, 208. For example, a first inlet port of the valve 210 (labelled "E" in FIG. 3) may be fluidically coupled to an outlet of the first pump 206 and a second inlet port of the valve 210 (labelled "B" in FIG. 3) may be fluidically coupled to an outlet of the second pump 208. In some implementations, the valve 210 is a commercially-available, off the shelf valve, and can be a Valvo Vici Cheminert 6 port valve or a Knauer Azura V 2.1S 6-port valve. The system 200 also includes a mixing assembly 212, which can include any or all of the features described herein for the mixing assembly 150, that is fluidically coupled to the valve 210. For example, a first mixing assembly inlet may be fluidically coupled to a first outlet port of the valve 210 (labelled "D" in FIG. 3) and a second mixing assembly inlet may be fluidically coupled to a second outlet port of the valve 210 (labelled "C" in FIG. 3).

As also illustrated in FIG. 3, the system 200 includes a reservoir 214 that is fluidically coupled to the mixing assembly 212. For example, an inlet of the reservoir 214 can be fluidically coupled to an outlet of the mixing assembly 212. During operation of the system 200, the reservoir 214 can hold formulated lipid nanoparticles produced as a result of the mixture of the two stock solutions. As also illustrated in FIG. 3, the valve 210 is fluidically coupled to the first and the second reservoirs 202 and 204. For example, a third outlet port of the valve 210 (labelled "F" in FIG. 3) may be fluidically coupled to an inlet of the first reservoir 202 and a fourth outlet port of the valve 210 (labelled "A" in FIG. 3) may be fluidically coupled to an inlet of the second reservoir 204.

Figure 4A:
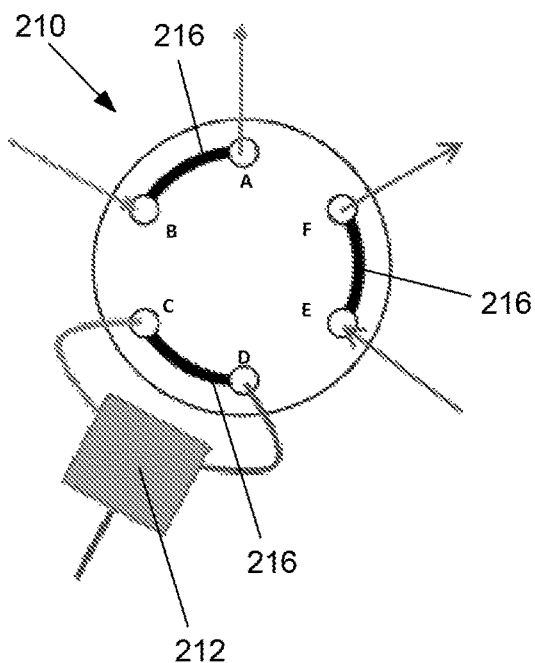
FIG. 4A illustrates a six-port, two-position valve for use in the method of FIG. 1 in a first position.
Figure 4B:
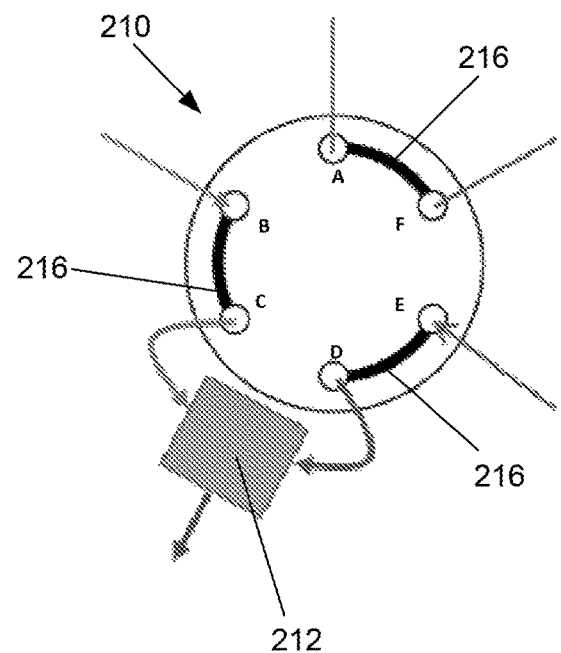
FIG. 4B illustrates the six-port, two-position valve of FIG. 4A in a second position.

FIG. 4A illustrates a first, recirculating or priming position of the valve 210 and FIG. 4B illustrates a second, mixing or operating position of the valve 210. As illustrated in FIGS. 4A and 4B, the six ports of the valve 210 are labelled alphabetically in order in a counter-clockwise direction, such that port "A" is adjacent to ports "B" and "F," port "B" is adjacent to ports "C" and "A," port "C" is adjacent to ports "D" and "B," port "D" is adjacent to ports "E" and "C," port "E" is adjacent to ports "D" and "F," and port "F" is adjacent to ports "A" and "E." The valve 210 includes three internal conduits 216, each of which fluidically couple two adjacent ports to one another.

The internal conduits 216 can be rotated and switched between two positions such that in the first operating position of the valve 210 illustrated in FIG. 4A, port "A" is fluidically coupled to port "B," port "C" is fluidically coupled to port "D," and port "E" is fluidically coupled to port "F." Thus, in the recirculating operating position of the valve 210, the first pump 206 pumps the first stock solution from the first reservoir 202, into the first inlet port "E" of the valve 210, out of the third outlet port "F" of the valve 210, and back to the first reservoir 202, while the second pump 208 pumps the second stock solution from the second reservoir 204, into the second inlet port "B" of the valve 210, out of the fourth outlet port "A" of the valve 210, and back to the second reservoir 204. In such an operating position of the valve 210, the first and second outlet ports "D" and "C" are fluidically coupled to one another.

The internal conduits 216 can also be rotated and switched between two positions such that in the second operating position of the valve 210 illustrated in FIG. 4B, port "F" is fluidically coupled to port "A," port "B" is fluidically coupled to port "C," and port "D" is fluidically coupled to port "E." Thus, in the mixing operating position of the valve 210, the first pump 206 pumps the first stock solution from the first reservoir 202, into the first inlet port "E" of the valve 210, out of the first outlet port "D" of the valve 210, and into the mixing assembly 212, while the second pump 208 pumps the second stock solution from the second reservoir 204, into the second inlet port "B" of the valve 210, out of the second outlet port "C" of the valve 210, and into the mixing assembly 212. In such an operating position of the valve 210, the third and fourth outlet ports "F" and "A" are fluidically coupled to one another.

The system 200 can be operated with the valve 210 initially in the recirculating operating position, such as in a "recirculating mode" or a "priming mode," such as to prime the first and second pumps 206, 208, and force air bubbles out of the conduits between the various components, prior to mixing the two stock solutions with one another. During this priming/recirculating mode, there is not loss or waste of stock solutions as they are returned to their first and second reservoirs 202 and 204. Once the components have been primed and adequately cleared of air, the valve 210 can be switched and the system 200 can be operated with the valve 210 in the mixing operating position, such as in a "mixing mode," a "formulating mode," or an "operating mode," such that the two stock solutions are simultaneously fed into the mixing assembly 212. The stock solutions can then mix within the mixing assembly 212, flow out of the mixing assembly 212 into the reservoir 214, and be stored therein for later use. In either the recirculating mode or the mixing mode or both, the first and second pumps 206, 208 can operate at either the same speed, to pump the respective stock solutions at the same rate, or at different speeds, to pump the respective stock solutions at different rates, such as to accommodate a desired mixing ratio for the two stock solutions within the mixing assembly 212. Throughout operation of the system 200, the first and second pumps 206 and 208 can each pump solution at a rate between 100-200 mL/min. In some embodiments, throughout operation of the system 200, the first and second pumps 206 and 208 can pump solutions at a combined rate up to 20,000 mL/min, for example, 100 mL/min, 250 mL/min, 500 mL/min, or 1000 mL/min (e.g., Knauer Azura pumps contain pump heads each rated to deliver about 10-100% of the nominal flow rate). In some embodiments, the combined flow rate is between 15-3,000 mL/min (e.g., 40 mL/min or 160 mL/min, up to 1,300 mL/min), 160-20,000 mL/min (e.g., up to 4,000 mL/min), or 100-200 mL/min. In some embodiments, the combined flow rate may be greater than 25,000 mL/min.

Figure 5:
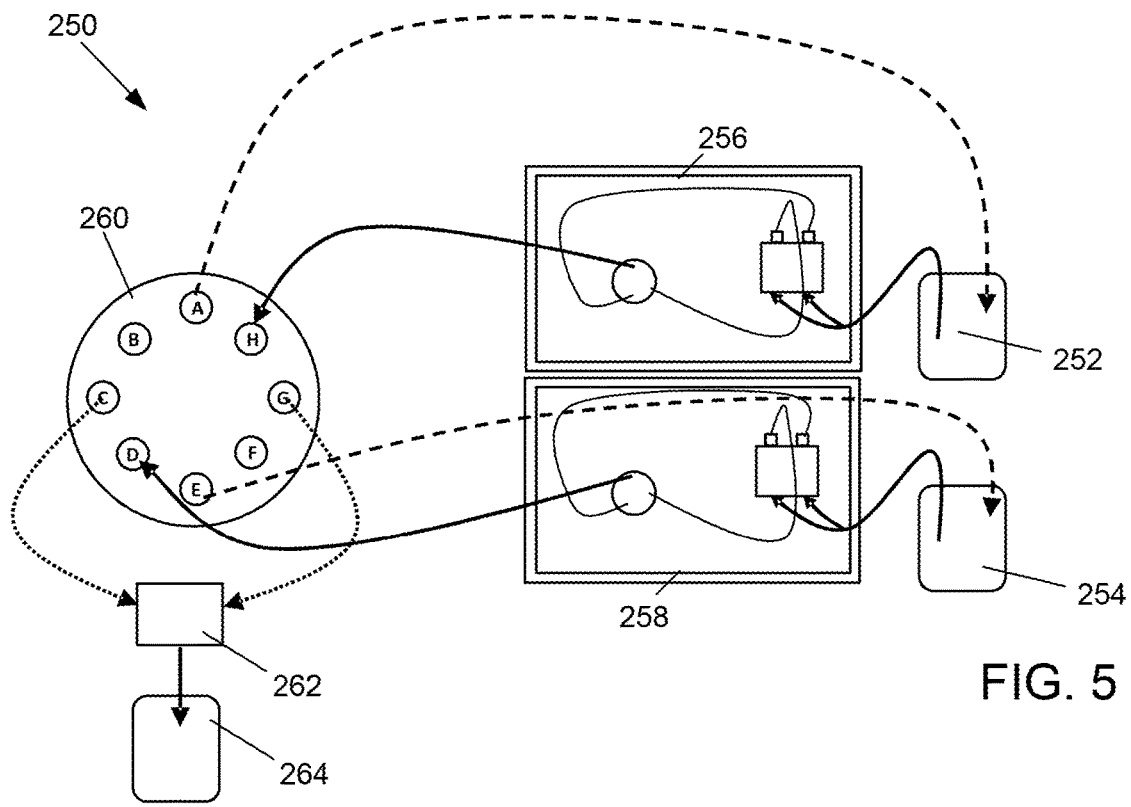
FIG. 5 illustrates another arrangement of pumps and valves for use in the method of FIG. 1.

FIG. 5 illustrates a system 250 for mixing two stock solutions, such as for use in the method 100. As illustrated in FIG. 5, the system 250 includes a first reservoir 252 for holding a first one of the stock solutions, which may be an organic lipid stock solution, as well as a second reservoir 254 for holding a second one of the stock solutions, which may be an aqueous nucleic acid stock solution. In some implementations, the first and second reservoirs 252 and 254 are commercially-available, off the shelf reservoirs, and can be made of polyethylene terephthalate copolyester (PETG) or polypropylene or polycarbonate. In some implementations, the first and second reservoirs 202 and 204 are commercially-available, off the shelf reservoirs, and can be bags comprising polyethylene (e.g., St. Gobain bioprocess bags). The system 250 also includes a first pump 256 that is fluidically coupled to the first reservoir 252 and a second pump 258 that is fluidically coupled to the second reservoir 254. For example, an inlet of the first pump 256 may be fluidically coupled to an outlet of the first reservoir 252 and an inlet of the second pump 258 may be fluidically coupled to an outlet of the second reservoir 254. In some implementations, the first pump 256 is a commercially-available, off the shelf pump, and can be a Knauer Azura 2.1—250 mL/min pump. In some implementations, the second pump 258 is a commercially-available, off the shelf pump, and can be a Knauer Azura 2.1—500 mL/min pump. In some implementations, the first pump 206 can be a a Knauer Azura 2.1—500 mL/min pump and the second pump 208 can be a Knauer Azura 2.1—1000 mL/min pump. In other implementations, however, the first and second pumps 256, 258 may be any other suitable pumps, including any suitable peristaltic pumps, syringe pumps, centrifugal pumps, diaphragm pumps, membrane pumps, any HPLC (high-performance liquid chromatography) or UHPLC (ultra-high-performance liquid chromatography)-type positive displacement piston pumps, and/or quaternary diaphragm pumps, e.g., those available under the brand name QUATTROFLOW.

As also illustrated in FIG. 5, the system 250 includes an 8-port, 2-position valve 260 that is fluidically coupled to the first and second pumps 256, 258. For example, a first inlet port of the valve 260 (labelled "H" in FIG. 5) may be fluidically coupled to an outlet of the first pump 256 and a second inlet port of the valve 260 (labelled "D" in FIG. 5) may be fluidically coupled to an outlet of the second pump 258. In some implementations, the valve 260 is a commercially-available, off the shelf valve, and can be a Valvo Vici Cheminert 8 port valve or a Knauer Azura V 2.1S 8 port valve. The system 250 also includes a mixing assembly 262, which can include any or all of the features described herein for the mixing assembly 150, that is fluidically coupled to the valve 260. For example, a first mixing assembly inlet may be fluidically coupled to a first outlet port of the valve 260 (labelled "G" in FIG. 5) and a second mixing assembly inlet may be fluidically coupled to a second outlet port of the valve 260 (labelled "C" in FIG. 5).

As also illustrated in FIG. 5, the system 250 includes a reservoir 264 that is fluidically coupled to the mixing assembly 262. For example, an inlet of the reservoir 264 can be fluidically coupled to an outlet of the mixing assembly 262. During operation of the system 250, the reservoir 264 can hold formulated lipid nanoparticles produced as a result of the mixture of the two stock solutions. As also illustrated in FIG. 5, the valve 260 is fluidically coupled to the first and the second reservoirs 252 and 254. For example, a third outlet port of the valve 260 (labelled "A" in FIG. 5) may be fluidically coupled to an inlet of the first reservoir 252 and a fourth outlet port of the valve 260 (labelled "E" in FIG. 5) may be fluidically coupled to an inlet of the second reservoir

254. As also illustrated in FIG. 5, the valve 260 includes a first open port (labelled "B" in FIG. 5) and a second open port (labelled "F" in FIG. 5). As used herein, the term "open port" may refer to a dummy port that is open to air or a stub or capped conduit rather than to other operating components of the system 250.

Figure 6A:
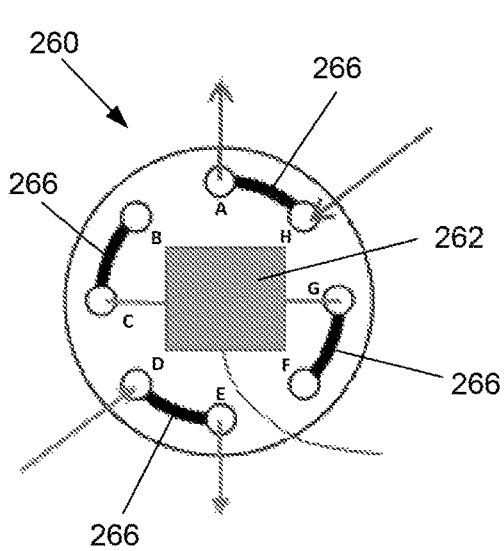
FIG. 6A illustrates an eight-port, two-position valve for use in the method of FIG. 1 in a first position.
Figure 6B:
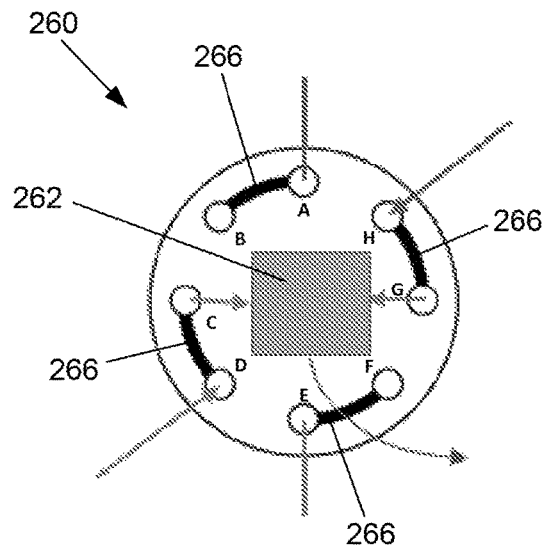
FIG. 6B illustrates the eight-port, two-position valve of FIG. 6A in a second position.

FIG. 6A illustrates a first, recirculating or priming position of the valve 260 and FIG. 6B illustrates a second, mixing or operating position of the valve 260. As illustrated in FIGS. 6A and 6B, the eight ports of the valve 260 are labelled alphabetically in order in a counter-clockwise direction, such that port "A" is adjacent to ports "B" and "H," port "B" is adjacent to ports "C" and "A," port "C" is adjacent to ports "D" and "B," port "D" is adjacent to ports "E" and "C," port "E" is adjacent to ports "D" and "F," port "F" is adjacent to ports "G" and "E," port "G" is adjacent to ports "H" and "F," and port "H" is adjacent to ports "A" and "G." The valve 260 includes four internal conduits 266, each of which fluidically couple two adjacent ports to one another.

The internal conduits 266 can be rotated and switched between two positions such that in the first operating position of the valve 260 illustrated in FIG. 6A, port "B" is fluidically coupled to port "C," port "D" is fluidically coupled to port "E," port "F" is fluidically coupled to port "G," and port "H" is fluidically coupled to port "A." Thus, in the recirculating operating position of the valve 260, the first pump 256 pumps the first stock solution from the first reservoir 252, into the first inlet port "H" of the valve 260, out of the third outlet port "A" of the valve 260, and back to the first reservoir 252, while the second pump 258 pumps the second stock solution from the second reservoir 254, into the second inlet port "D" of the valve 260, out of the fourth outlet port "E" of the valve 260, and back to the second reservoir 254. In such an operating position of the valve 260, the first outlet port "G" and the second open port "F" are fluidically coupled to one another and the second outlet port "C" and the first open port "B" are fluidically coupled to one another.

The internal conduits 266 can also be rotated and switched between two positions such that in the second operating position of the valve 260 illustrated in FIG. 6B, port "A" is fluidically coupled to port "B," port "C" is fluidically coupled to port "D," port "E" is fluidically coupled to port "F," and port "G" is fluidically coupled to port "H." Thus, in the mixing operating position of the valve 260, the first pump 256 pumps the first stock solution from the first reservoir 252, into the first inlet port "H" of the valve 260, out of the first outlet port "G" of the valve 260, and into the mixing assembly 262, while the second pump 258 pumps the second stock solution from the second reservoir 254, into the second inlet port "D" of the valve 260, out of the second outlet port "C" of the valve 260, and into the mixing assembly 262. In such an operating position of the valve 260, the third outlet port "A" and the first open port "B" are fluidically coupled to one another and the fourth outlet port "E" and the second open port "F" are fluidically coupled to one another.

The system 250 can be operated with the valve 260 initially in the recirculating operating position, such as in a "recirculating mode" or a "priming mode," such as to prime the first and second pumps 256, 258, and force air bubbles out of the conduits between the various components, prior to mixing the two stock solutions with one another. During this priming/recirculating mode, there is not loss or waste of stock solutions as they are returned to their first and second reservoirs 202 and 204. Once the components have been primed and adequately cleared of air, the valve 260 can be switched and the system 250 can be operated with the valve 260 in the mixing operating position, such as in a "mixing mode," a "formulating mode," or an "operating mode," such that the two stock solutions are simultaneously fed into the mixing assembly 262. The stock solutions can then mix within the mixing assembly 262, flow out of the mixing assembly 262 into the reservoir 264, and be stored therein for later use. In either the recirculating mode or the mixing mode or both, the first and second pumps 256, 258 can operate at either the same speed, to pump the respective stock solutions at the same rate, or at different speeds, to pump the respective stock solutions at different rates, such as to accommodate a desired mixing ratio for the two stock solutions within the mixing assembly 262. Throughout operation of the system 250, the first and second pumps 256 and 258 can pump solution at a combined rate between 100-200 mL/min.

In some implementations, the system 250 has certain advantages over the system 200 due to its use of an 8-port valve with two open ports rather than a 6-port valve with no open ports. In particular, the use of the open ports "B" and "F" in the 8-port valve 260 prevent or at least reduce or minimize the degree to which the two stock solutions mix with one another other than within the mixing assembly 262. For example, when the system 250 is operating in the recirculating mode, any residual stock solution remaining at the first and second outlet ports "C" and "G" are fluidically coupled to the open ports and thus to air or other inert media, rather than to each other such that the two stock solutions might mix prior to entering the mixing assembly 262. Similarly, when the system 250 is operating in the mixing mode, any stock solution present at the third and fourth outlet ports "A" and "E" are fluidically coupled to the open ports and thus to air or other inert media, rather than to each other such that the two stock solutions might mix prior to entering the mixing assembly 262 or returning to the first and second reservoirs 252 and 254.

In either of the systems 200 and 250, any of the conduits described herein may include one or more check valves, such as to prevent backflow and/or siphoning of the respective solutions through the respective conduits, such as to the open ports of the valve 210 and/or 260, such as at times when the respective conduits are not receiving solution pumped therethrough by the pumps 206, 208, 256, and/or 258.

Figure 7A:
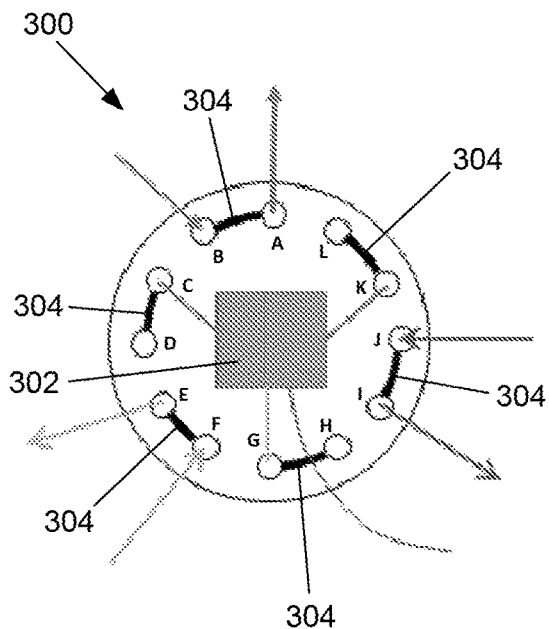
FIG. 7A illustrates a twelve-port, two-position valve for use in the method of FIG. 1 in a first position, where the twelve-port, two-position valve is coupled to other components in a first arrangement.
Figure 7B:
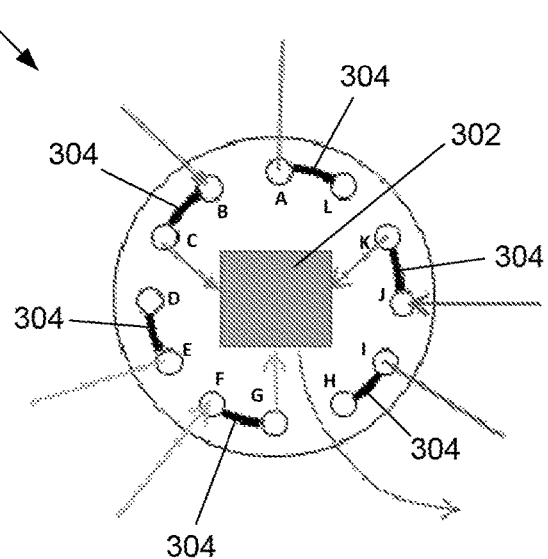
FIG. 7B illustrates the twelve-port, two-position valve of FIG. 7A in a second position.

FIG. 7A illustrates a first, recirculating or priming position of a twelve-port, two-position valve 300 that can be used in place of the valve 210 of system 200 or the valve 260 of system 250 to control the flow of three different solutions to a mixing assembly 302. FIG. 7B illustrates a second, mixing or operating position of the valve 300. As illustrated in FIGS. 7A and 7B, the twelve ports of the valve 300 are labelled alphabetically in order in a counter-clockwise direction, such that port "A" is adjacent to ports "B" and "L," port "B" is adjacent to ports "C" and "A," port "C" is adjacent to ports "D" and "B," port "D" is adjacent to ports "E" and "C," port "E" is adjacent to ports "D" and "F," port "F" is adjacent to ports "G" and "E," port "G" is adjacent to ports "H" and "F," port "H" is adjacent to ports "I" and "G," port "I" is adjacent to ports "J" and "H," port "J" is adjacent to ports "K" and "I," port "K" is adjacent to ports "L" and "J," and port "L" is adjacent to ports "A" and "K." The valve 300 includes six internal conduits 304, each of which fluidically couple two adjacent ports to one another.

Port "B" can be a first inlet port that is fluidically coupled to a source of a first solution to be mixed within the mixing assembly 302, port "F" can be a second inlet port that is fluidically coupled to a source of a second solution to be mixed within the mixing assembly 302, and port "J" can be a third inlet port that is fluidically coupled to a source of a third solution to be mixed within the mixing assembly 302. Port "C" can be a first outlet port that is fluidically coupled to a first inlet of the mixing assembly 302, port "G" can be a second outlet port that is fluidically coupled to a second inlet of the mixing assembly 302, and port "K" can be a third outlet port that is fluidically coupled to a third inlet of the mixing assembly 302. Port "A" can be a fourth outlet port that is fluidically coupled to the source of the first solution, port "E" can be a fifth outlet port that is fluidically coupled to the source of the second solution, and port "I" can be a sixth outlet port that is fluidically coupled to the source of the third solution. Port "D" can be a first open port, port "H" can be a second open port, and port "L" can be a third open port.

The internal conduits 304 can be rotated and switched between two positions such that in the first operating position of the valve 300 illustrated in FIG. 7A, port "A" is fluidically coupled to port "B," port "C" is fluidically coupled to port "D," port "E" is fluidically coupled to port "F," port "G" is fluidically coupled to port "H," port "I" is fluidically coupled to port "J," and port "K" is fluidically coupled to port "L." Thus, in the recirculating operating position of the valve 300, a first pump can pump the first solution into the first inlet port "B" of the valve 300, out of the fourth outlet port "A" of the valve 300, and back to the source of the first solution, while a second pump pumps the second solution into the second inlet port "F" of the valve 300, out of the fifth outlet port "E" of the valve 300, and back to the source of the second solution and while a third pump pumps the third solution into the third inlet port "J" of the valve 300, out of the sixth outlet port "I" of the valve 300, and back to the source of the third solution. In such an operating position of the valve 300, the first outlet port "C" and the first open port "D" are fluidically coupled to one another, the second outlet port "G" and the second open port "H" are fluidically coupled to one another, and the third outlet port "K" and the third open port "L" are fluidically coupled to one another.

The internal conduits 304 can also be rotated and switched between two positions such that in the second operating position of the valve 300 illustrated in FIG. 7B, port "B" is fluidically coupled to port "C," port "D" is fluidically coupled to port "E," port "F" is fluidically coupled to port "G," port "H" is fluidically coupled to port "I," port "J" is fluidically coupled to port "K," and port "L" is fluidically coupled to port "A." Thus, in the mixing operating position of the valve 300, the first pump pumps the first solution into the first inlet port "B" of the valve 300, out of the first outlet port "C" of the valve 300, and into the mixing assembly 302, while the second pump pumps the second solution into the second inlet port "F" of the valve 300, out of the second outlet port "G" of the valve 300, and into the mixing assembly 302, and while the third pump pumps the third solution into the third inlet port "J" of the valve 300, out of the third outlet port "K" of the valve 300, and into the mixing assembly 302. In such an operating position of the valve 300, the fourth outlet port "A" and the third open port "L" are fluidically coupled to one another, the fifth outlet port "E" and the first open port "D" are fluidically coupled to one another, and the sixth outlet port "I" and the second open port "H" are fluidically coupled to one another.

Figure 8A:
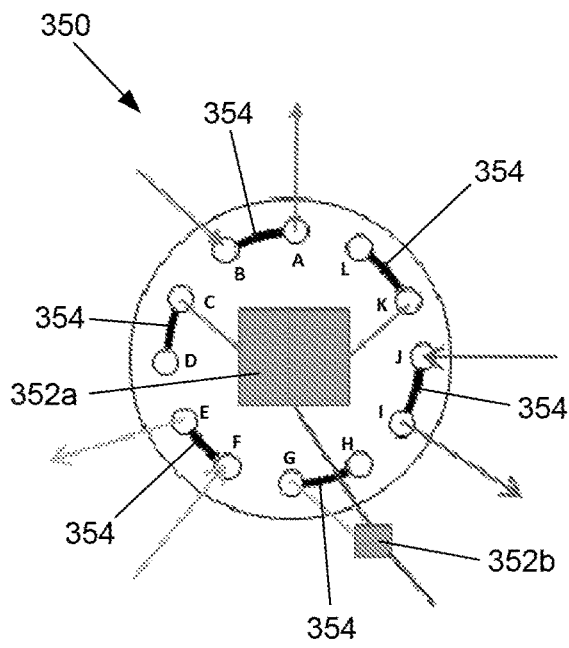
FIG. 8A illustrates a twelve-port, two-position valve for use in the method of FIG. 1 in a first position, where the twelve-port, two-position valve is coupled to other components in a second arrangement.
Figure 8B:
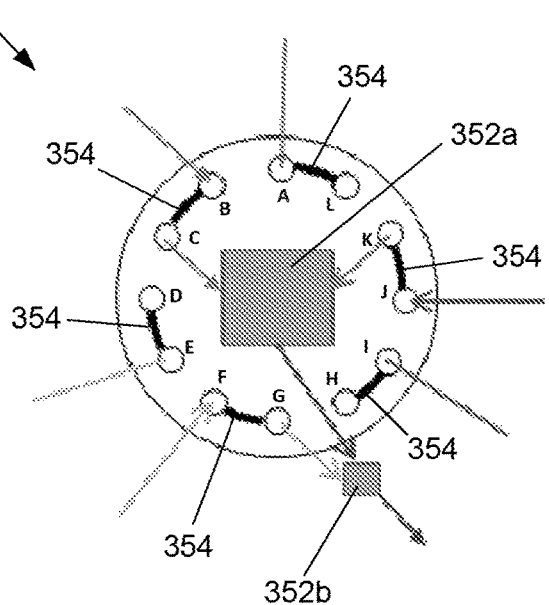
FIG. 8B illustrates the twelve-port, two-position valve of FIG. 8A in a second position.

FIG. 8A illustrates a first, recirculating or priming position of a twelve-port, two-position valve 350 that can be used in place of the valve 210 of system 200 or the valve 260 of system 250 to control the flow of three different solutions to a mixing assembly 352 including a first mixing assembly portion 352a and a second mixing assembly portion 352b. FIG. 8B illustrates a second, mixing or operating position of the valve 350. As illustrated in FIGS. 8A and 8B, the twelve ports of the valve 350 are labelled alphabetically in order in a counter-clockwise direction, such that port "A" is adjacent to ports "B" and "L," port "B" is adjacent to ports "C" and "A," port "C" is adjacent to ports "D" and "B," port "D" is adjacent to ports "E" and "C," port "E" is adjacent to ports "D" and "F," port "F" is adjacent to ports "G" and "E," port "G" is adjacent to ports "H" and "F," port "H" is adjacent to ports "I" and "G," port "I" is adjacent to ports "J" and "H," port "J" is adjacent to ports "K" and "I," port "K" is adjacent to ports "L" and "J," and port "L" is adjacent to ports "A" and "K." The valve 350 includes six internal conduits 354, each of which fluidically couple two adjacent ports to one another.

Port "B" can be a first inlet port that is fluidically coupled to a source of a first solution to be mixed within the mixing assembly 352, port "F" can be a second inlet port that is fluidically coupled to a source of a second solution to be mixed within the mixing assembly 352, and port "J" can be a third inlet port that is fluidically coupled to a source of a third solution to be mixed within the mixing assembly 352. Port "C" can be a first outlet port that is fluidically coupled to a first inlet of the mixing assembly 352, port "G" can be a second outlet port that is fluidically coupled to a second inlet of the mixing assembly 352, and port "K" can be a third outlet port that is fluidically coupled to a third inlet of the mixing assembly 352. Port "A" can be a fourth outlet port that is fluidically coupled to the source of the first solution, port "E" can be a fifth outlet port that is fluidically coupled to the source of the second solution, and port "I" can be a sixth outlet port that is fluidically coupled to the source of the third solution. Port "D" can be a first open port, port "H" can be a second open port, and port "L" can be a third open port.

The internal conduits 354 can be rotated and switched between two positions such that in the first operating position of the valve 350 illustrated in FIG. 8A, port "A" is fluidically coupled to port "B," port "C" is fluidically coupled to port "D," port "E" is fluidically coupled to port "F," port "G" is fluidically coupled to port "H," port "I" is fluidically coupled to port "J," and port "K" is fluidically coupled to port "L." Thus, in the recirculating operating position of the valve 350, a first pump can pump the first solution into the first inlet port "B" of the valve 350, out of the fourth outlet port "A" of the valve 350, and back to the source of the first solution, while a second pump pumps the second solution into the second inlet port "F" of the valve 350, out of the fifth outlet port "E" of the valve 350, and back to the source of the second solution and while a third pump pumps the third solution into the third inlet port "J" of the valve 350, out of the sixth outlet port "I" of the valve 350, and back to the source of the third solution. In such an operating position of the valve 350, the first outlet port "C" and the first open port "D" are fluidically coupled to one another, the second outlet port "G" and the second open port "H" are fluidically coupled to one another, and the third outlet port "K" and the third open port "L" are fluidically coupled to one another.

The internal conduits 354 can also be rotated and switched between two positions such that in the second operating position of the valve 350 illustrated in FIG. 8B, port "B" is fluidically coupled to port "C," port "D" is fluidically coupled to port "E," port "F" is fluidically coupled to port "G," port "H" is fluidically coupled to port "I," port "J" is fluidically coupled to port "K," and port "L" is fluidically coupled to port "A." Thus, in the mixing operating position of the valve 350, the first pump pumps the first solution into the first inlet port "B" of the valve 350, out of the first outlet port "C" of the valve 350, and into the mixing assembly 352, while the second pump pumps the second solution into the second inlet port "F" of the valve 350, out of the second outlet port "G" of the valve 350, and into the mixing assembly 352, and while the third pump pumps the third solution into the third inlet port "J" of the valve 350, out of the third outlet port "K" of the valve 350, and into the mixing assembly 352. In such an operating position of the valve 350, the fourth outlet port "A" and the third open port "L" are fluidically coupled to one another, the fifth outlet port "E" and the first open port "D" are fluidically coupled to one another, and the sixth outlet port "I" and the second open port "H" are fluidically coupled to one another.

The valve 300 and its various connections, including to the mixing assembly 302, as illustrated in FIGS. 7A and 7B, can be used to control the flow of three solutions to be mixed together simultaneously within a single mixing chamber within the mixing assembly 302. The mixing assembly 302 can be a cross-type mixing assembly and operate using vortex-type mixing techniques. Thus, as illustrated in FIGS. 7A and 7B, the first mixing assembly inlet, the second mixing assembly inlet, the third mixing assembly inlet, and a mixing assembly outlet of the mixing assembly 302 are each directly fluidically coupled to the single mixing chamber. In this sense, "direct" coupling means there is a direct path through a single conduit between the components that is uninterrupted by other elements.

The valve 350 and its various connections, including to the mixing assembly 352, as illustrated in FIGS. 8A and 8B, can be used to control the flow of three solutions to be mixed together sequentially, first within a first mixing chamber within the first mixing assembly portion 352a and then within a second mixing chamber within the second mixing assembly portion 352b. The first and second mixing assembly portions 352a and 352b can each be tee-type mixing assemblies (e.g., "T-connector" or "T-junction"). Thus, the first mixing assembly portion 352a can have first and second inlets that are fluidically coupled to the first outlet port "C" and to the third outlet port "K," respectively, of the valve 350. The second mixing assembly portion 352b can have first and second inlets that are fluidically coupled to the second outlet port "G" of the valve 350 and to an outlet of the first mixing assembly portion 352a, respectively, as well as a second mixing assembly portion outlet.

The valve 350 can control the flow of the first and third solutions to the first mixing assembly portion 352a where the first and third solutions can be mixed with one another, such as to form lipid nanoparticles as described elsewhere herein. At the same time, the valve 350 can control the flow of the second solution to the second mixing assembly portion 352, where the mixture including the lipid nanoparticles and the second solution, which can be a diluent, can mix, such as to dilute the initial mixture, as described elsewhere herein.

Any of the systems and components thereof described herein, including the various pumps and valves described herein, can be controlled using any known control techniques and/or any known control systems. For example, in some implementations, such components can be controlled manually, electronically, and/or hydraulically. In some specific implementations, the systems described herein can include a manual push button or switch, such as physically located on and/or integrated with the respective component (s), such as the pumps and/or the valves, which can be actuated by an operator to initiate or terminate operation, or otherwise control the operation of, such components. In other specific implementations, the systems described herein can include a laptop, tablet, or other computing device running control software that is communicatively coupled to the components of the systems described herein, such as through a router, and which can be controlled by an operator to initiate or terminate operation, or otherwise control the operation of, such components.

As noted elsewhere herein, different pumps within a single system may pump respective solutions toward a mixing assembly at different rates, such as to accommodate a desired mixing ratio for the solutions within the mixing assembly. Nevertheless, it can be advantageous that the solutions meet each other at a desired location, such as within a mixing chamber within the mixing assembly, at the same time. Thus, the use of a single flow control valve to control the flow of multiple solutions to the mixing assembly can be advantageous, because it can help to improve the timing of the flows and the simultaneity of the flows reaching the mixing chamber. Further, the dimensions, such as the inside diameters and the lengths, of the mixing assembly inlets, such as the first and second mixing assembly inlets 152 and 154, can be selected and precisely controlled based on the desired mixing ratio for the solutions to ensure that the solutions reach the mixing chamber(s) at the same time (i.e., to improve or increase the simultaneity of the flows reaching the mixing chambers). Such improvements are advantageous in turn because they reduce an amount of an initial mixture that is wasted at start-up of the system. For example, in some implementations, the systems and techniques described herein can reduce an amount of an initial mixture that is wasted from about 10-15 mL to about 0 mL.

Methods of Manufacture

In certain embodiments, the present disclosure provides a method for mixing and manufacturing lipid nanoparticles. Advantageously, the present disclosure provides embodiments of a method that minimizes reagent waste and increases efficiency in manufacturing lipid nanoparticles.

Accordingly, one embodiment provides a method of manufacturing lipid nanoparticles, comprising providing an organic lipid stock solution within a first reservoir, providing an aqueous nucleic acid stock solution within a second reservoir, pumping the organic lipid stock solution from the first reservoir to a first valve inlet port of a valve, pumping the aqueous nucleic acid stock solution from the second reservoir to a second valve inlet port of the valve, flowing the organic lipid stock solution and the aqueous nucleic acid stock through the valve and operating the valve in a second operating position in which the first valve inlet port is not fluidically connected to a first mixing assembly inlet of a mixing assembly and the second valve inlet port is not fluidically connected to a second mixing assembly inlet of the mixing assembly in the second operating position, and switching the valve to a first operating position and flowing the organic lipid stock solution through the valve to the first mixing assembly inlet of a mixing assembly and flowing the aqueous nucleic acid stock solution through the valve to the second mixing assembly inlet of the mixing assembly thereby mixing the organic lipid stock solution and the aqueous nucleic acid stock solution within the mixing assembly to create a first mixture and flowing the first mixture out of the mixing assembly through a mixing assembly outlet.

In some more specific embodiments, the method further comprising flowing the organic lipid stock solution through the valve to the first reservoir and flowing the aqueous nucleic acid stock solution through the valve to the second reservoir.

In other specific embodiments, the method further comprises providing a diluent within a third reservoir and pumping the diluent from the third reservoir to a third valve inlet port of the valve, wherein switching the valve to the first operating position further comprises flowing the diluent through the valve to a third mixing assembly inlet of the mixing assembly thereby mixing the diluent with the first mixture within the mixing assembly and flowing the diluent and first mixture out of the mixing assembly through the mixing assembly outlet.

In certain embodiments, operating the valve to the second operating position further comprises preventing the diluent from flowing through the valve to the third mixing assembly inlet of the mixing assembly.

One specific embodiment provides a method of manufacturing lipid nanoparticles, comprising providing the system of any one of the foregoing embodiments, pumping the organic lipid stock solution from the first reservoir to the first valve inlet port of the valve, pumping the aqueous nucleic acid stock solution from the second reservoir to the second valve inlet port of the valve, flowing the organic lipid stock solution and the aqueous nucleic acid stock through the valve and operating the valve in the second operating position in which the first valve inlet port is not fluidically connected to a first mixing assembly of a mixing assembly and the second valve inlet port is not fluidically connected to a second mixing assembly of the mixing assembly in the second operating position, and switching the valve to the first operating position and flowing the organic lipid stock solution through the valve to the first mixing assembly inlet of the mixing assembly and flowing the aqueous nucleic acid stock solution through the valve to the second mixing assembly inlet of the mixing assembly thereby mixing the organic lipid stock solution and the aqueous nucleic acid stock solution within the mixing assembly to create a first mixture and flowing the first mixture out of the mixing assembly through the mixing assembly outlet.

The present disclosure provides methods that advantageously avoid loss of valuable reagents (e.g., organic lipid stock solution, aqueous nucleic acid stock solution, etc.). Additionally, embodiments of the methods of this disclosure are adaptable to a wide variety of reagents, concentrations, flow rates, and other parameters. Parameters of the present disclosure can be adjusted to achieve a desired result (e.g., encapsulation percentage, particle size distribution, etc.). Some specific non-limiting embodiments of these parameters are disclosed herein.

For example, in some embodiments the methods disclosed herein reduce expensive and wasteful production losses in the prior art caused by failure of stream flows to initiate the mixing process in precise co-ordination, resulting in improper and out-of-specification particle generation. In certain embodiments the methods avoid the previously unavoidable loss of 0.5%, 1%, 2%, 3%, 4%, 5% or more by mass of one or more of the stock solutions. In certain other embodiments the methods avoid the previously unavoidable loss of 0.5 ml, 1 ml, 2 ml, 3 ml, 4 ml, 5 ml, or more of one or more of the stock solutions.

Organic Lipid Stock Solution and Lipid Nanoparticles

One embodiment of the foregoing system or method provides an organic lipid stock solution comprising a cationic lipid or mixtures thereof. For example, in some embodiments, the cationic lipid(s) can be any of a number of lipid species which carry a net positive charge at a selected pH, such as physiological pH. The cationic lipids may be prepared according to the procedures set forth in the Examples or according to methods known or derivable by one of ordinary skill in the art.

Cationic Lipids

Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3dioleoyloxy)propyl)-N,N,N-trimethylammonium chloride (DOTAP); 3-(N—(N',N'dimethylaminoethane)-carbamoyl) cholesterol (DC-Chol), N-(1-(2,3-dioleoyloxy)propyl)N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE).

Additionally, a number of commercial preparations of cationic lipids are available which can be used according to the present disclosure. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one specific embodiment, the cationic lipid is an amino lipid. Suitable amino lipids include those described in PCT Pub. No. WO 2012/016184, which is incorporated herein by reference in its entirety. Representative amino lipids include, but are not limited to, 1,2-dilinoleyoxy-3-(dimethylamino) acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,Ndilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

In some embodiments, the cationic lipid has the following formula:

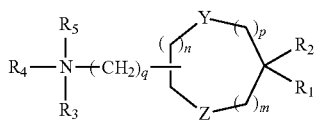

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl; m, n, and p are either the same or different and independently either 0 or 1 with the proviso that m, n, and p are not simultaneously 0; q is 0, 1, 2, 3, or 4; and Y and Z are either the same or different and independently O, S, or NH.

In one embodiment, $R_1$ and $R_2$ are each linoleyl, and the amino lipid is a dilinoleyl amino lipid. In one embodiment, the amino lipid is a dilinoleyl amino lipid.

In various other embodiments, the cationic lipid has the following structure:

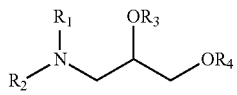

or a pharmaceutically acceptable salt, tautomer, prodrug or stereoisomer thereof, wherein:

$R_1$ and $R_2$ are independently selected from the group consisting of H, and $C_1$-$C_3$ alkyls;

$R_3$ and $R_4$ are independently selected from the group consisting of alkyl groups having from about 10 to about 20 carbon atoms, wherein at least one of $R_3$ and $R_4$ comprises at least two sites of unsaturation. (e.g., $R_3$ and $R_4$ may be, for example, dodecadienyl, tetradecadienyl, hexadecadienyl, linoleyl, and icosadienyl. In a preferred embodiment, $R_3$ and $R_4$ are both linoleyl, $R_3$ and $R_4$ may comprise at least three sites of unsaturation (e.g., $R_3$ and $R_4$ may be, for example, dodecatrienyl, tetradectrienyl, hexadecatrienyl, linolenyl, and icosatrienyl).

In some embodiments, the cationic lipid has the following structure:

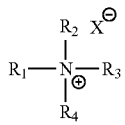

or a pharmaceutically acceptable salt, tautomer, prodrug or stereoisomer thereof, wherein:

$R_1$ and $R_2$ are independently selected and are H or $C_1$-$C_3$ alkyls. $R_3$ and $R_4$ are independently selected and are alkyl groups having from about 10 to about 20 carbon atoms, wherein at least one of $R_4$ and $R_4$ comprises at least two sites of unsaturation. In one embodiment, $R_3$ and $R_4$ are both the same, for example, in some embodiments $R_3$ and $R_4$ are both linoleyl (i.e., $C_{18}$), etc. In another embodiment, $R_3$ and $R_4$ are different, for example, in some embodiments $R_3$ is tetradectrienyl ($C_4$) and $R_4$ is linoleyl ($C_{18}$). In a preferred embodiment, the cationic lipid(s) of the present invention are symmetrical, i.e., $R_3$ and $R_4$ are the same. In another preferred embodiment, both $R_3$ and $R_4$ comprise at least two sites of unsaturation. In some embodiments, $R_3$ and $R_4$ are independently selected from dodecadienyl, tetradecadienyl, hexadecadienyl, linoleyl, and icosadienyl. In a preferred embodiment, $R_3$ and $R_4$ are both linoleyl. In some embodiments, $R_4$ and $R_4$ comprise at least three sites of unsaturation and are independently selected from, e.g., dodecatrienyl, tetradectrienyl, hexadecatrienyl, linolenyl, and icosatrienyl.

In various embodiments, the cationic lipid has the formula:

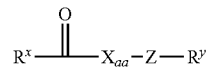

or a pharmaceutically acceptable salt, tautomer, prodrug or stereoisomer thereof, wherein:

$X_{aa}$ is a D- or L-amino acid residue having the formula —$NR^N$—$CR^1R^2$—$C(C=O)$—, or a peptide or a peptide of amino acid residues having the formula $\{NR^N$—$CR^1R^2$—$(C=O)\}_n$—, wherein n is 2 to 20;

$R^1$ is independently, for each occurrence, a non-hydrogen, substituted or unsubstituted side chain of an amino acid;

$R^2$ and $R^N$ are independently, for each occurrence, hydrogen, an organic group consisting of carbon, oxygen, nitrogen, sulfur, and hydrogen atoms, or any combination of the foregoing, and having from 1 to 20 carbon atoms, $C_{(1-5)}$alkyl, cycloalkyl, cycloalkylalkyl, $C_{(3-5)}$alkenyl, $C_{(3-5)}$alkynyl, $C_{(1-5)}$alkanoyl, $C_{(1-5)}$alkanoyloxy, $C_{(1-5)}$alkoxy, $C_{(1-5)}$alkoxy-$C_{(1-5)}$alkyl, $C_{(1-5)}$alkoxy-$C_{(1-5)}$alkoxy, $C_{(1-5)}$alkyl-amino-$C_{(1-5)}$alkyl-, $C_{(1-5)}$dialkyl-amino-$C_{(1-5)}$alkyl-, nitro-$C_{(1-5)}$alkyl, cyano-$C_{(1-5)}$alkyl, aryl-$C_{(1-5)}$alkyl, 4-biphenyl-$C_{(1-5)}$alkyl, carboxyl, or hydroxyl;

Z is NH, O, S, —$CH_2S$—, —$CH_2S(O)$—, or an organic linker consisting of 1-40 atoms selected from hydrogen, carbon, oxygen, nitrogen, and sulfur atoms (preferably, Z is NH or O);

$R^x$ and $R^y$ are, independently, (i) a lipophilic tail derived from a lipid (which can be naturally-occurring or synthetic), phospholipid, glycolipid, triacylglycerol, glycerophospholipid, sphingolipid, ceramide, sphingomyelin, cerebroside, or ganglioside, wherein the tail optionally includes a steroid; (ii) an amino acid terminal group selected from hydrogen, hydroxyl, amino, and an organic protecting group; or (iii) a substituted or unsubstituted $C_{(3-22)}$alkyl, $C_{(6-12)}$cycloalkyl, $C_{(6-12)}$cycloalkyl-$C_{(3-22)}$alkyl, $C_{(3-22)}$alkenyl, $C_{(3-22)}$alkynyl, $C_{(3-22)}$alkoxy, or $C_{(6-12)}$alkoxy-$C_{(3-22)}$alkyl;

one of $R^x$ and $R^y$ is a lipophilic tail as defined above and the other is an amino acid terminal group, or both $R^x$ and $R^y$ are lipophilic tails;

at least one of $R^x$ and $R^y$ is interrupted by one or more biodegradable groups (e.g., —OC(O)—, —C(O)O—, —SC(O)—, —C(O)S—, —OC(S)—, —C(S)O—, —S—S—, —C(R$^5$)=N—, —N=C(R$^5$)—, —C(R$^5$)=N—O—, —O—N=C(R$^5$)—, —C(O)(NR$^5$)—, —N(R$^5$)C(O)—, —C(S)(NR$^5$)—, —N(R$^5$)C(O)—, —N(R$^5$)C(O)N(R$^5$)—, OC(O)O—, —OSi(R$^5$)$_2$O—, C(O)(CR$^3$R$^4$)C(O)O—, —OC(O)(CR$^3$R$^4$)C(O)— or

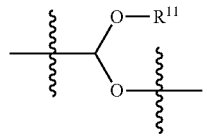

wherein R$^{11}$ is a C$_2$-C$_8$ alkyl or alkenyl and each occurrence of R$^5$ is, independently, H or alkyl; and each occurrence of R$^3$ and R$^4$ are, independently H, halogen, OH, alkyl, alkoxy, —NH$_2$, alkylamino, or dialkylamino; or R$^3$ and R$^4$, together with the carbon atom to which they are directly attached, form a cycloalkyl group (in one preferred embodiment, each occurrence of R$^3$ and R$^4$ are, independently H or C$_1$-C$_4$ alkyl)); and R$^x$ and R$^y$ each, independently, optionally have one or more carbon-carbon double bonds.

In some embodiments, the cationic lipid has one of the following structures:

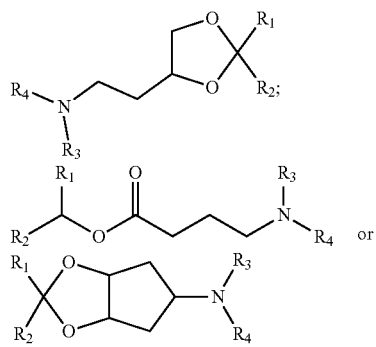

or a pharmaceutically acceptable salt, tautomer, prodrug or stereoisomer thereof, wherein:

R$_1$ and R$_2$ are independently alkyl, alkenyl or alkynyl, and each can be optionally substituted;
R$_3$ and R$_4$ are independently a C$_1$-C$_6$ alkyl, or R$_3$ and R$_4$ can be taken together to form an optionally substituted heterocyclic ring.

A representative useful dilinoleyl amino lipid has the formula:

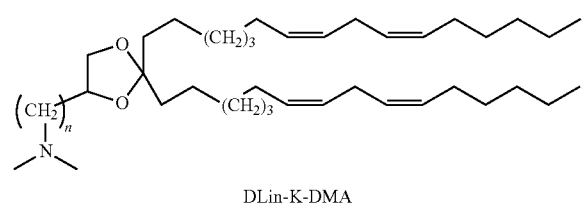

DLin-K-DMA wherein n is 0, 1, 2, 3, or 4.

In one embodiment, the cationic lipid is DLin-K-DMA. In one embodiment, a cationic lipid of any one of the disclosed embodiments is DLin-KC2-DMA (DLin-K-DMA above, wherein n is 2).

In one embodiment, the cationic lipid has the following structure:

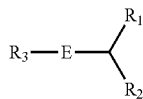

or a pharmaceutically acceptable salt, tautomer, prodrug or stereoisomer thereof, wherein:

R$_1$ and R$_2$ are each independently for each occurrence optionally substituted C$_{10}$-C$_{30}$ alkyl, optionally substituted C$_{10}$-C$_{30}$ alkenyl, optionally substituted C$_{10}$-C$_{30}$ alkynyl or optionally substituted C$_{10}$-C$_{30}$ acyl;

R$_3$ is H, optionally substituted C$_{10}$-C$_{10}$ alkyl, optionally substituted C$_2$-C$_{10}$ alkenyl, optionally substituted C$_2$-C$_{10}$ alkynyl, alkylheterocycle, alkylphosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K), heteroaryl, or heterocycle, or linker-ligand, for example in some embodiments R$_3$ is (CH$_3$)$_2$N(CH$_2$)$_n$—, wherein n is 1, 2, 3 or 4;

E is O, S, N(Q), C(O), OC(O), C(O)O, N(Q)C(O), C(O)N(Q), (Q)N(CO))O, O(CO)N(Q), S(O), NS(O)$_2$N(Q), S(O)$_2$, N(O)S(O)$_2$, SS, O=N, aryl, heteroaryl, cyclic or heterocycle, for example —C(O)O, wherein— is a point of connection to R$_3$; and Q is H, alkyl, ω-aminoalkyl, ω-(substituted)aminoalkyl, ω-phosphoalkyl or ω-thiophosphoalkyl.

In one specific embodiment, the cationic lipid has the following structure:

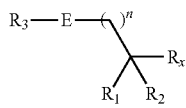

or a pharmaceutically acceptable salt, tautomer, prodrug or stereoisomer thereof, wherein:

E is O, S, N(Q) C(O), N(Q)C(O), C(O)N(Q), (Q)N(CO)O, O(CO)N(Q), S(O), NS(O)$_2$N(Q), S(O)$_2$, N(Q)S(O)$_2$, SS, O=N, aryl, heteroaryl, cyclic or heterocycle;

Q is H, alkyl, ω-aminoalkyl, ω-(substituted)aminoalkyl, ω-phosphoalkyl or ω-thiophosphoalkyl;

R$_1$ and R$_2$ and R$_x$ are each independently for each occurrence H, optionally substituted C$_1$-C$_{10}$ alkyl, optionally substituted C$_{10}$-C$_{30}$ alkyl, optionally substituted C$_{10}$-C$_{30}$ alkenyl, optionally substituted C$_{10}$-C$_{30}$ alkynyl, optionally substituted C$_{10}$-C$_{30}$ acyl, or linker-ligand, provided that at least one of R$_1$, R$_2$ and R$_x$ is not H;

R$_3$ is H, optionally substituted C$_1$-C$_{10}$ alkyl, optionally substituted C$_2$-C$_{10}$ alkenyl, optionally substituted C$_2$-C$_{10}$ alkynyl, alkylheterocycle, alkylphosphate, alkylphosphorothioate, alkylphosphorodithioate, alkylphosphonate, alkylamine, hydroxyalkyl, ω-aminoalkyl, ω-(substituted)aminoalkyl, ω-phosphoalkyl, ω-thiophosphoalkyl, optionally substituted polyethylene glycol (PEG, mw 100-40K), optionally substituted mPEG (mw 120-40K), heteroaryl, or heterocycle, or linker-ligand; and n is 0, 1, 2, or 3.

Cationic Lipids of Formula I

In one embodiment, the cationic lipid has the structure of Formula I:

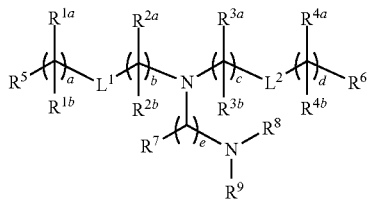

I or a pharmaceutically acceptable salt, tautomer or stereoisomer thereof, wherein:
one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;
$R^a$ is H or $C_1$-$C_{12}$ alkyl;
$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;
$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;
$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;
$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;
$R^5$ and $R^6$ are each independently methyl or cycloalkyl;
$R^7$ is, at each occurrence, independently H or $C_1$-$C_{12}$ alkyl;
$R^8$ and $R^9$ are each independently unsubstituted $C_1$-$C_{12}$ alkyl; or $R^8$ and
$R^9$, together with the nitrogen atom to which they are attached, form a 5, 6 or 7-membered heterocyclic ring comprising one nitrogen atom;
a and d are each independently an integer from 0 to 24;
b and c are each independently an integer from 1 to 24;
e is 1 or 2; and
x is 0, 1 or 2.

In some embodiments of Formula I, $L^1$ and $L^2$ are independently —O(C=O)— or —(C=O)O—.

In certain embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—. In other embodiments, $R^{1a}$ and $R^{1b}$ are not isopropyl when a is 6 or n-butyl when a is 8.

In still further embodiments of Formula I, at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—; and
$R^{1a}$ and $R^{1b}$ are not isopropyl when a is 6 or n-butyl when a is 8.

In other embodiments of Formula I, $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula I, any one of $L^1$ or $L^2$ may be —O(C=O)— or a carbon-carbon double bond. $L^1$ and $L^2$ may each be —O(C=O)— or may each be a carbon-carbon double bond.

In some embodiments of Formula I, one of $L^1$ or $L^2$ is —O(C=O)—. In other embodiments, both $L^1$ and $L^2$ are —O(C=O)—.

In some embodiments of Formula I, one of $L^1$ or $L^2$ is —(C=O)O—. In other embodiments, both $L^1$ and $L^2$ are —(C=O)O—.

In some other embodiments of Formula I, one of $L^1$ or $L^2$ is a carbon-carbon double bond. In other embodiments, both $L^1$ and $L^2$ are a carbon-carbon double bond.

In still other embodiments of Formula I, one of $L^1$ or $L^2$ is —O(C=O)— and the other of $L^1$ or $L^2$ is —(C=O)O—. In more embodiments, one of $L^1$ or $L^2$ is —O(C=O)— and the other of $L^1$ or $L^2$ is a carbon-carbon double bond. In yet more embodiments, one of $L^1$ or $L^2$ is —(C=O)O— and the other of $L^1$ or $L^2$ is a carbon-carbon double bond.

It is understood that "carbon-carbon" double bond, as used throughout the specification, refers to one of the following structures:

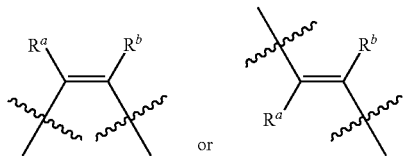

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula I have the following Formula (Ia):

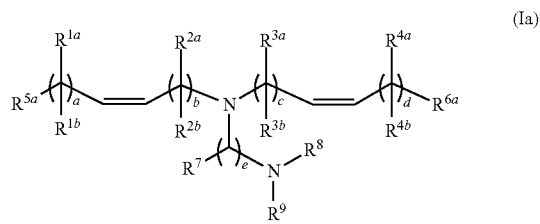

(Ia)

In other embodiments, the lipid compounds of Formula I have the following Formula (Ib):

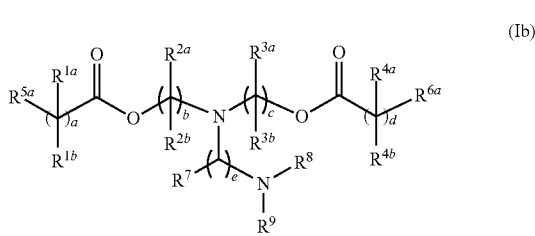

(Ib)

In yet other embodiments, the lipid compounds of Formula I have the following Formula (Ic):

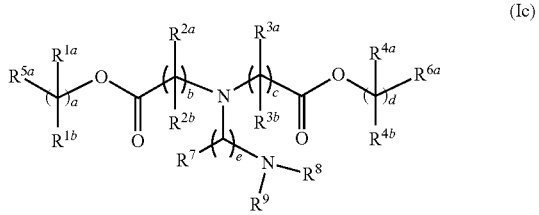

(Ic)

In certain embodiments of the cationic lipid of Formula I, a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula I, b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula I, c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain other embodiments of Formula I, d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula I, a and d are the same. In some other embodiments, b and c are the same. In some other specific embodiments, a and d are the same and b and c are the same.

The sum of a and b and the sum of c and d in Formula I are factors which may be varied to obtain a lipid of formula I having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a, b, c and d are selected such the sum of a and b and the sum of c and d is 12 or greater.

In some embodiments of Formula I, e is 1. In other embodiments, e is 2.

The substituents at $R^{1a}$, $R^{2a}$, $R^{3a}$ and $R^{4a}$ of Formula I are not particularly limited. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula I, $R^{1a}$, $R^{1b}$, $R^{4a}$ and $R^{4b}$ are $C_1$-$C_{12}$ alkyl at each occurrence.

In further embodiments of Formula I, at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula I, $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula I are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments the cycloalkyl may be substituted or not substituted. In certain other embodiments the cycloalkyl is substituted with $C_1$-$C_{12}$ alkyl, for example tert-butyl.

The substituents at $R^7$ are not particularly limited in the foregoing embodiments of Formula I. In certain embodiments at least one $R^7$ is H. In some other embodiments, $R^7$ is H at each occurrence. In certain other embodiments $R^7$ is $C_1$-$C_{12}$ alkyl.

In certain other of the foregoing embodiments of Formula I, one of $R^8$ or $R^9$ is methyl. In other embodiments, both $R^8$ and $R^9$ are methyl.

In some different embodiments of Formula I, $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In various different embodiments, the lipid of Formula I has one of the structures set forth in Table 1 below.

TABLE 1
Representative Lipids of Formula I
| No. | Structure | pKa |
|---|---|---|
| I-1 | 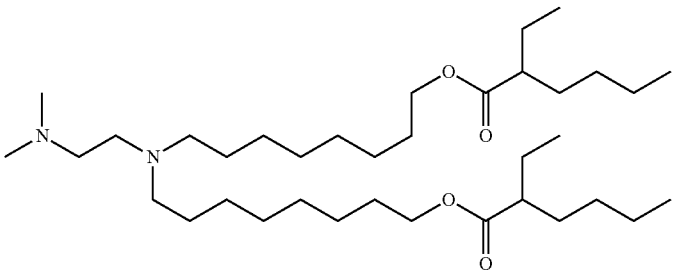 [SMILES: CCCCC(CC)C(=O)OCCCCCCCCN(CCCCCCCCOC(=O)C(CC)CCCC)CCN(C)C] | — |
| I-2 | 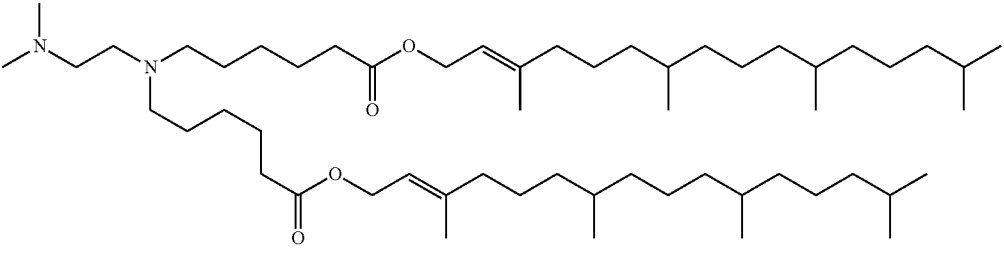 [SMILES: C/C(=C\COC(=O)CCCCCN(CCCCCC(=O)OC/C=C(\C)CCCC(C)CCCC(C)CCCC(C)C)CCN(C)C)CCCC(C)CCCC(C)CCCC(C)C] | 5.64 |
| I-3 | 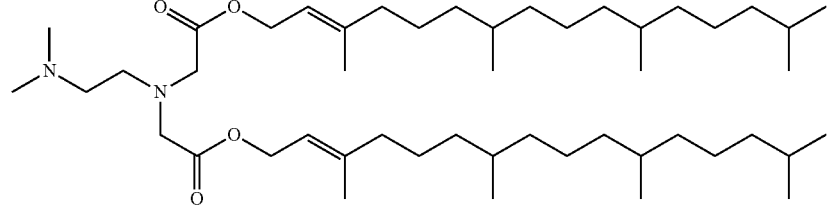 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | 7.15 |
| I-4 | 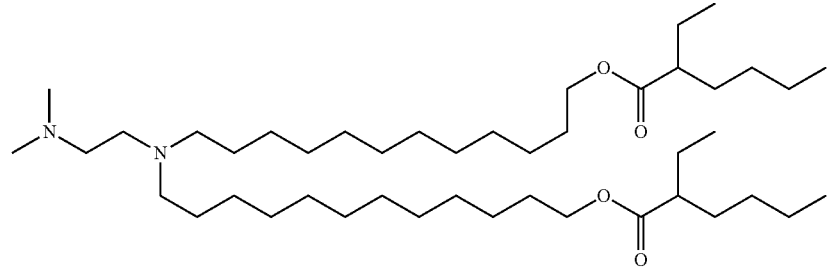 [SMILES: CCCCC(CC)C(=O)OCCCCCCCCCCCCN(CCCCCCCCCCCCOC(=O)C(CC)CCCC)CCN(C)C] | 6.43 |
| I-5 | 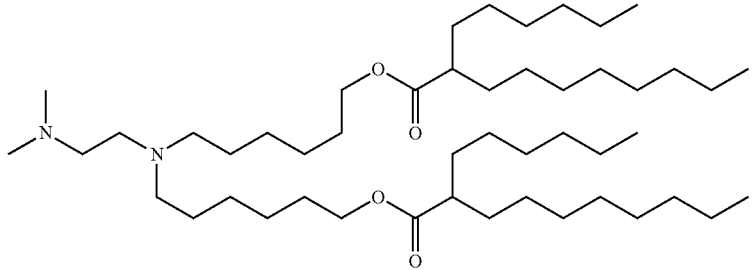 [SMILES: CCCCCCCCC(CCCCCC)C(=O)OCCCCCCN(CCCCCCOC(=O)C(CCCCCC)CCCCCCCC)CCN(C)C] | 6.28 |

TABLE 1-continued

Representative Lipids of Formula I

| No. | Structure | pKa |
|-----|-----------|-----|
| I-6 | 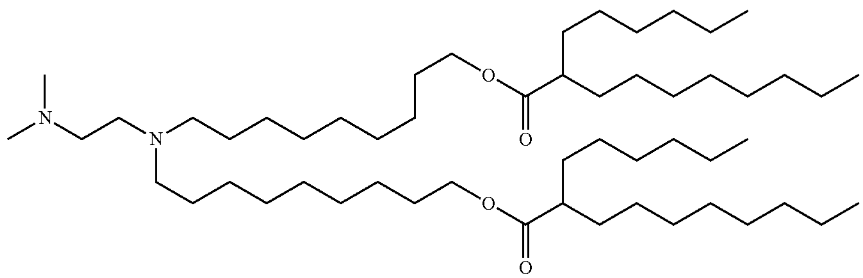 [SMILES: CCCCCCCCC(CCCCCC)C(=O)OCCCCCCCCCN(CCCCCCCCCOC(=O)C(CCCCCC)CCCCCCCC)CCN(C)C] | 6.12 |
| I-7 | 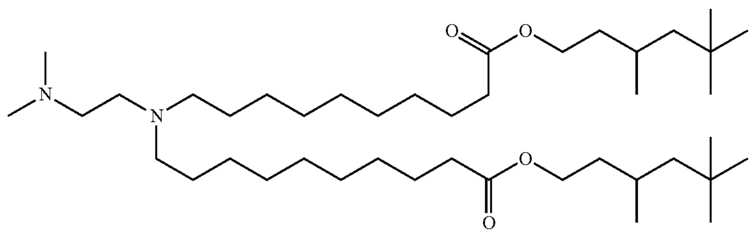 [SMILES: CC(CCOC(=O)CCCCCCCCCN(CCCCCCCCCC(=O)OCCC(C)CC(C)(C)C)CCN(C)C)CC(C)(C)C] | — |
| I-8 | 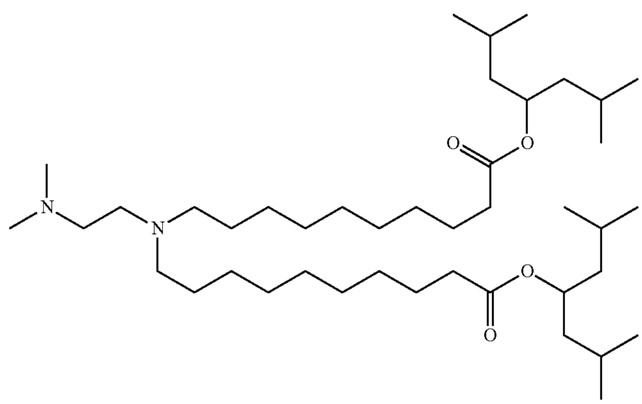 [SMILES: CC(C)CC(CC(C)C)OC(=O)CCCCCCCCCN(CCCCCCCCCC(=O)OC(CC(C)C)CC(C)C)CCN(C)C] | — |
| I-9 | 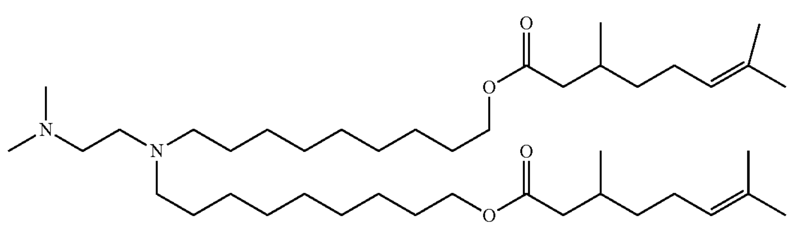 [SMILES: CC(C)=CCCC(C)CC(=O)OCCCCCCCCCN(CCCCCCCCCOC(=O)CC(C)CCC=C(C)C)CCN(C)C] | — |
| I-10 | 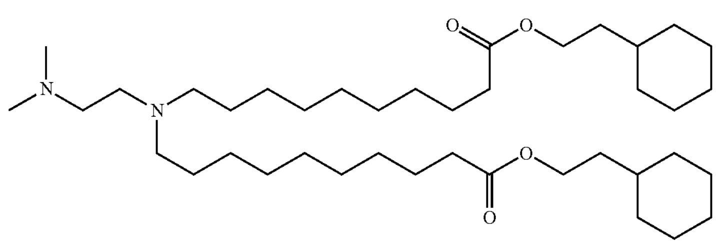 [SMILES: CN(C)CCN(CCCCCCCCCC(=O)OCCC1CCCCC1)CCCCCCCCCC(=O)OCCC1CCCCC1] | — |

TABLE 1-continued

Representative Lipids of Formula I

| No. | Structure | pKa |
|---|---|---|
| I-11 | 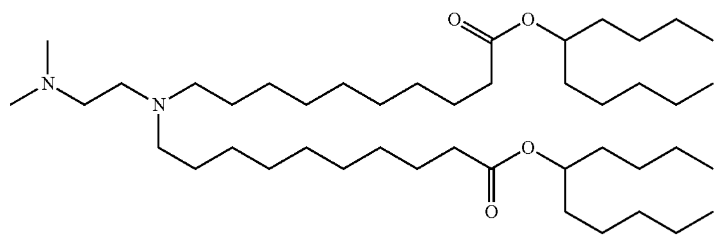 [SMILES: CCCCCC(CCCC)OC(=O)CCCCCCCCCN(CCCCCCCCCC(=O)OC(CCCC)CCCCC)CCN(C)C] | 6.36 |
| I-12 | 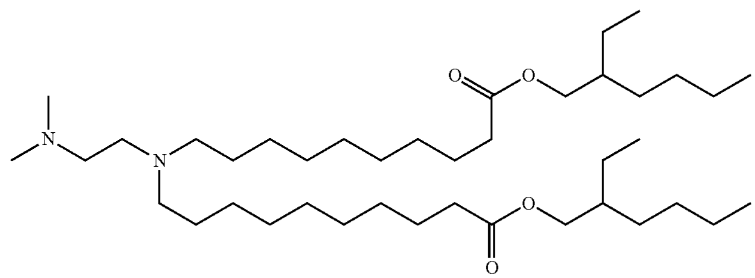 [SMILES: CCCCC(CC)COC(=O)CCCCCCCCCN(CCCCCCCCCC(=O)OCC(CC)CCCC)CCN(C)C] | — |
| I-13 | 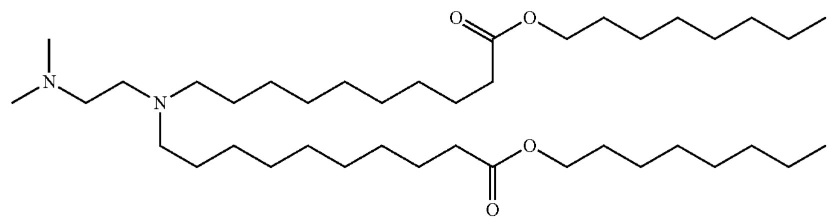 [SMILES: CCCCCCCCOC(=O)CCCCCCCCCN(CCCCCCCCCC(=O)OCCCCCCCC)CCN(C)C] | 6.51 |
| I-14 | 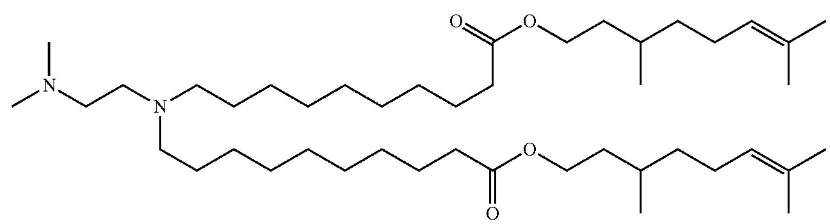 [SMILES: CC(C)=CCCC(C)CCOC(=O)CCCCCCCCCN(CCCCCCCCCC(=O)OCCC(C)CCC=C(C)C)CCN(C)C] | — |
| I-15 | 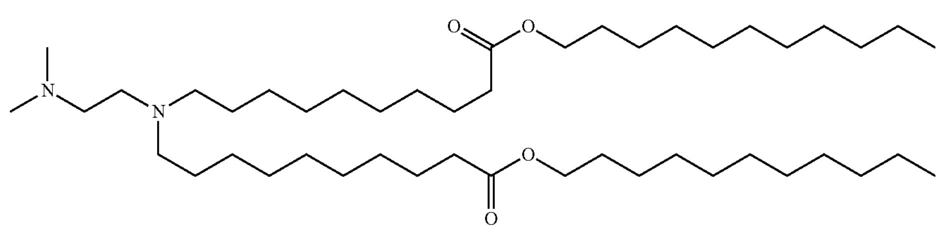 [SMILES: CCCCCCCCCCCOC(=O)CCCCCCCCCN(CCCCCCCCCC(=O)OCCCCCCCCCCC)CCN(C)C] | 6.30 |
| I-16 | 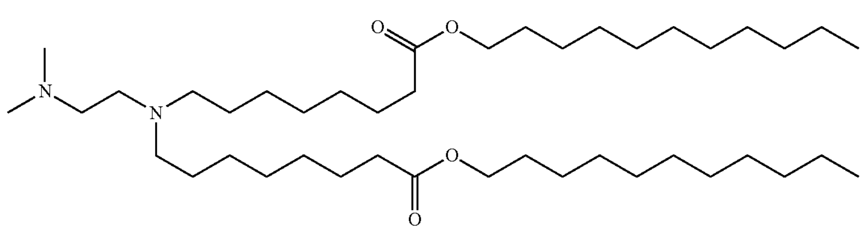 [SMILES: CCCCCCCCCCCOC(=O)CCCCCCCN(CCCCCCCC(=O)OCCCCCCCCCCC)CCN(C)C] | 6.63 |

TABLE 1-continued

Representative Lipids of Formula I

| No. | Structure | pKa |
|---|---|---|
| I-17 | 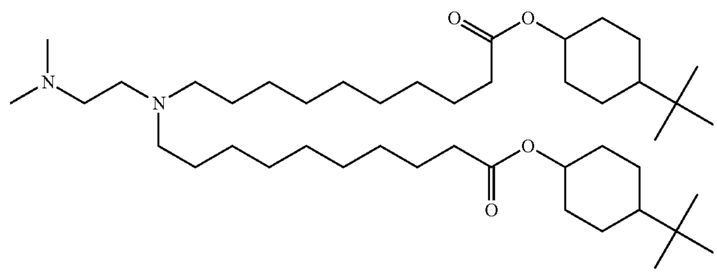 [SMILES: CN(C)CCN(CCCCCCCCCC(=O)OC1CCC(C(C)(C)C)CC1)CCCCCCCCCC(=O)OC1CCC(C(C)(C)C)CC1] | — |
| I-18 | 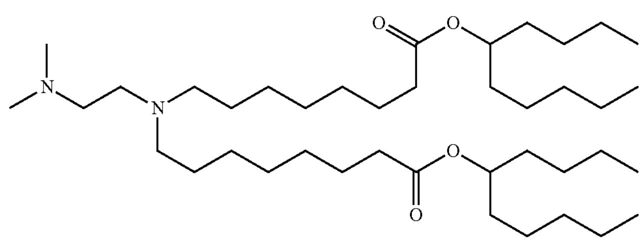 [SMILES: CCCCCC(CCCC)OC(=O)CCCCCCCN(CCCCCCCC(=O)OC(CCCC)CCCCC)CCN(C)C] | — |
| I-19 | 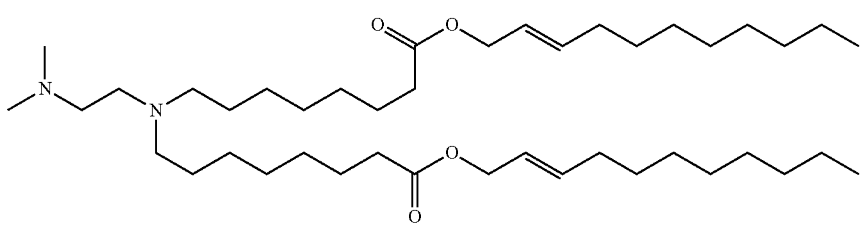 [SMILES: CCCCCCCC/C=C/COC(=O)CCCCCCCN(CCCCCCCC(=O)OC/C=C/CCCCCCCC)CCN(C)C] | 6.72 |
| I-20 | 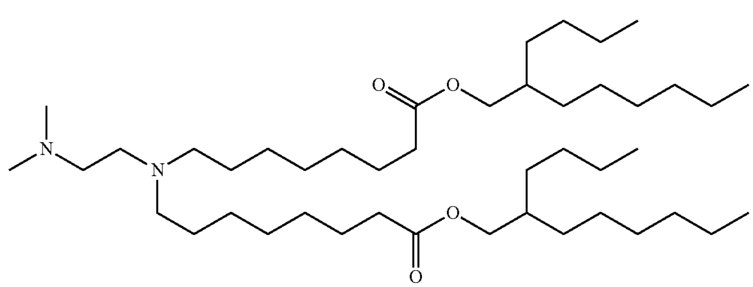 [SMILES: CCCCCCC(CCCC)COC(=O)CCCCCCCN(CCCCCCCC(=O)OCC(CCCC)CCCCCC)CCN(C)C] | 6.44 |
| I-21 | 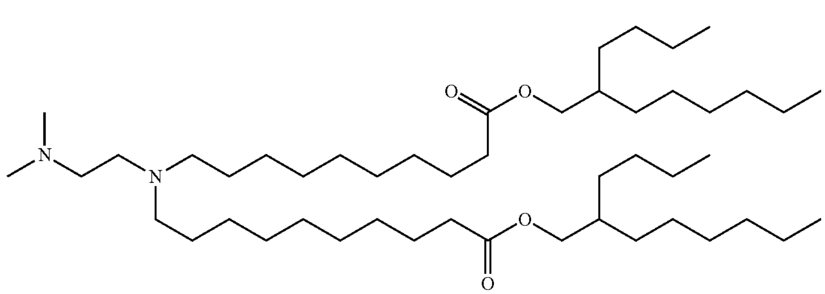 [SMILES: CCCCCCC(CCCC)COC(=O)CCCCCCCCCN(CCCCCCCCCC(=O)OCC(CCCC)CCCCCC)CCN(C)C] | 6.28 |

TABLE 1-continued
Representative Lipids of Formula I
| No. | Structure | pKa |
|---|---|---|
| I-22 | 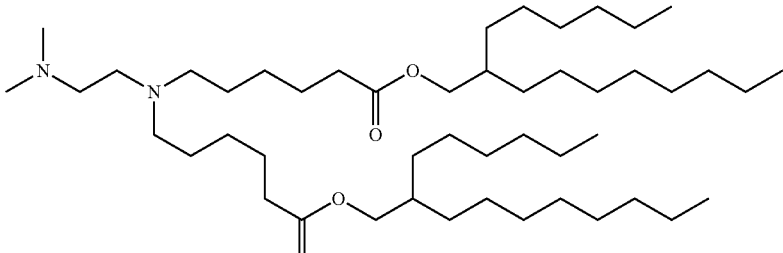 | 6.53 |
| I-23 | 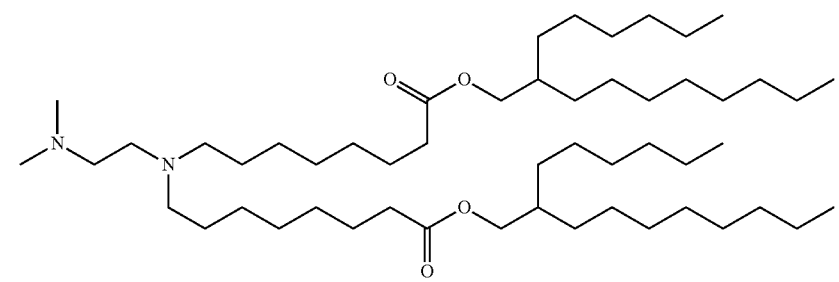 [SMILES: CCCCCCCCC(CCCCCC)COC(=O)CCCCCCCN(CCCCCCCC(=O)OCC(CCCCCC)CCCCCCCC)CCN(C)C] | 6.24 |
| I-24 | 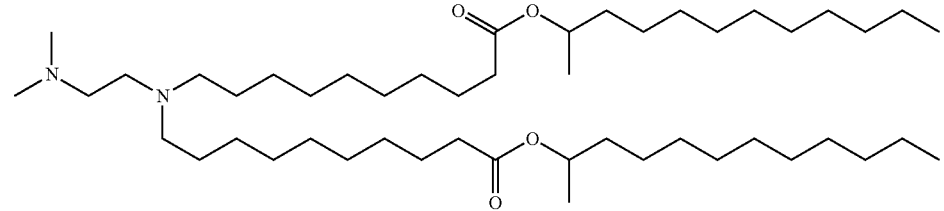 [SMILES: CCCCCCCCCCC(C)OC(=O)CCCCCCCCCN(CCCCCCCCCC(=O)OC(C)CCCCCCCCCC)CCN(C)C] | 6.28 |
| I-25 | 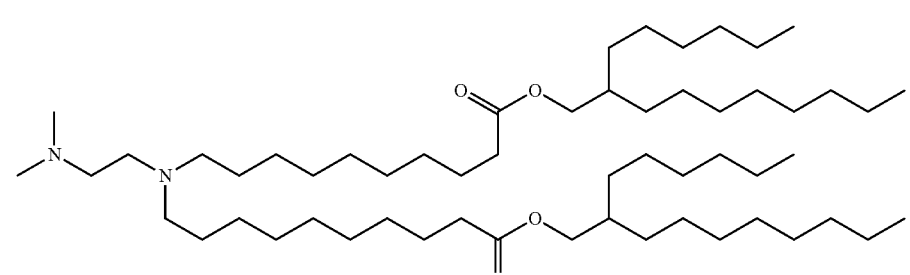 | 6.20 |
| I-26 | 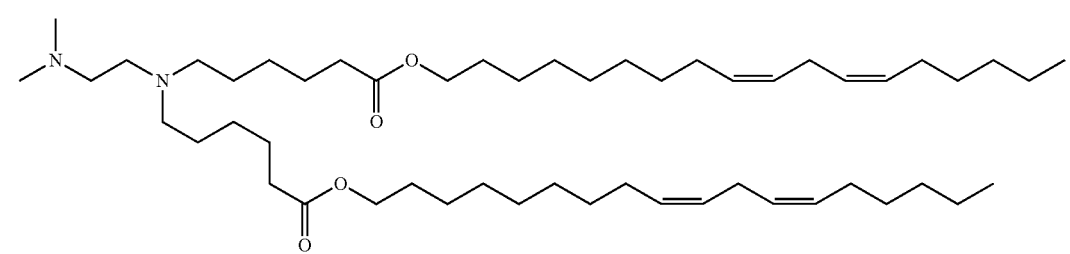 [SMILES: CCCCC/C=C\C/C=C\CCCCCCCCOC(=O)CCCCCN(CCCCCC(=O)OCCCCCCCC/C=C\C/C=C\CCCCC)CCN(C)C] | 6.89 |

TABLE 1-continued

Representative Lipids of Formula I

| No. | Structure | pKa |
|---|---|---|
| I-27 | 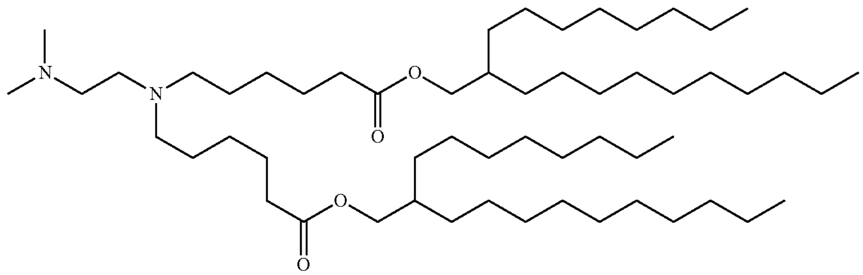 [SMILES: CCCCCCCCCCC(CCCCCCCC)COC(=O)CCCCCN(CCCCCC(=O)OCC(CCCCCCCC)CCCCCCCCCC)CCN(C)C] | 6.30 |
| I-28 | 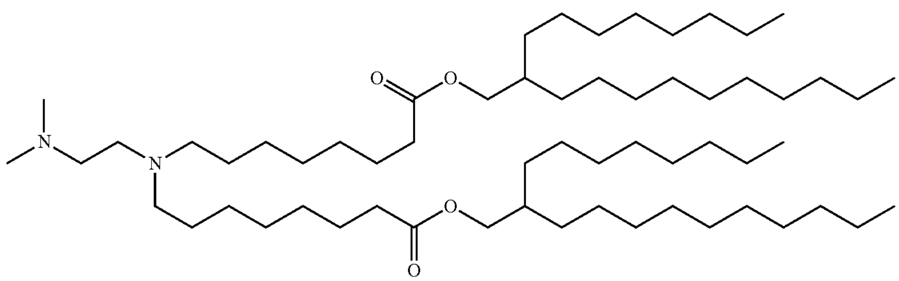 [SMILES: CCCCCCCCCCC(CCCCCCCC)COC(=O)CCCCCCCN(CCCCCCCC(=O)OCC(CCCCCCCC)CCCCCCCCCC)CCN(C)C] | 6.20 |
| I-29 | 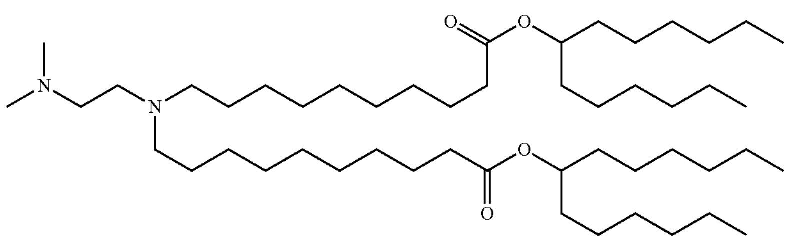 [SMILES: CCCCCCC(CCCCCC)OC(=O)CCCCCCCCCN(CCCCCCCCCC(=O)OC(CCCCCC)CCCCCC)CCN(C)C] | 6.22 |
| I-30 | 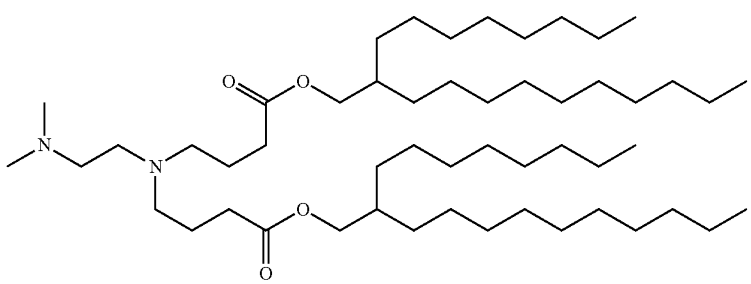 [SMILES: CCCCCCCCCCC(CCCCCCCC)COC(=O)CCCN(CCCC(=O)OCC(CCCCCCCC)CCCCCCCCCC)CCN(C)C] | — |
| I-31 | 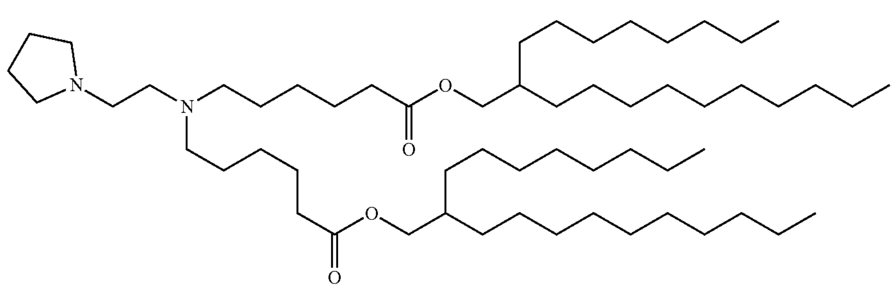 [SMILES: CCCCCCCCCCC(CCCCCCCC)COC(=O)CCCCCN(CCCCCC(=O)OCC(CCCCCCCC)CCCCCCCCCC)CCN1CCCC1] | 6.33 |

TABLE 1-continued
Representative Lipids of Formula I
| No. | Structure | pKa |
|---|---|---|
| I-32 | 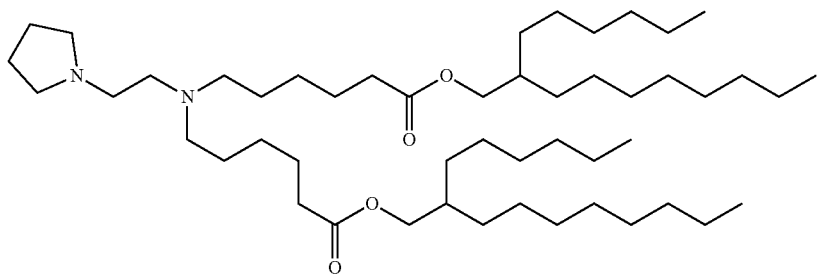 [SMILES: CCCCCCCCC(CCCCCC)COC(=O)CCCCCN(CCCCCC(=O)OCC(CCCCCC)CCCCCCCC)CCN1CCCC1] | 6.47 |
| I-33 | 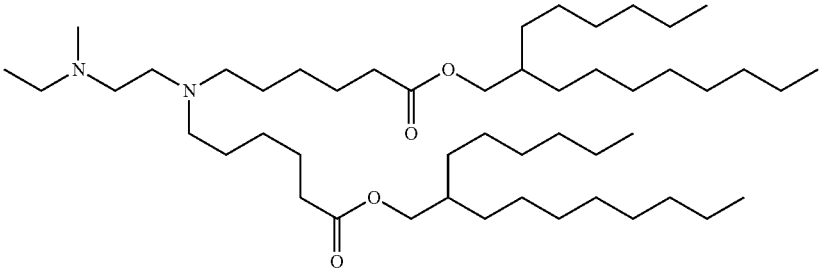 [SMILES: CCCCCCCCC(CCCCCC)COC(=O)CCCCCN(CCCCCC(=O)OCC(CCCCCC)CCCCCCCC)CCN(C)CC] | 6.27 |
| I-34 | 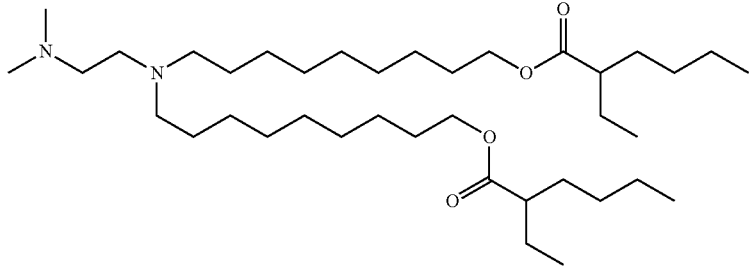 [SMILES: CCCCC(CC)C(=O)OCCCCCCCCCN(CCCCCCCCCOC(=O)C(CC)CCCC)CCN(C)C] | — |
| I-35 | 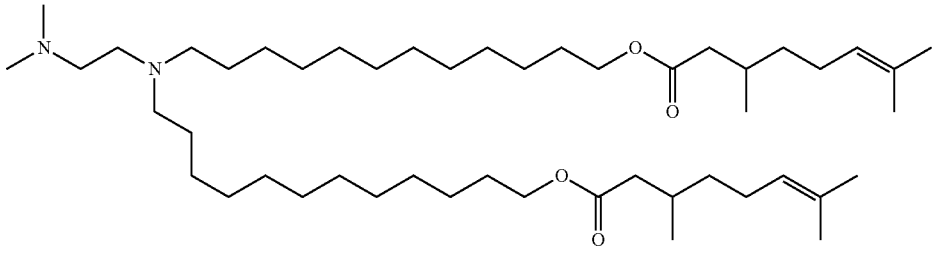 [SMILES: CC(C)=CCCC(C)CC(=O)OCCCCCCCCCCCCN(CCCCCCCCCCCCOC(=O)CC(C)CCC=C(C)C)CCN(C)C] | 6.21 |
| I-36 | 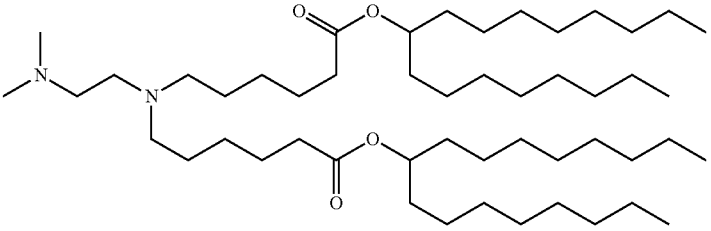 [SMILES: CCCCCCCCC(CCCCCCCC)OC(=O)CCCCCN(CCCCCC(=O)OC(CCCCCCCC)CCCCCCCC)CCN(C)C] | — |

TABLE 1-continued
Representative Lipids of Formula I
| No. | Structure | pKa |
|---|---|---|
| I-37 | 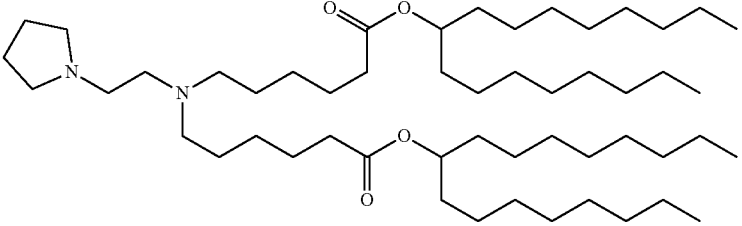 [SMILES: CCCCCCCCC(CCCCCCCC)OC(=O)CCCCCN(CCCCCC(=O)OC(CCCCCCCC)CCCCCCCC)CCN1CCCC1] | — |
| I-38 | 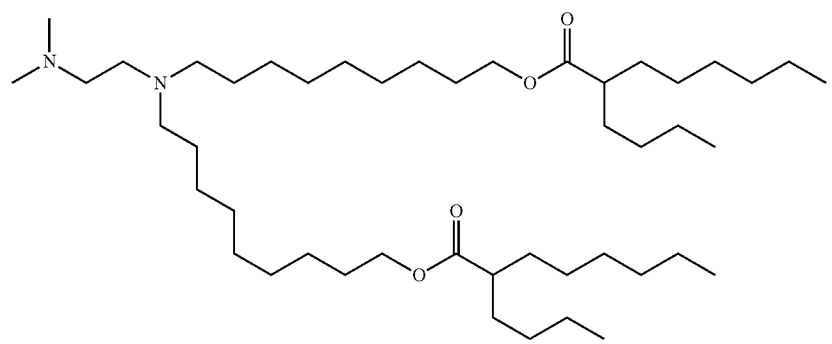 [SMILES: CCCCCCC(CCCC)C(=O)OCCCCCCCCCN(CCCCCCCCCOC(=O)C(CCCC)CCCCCC)CCN(C)C] | 6.24 |
| I-39 | 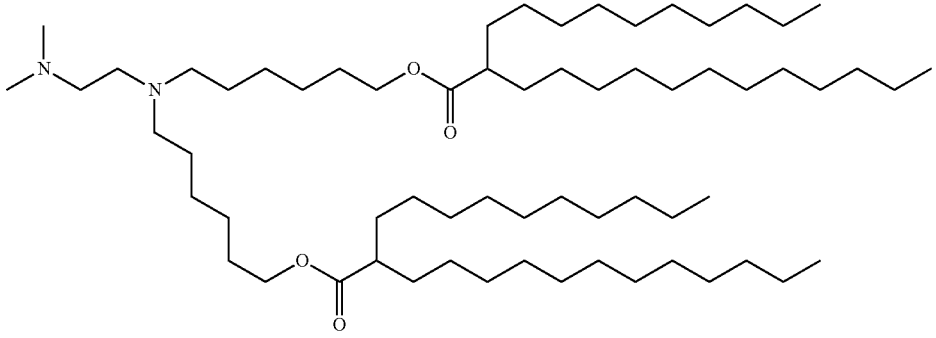 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] | 5.82 |
| I-40 | 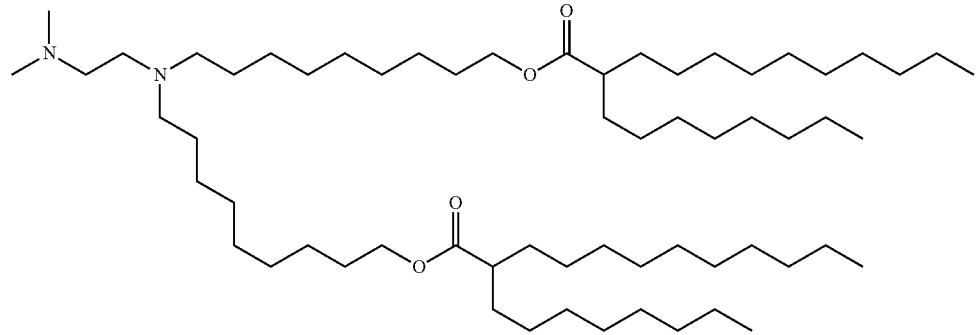 [SMILES: CCCCCCCCCCC(CCCCCCCC)C(=O)OCCCCCCCCCN(CCCCCCCCCOC(=O)C(CCCCCCCC)CCCCCCCCCC)CCN(C)C] | 6.38 |

TABLE 1-continued

Representative Lipids of Formula I

| No. | Structure | pKa |
|---|---|---|
| I-41 | 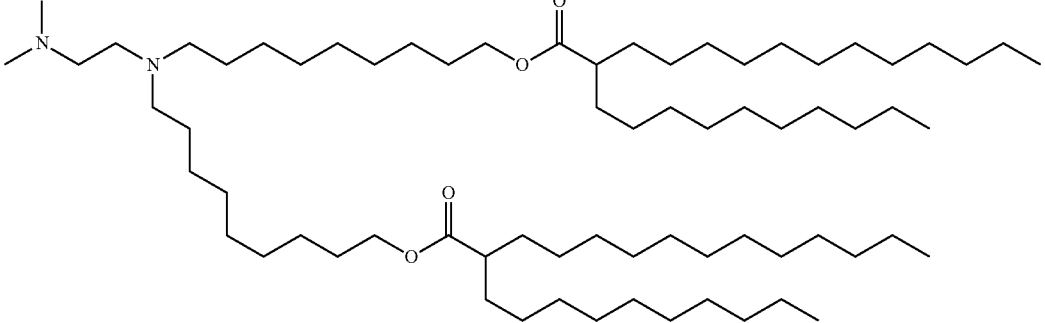 | 5.91 |

Compounds of Formula (I) can be prepared and tested according to the procedures set forth in PCT Pub. No. WO 2015/199952, the full disclosure of which is incorporated by reference in its entirety.

Cationic Lipids of Formula II

In some embodiments, the cationic lipid has a structure of Formula II:

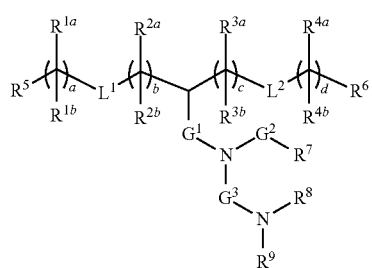  II or a pharmaceutically acceptable salt, tautomer or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either:
(a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either:
(a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either:
(a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either:
(a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C=O)—, —(C=O)O— or a direct bond. In other embodiments, $G^1$ and $G^2$ are each independently —(C=O)— or a direct bond. In some different embodiments, $L^1$ and $L^2$ are each independently —O(C=O)—, —(C=O)O— or a direct bond; and $G^1$ and $G^2$ are each independently —(C=O)— or a direct bond.

In some different embodiments of Formula (II), $L^1$ and $L^2$ are each independently —C(=O)—, —O—, —S(O)$_x$—, —S—S—, —C(=O)S—, —SC(=O)—, —NR$^a$—, —NR$^a$C(=O)—, —C(=O)NR$^a$—, —NR$^a$C(=O)NR$^a$, —OC(=O)NR$^a$—, —NR$^a$C(=O)O—, —NR$^a$S(O)$_x$NR$^a$—, —NR$^a$S(O)$_x$— or —S(O)$_x$NR$^a$—.

In other of the foregoing embodiments of Formula (II), the lipid compound has one of the following Formulae (IIA) or (IIB):

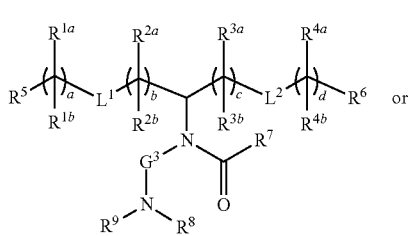

(IIA)

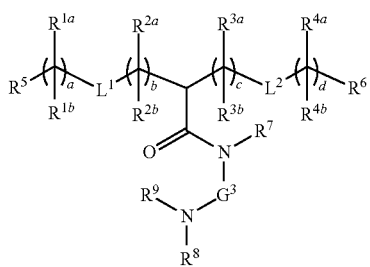

(IIB)

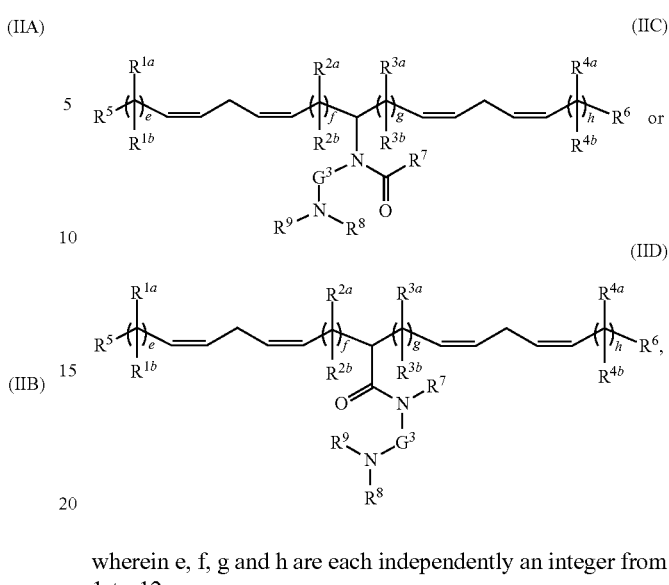

In some embodiments of Formula (II), the lipid compound has Formula (IIA). In other embodiments, the lipid compound has Formula (IIB).

In any of the foregoing embodiments of Formula (II), one of $L^1$ or $L^2$ is —O(C=O)—. For example, in some embodiments each of $L^1$ and $L^2$ are —O(C=O)—.

In some different embodiments of Formula (II), one of $L^1$ or $L^2$ is —(C=O)O—. For example, in some embodiments each of $L^1$ and $L^2$ is —(C=O)O—.

In different embodiments of Formula (II), one of $L^1$ or $L^2$ is a direct bond. As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following Formulae (IIC) or (IID):

wherein e, f, g and h are each independently an integer from 1 to 12.

In some embodiments of Formula (II), the lipid compound has Formula (IIC). In other embodiments, the lipid compound has Formula (IID).

In various embodiments of Formulae (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_{12}$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C═O)O$R^b$, —O(C═O)$R^b$, —C(═O)$R^b$, —O$R^b$, —S(O)$_x$$R^b$, —S—S$R^b$, —C(═O)S$R^b$, —SC(═O)$R^b$, —N$R^a$$R^b$, —N$R^a$C(═O)$R^b$, —C(═O)N$R^a$$R^b$, —N$R^a$C(═O)N$R^a$$R^b$, —OC(═O)N$R^a$$R^b$, —N$R^a$C(═O)O$R^b$, —N$R^a$S(O)$_x$N$R^a$$R^b$, —N$R^a$S(O)$_x$$R^b$ or —S(O)$_x$N$R^a$$R^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C═O)O$R^b$ or —O(C═O)$R^b$.

In some of the foregoing embodiments of Formula (II), $R^b$ is branched $C_1$-$C_{16}$ alkyl. For example, in some embodiments $R^b$ has one of the following structures:

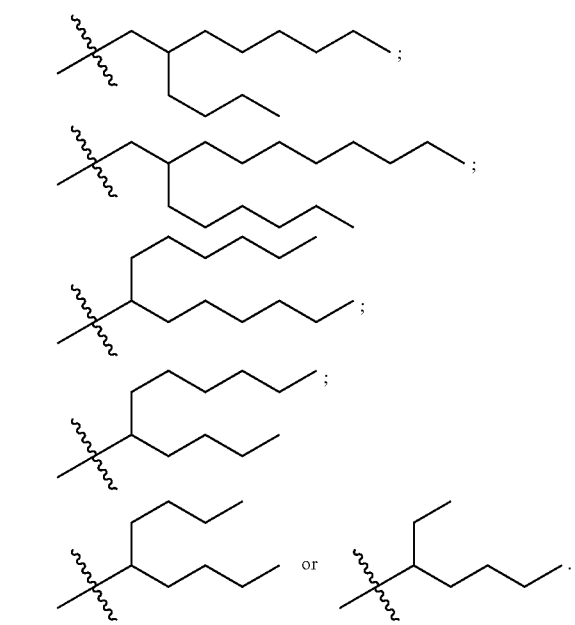

In certain other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In still other embodiments of the foregoing lipids of Formula (II), $G^3$ is $C_2$-$C_4$ alkylene, for example $C_3$ alkylene. In various different embodiments, the lipid compound has one of the structures set forth in Table 2 below:

TABLE 2
| | Representative Lipids of Formula (II) | |
|---|---|---|
| No. | Structure | pKa |
| II-1 | 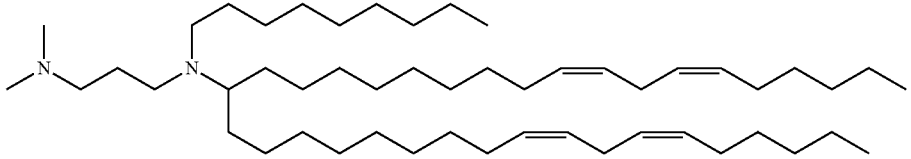 [SMILES: CCCCC/C=C\C/C=C\CCCCCCCCC(CCCCCCCC/C=C\C/C=C\CCCCC)N(CCCCCCCCC)CCCN(C)C] | 5.64 |
| II-2 | 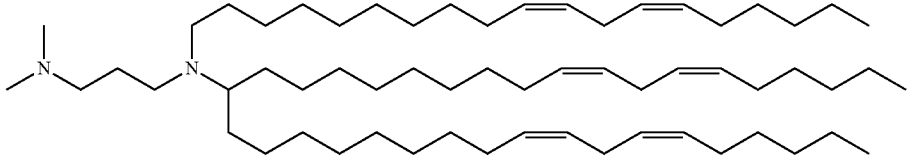 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | — |
| II-3 | 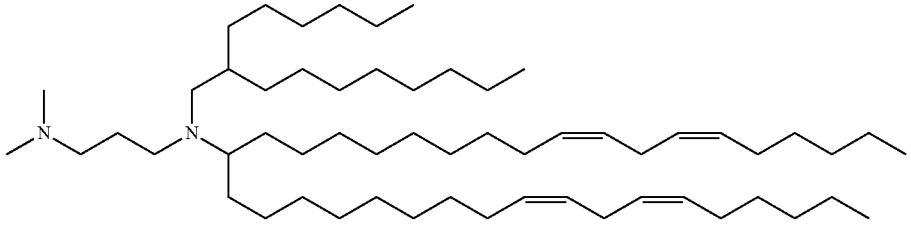 [SMILES: CCCCC/C=C\C/C=C\CCCCCCCCC(CCCCCCCC/C=C\C/C=C\CCCCC)N(CCCN(C)C)CC(CCCCCC)CCCCCCCC] | — |
| II-4 | 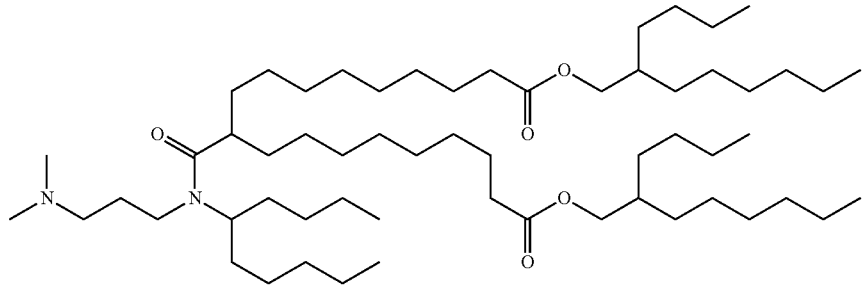 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | — |
| II-5 | 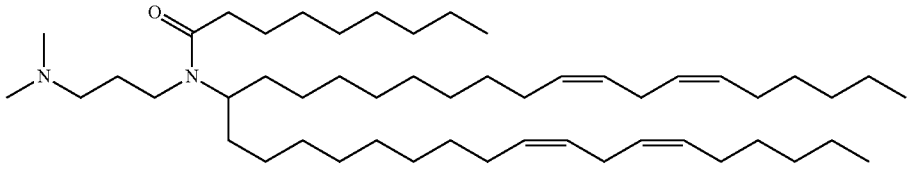 [SMILES: CCCCC/C=C\C/C=C\CCCCCCCCC(CCCCCCCC/C=C\C/C=C\CCCCC)N(CCCN(C)C)C(=O)CCCCCCCC] | 6.27 |
| II-6 | 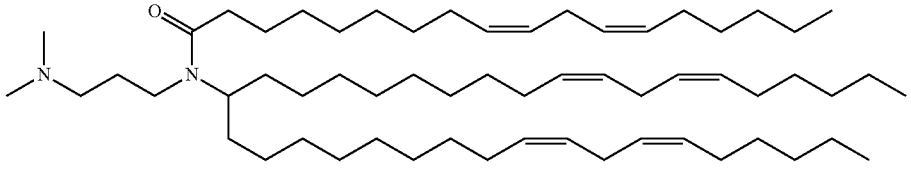 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | 6.14 |
| II-7 | 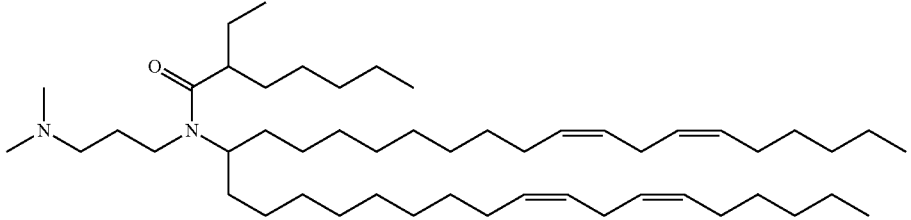 [SMILES: CCCCC/C=C\C/C=C\CCCCCCCCC(CCCCCCCC/C=C\C/C=C\CCCCC)N(CCCN(C)C)C(=O)C(CC)CCCCC] | 5.93 |

TABLE 2-continued

Representative Lipids of Formula (II)

| No. | Structure | pKa |
|---|---|---|
| II-8 | 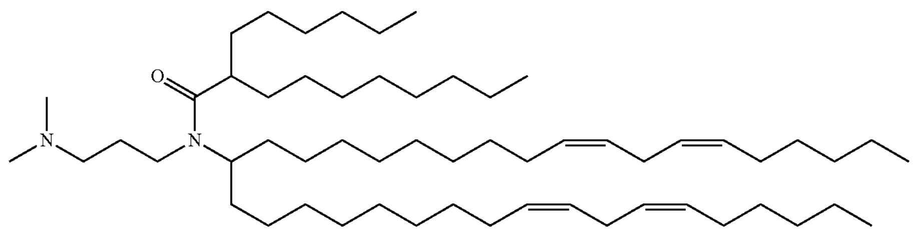 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | 5.35 |
| II-9 | 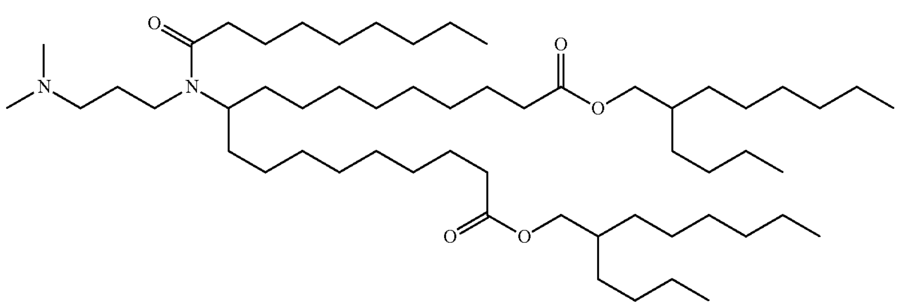 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | 6.27 |
| II-10 | 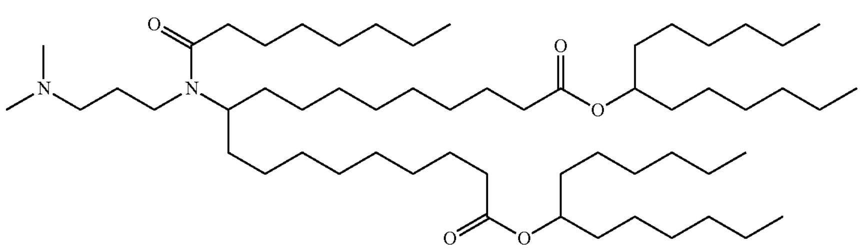 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | 6.16 |
| II-11 | 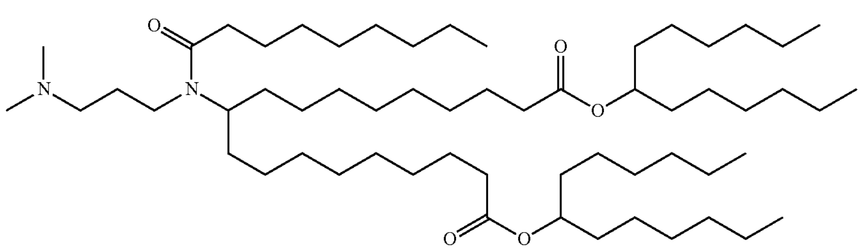 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | 6.13 |
| II-12 | 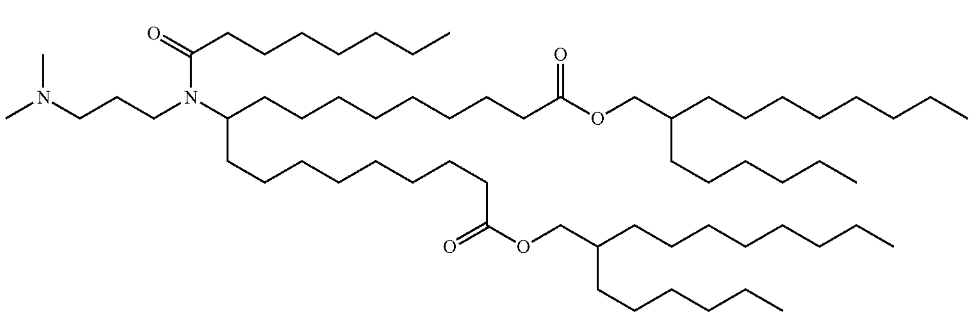 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | 6.21 |

TABLE 2-continued

Representative Lipids of Formula (II)

| No. | Structure | pKa |
|---|---|---|
| II-13 | 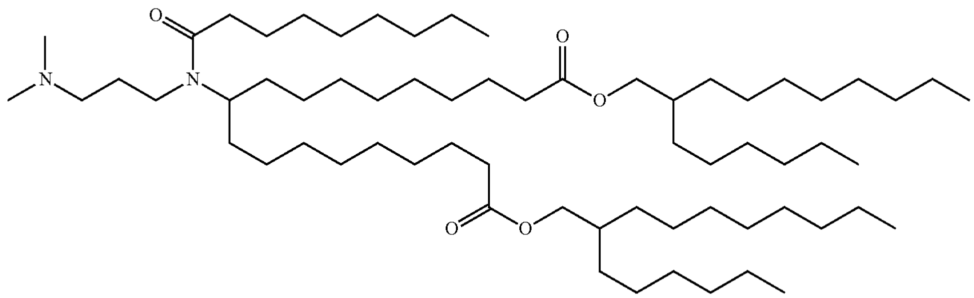 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] | 6.22 |
| II-14 | 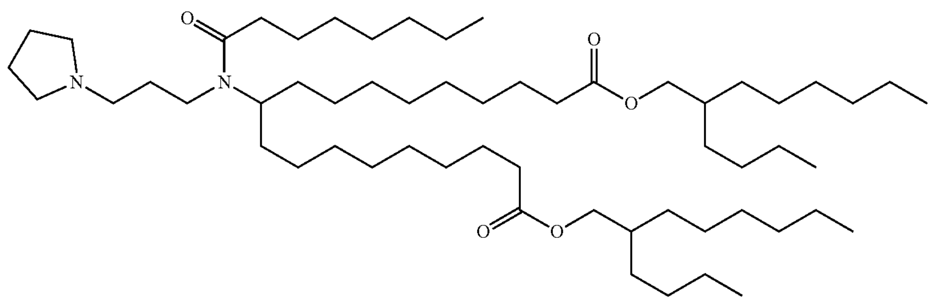 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC] | 6.33 |
| II-15 | 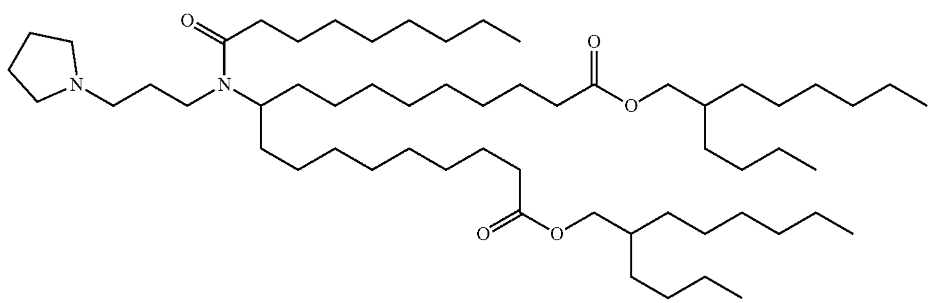 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC] | 6.32 |
| II-16 | 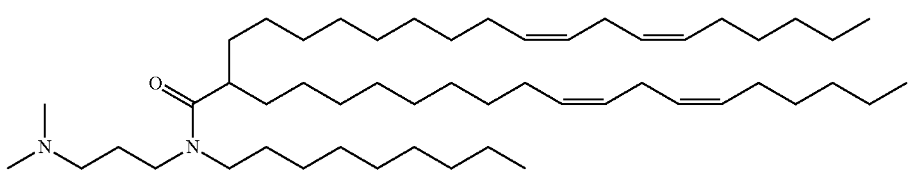 [SMILES: CCCCC/C=C\C/C=C\CCCCCCCCC(CCCCCCCC/C=C\C/C=C\CCCCC)C(=O)N(CCCCCCCCC)CCCN(C)C] | 6.37 |
| II-17 | 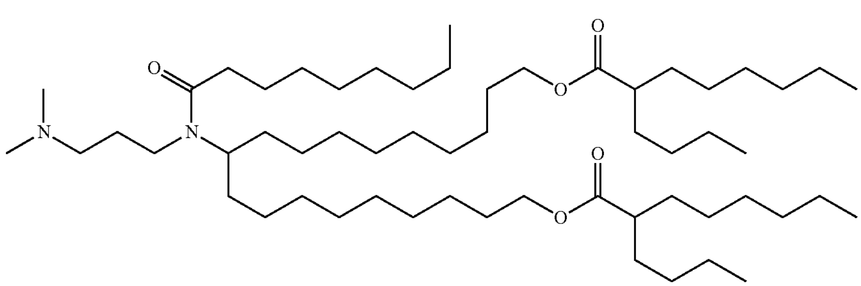 | 6.27 |

TABLE 2-continued

Representative Lipids of Formula (II)

| No. | Structure | pKa |
|---|---|---|
| II-18 | 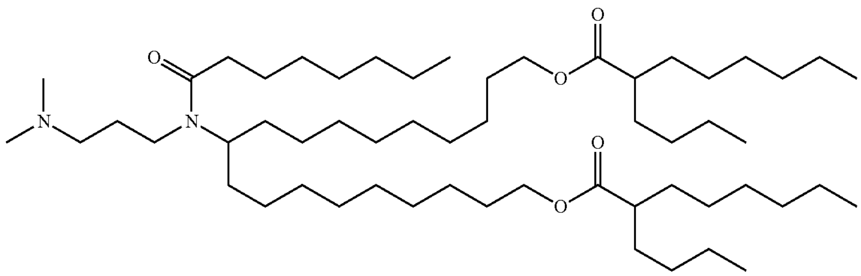 | — |
| II-19 | 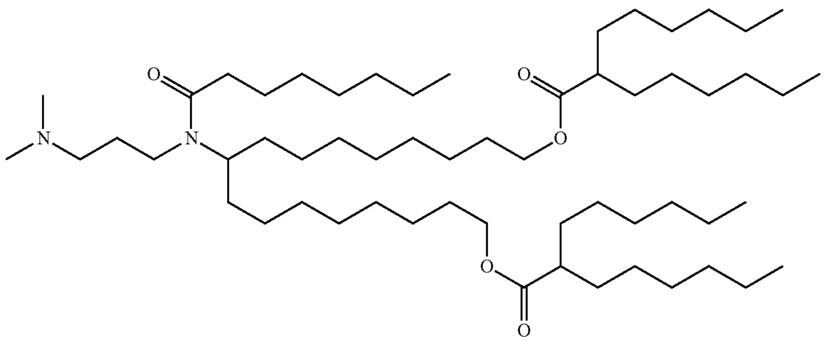 [SMILES: CCCCCCCC(=O)N(CCCN(C)C)C(CCCCCCCCOC(=O)C(CCCCCC)CCCCCC)CCCCCCCCOC(=O)C(CCCCCC)CCCCCC] | — |
| II-20 | 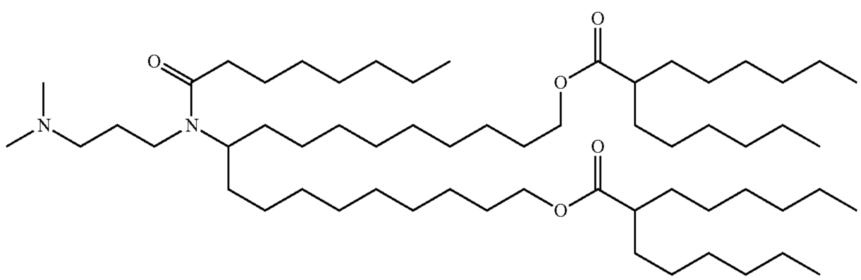 | — |
| II-21 | 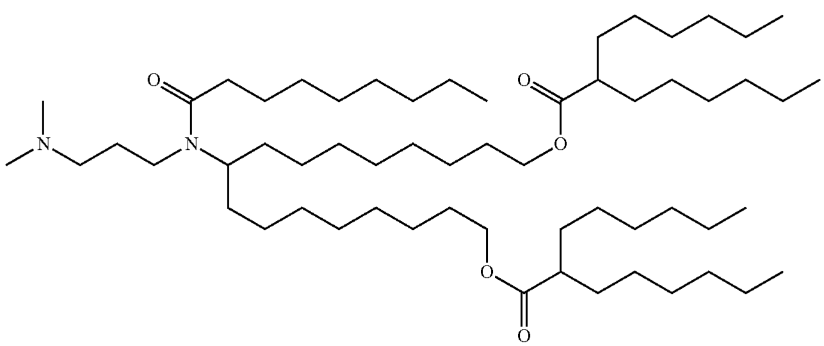 [SMILES: CCCCCCCCC(=O)N(CCCN(C)C)C(CCCCCCCCOC(=O)C(CCCCCC)CCCCCC)CCCCCCCCOC(=O)C(CCCCCC)CCCCCC] | — |
| II-22 | 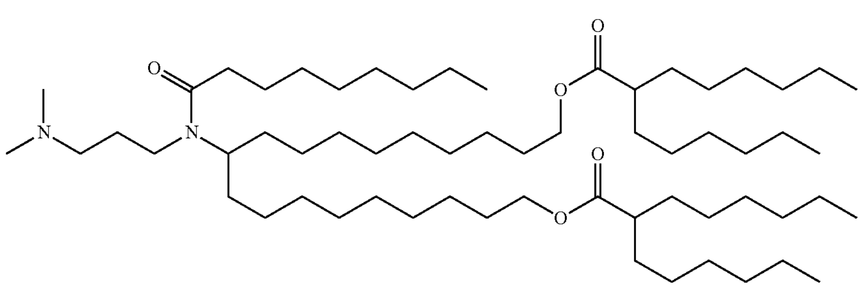 | — |

TABLE 2-continued

Representative Lipids of Formula (II)

| No. | Structure | pKa |
|---|---|---|
| II-23 | 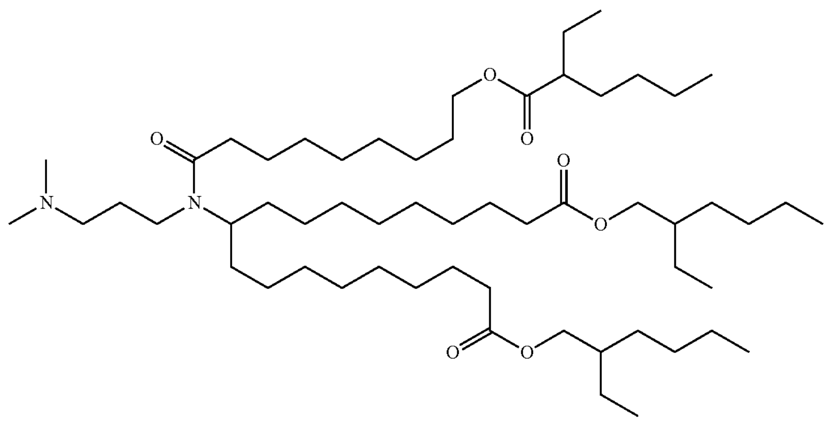 | — |
| II-24 | 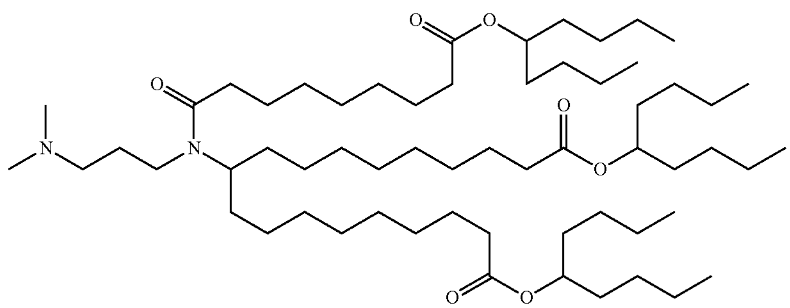 | 6.14 |
| II-25 | 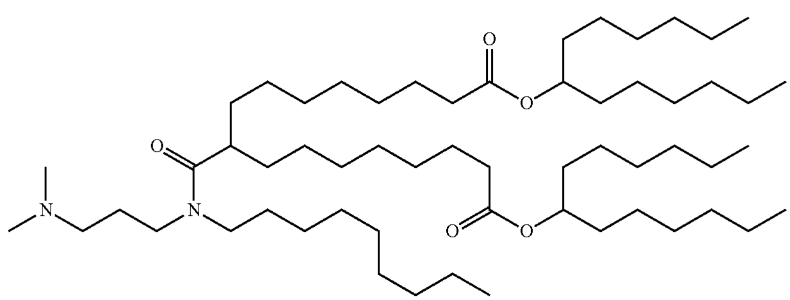 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | — |
| II-26 | 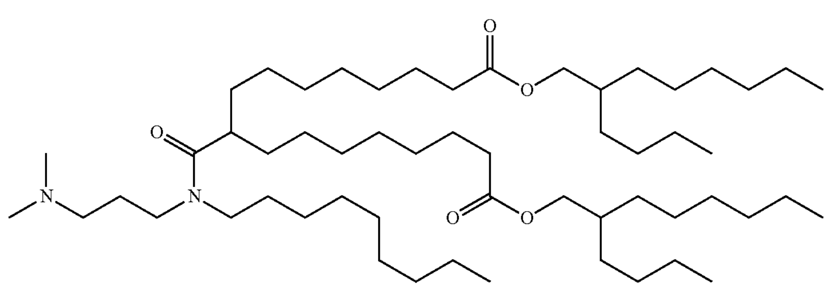 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | — |

TABLE 2-continued

Representative Lipids of Formula (II)

| No. | Structure | pKa |
|---|---|---|
| II-27 | 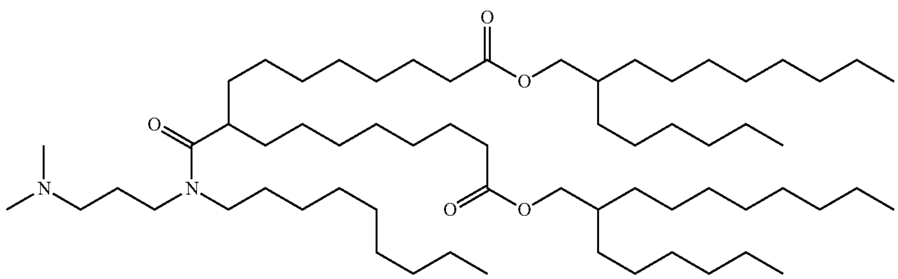 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | — |
| II-28 | 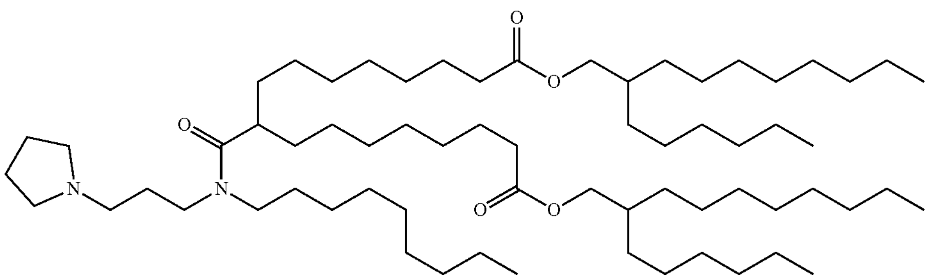 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | — |
| II-29 | 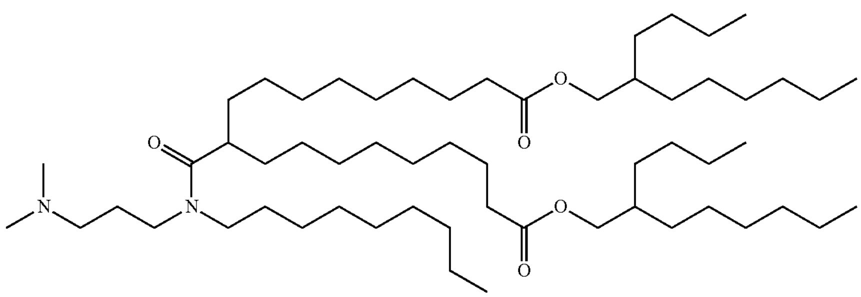 | — |
| II-30 | 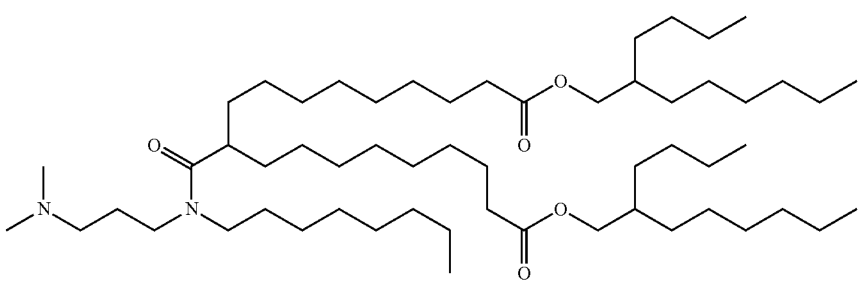 | — |
| II-31 | 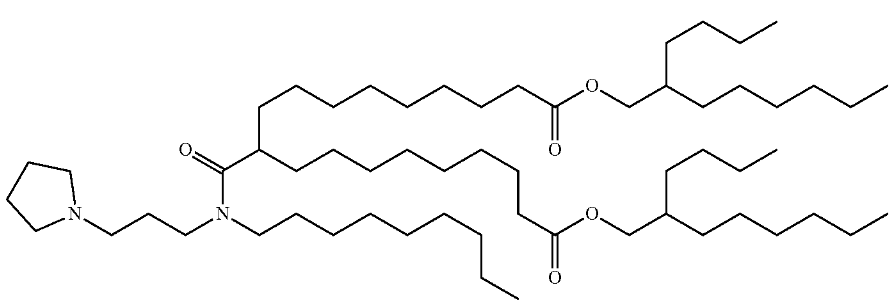 | — |

TABLE 2-continued
Representative Lipids of Formula (II)
| No. | Structure | pKa |
|---|---|---|
| II-32 | 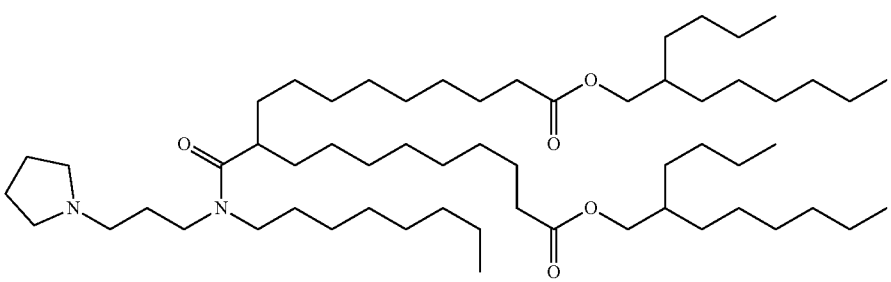 | — |
| II-33 | 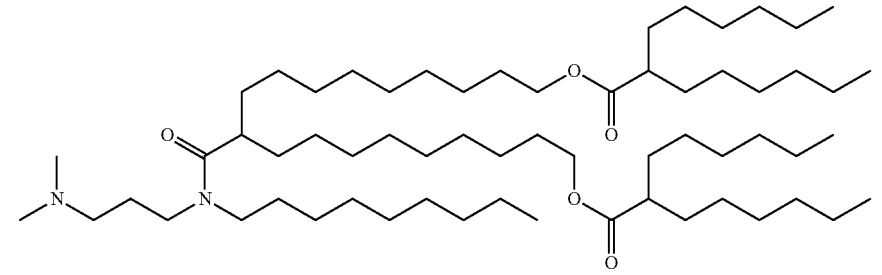 | — |
| II-34 | 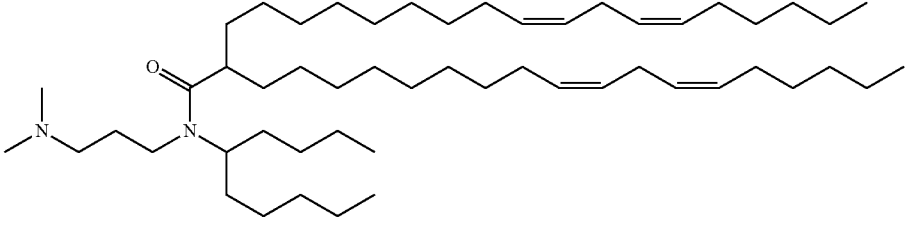 [SMILES: CCCCC/C=C\C/C=C\CCCCCCCCC(CCCCCCCC/C=C\C/C=C\CCCCC)C(=O)N(CCCN(C)C)C(CCCC)CCCCC] | — |
| II-35 | 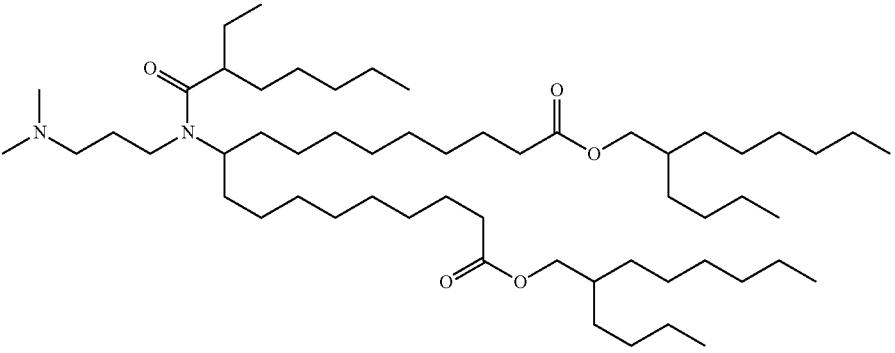 | 5.97 |
| II-36 | 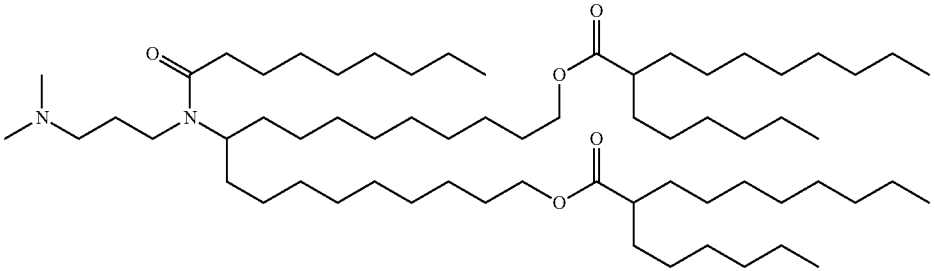 | 6.13 |

TABLE 2-continued

Representative Lipids of Formula (II)

| No. | Structure | pKa |
|---|---|---|
| II-37 | 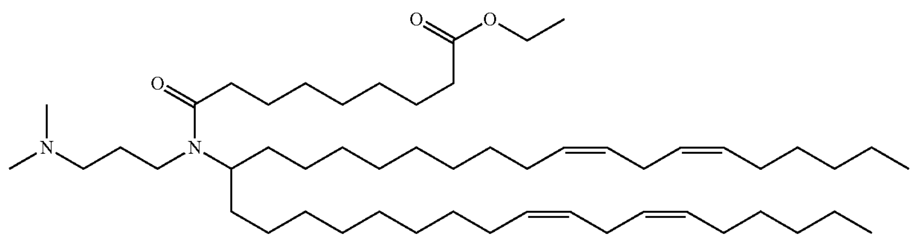 [SMILES: CCCCC/C=C\C/C=C\CCCCCCCCC(CCCCCCCC/C=C\C/C=C\CCCCC)N(CCCN(C)C)C(=O)CCCCCCCC(=O)OCC] | 5.61 |
| II-38 | 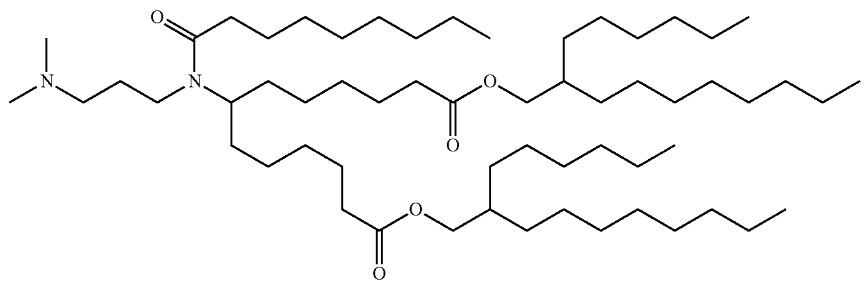 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC] | 6.45 |
| II-39 | 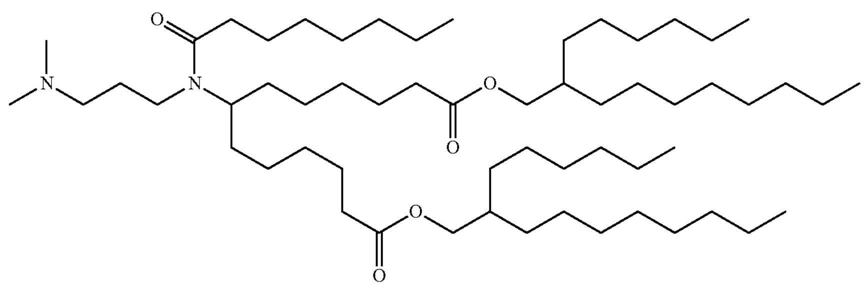 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC] | 6.45 |
| II-40 | 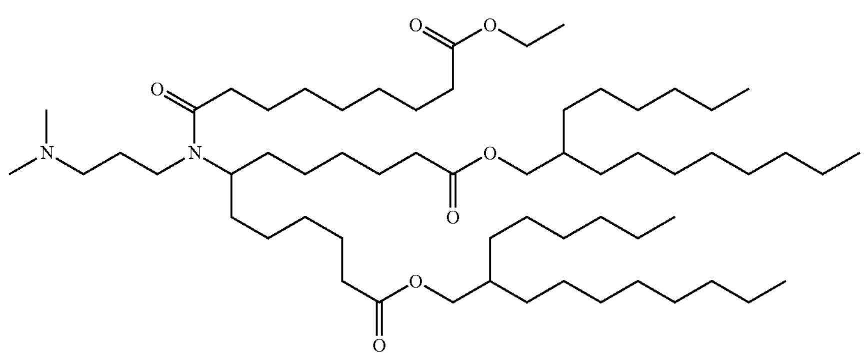 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC] | 6.57 |
| II-41 | 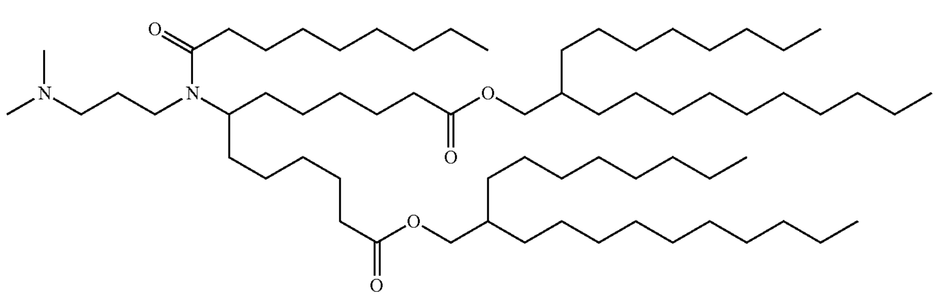 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC] | — |

TABLE 2-continued

Representative Lipids of Formula (II)

| No. | Structure | pKa |
|---|---|---|
| II-42 | 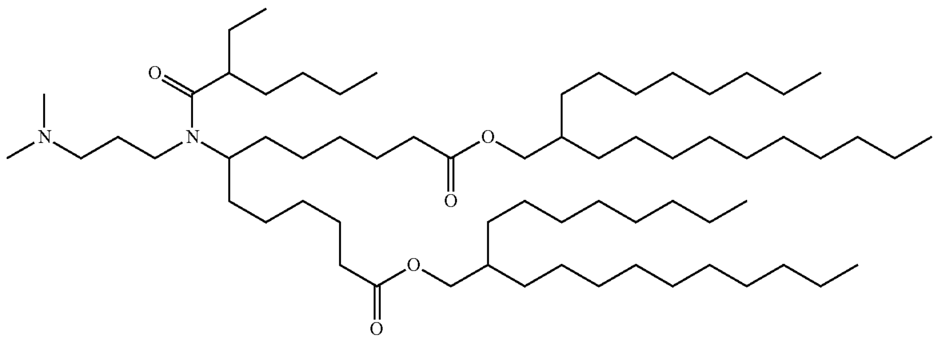 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)C(CC)CCCC] | — |
| II-43 | 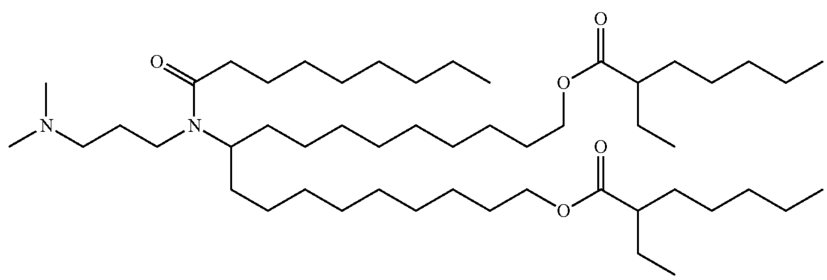 | — |
| II-44 | 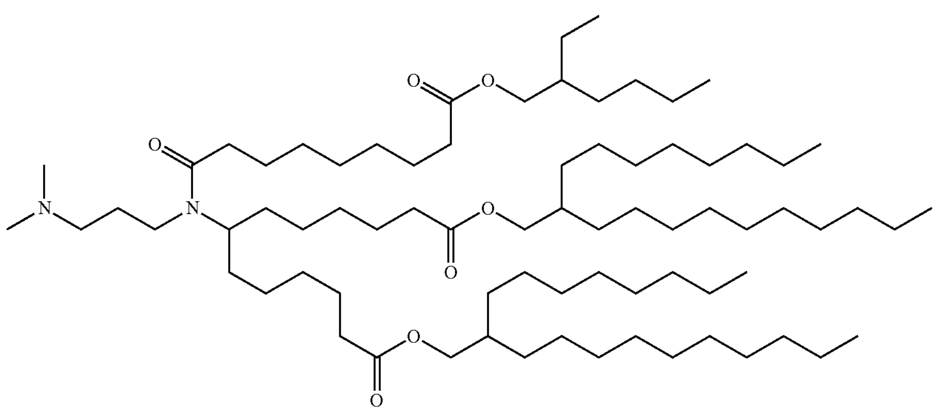 | — |
| II-45 | 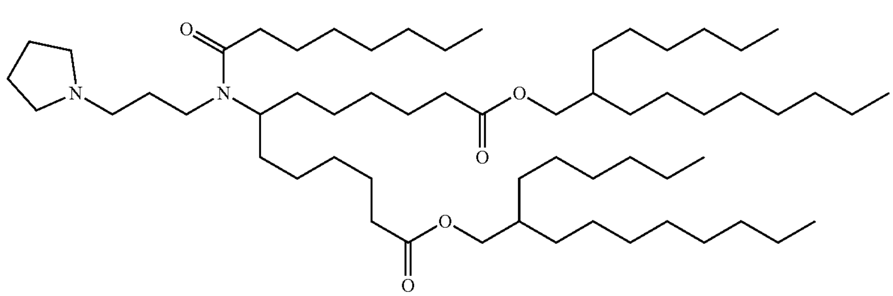 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | — |

TABLE 2-continued

Representative Lipids of Formula (II)

| No. | Structure | pKa |
|---|---|---|
| II-46 | 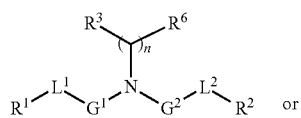 | — |

Compounds of Formula (II) can be prepared and tested according to the procedures set forth in PCT Pub. No. WO 2017/004143, the full disclosure of which is incorporated by reference in its entirety.

Cationic Lipids of Formula III

In some other embodiments, the cationic lipid has a structure of Formula III:

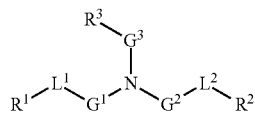
(III)

or a pharmaceutically acceptable salt or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, OR$^5$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the cationic lipid has one of the following Formulae (IIIA) or (IIIB):

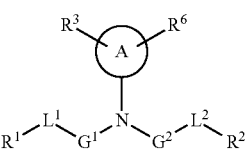
(IIIA)

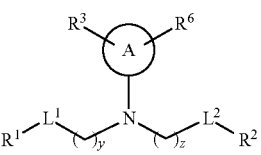
(IIIB)

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has Formula (IIIA), and in other embodiments, the lipid has Formula (IIIB).

In other embodiments of Formula (III), the lipid has one of the following Formulae (IIIC) or (IIID):

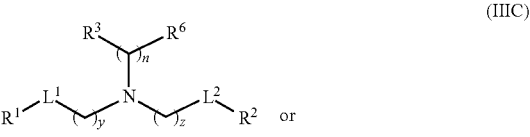

wherein y and z are each independently integers ranging from 1 to 12.

In any of the foregoing embodiments of Formula (III), one of $L^1$ or $L^2$ is —O(C=O)—. For example, in some embodiments each of $L^1$ and $L^2$ are —O(C=O)—. In some different embodiments of any of the foregoing, $L^1$ and $L^2$ are each independently —(C=O)O— or —O(C=O)—. For example, in some embodiments each of L and $L^2$ is —(C=O)O—.

In some different embodiments of Formula (III), the cationic lipid has one of the following Formulae (IIIE) or (IIIF):

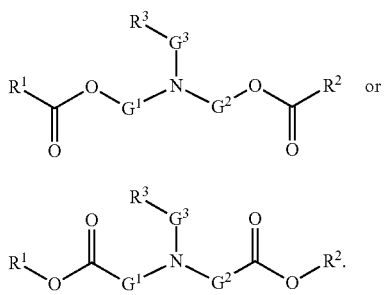

(IIIE)

(IIIF)

In some of the foregoing embodiments of Formula (III), the cationic lipid has one of the following Formulae (IIIG), (IIIH), (IIIJ), or (IIIK):

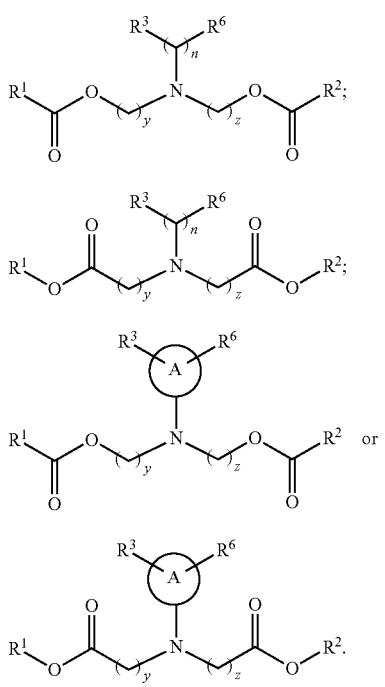

(IIIG)

(IIIH)

(IIIJ)

(IIIK)

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

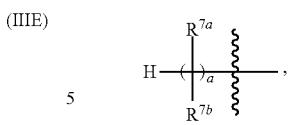

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

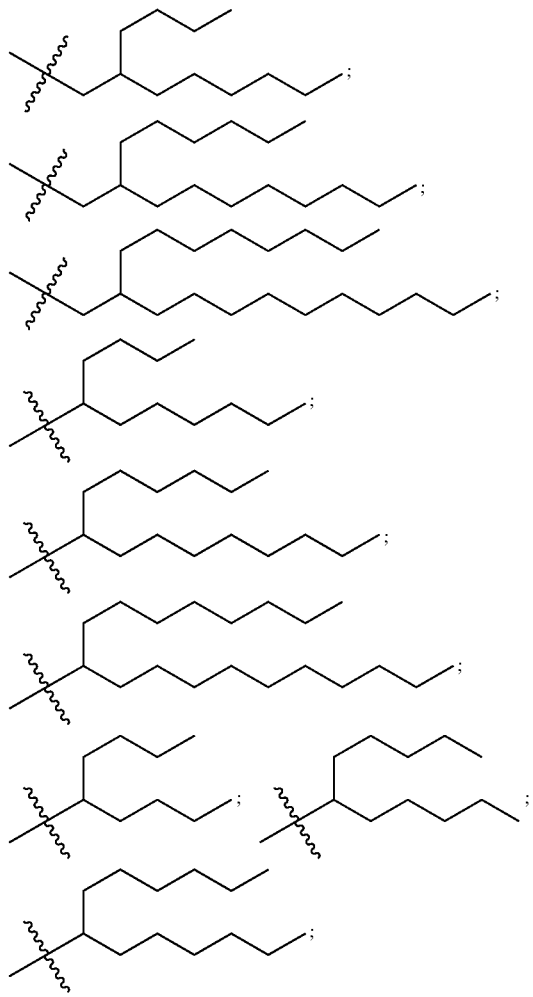

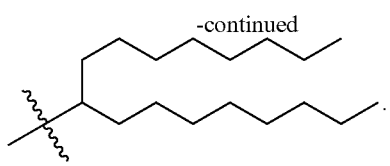

In some of the foregoing embodiments of Formula (III), $R^3$ is OH, CN, —C(=O)OR$^4$, —OC(=O)R$^4$ or —NHC(=O)R$^4$. In some embodiments, $R^4$ is methyl or ethyl.

In various different embodiments, a cationic lipid of any one of the disclosed embodiments of Formula (III) has one of the structures set forth in Table 3 below.

TABLE 3

Representative Compounds of Formula (III)

| No. | Structure | pKa |
|---|---|---|
| III-1 | 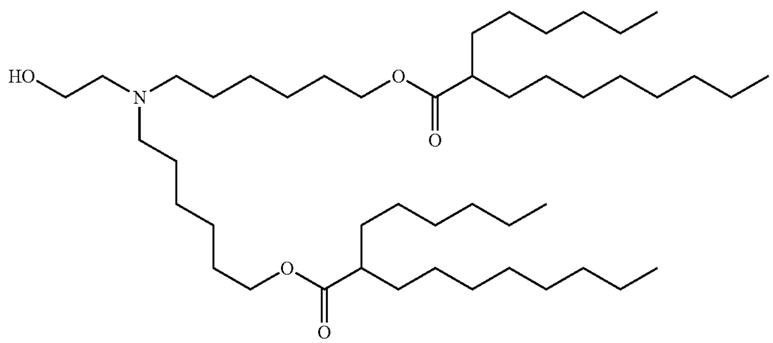 [SMILES: CCCCCCCCC(CCCCCC)C(=O)OCCCCCCN(CCO)CCCCCCOC(=O)C(CCCCCC)CCCCCCCC] | 5.89 |
| III-2 | 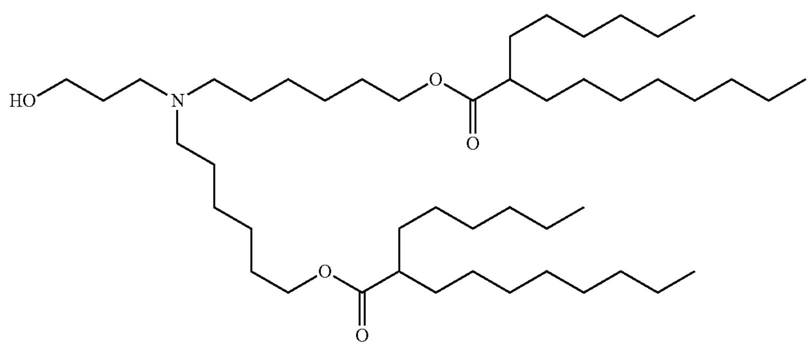 [SMILES: CCCCCCCCC(CCCCCC)C(=O)OCCCCCCN(CCCO)CCCCCCOC(=O)C(CCCCCC)CCCCCCCC] | 6.05 |
| III-3 | 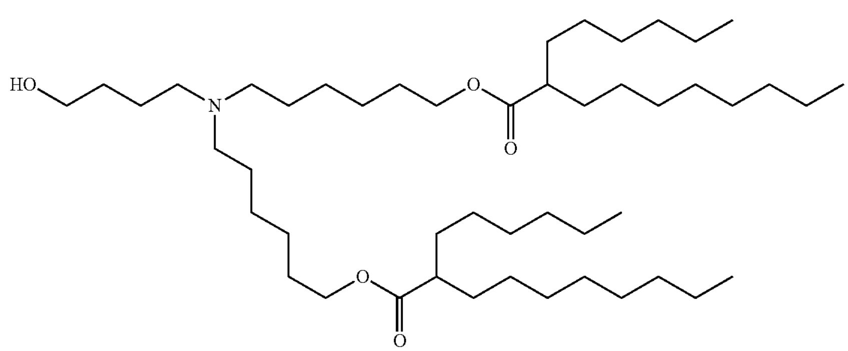 [SMILES: CCCCCCCCC(CCCCCC)C(=O)OCCCCCCN(CCCCO)CCCCCCOC(=O)C(CCCCCC)CCCCCCCC] | 6.09 |

TABLE 3-continued
Representative Compounds of Formula (III)
| No. | Structure | pKa |
|---|---|---|
| III-4 | 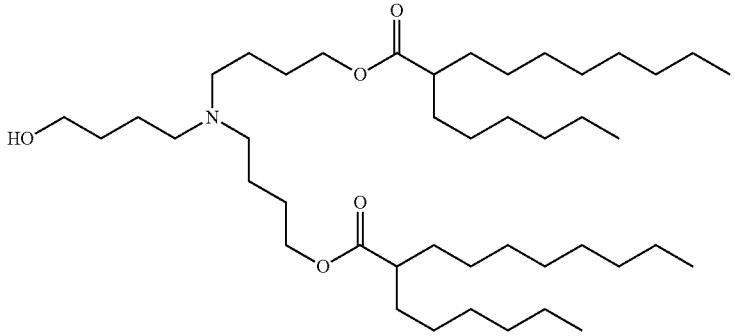 [SMILES: CCCCCCCCC(CCCCCC)C(=O)OCCCCN(CCCCO)CCCCOC(=O)C(CCCCCC)CCCCCCCC] | 5.60 |
| III-5 | 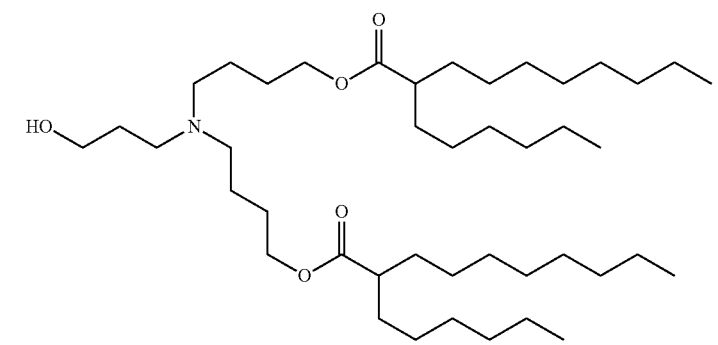 [SMILES: CCCCCCCCC(CCCCCC)C(=O)OCCCCN(CCCO)CCCCOC(=O)C(CCCCCC)CCCCCCCC] | 5.59 |
| III-6 | 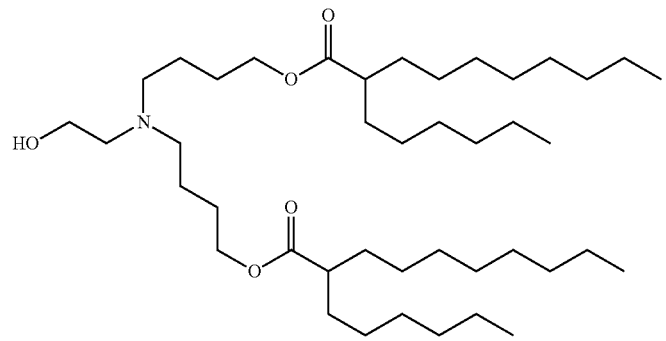 [SMILES: CCCCCCCCC(CCCCCC)C(=O)OCCCCN(CCO)CCCCOC(=O)C(CCCCCC)CCCCCCCC] | 5.42 |
| III-7 | 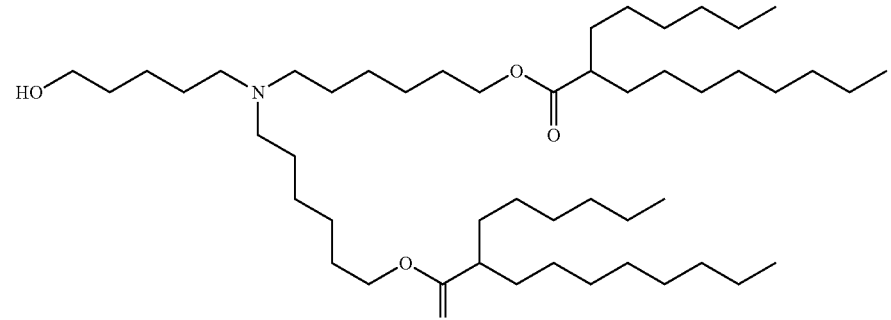 | 6.11 |

TABLE 3-continued

Representative Compounds of Formula (III)

| No. | Structure | pKa |
|---|---|---|
| III-8 | 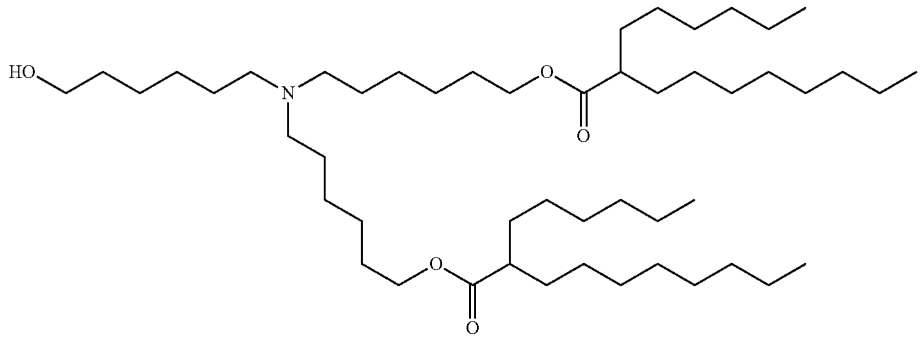 [SMILES: CCCCCCCCC(CCCCCC)C(=O)OCCCCCCN(CCCCCCO)CCCCCCOC(=O)C(CCCCCC)CCCCCCCC] | 5.84 |
| III-9 | 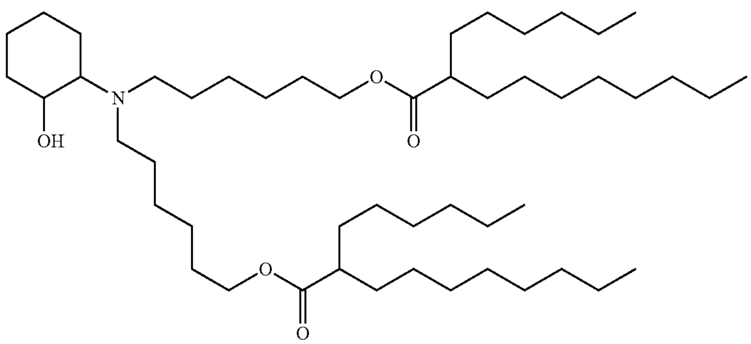 [SMILES: CCCCCCCCC(CCCCCC)C(=O)OCCCCCCN(CCCCCCOC(=O)C(CCCCCC)CCCCCCCC)C1CCCCC1O] | — |
| III-10 | 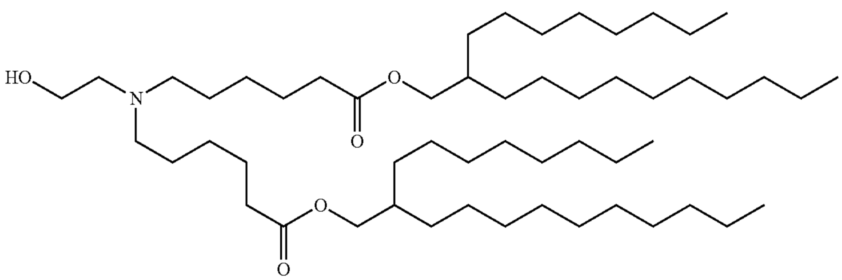 | — |
| III-11 | 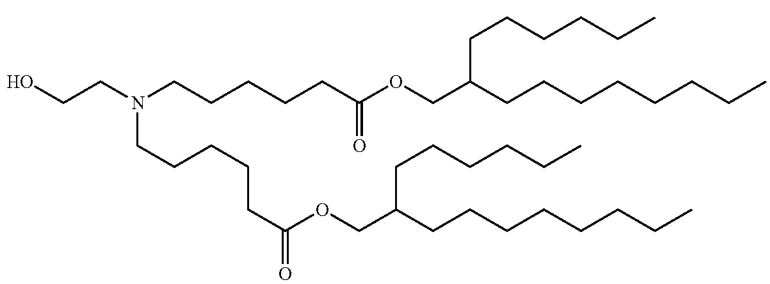 | — |
| III-12 | 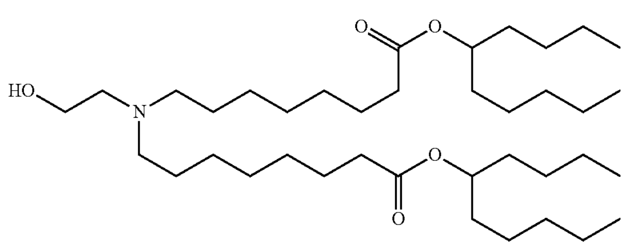 [SMILES: CCCCCC(CCCC)OC(=O)CCCCCCCN(CCO)CCCCCCCC(=O)OC(CCCC)CCCCC] | — |

TABLE 3-continued

Representative Compounds of Formula (III)

| No. | Structure | pKa |
|---|---|---|
| III-13 | 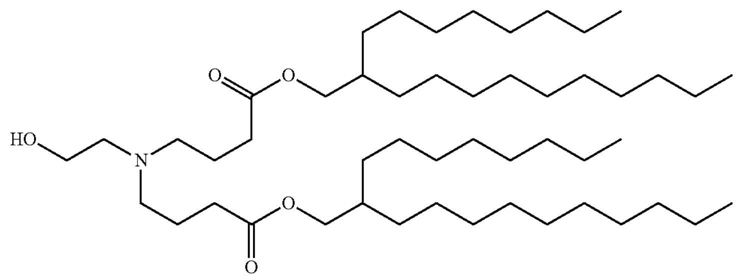 [SMILES: CCCCCCCCCCC(CCCCCCCC)COC(=O)CCCN(CCO)CCCC(=O)OCC(CCCCCCCC)CCCCCCCCCC] | — |
| III-14 | 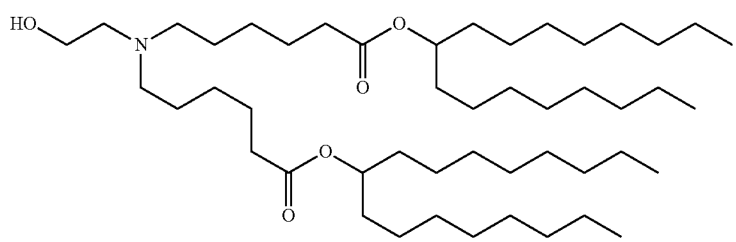 [SMILES: CCCCCCCCC(CCCCCCCC)OC(=O)CCCCCN(CCO)CCCCCC(=O)OC(CCCCCCCC)CCCCCCCC] | — |
| III-15 | 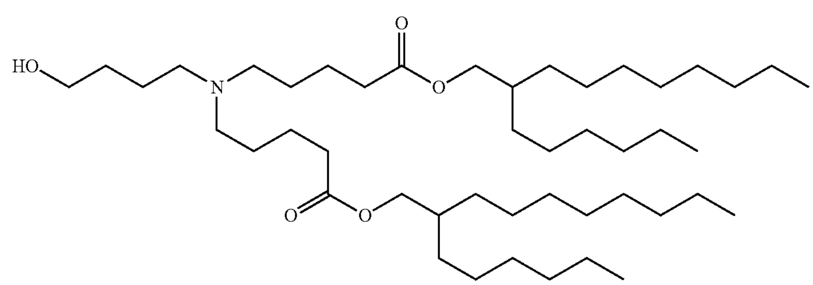 [SMILES: CCCCCCCCC(CCCCCC)COC(=O)CCCCN(CCCCO)CCCCC(=O)OCC(CCCCCC)CCCCCCCC] | 6.14 |
| III-16 | 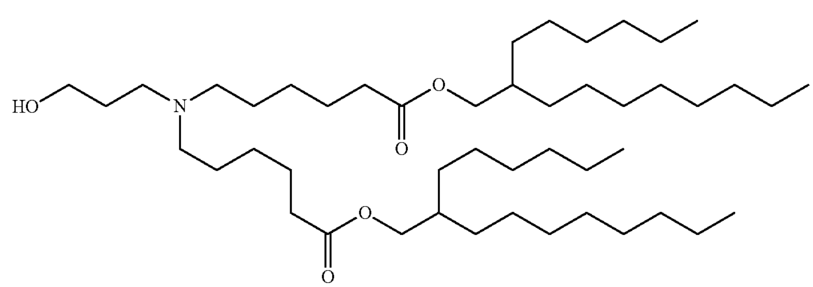 [SMILES: CCCCCCCCC(CCCCCC)COC(=O)CCCCCN(CCCO)CCCCCC(=O)OCC(CCCCCC)CCCCCCCC] | 6.31 |
| III-17 | 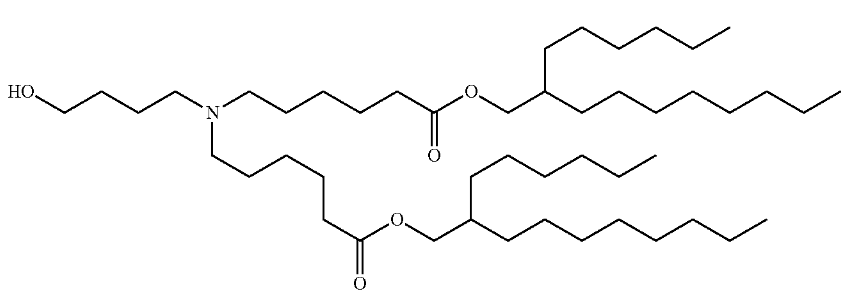 [SMILES: CCCCCCCCC(CCCCCC)COC(=O)CCCCCN(CCCCO)CCCCCC(=O)OCC(CCCCCC)CCCCCCCC] | 6.28 |

TABLE 3-continued

Representative Compounds of Formula (III)

| No. | Structure | pKa |
|---|---|---|
| III-18 | 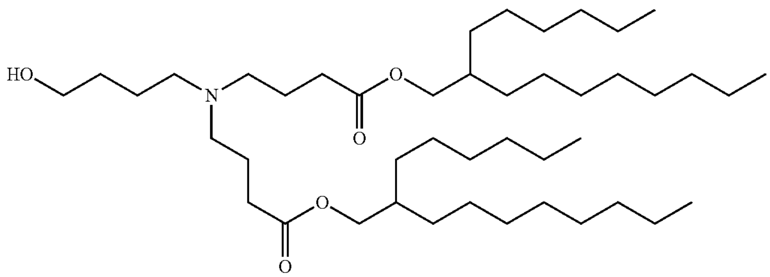 [SMILES: CCCCCCCCC(CCCCCC)COC(=O)CCCN(CCCCO)CCCC(=O)OCC(CCCCCC)CCCCCCCC] | — |
| III-19 | 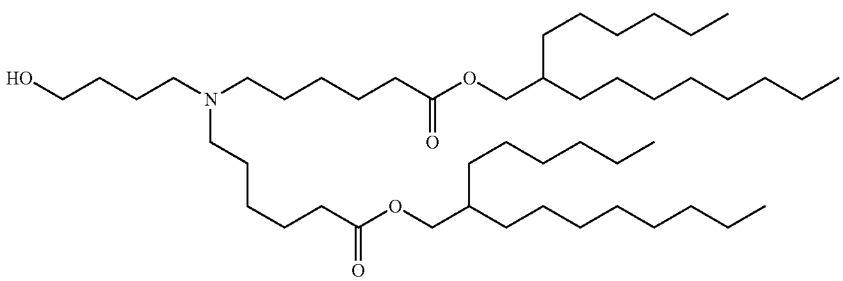 [SMILES: CCCCCCCCC(CCCCCC)COC(=O)CCCCCN(CCCCO)CCCCCC(=O)OCC(CCCCCC)CCCCCCCC] | — |
| III-20 | 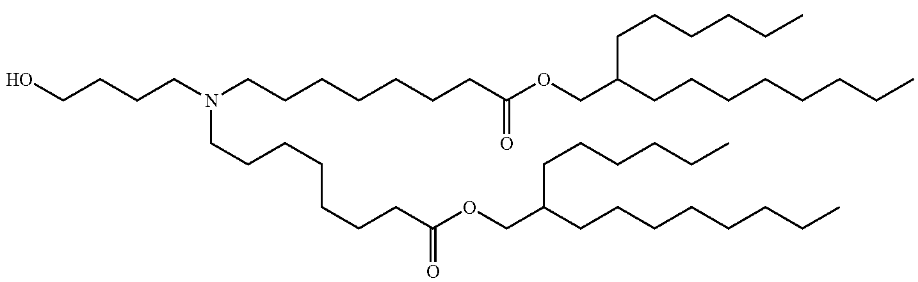 [SMILES: CCCCCCCCC(CCCCCC)COC(=O)CCCCCCCN(CCCCO)CCCCCCCC(=O)OCC(CCCCCC)CCCCCCCC] | 6.36 |
| III-21 | 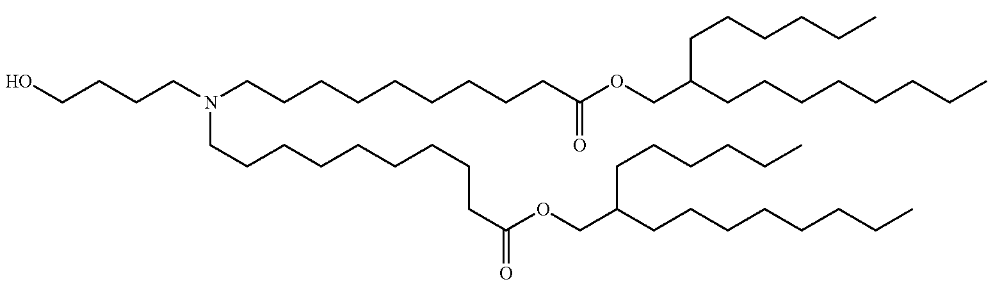 [SMILES: CCCCCCCCC(CCCCCC)COC(=O)CCCCCCCCCN(CCCCO)CCCCCCCCCC(=O)OCC(CCCCCC)CCCCCCCC] | — |
| III-22 | 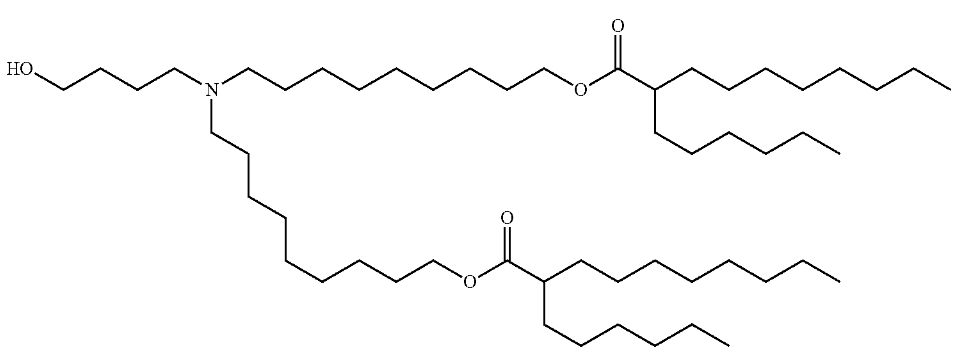 [SMILES: CCCCCCCCC(CCCCCC)C(=O)OCCCCCCCCCN(CCCCO)CCCCCCCCCOC(=O)C(CCCCCC)CCCCCCCC] | 6.10 |

TABLE 3-continued

Representative Compounds of Formula (III)

| No. | Structure | pKa |
|---|---|---|
| III-23 | 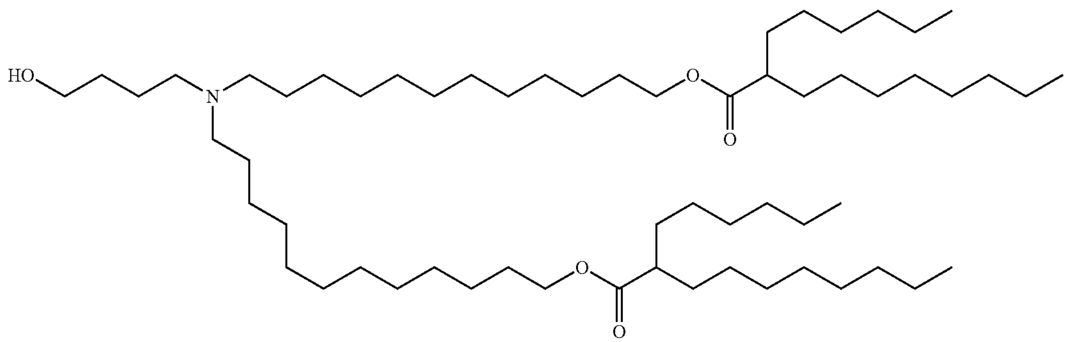 [SMILES: CCCCCCCCC(CCCCCC)C(=O)OCCCCCCCCCCCCN(CCCCO)CCCCCCCCCCCCOC(=O)C(CCCCCC)CCCCCCCC] | 5.98 |
| III-24 | 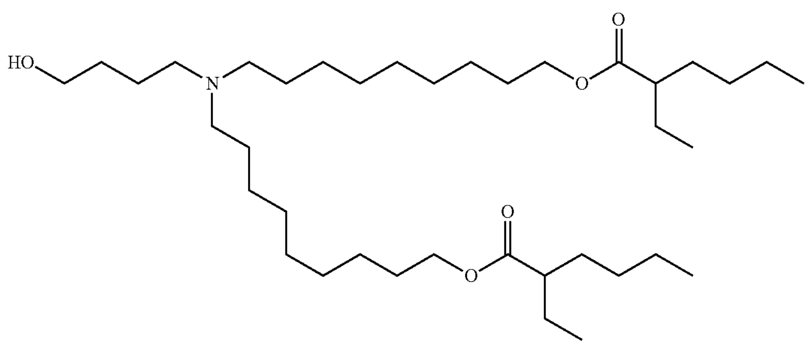 [SMILES: CCCCC(CC)C(=O)OCCCCCCCCCN(CCCCO)CCCCCCCCCOC(=O)C(CC)CCCC] | — |
| III-25 | 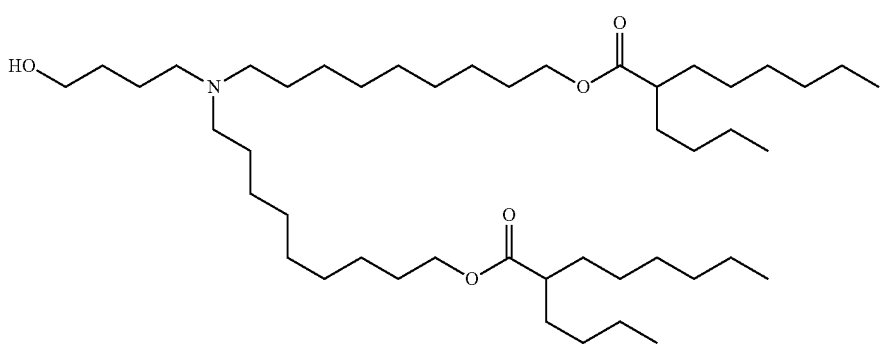 [SMILES: CCCCCCC(CCCC)C(=O)OCCCCCCCCCN(CCCCO)CCCCCCCCCOC(=O)C(CCCC)CCCCCC] | 6.22 |
| III-26 | 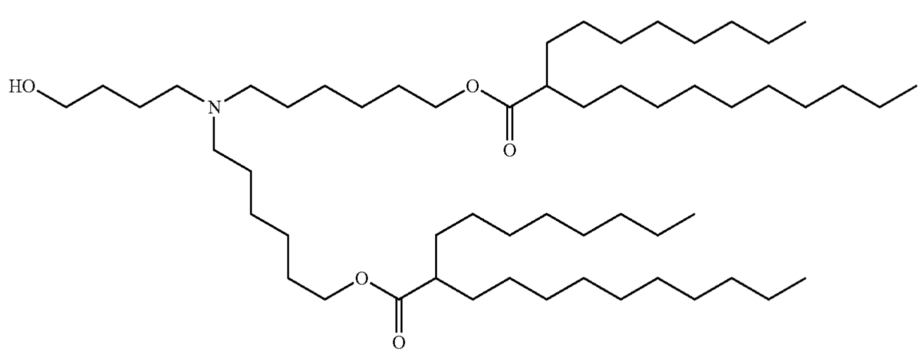 [SMILES: CCCCCCCCCCC(CCCCCCCC)C(=O)OCCCCCCN(CCCCO)CCCCCCOC(=O)C(CCCCCCCC)CCCCCCCCCC] | 5.84 |

TABLE 3-continued

Representative Compounds of Formula (III)

| No. | Structure | pKa |
|---|---|---|
| III-27 | 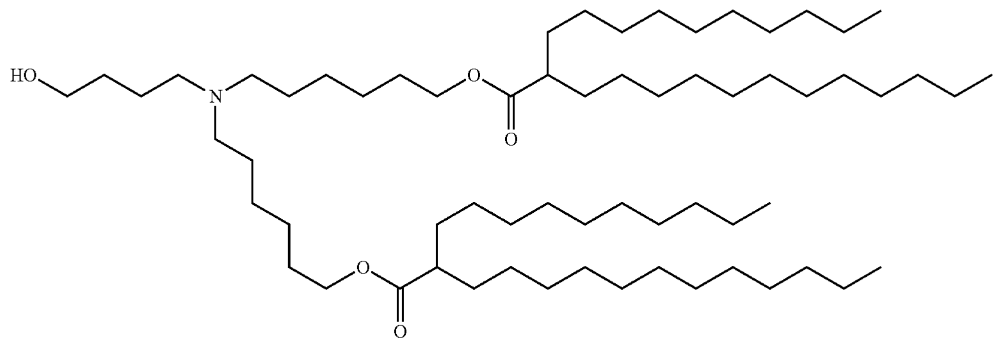 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] | 5.77 |
| III-28 | 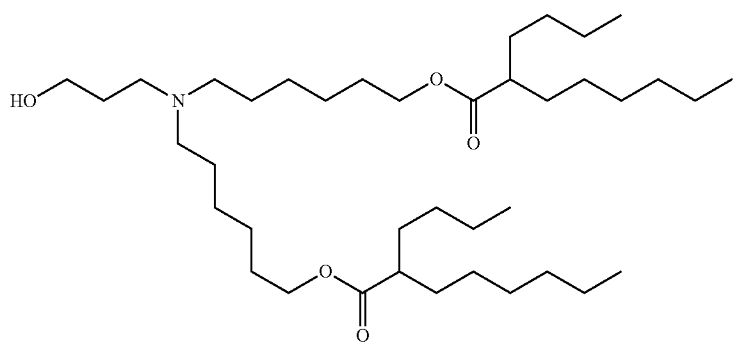 [SMILES: CCCCCCC(CCCC)C(=O)OCCCCCCN(CCCO)CCCCCCOC(=O)C(CCCC)CCCCCC] | — |
| III-29 | 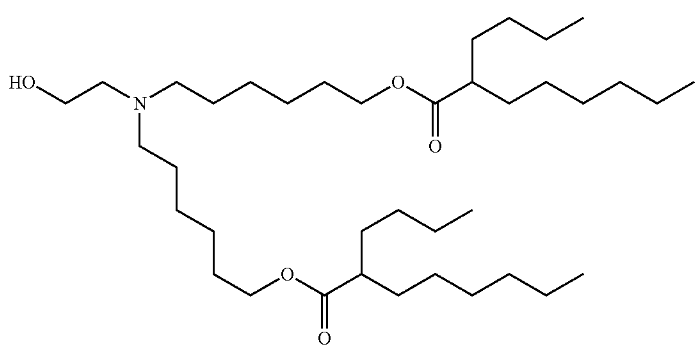 [SMILES: CCCCCCC(CCCC)C(=O)OCCCCCCN(CCO)CCCCCCOC(=O)C(CCCC)CCCCCC] | — |
| III-30 | 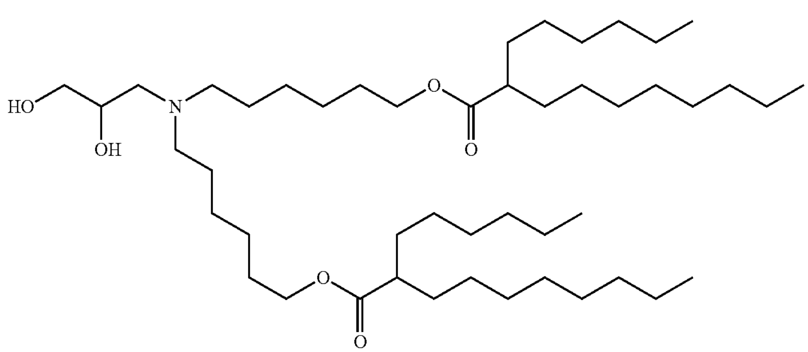 [SMILES: CCCCCCCCC(CCCCCC)C(=O)OCCCCCCN(CCCCCCOC(=O)C(CCCCCC)CCCCCCCC)CC(O)CO] | 6.09 |

TABLE 3-continued
Representative Compounds of Formula (III)
| No. | Structure | pKa |
|---|---|---|
| III-31 | 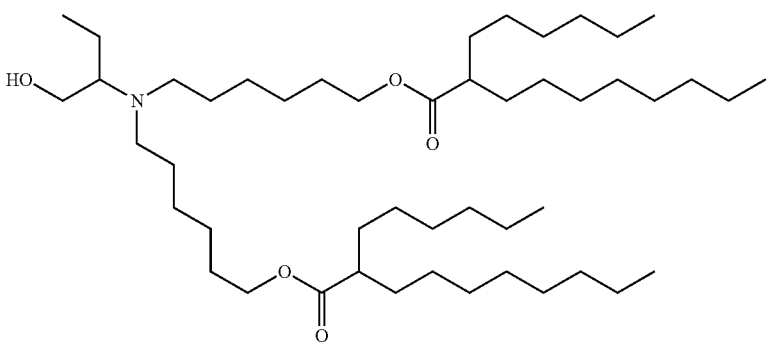 [SMILES: CCCCCCCCC(CCCCCC)C(=O)OCCCCCCN(CCCCCCOC(=O)C(CCCCCC)CCCCCCCC)C(CC)CO] | — |
| III-32 | 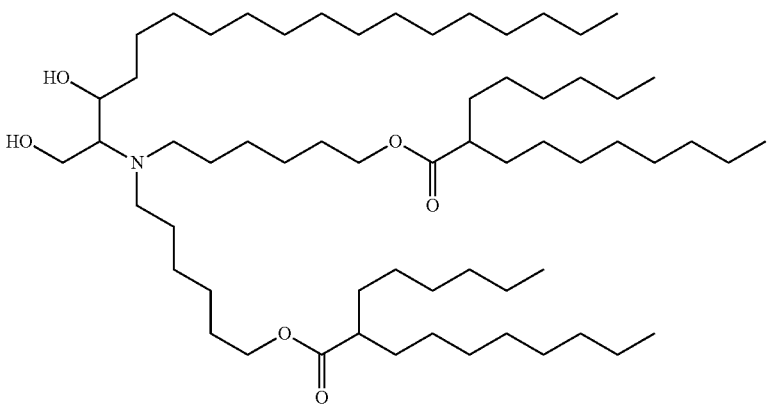 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | — |
| III-33 | 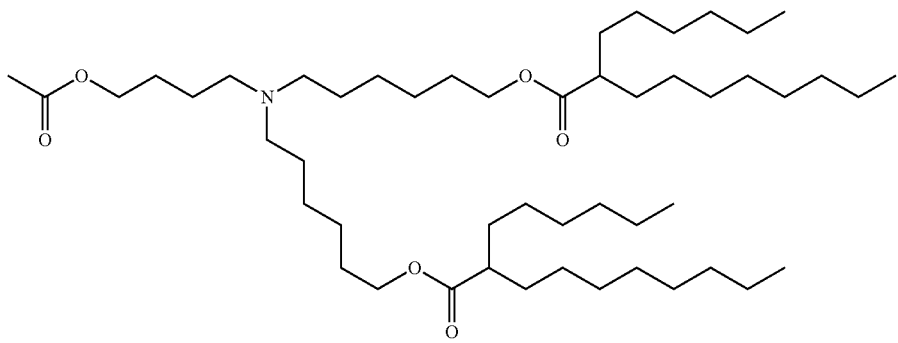 | — |
| III-34 | 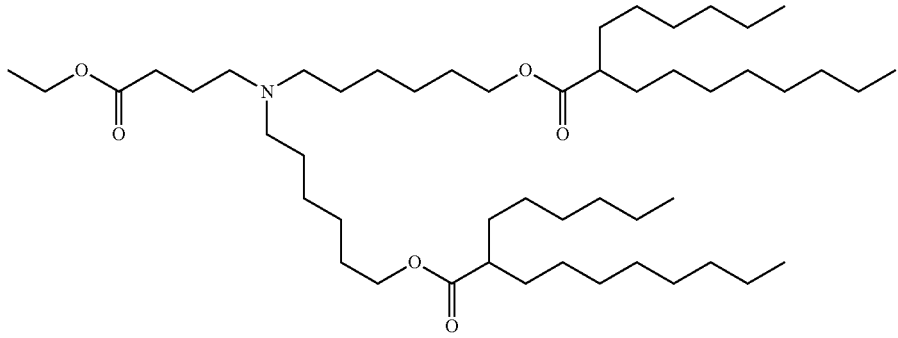 [SMILES: CCCCCCCCC(CCCCCC)C(=O)OCCCCCCN(CCCCCCOC(=O)C(CCCCCC)CCCCCCCC)CCCC(=O)OCC] | — |

TABLE 3-continued
Representative Compounds of Formula (III)
| No. | Structure | pKa |
|---|---|---|
| III-35 | 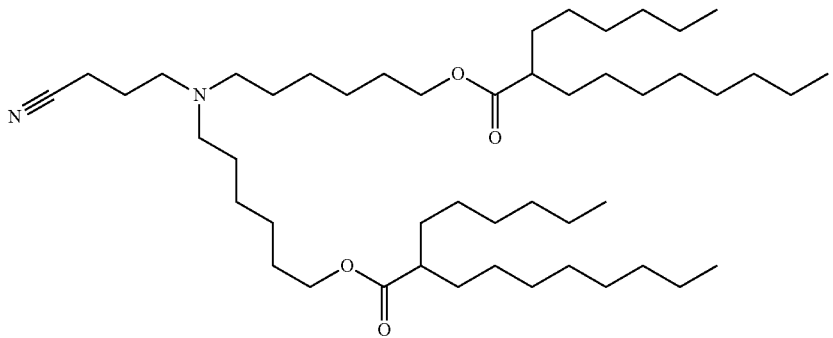 [SMILES: CCCCCCCCC(CCCCCC)C(=O)OCCCCCCN(CCCC#N)CCCCCCOC(=O)C(CCCCCC)CCCCCCCC] | — |
| III-36 | 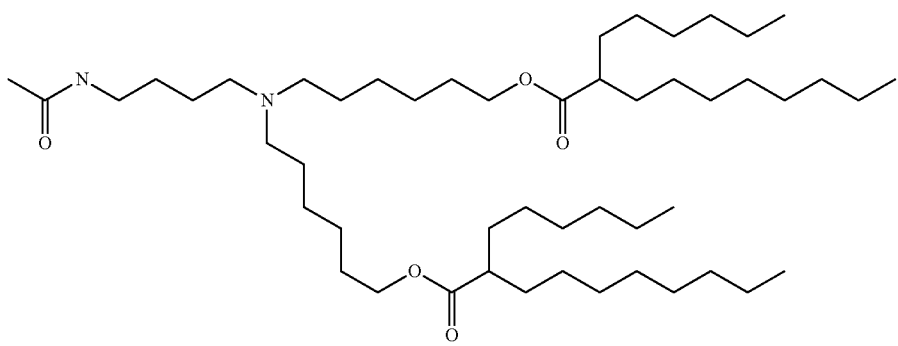 [SMILES: CCCCCCCCC(CCCCCC)C(=O)OCCCCCCN(CCCCCCOC(=O)C(CCCCCC)CCCCCCCC)CCCCNC(C)=O] | — |
| III-37 | 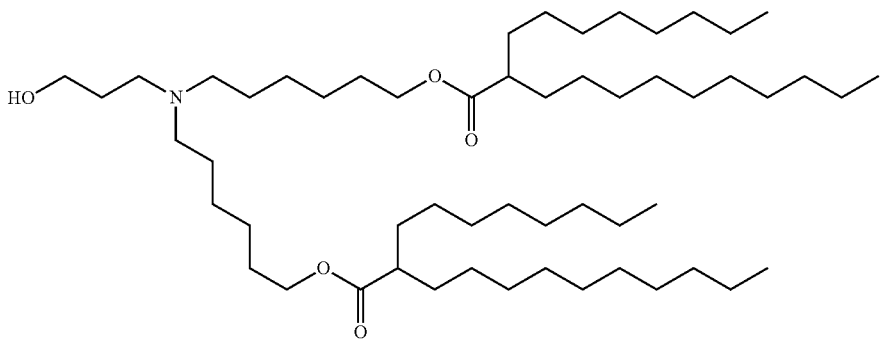 [SMILES: CCCCCCCCCCC(CCCCCCCC)C(=O)OCCCCCCN(CCCO)CCCCCCOC(=O)C(CCCCCCCC)CCCCCCCCCC] | — |
| III-38 | 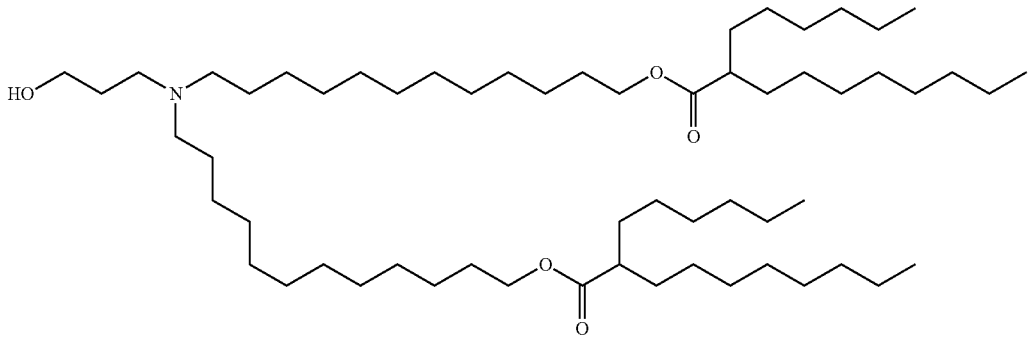 [SMILES: CCCCCCCCC(CCCCCC)C(=O)OCCCCCCCCCCCCN(CCCO)CCCCCCCCCCCCOC(=O)C(CCCCCC)CCCCCCCC] | — |

TABLE 3-continued

Representative Compounds of Formula (III)

| No. | Structure | pKa |
|---|---|---|
| III-39 | 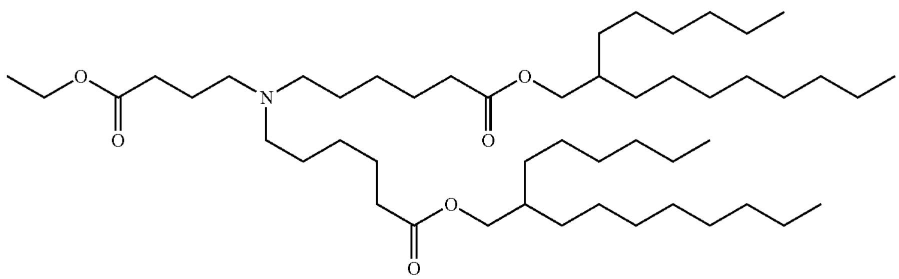 [SMILES: CCCCCCCCC(CCCCCC)COC(=O)CCCCCN(CCCCCC(=O)OCC(CCCCCC)CCCCCCCC)CCCC(=O)OCC] | — |
| III-40 | 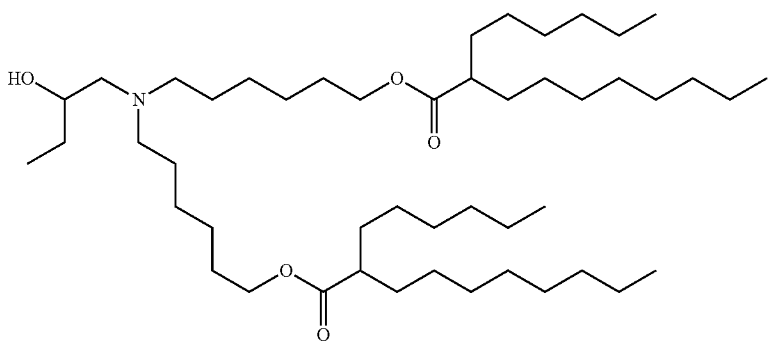 [SMILES: CCCCCCCCC(CCCCCC)C(=O)OCCCCCCN(CCCCCCOC(=O)C(CCCCCC)CCCCCCCC)CC(O)CC] | — |
| III-41 | 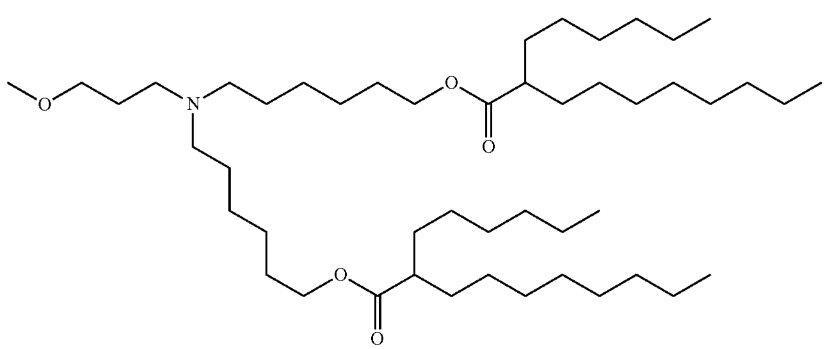 [SMILES: CCCCCCCCC(CCCCCC)C(=O)OCCCCCCN(CCCCCCOC(=O)C(CCCCCC)CCCCCCCC)CCCOC] | — |
| III-42 | 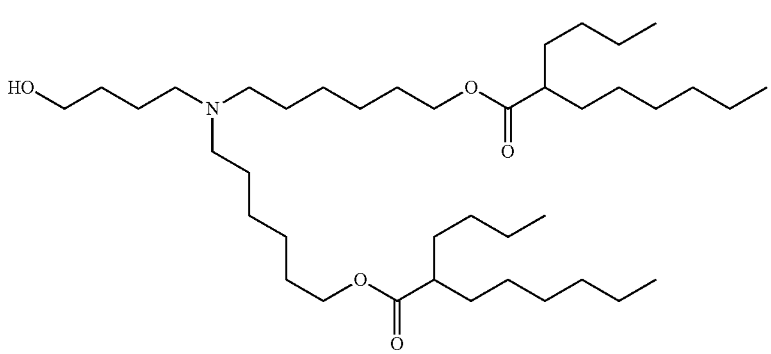 [SMILES: CCCCCCC(CCCC)C(=O)OCCCCCCN(CCCCO)CCCCCCOC(=O)C(CCCC)CCCCCC] | — |

TABLE 3-continued

Representative Compounds of Formula (III)

| No. | Structure | pKa |
|-----|-----------|-----|
| III-43 | 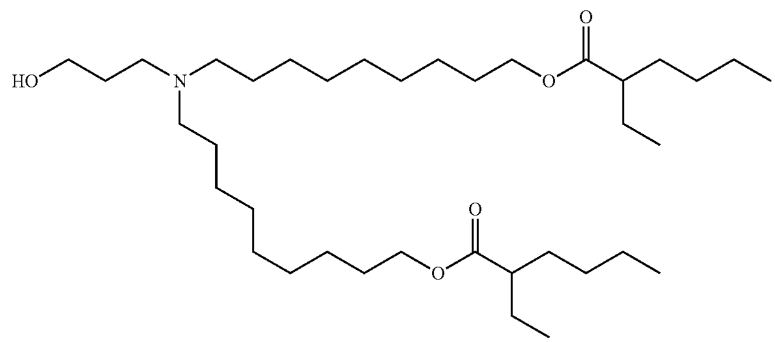 [SMILES: CCCCC(CC)C(=O)OCCCCCCCCCN(CCCO)CCCCCCCCCOC(=O)C(CC)CCCC] | — |
| III-44 | 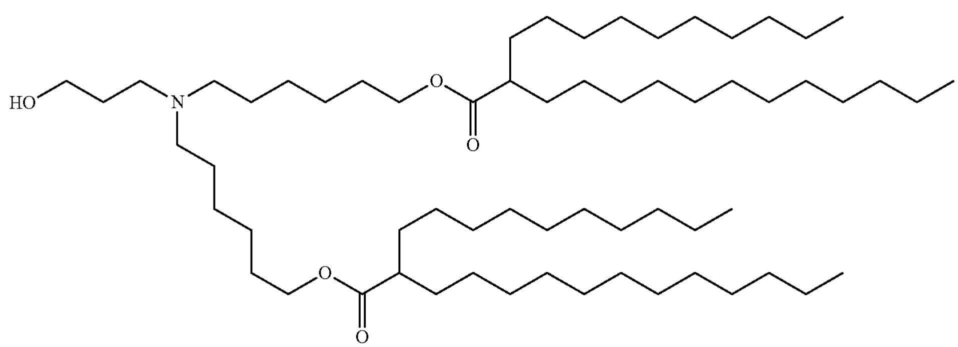 [SMILES: CCCCCCCCCCCCC(CCCCCCCCCC)C(=O)OCCCCCCN(CCCO)CCCCCCOC(=O)C(CCCCCCCCCC)CCCCCCCCCCCC] | — |
| III-45 | 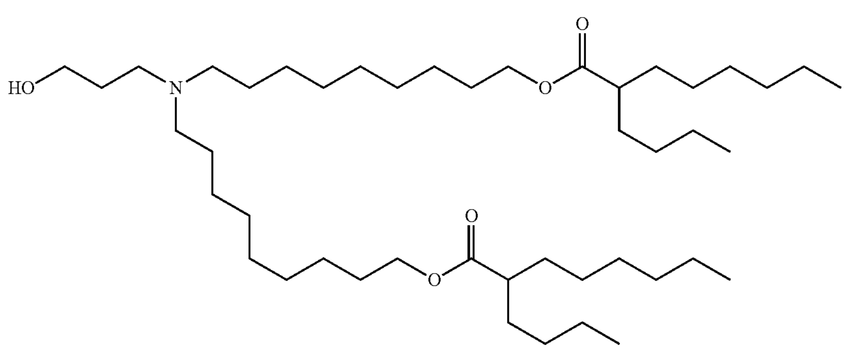 [SMILES: CCCCCCC(CCCC)C(=O)OCCCCCCCCCN(CCCO)CCCCCCCCCOC(=O)C(CCCC)CCCCCC] | — |
| III-46 | 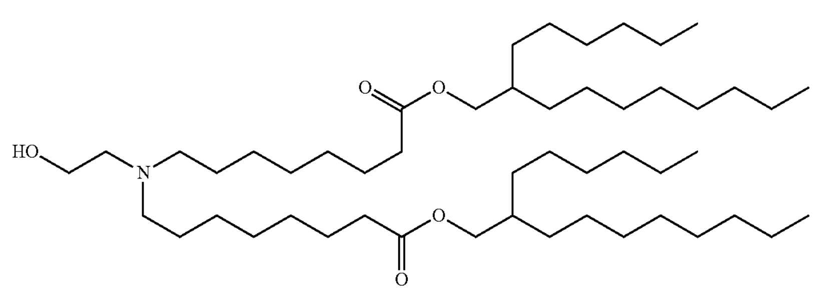 [SMILES: CCCCCCCCC(CCCCCC)COC(=O)CCCCCCCN(CCO)CCCCCCCC(=O)OCC(CCCCCC)CCCCCCCC] | — |

TABLE 3-continued

Representative Compounds of Formula (III)

| No. | Structure | pKa |
|---|---|---|
| III-47 | 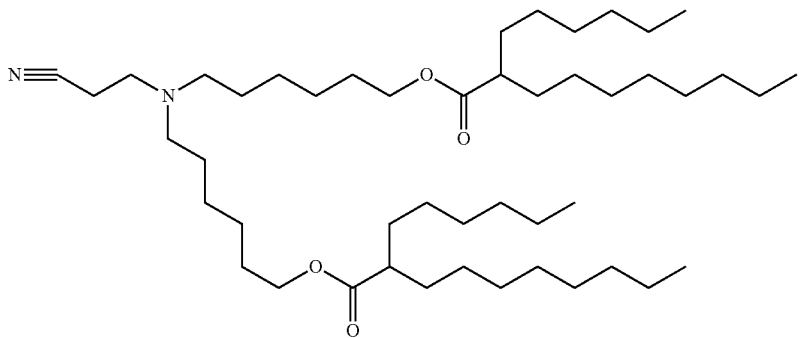 [SMILES: CCCCCCCCC(CCCCCC)C(=O)OCCCCCCN(CCC#N)CCCCCCOC(=O)C(CCCCCC)CCCCCCCC] | — |
| III-48 | 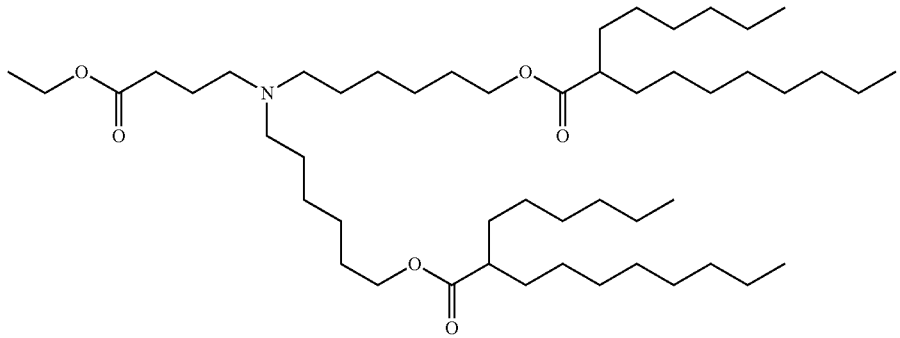 [SMILES: CCCCCCCCC(CCCCCC)C(=O)OCCCCCCN(CCCCCCOC(=O)C(CCCCCC)CCCCCCCC)CCCC(=O)OCC] | — |
| III-49 | 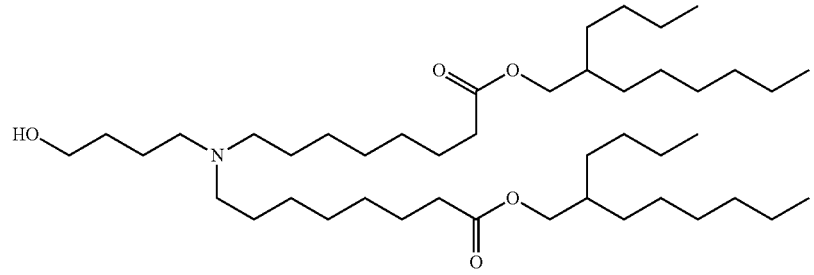 [SMILES: CCCCCCC(CCCC)COC(=O)CCCCCCCN(CCCCO)CCCCCCCC(=O)OCC(CCCC)CCCCCC] | — |

Compounds of Formula (III) can be prepared and tested according to the procedures set forth in PCT Pub. No. WO 2017/075531, the full disclosure of which is incorporated by reference in its entirety.

Cationic Lipids of Formula IV

In one embodiment, the cationic lipid has a structure of Formula (IV):

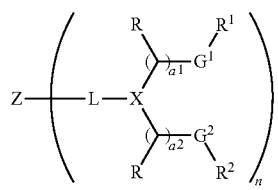

(IV)

or a pharmaceutically acceptable salt or stereoisomer thereof, wherein:

one of $G^1$ or $G^2$ is, at each occurrence, —O(C=O)—, —(C=O)O—, —C(=O)—, —O—, —S(O)$_y$—, —S—S—, —C(=O)S—, —SC(=O)—, —N(R$^a$)C(=O)—, —C(=O)N(R$^a$)—, —N(R$^a$)C(=O)N(R$^a$)—, —OC(=O)N(R$^a$)— or —N(R$^a$)C(=O)O—, and the other of $G^1$ or $G^2$ is, at each occurrence, —O(C=O)—, —(C=O)O—, —C(=O)—, —O—, —S(O)$_y$—, —S—S—, —C(=O)S—, —SC(=O)—, —N(R$^a$)C(=O)—, —C(=O)N(R$^a$)—, —N(R$^a$)C(=O)N(R$^a$)—, —OC(=O)N(R$^a$)— or —N(R$^a$)C(=O)O— or a direct bond;

L is, at each occurrence, ~O(C=O)—, wherein ~ represents a covalent bond to X;

X is CR$^a$.

Z is alkyl, cycloalkyl or a monovalent moiety comprising at least one polar functional group when n is 1; or Z is alkylene, cycloalkylene or a polyvalent moiety comprising at least one polar functional group when n is greater than 1;

R$^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

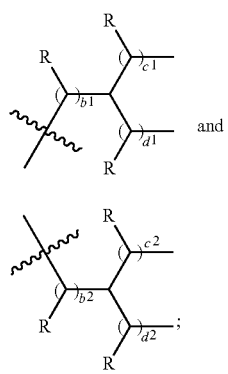

$a^1$ and $a^2$ are, at each occurrence, independently an integer from 3 to 12;
$b^1$ and $b^2$ are, at each occurrence, independently 0 or 1;
$c^1$ and $c^2$ are, at each occurrence, independently an integer from 5 to 10;
$d^1$ and $d^2$ are, at each occurrence, independently an integer from 5 to 10;
y is, at each occurrence, independently an integer from 0 to 2; and
n is an integer from 1 to 6,
wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In some embodiments of Formula (IV), $G^1$ and $G^2$ are each independently
—O(C=O)— or —(C=O)O—.

In other embodiments of Formula (IV), X is CH.

In different embodiments of Formula (IV), the sum of $a^1+b^1+c^1$ or the sum of $a^2+b^2+c^2$ is an integer from 12 to 26.

In still other embodiments of Formula (IV), $a^1$ and $a^2$ are independently an integer from 3 to 10. For example, in some embodiments $a^1$ and $a^2$ are independently an integer from 4 to 9.

In various embodiments of Formula (IV), $b^1$ and $b^2$ are 0. In different embodiments, $b^1$ and $b^2$ are 1.

In more embodiments of Formula (IV), $c^1$, $c^2$, $d^1$ and $d^2$ are independently an integer from 6 to 8.

In other embodiments of Formula (IV), $c^1$ and $c^2$ are, at each occurrence, independently an integer from 6 to 10, and $d^1$ and $d^2$ are, at each occurrence, independently an integer from 6 to 10.

In other embodiments of Formula (IV), $c^1$ and $c^2$ are, at each occurrence, independently an integer from 5 to 9, and $d^1$ and $d^2$ are, at each occurrence, independently an integer from 5 to 9.

In more embodiments of Formula (IV), Z is alkyl, cycloalkyl or a monovalent moiety comprising at least one polar functional group when n is 1. In other embodiments, Z is alkyl.

In various embodiments of the foregoing Formula (IV), R is, at each occurrence, independently either: (a) H or methyl; or (b) R together with the carbon atom to which it is bound is taken together with an adjacent R and the carbon atom to which it is bound to form a carbon-carbon double bond. In certain embodiments, each R is H. In other embodiments at least one R together with the carbon atom to which it is bound is taken together with an adjacent R and the carbon atom to which it is bound to form a carbon-carbon double bond.

In other embodiments of the compound of Formula (IV), $R^1$ and $R^2$ independently have one of the following structures:

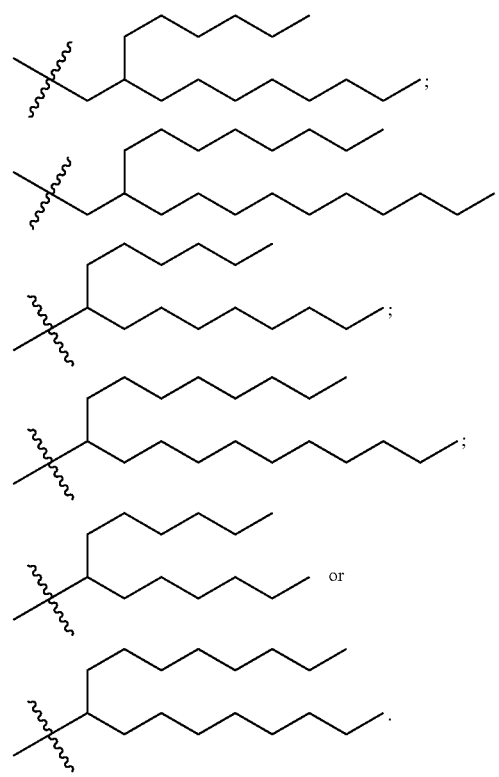

In certain embodiments of Formula (IV), the compound has one of the following structures:

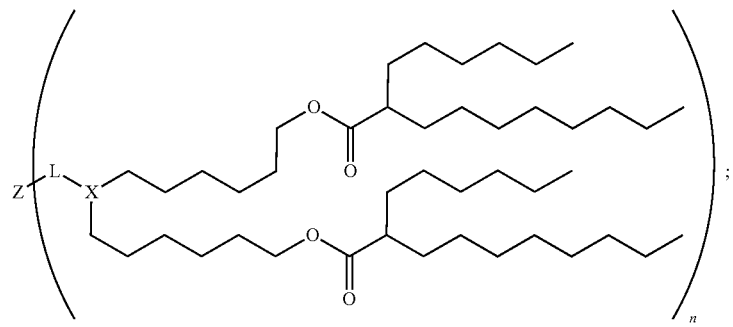

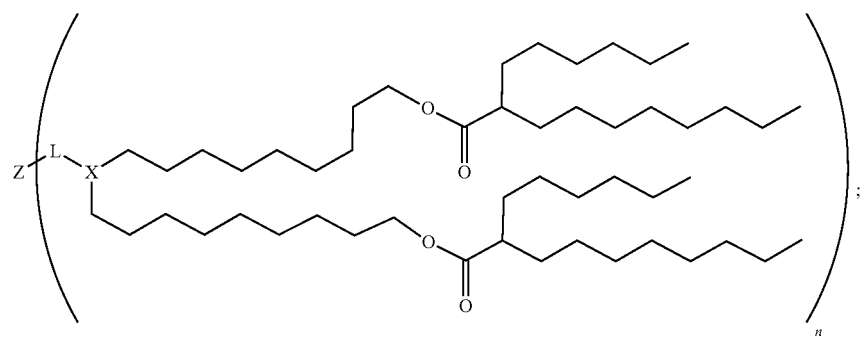;
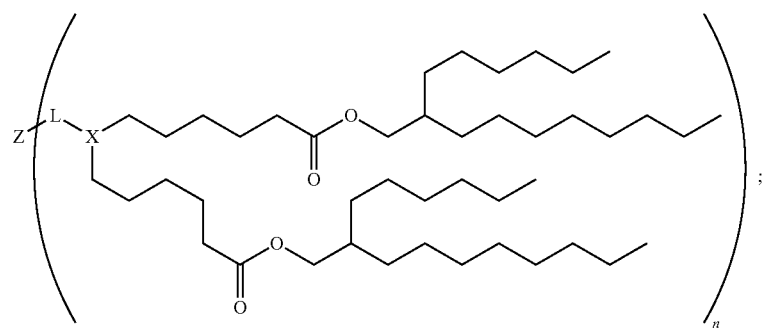;
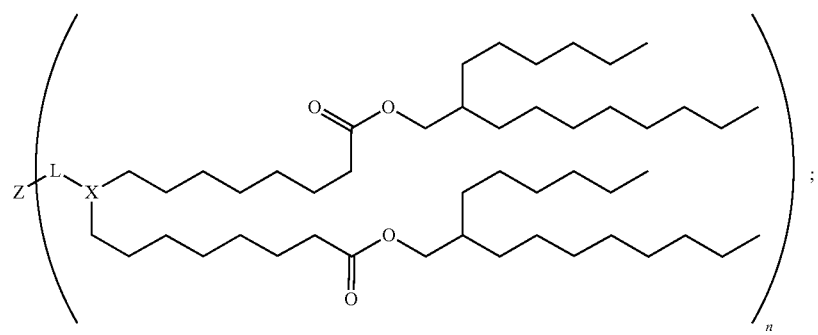;
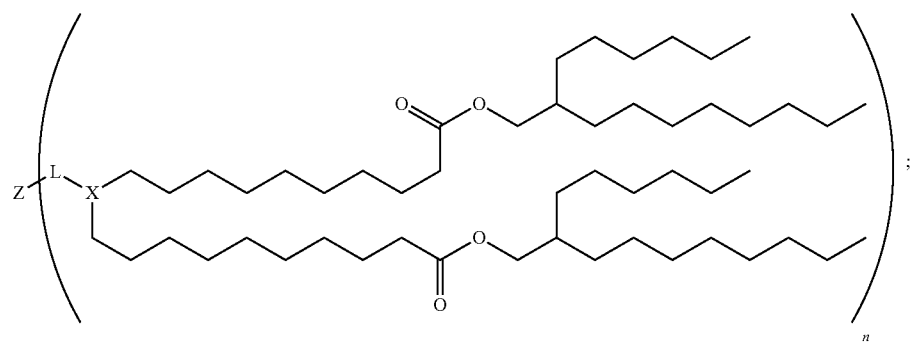;
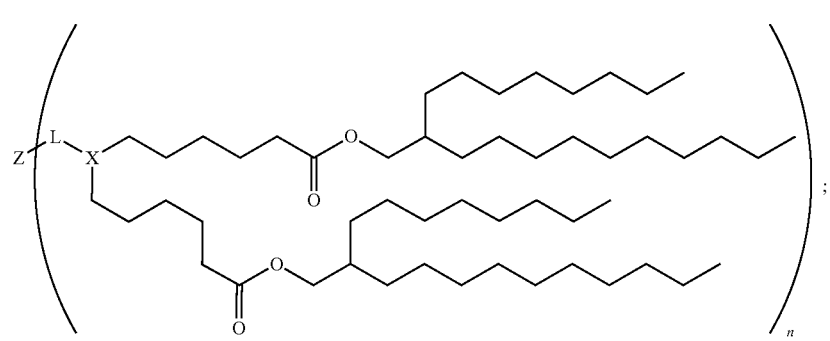;

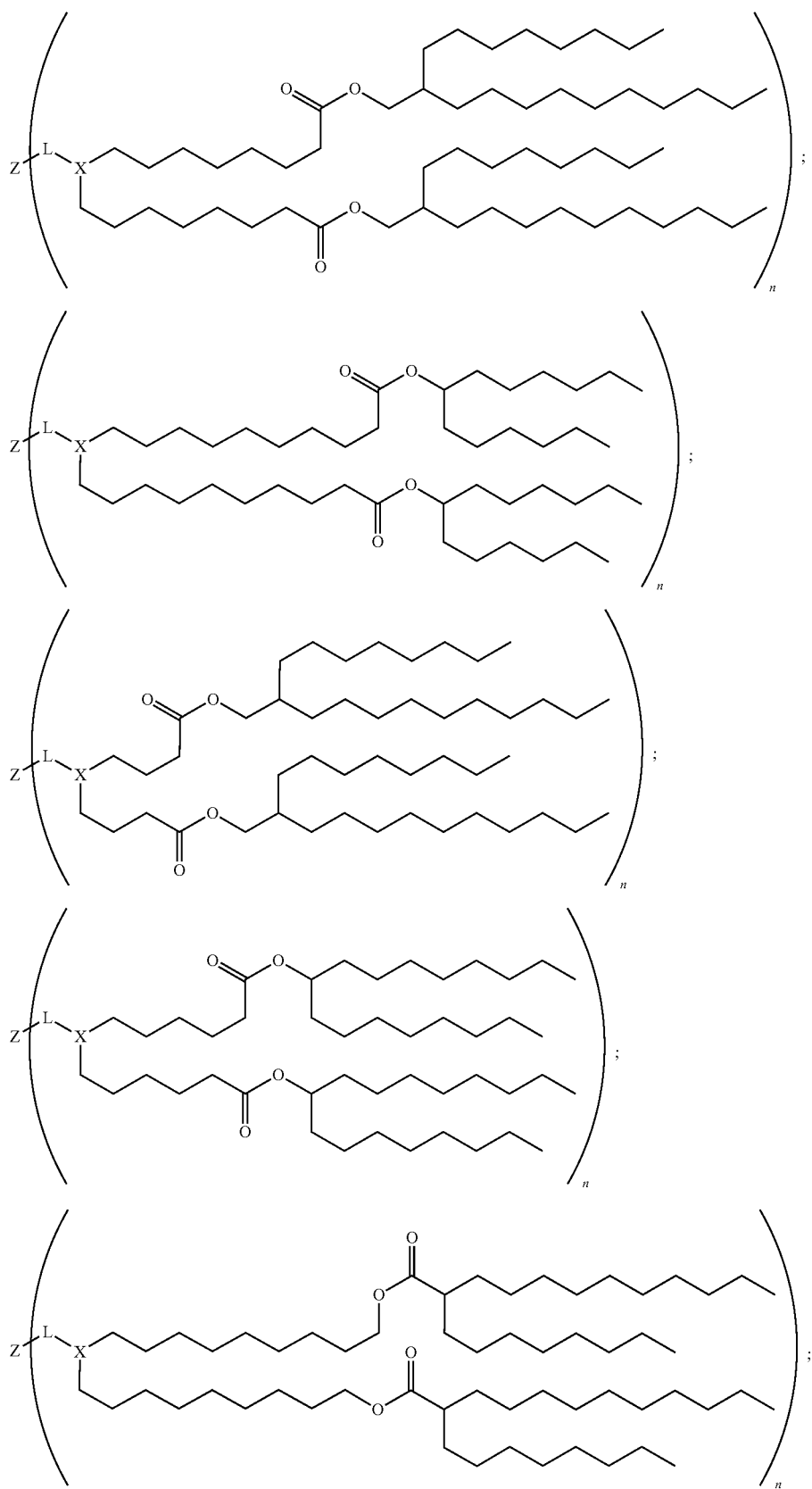

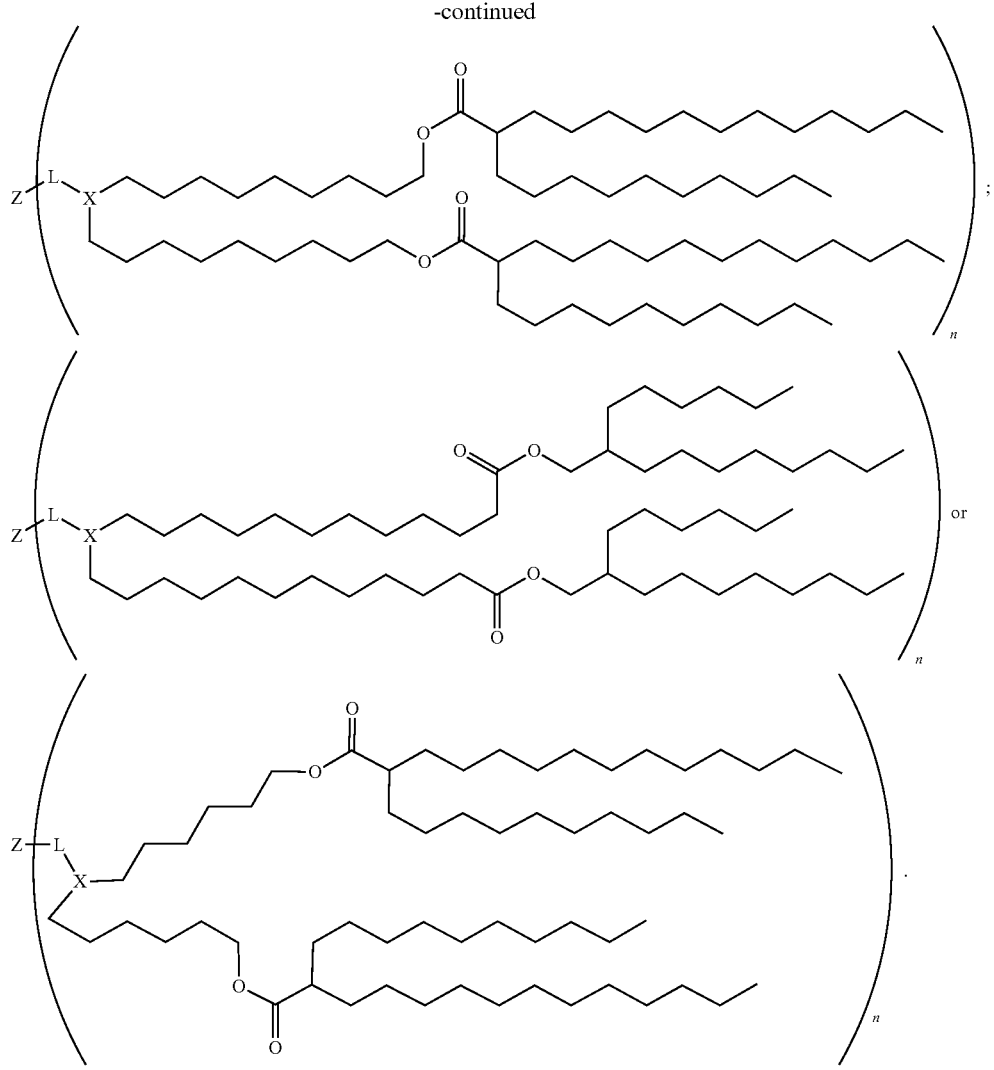

Cationic Lipids of Formula V

In still different embodiments the cationic lipid has the structure of Formula (V):

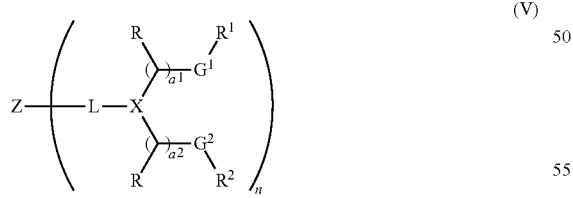

(V)

or a pharmaceutically acceptable salt or stereoisomer thereof, wherein:

one of $G^1$ or $G^2$ is, at each occurrence, —O(C=O)—, —(C=O)O—, —C(=O)—, —O—, —S(O)$_y$—, —S—S—, —C(=O)S—, —SC(=O)—, —N(R$^a$)C(=O)—, —C(=O)N(R$^a$)—, —N(R$^a$)C(=O)N(R$^a$)—, —OC(=O)N(R$^a$)— or —N(R$^a$)C(=O)O—, and the other of $G^1$ or $G^2$ is, at each occurrence, —O(C=O)—, —(C=O)O—, —C(=O)—, —O—, —S(O)$_y$—, —S—S—, —C(=O)S—, —SC(=O)—, —N(R$^a$)C(=O)—, —C(=O)N(R$^a$)—, —N(R$^a$)C(=O)N(R$^a$)—, —OC(=O)N(R$^a$)— or —N(R$^a$)C(=O)O— or a direct bond;

L is, at each occurrence, ~O(C=O)—, wherein ~ represents a covalent bond to X;

X is CR$^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

R$^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

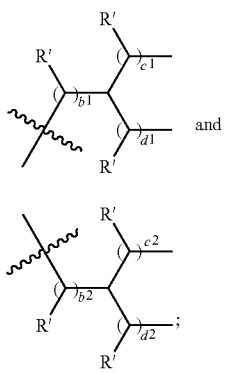

and

R' is, at each occurrence, independently H or $C_1$-$C_{12}$ alkyl;

$a^1$ and $a^2$ are, at each occurrence, independently an integer from 3 to 12;

$b^1$ and $b^2$ are, at each occurrence, independently 0 or 1;

$c^1$ and $c^2$ are, at each occurrence, independently an integer from 2 to 12;

$d^1$ and $d^2$ are, at each occurrence, independently an integer from 2 to 12;

y is, at each occurrence, independently an integer from 0 to 2; and n is an integer from 1 to 6, wherein $a^1$, $a^2$, $c^1$, $c^2$, $d^1$ and $d^2$ are selected such that the sum of $a^1+c^1+d^1$ is an integer from 18 to 30, and the sum of $a^2+c^2+d^2$ is an integer from 18 to 30, and wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In certain embodiments of Formula (V), $G^1$ and $G^2$ are each independently

—O(C=O)— or —(C=O)O—.

In other embodiments of Formula (V), X is CH.

In some embodiments of Formula (V), the sum of $a^1+c^1+d^1$ is an integer from 20 to 30, and the sum of $a^2+c^2+d^2$ is an integer from 18 to 30. In other embodiments, the sum of $a^1+c^1+d^1$ is an integer from 20 to 30, and the sum of $a^2+c^2+d^2$ is an integer from 20 to 30. In more embodiments of Formula (V), the sum of $a^1+b^1+c^1$ or the sum of $a^2+b^2+c^2$ is an integer from 12 to 26. In other embodiments, $a^1$, $a^2$, $c^1$, $c^2$, $d^1$ and $d^2$ are selected such that the sum of $a^1+c^1+d^1$ is an integer from 18 to 28, and the sum of $a^2+c^2+d^2$ is an integer from 18 to 28, In still other embodiments of Formula (V), $a^1$ and $a^2$ are independently an integer from 3 to 10, for example an integer from 4 to 9.

In yet other embodiments of Formula (V), $b^1$ and $b^2$ are 0. In different embodiments $b^1$ and $b^2$ are 1.

In certain other embodiments of Formula (V), $c^1$, $c^2$, $d^1$ and $d^2$ are independently an integer from 6 to 8.

In different other embodiments of Formula (V), Z is alkyl or a monovalent moiety comprising at least one polar functional group when n is 1; or Z is alkylene or a polyvalent moiety comprising at least one polar functional group when n is greater than 1.

In more embodiments of Formula (V), Z is alkyl, cycloalkyl or a monovalent moiety comprising at least one polar functional group when n is 1. In other embodiments, Z is alkyl.

In other different embodiments of Formula (V), R is, at each occurrence, independently either: (a) H or methyl; or (b) R together with the carbon atom to which it is bound is taken together with an adjacent R and the carbon atom to which it is bound to form a carbon-carbon double bond. For example in some embodiments each R is H. In other embodiments at least one R together with the carbon atom to which it is bound is taken together with an adjacent R and the carbon atom to which it is bound to form a carbon-carbon double bond.

In more embodiments, each R' is H.

In certain embodiments of Formula (V), the sum of $a^1+c^1+d^1$ is an integer from 20 to 25, and the sum of $a^2+c^2+d^2$ is an integer from 20 to 25.

In other embodiments of Formula (V), $R^1$ and $R^2$ independently have one of the following structures:

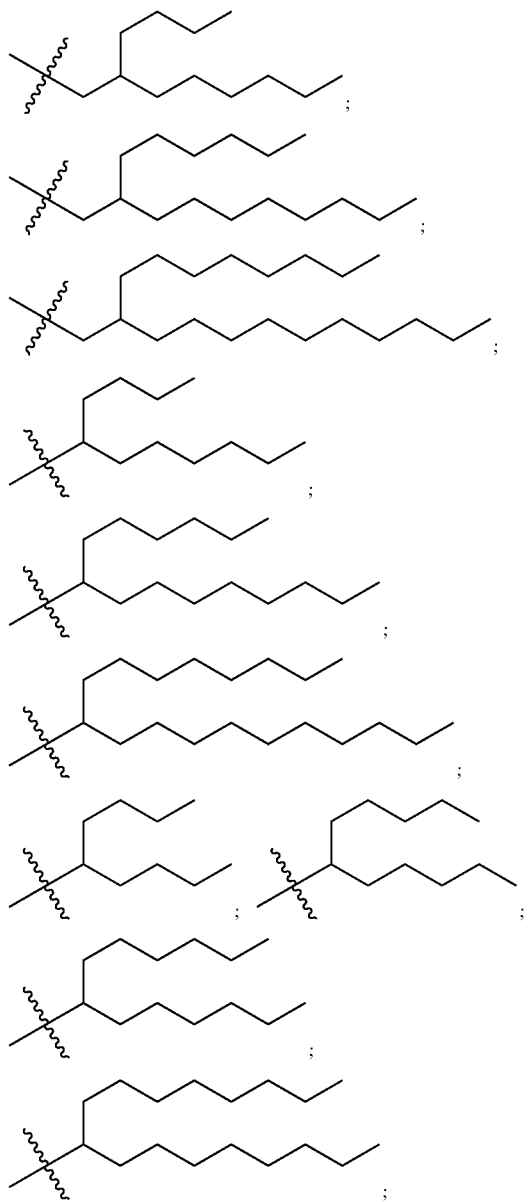

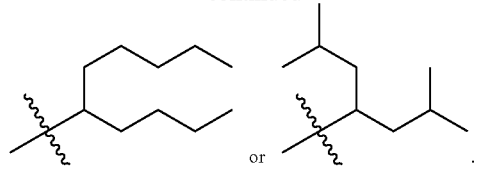
In more embodiments of Formula (V), the compound has one of the following structures
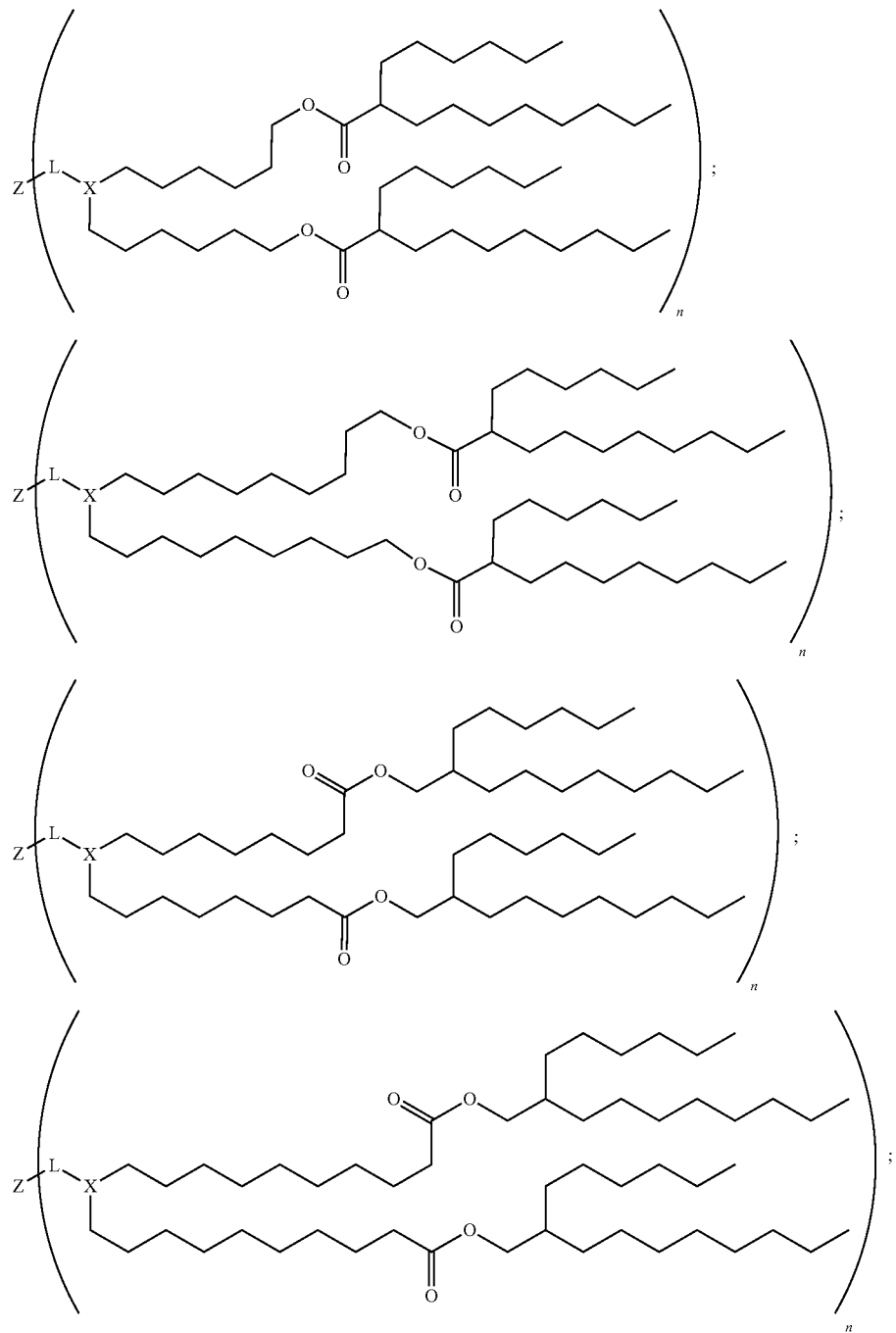

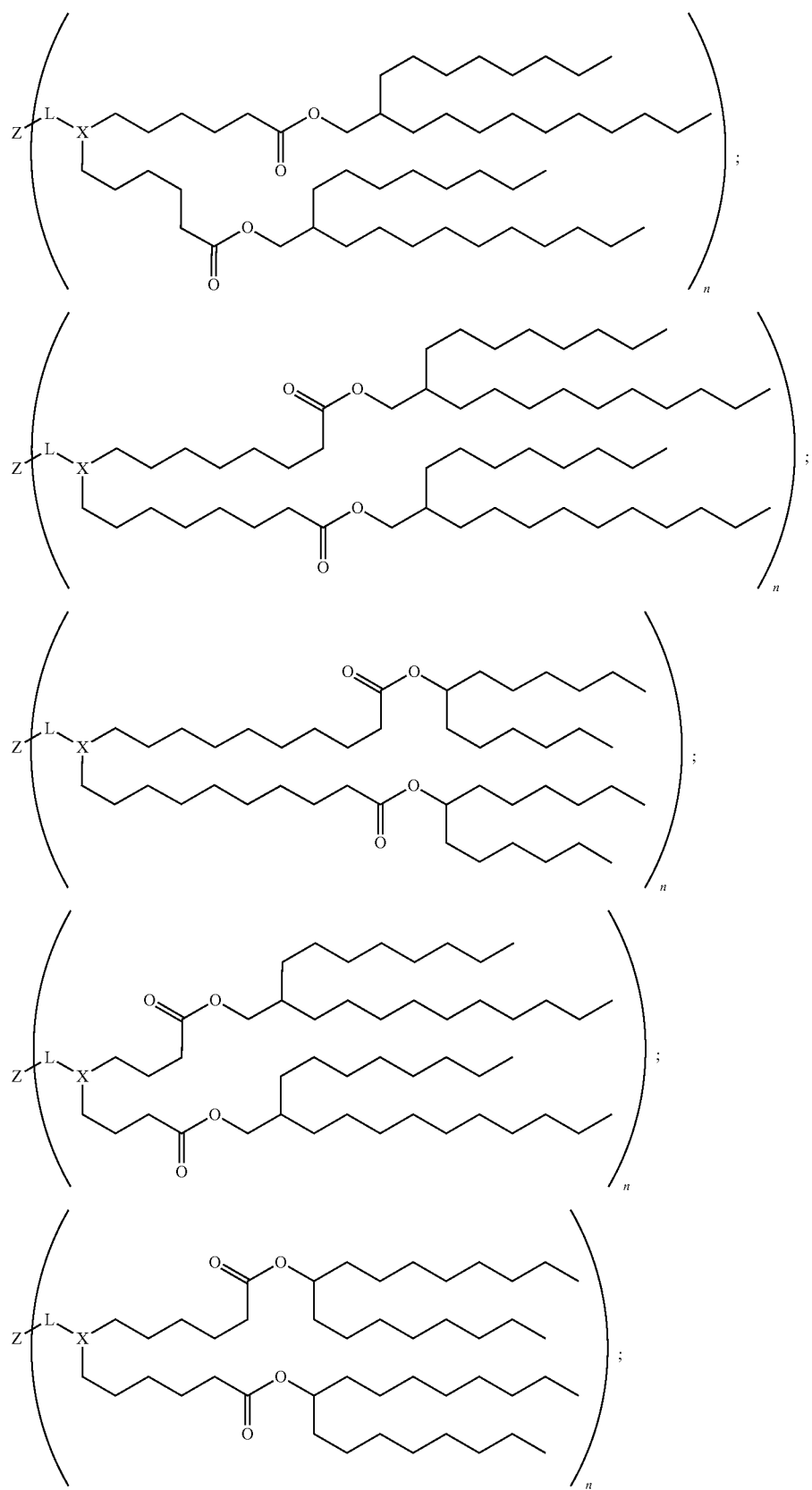

-continued

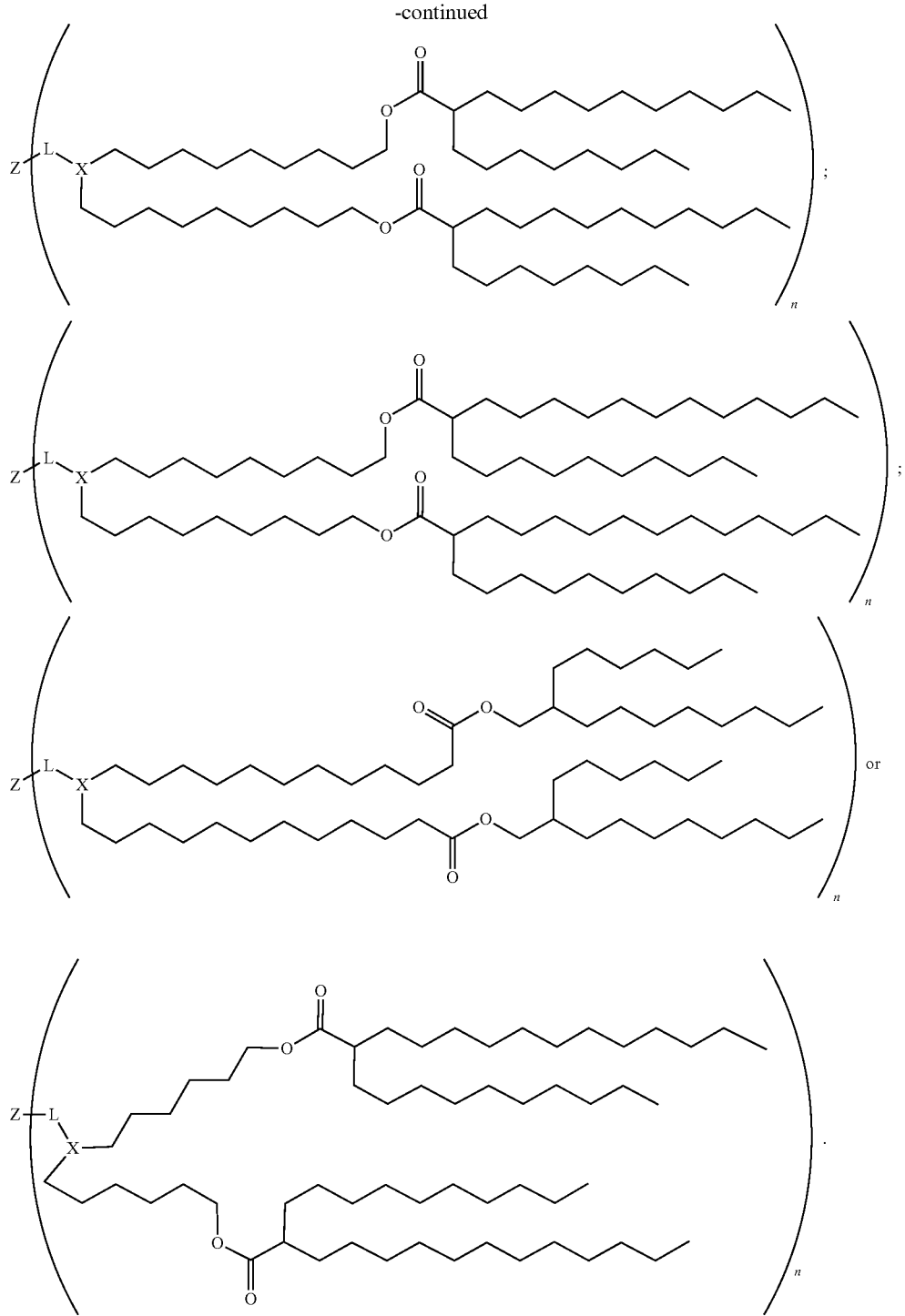

In any of the foregoing embodiments of Formula (IV) or (V), n is 1. In other of the foregoing embodiments of Formula (IV) or (V), n is greater than 1.

In more of any of the foregoing embodiments of Formula (IV) or (V), Z is a mono- or polyvalent moiety comprising at least one polar functional group. In some embodiments, Z is a monovalent moiety comprising at least one polar functional group. In other embodiments, Z is a polyvalent moiety comprising at least one polar functional group.

In more of any of the foregoing embodiments of Formula (IV) or (V), the polar functional group is a hydroxyl, alkoxy, ester, cyano, amide, amino, alkylaminyl, heterocyclyl or heteroaryl functional group.

In any of the foregoing embodiments of Formula (IV) or (V), Z is hydroxyl, hydroxylalkyl, alkoxyalkyl, amino, aminoalkyl, alkylaminyl, alkylaminylalkyl, heterocyclyl or heterocyclylalkyl.

In some other embodiments of Formula (IV) or (V), Z has the following structure:

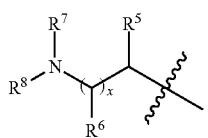

wherein:
 $R^5$ and $R^6$ are independently H or $C_1$-$C_6$ alkyl;
 $R^7$ and $R^8$ are independently H or $C_1$-$C_6$ alkyl or $R^7$ and $R^8$, together with the nitrogen atom to which they are attached, join to form a 3-7 membered heterocyclic ring; and
 x is an integer from 0 to 6.

In still different embodiments of Formula (IV) or (V), Z has the following structure:

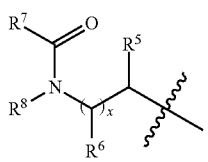

wherein:
 $R^5$ and $R^6$ are independently H or $C_1$-$C_6$ alkyl;
 $R^7$ and $R^8$ are independently H or $C_1$-$C_6$ alkyl or $R^7$ and $R^8$, together with the nitrogen atom to which they are attached, join to form a 3-7 membered heterocyclic ring; and
 x is an integer from 0 to 6.

In still different embodiments of formula (IV) or (V), Z has the following structure:

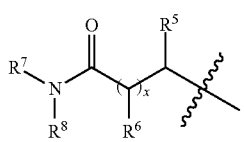

wherein:
 $R^5$ and $R^6$ are independently H or $C_1$-$C_6$ alkyl;
 $R^7$ and $R^8$ are independently H or $C_1$-$C_6$ alkyl or $R^7$ and $R^8$, together with the nitrogen atom to which they are attached, join to form a 3-7 membered heterocyclic ring; and
 x is an integer from 0 to 6.

In some other embodiments of Formula (IV) or (V), Z is hydroxylalkyl, cyanoalkyl or an alkyl substituted with one or more ester or amide groups.

For example, in any of the foregoing embodiments of Formula (IV) or (V), Z has one of the following structures:

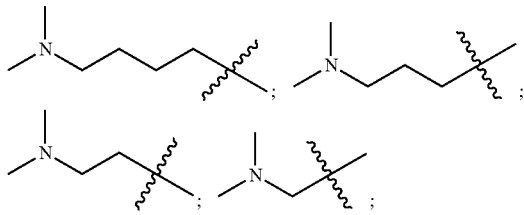

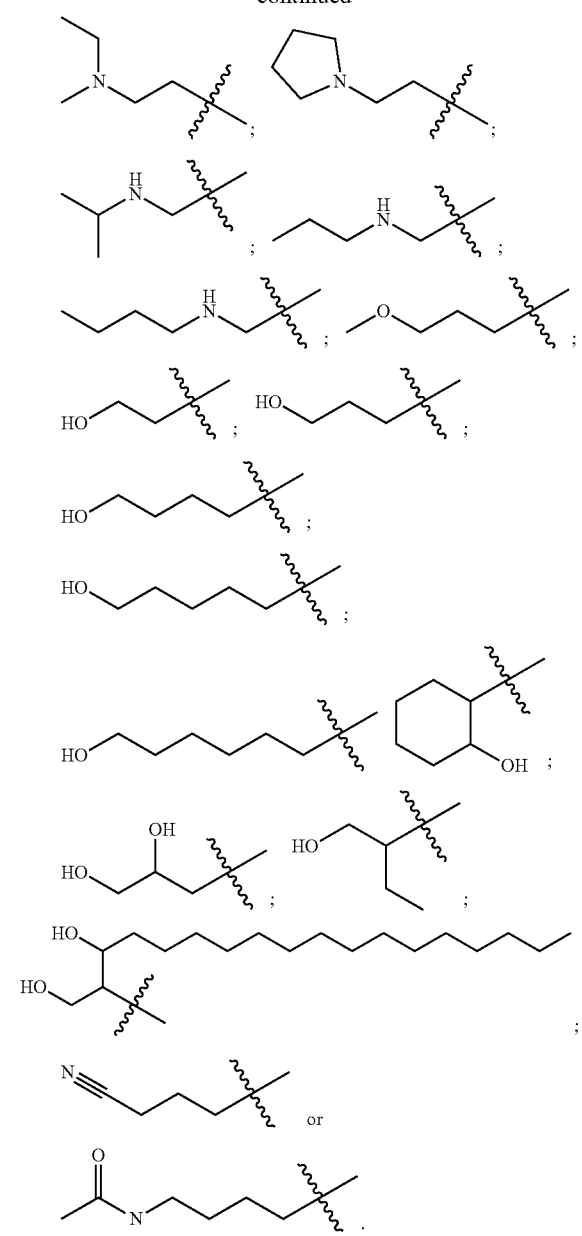

In other embodiments of Formula (IV) or (V), Z-L has one of the following structures:

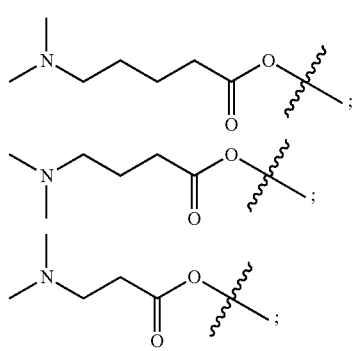

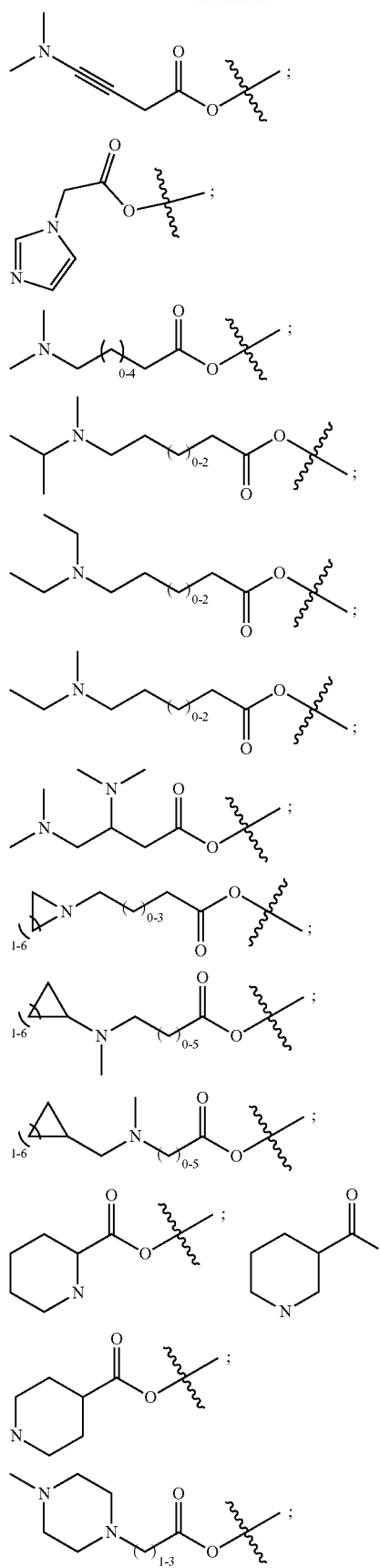
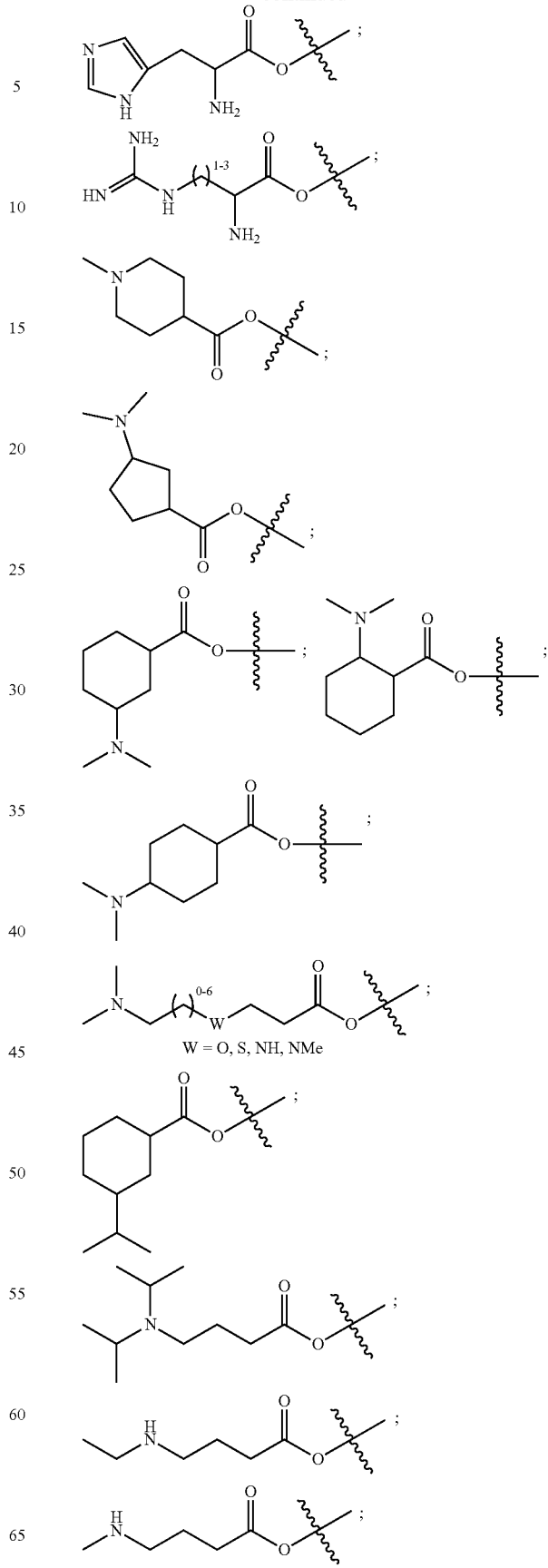

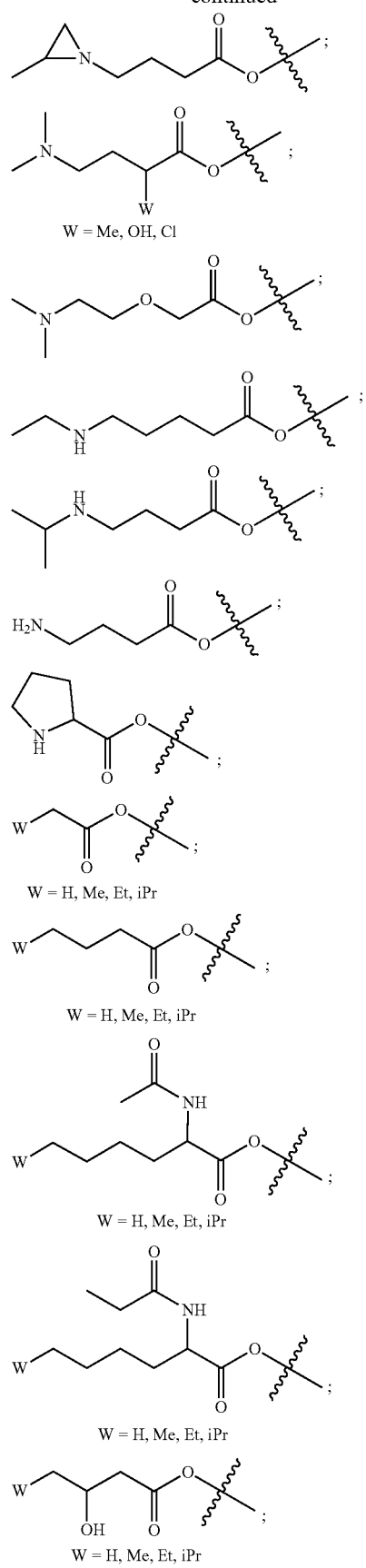
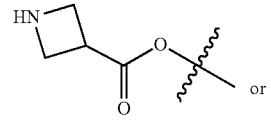

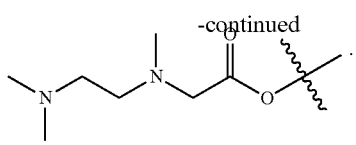
In other embodiments, Z-L has one of the following structures:
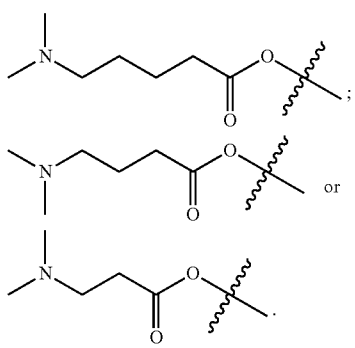
In still other embodiments, X is CH and Z-L has one of the following structures:
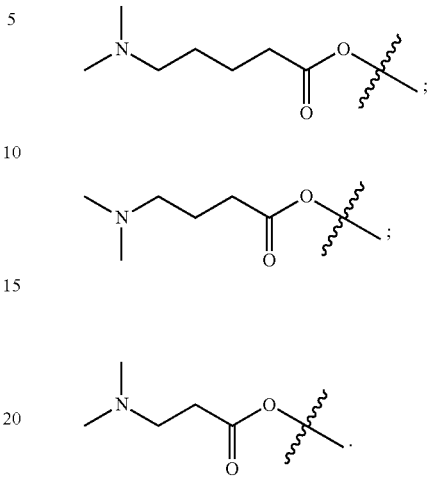
In various different embodiments, a cationic lipid has one of the structures set forth in Table 4 below.
TABLE 4
Representative Compounds of Formula (IV) or (V)
| No. | Structure |
| --- | --- |
| IV-1 | 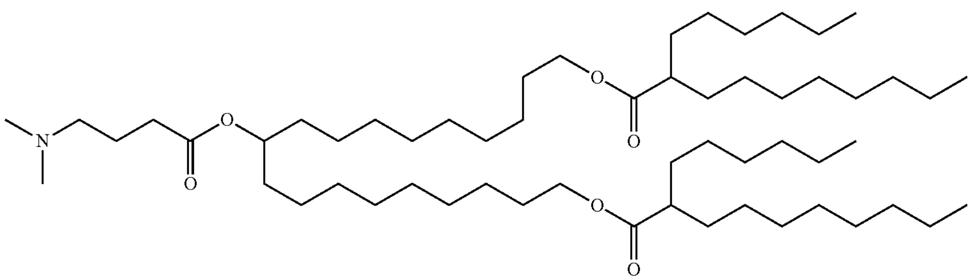 [SMILES: CCCCCCCCC(CCCCCC)C(=O)OCCCCCCCCCC(CCCCCCCCCOC(=O)C(CCCCCC)CCCCCCCC)OC(=O)CCCN(C)C] |
| IV-2 | 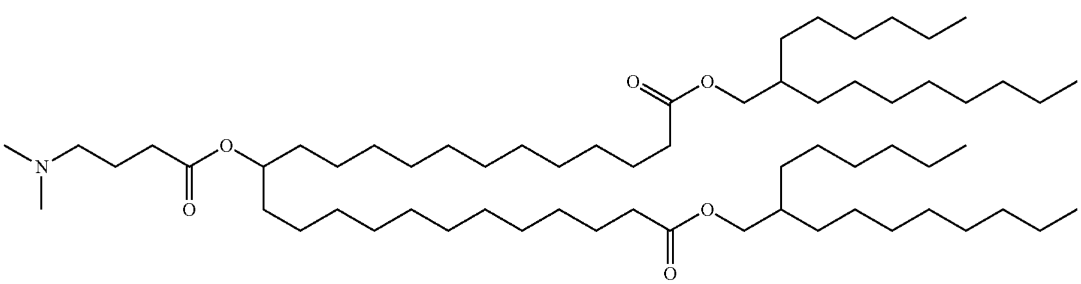 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C] |
| IV-3 | 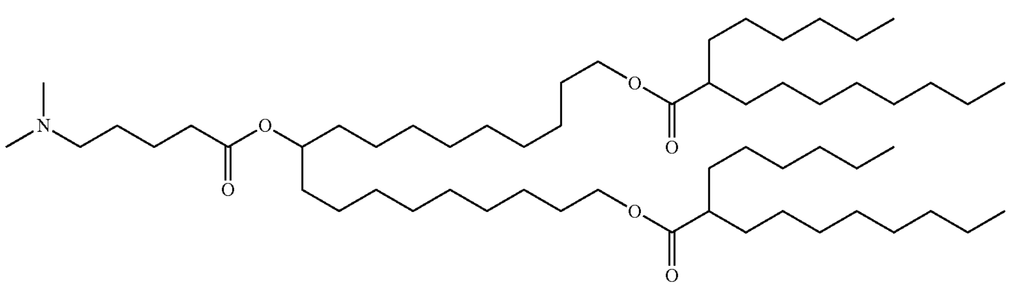 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] |

Compounds of Formula (IV) and (V) can be prepared and tested according to the procedures set forth in PCT Pub. No. WO 2017/117528, the full disclosure of which is incorporated by reference in its entirety.

Cationic Lipids of Formula VI

In still different embodiments the cationic lipid has the structure of Formula (VI):

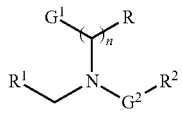

(VI)

or a pharmaceutically acceptable salt, tautomer or stereoisomer thereof, wherein:

$G^1$ is —OH, —NR$^3$R$^4$, —(C=O)NR$^5$ or —NR$^3$(C=O)R$^5$;

$G^2$ is —CH$_2$— or —(C=O)—;

R is, at each occurrence, independently H or OH;

$R^1$ and $R^2$ are each independently branched, saturated or unsaturated $C_{12}$-$C_{36}$ alkyl;

$R^3$ and $R^4$ are each independently H or straight or branched, saturated or unsaturated $C_1$-$C_6$ alkyl;

$R^5$ is straight or branched, saturated or unsaturated $C_1$-$C_6$ alkyl; and n is an integer from 2 to 6.

In some embodiments of (VI), $R^1$ and $R^2$ are each independently branched, saturated or unsaturated $C_{12}$-$C_{30}$ alkyl, $C_{12}$-$C_{20}$ alkyl, or $C_{15}$-$C_{20}$ alkyl. In some specific embodiments, $R^1$ and $R^2$ are each saturated. In certain embodiments, at least one of $R^1$ and $R^2$ is unsaturated.

In some of the foregoing embodiments of (VI), $R^1$ and $R^2$ have the following structure:

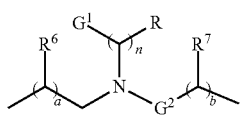

In some of the foregoing embodiments of (VI), the compound has the following structure (VIA):

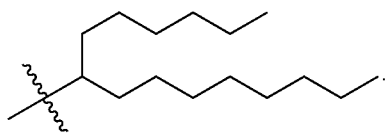 [SMILES: *C(CCCCCC)CCCCCCCC]

(VIA)

wherein:

$R^6$ and $R^7$ are, at each occurrence, independently H or straight or branched, saturated or unsaturated $C_1$-$C_{14}$ alkyl;

a and b are each independently an integer ranging from 1 to 15, provided that $R^6$ and a, and $R^7$ and b, are each independently selected such that $R^1$ and $R^2$, respectively, are each independently branched, saturated or unsaturated $C_{12}$-$C_{36}$ alkyl.

In some of the foregoing embodiments of (VI), the compound has the following structure (VIB):

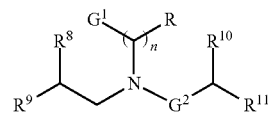

(VIB)

wherein:

$R^8$, $R^9$, $R^{10}$ and $R^{11}$ are each independently straight or branched, saturated or unsaturated $C_4$-$C_{12}$ alkyl, provided that $R^8$ and $R^9$, and $R^{10}$ and $R^{11}$, are each independently selected such that $R^1$ and $R^2$, respectively, are each independently branched, saturated or unsaturated $C_{12}$-$C_{36}$ alkyl. In some embodiments of (IB), $R^8$, $R^9$, $R^{10}$ and $R^{11}$ are each independently straight or branched, saturated or unsaturated $C_6$-$C_{10}$ alkyl. In certain embodiments of (VIB), at least one of $R^8$, $R^9$, $R^{10}$ and $R^{11}$ is unsaturated. In other certain specific embodiments of (VIB), each of $R^8$, $R^9$, $R^{10}$ and $R^{11}$ is saturated.

In some of the foregoing embodiments of (VI), the compound has structure (VIA), and in other embodiments, the compound has structure (VIB).

In some of the foregoing embodiments of (VI), $G^1$ is —OH, and in some embodiments $G^1$ is —NR$^3$R$^4$. For example, in some embodiments, $G^1$ is —NH$_2$, —NHCH$_3$ or —N(CH$_3$)$_2$. In certain embodiments, $G^1$ is —(C=O)NR$^5$. In certain other embodiments, $G^1$ is —NR$^3$(C=O)R$^5$. For example, in some embodiments $G^1$ is —NH(C=O)CH$_3$ or —NH(C=O)CH$_2$CH$_2$CH$_3$.

In some of the foregoing embodiments of (VI), $G^2$ is —CH$_2$—. In some different embodiments, $G^2$ is —(C=O)—.

In some of the foregoing embodiments of (VI), n is an integer ranging from 2 to 6, for example, in some embodiments n is 2, 3, 4, 5 or 6. In some embodiments, n is 2. In some embodiments, n is 3. In some embodiments, n is 4.

In certain of the foregoing embodiments of (VI), at least one of $R^1$, $R^2$, $R^3$, $R^4$ and $R^5$ is unsubstituted. For example, in some embodiments, $R^1$, $R^2$, $R^3$, $R^4$ and $R^5$ are each unsubstituted. In some embodiments, $R^3$ is substituted. In other embodiments $R^4$ is substituted. In still more embodiments, $R^5$ is substituted. In certain specific embodiments, each of $R^3$ and $R^4$ are substituted. In some embodiments, a substituent on $R^3$, $R^4$ or $R^5$ is hydroxyl. In certain embodiments, $R^3$ and $R^4$ are each substituted with hydroxyl.

In some of the foregoing embodiments of (VI), at least one R is OH. In other embodiments, each R is H.

In various different embodiments of (VI), the compound has one of the structures set forth in Table 5 below.

TABLE 5

Representative Compounds of Formula (VI)

| No. | Structure |
|---|---|
| VI-1 | 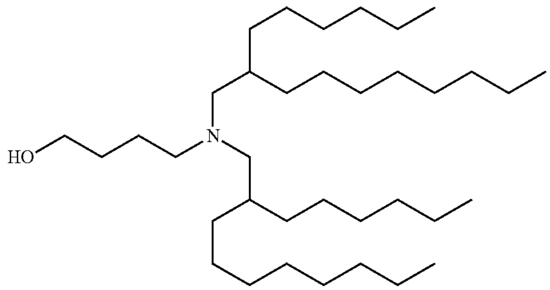 [SMILES: CCCCCCCCC(CCCCCC)CN(CCCCO)CC(CCCCCC)CCCCCCCC] |
| VI-2 | 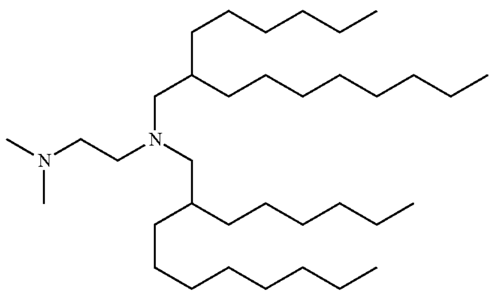 [SMILES: CCCCCCCCC(CCCCCC)CN(CCN(C)C)CC(CCCCCC)CCCCCCCC] |
| VI-3 | 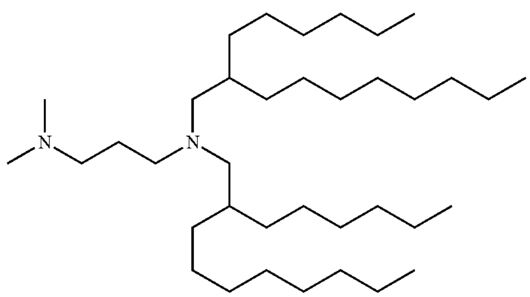 [SMILES: CCCCCCCCC(CCCCCC)CN(CCCN(C)C)CC(CCCCCC)CCCCCCCC] |
| VI-4 | 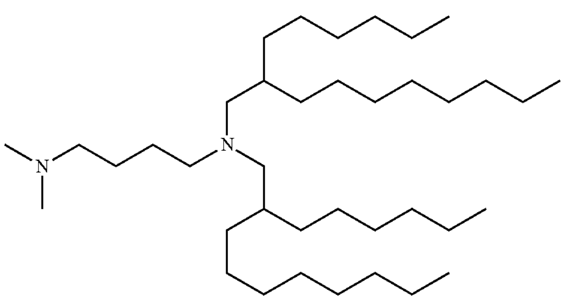 [SMILES: CCCCCCCCC(CCCCCC)CN(CCCCN(C)C)CC(CCCCCC)CCCCCCCC] |
| VI-5 | 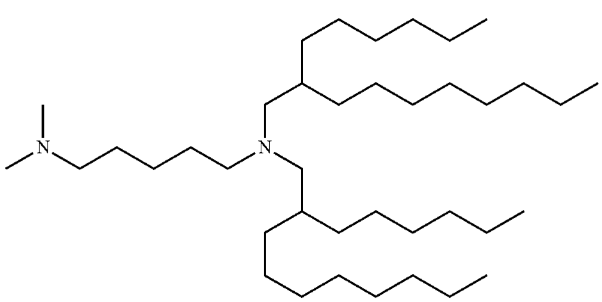 [SMILES: CCCCCCCCC(CCCCCC)CN(CCCCCN(C)C)CC(CCCCCC)CCCCCCCC] |

TABLE 5-continued
Representative Compounds of Formula (VI)
| No. | Structure |
|---|---|
| VI-6 | 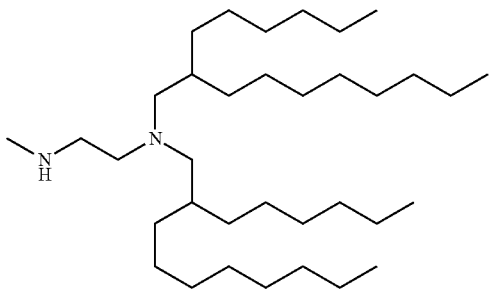 [SMILES: CCCCCCCCC(CCCCCC)CN(CCNC)CC(CCCCCC)CCCCCCCC] |
| VI-7 | 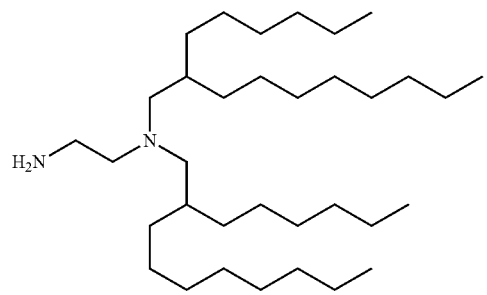 [SMILES: CCCCCCCCC(CCCCCC)CN(CCN)CC(CCCCCC)CCCCCCCC] |
| VI-8 | 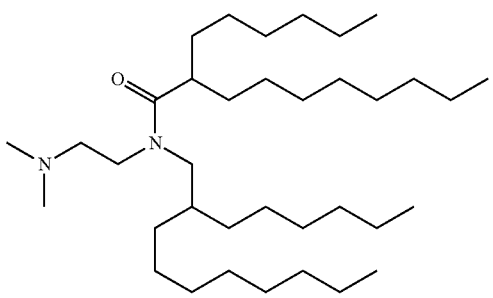 [SMILES: CCCCCCCCC(CCCCCC)CN(CCN(C)C)C(=O)C(CCCCCC)CCCCCCCC] |
| VI-9 | 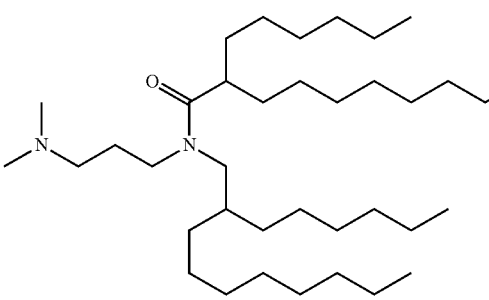 |
| VI-10 | 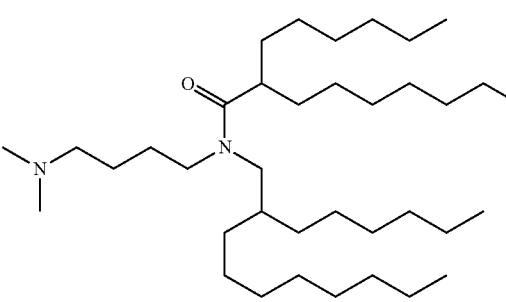 |

TABLE 5-continued

Representative Compounds of Formula (VI)

| No. | Structure |
| --- | --- |
| VI-11 | 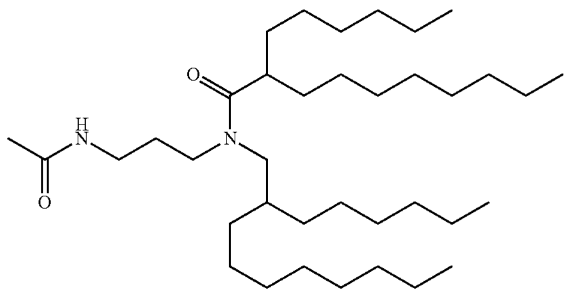 [SMILES: CCCCCCCCC(CCCCCC)CN(CCCNC(C)=O)C(=O)C(CCCCCC)CCCCCCCC] |
| VI-12 | 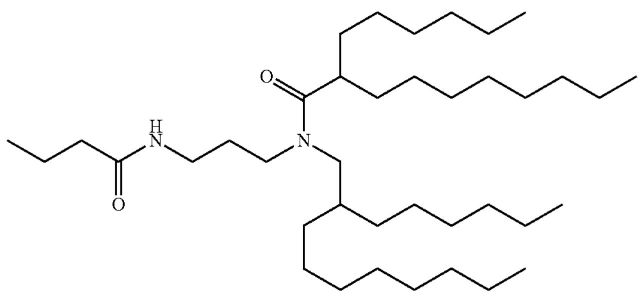 [SMILES: CCCCCCCCC(CCCCCC)CN(CCCNC(=O)CCC)C(=O)C(CCCCCC)CCCCCCCC] |
| VI-13 | 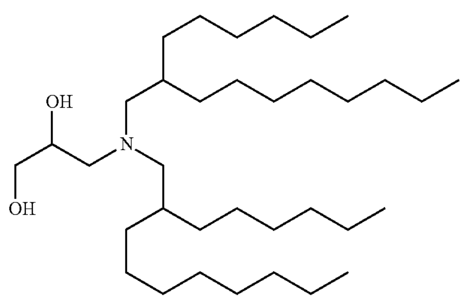 [SMILES: CCCCCCCCC(CCCCCC)CN(CC(O)CO)CC(CCCCCC)CCCCCCCC] |
| VI-14 | 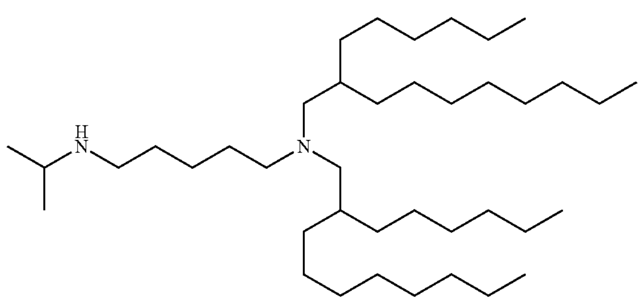 [SMILES: CCCCCCCCC(CCCCCC)CN(CCCCCNC(C)C)CC(CCCCCC)CCCCCCCC] |
| VI-15 | 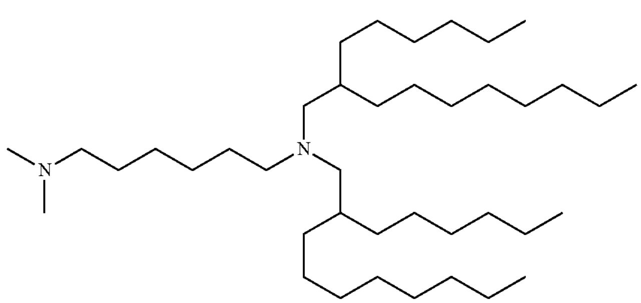 [SMILES: CCCCCCCCC(CCCCCC)CN(CCCCCCN(C)C)CC(CCCCCC)CCCCCCCC] |

TABLE 5-continued

Representative Compounds of Formula (VI)

| No. | Structure |
|---|---|
| VI-16 | 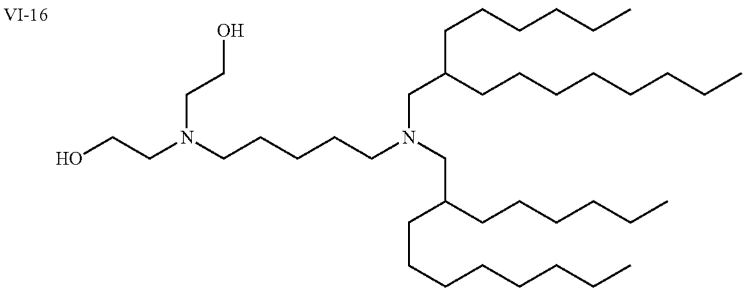 |
| VI-17 | 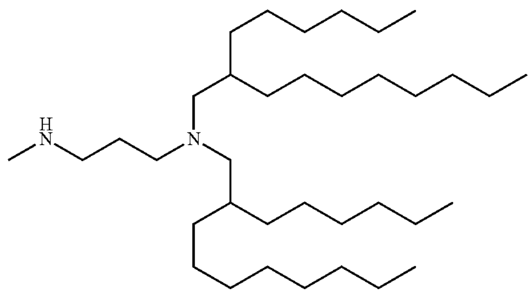 [SMILES: CCCCCCCCC(CCCCCC)CN(CCCNC)CC(CCCCCC)CCCCCCCC] |

Compounds of Formula (VI) can be prepared and tested according to the procedures set forth in PCT Pub. No. WO 2018/191657, the full disclosure of which is incorporated by reference in its entirety.

Cationic Lipids of Formula VII

In still different embodiments the cationic lipid has the structure of Formula (VII):

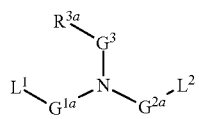

(VII)

or a pharmaceutically acceptable salt, tautomer or stereoisomer thereof, wherein:

$L^1$ is —O(C=O)R$^1$, —(C=O)OR$^1$, —C(=O)R$^1$, —OR$^1$, —S(O)$_x$R$^1$, —S—SR$^1$, —C(=O)SR$^1$, —SC(=O)R$^1$, —NR$^a$C(=O)R$^1$, —C(=O)NR$^b$R$^c$, —NR$^a$C(=O)NR$^b$R$^c$, —OC(=O)NR$^b$R$^c$ or —NR$^a$C(=O)OR$^1$;

$L^2$ is —O(C=O)R$^2$, —(C=O)OR$^2$, —C(=O)R$^2$, —OR$^2$, —S(O)$_x$R$^2$, —S—SR$^2$, —C(=O)SR$^2$, —SC(=O)R$^2$, —NR$^d$C(=O)R$^2$, —C(=O)NR$^e$R$^f$, —NR$^d$C(=O)NR$^e$R$^f$, —OC(=O)NR$^e$R$^f$; —NR$^d$C(=O)OR$^2$ or a direct bond to R$^2$;

$G^{1a}$ and $G^{2a}$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3a}$ is —C(=O)N(R$^{4a}$)R$^{5a}$ or —C(=O)OR$^6$;

$R^{4a}$ is $C_1$-$C_{12}$ alkyl;

$R^{5a}$ is H or $C_1$-$C_8$ alkyl or $C_2$-$C_8$ alkenyl;

$R^6$ is H, aryl or aralkyl; and x is 0, 1 or 2, and wherein each alkyl, alkenyl, alkylene, alkenylene, cycloalkylene, cycloalkenylene, aryl and aralkyl is independently substituted or unsubstituted.

In certain embodiments of structure (VII), $G^3$ is unsubstituted. In more specific embodiments of structure (VII), $G^3$ is $C_2$-$C_{12}$ alkylene, for example, in some embodiments of structure (VII), $G^3$ is $C_3$-$C_7$ alkylene, or in other embodiments of structure (I), $G^3$ is $C_3$-$C_{12}$ alkylene. In some embodiments of structure (VII), $G^3$ is $C_2$ or $C_3$ alkylene.

In some of the foregoing embodiments of structure (VII), the compound has the following structure (VIIA):

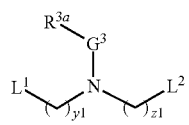

(IA)

wherein y1 and z1 are each independently integers ranging from 2 to 12, for example an integer from 2 to 6, for example 4.

In some of the foregoing embodiments of structure (VII), $L^1$ is —O(C=O)R$^1$, —(C=O)OR$^1$ or —C(=O)NR$^b$R$^c$, and $L^2$ is —O(C=O)R$^2$, —(C=O)OR$^2$ or —C(=O)NR$^e$R$^f$. For example, in some embodiments of structure (VII) $L^1$ and $L^2$ are —(C=O)OR$^1$ and —(C=O)OR$^2$, respectively. In other embodiments of structure (VII) $L^1$ is —(C=O)OR$^1$ and $L^2$ is —C(=O)NR$^e$R$^f$. In other embodiments of structure (VII) $L^1$ is —C(=O)NR$^b$R$^c$ and $L^2$ is —C(=O)NR$^e$R$^f$.

In other embodiments of the foregoing, the compound has one of the following structures (VIIB), (VIIC), (VIID) or (VIIE):

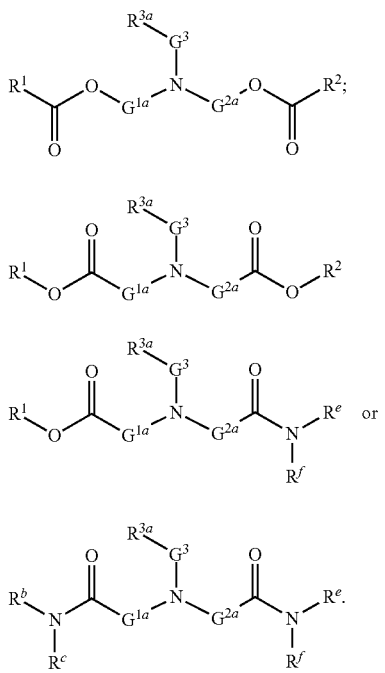

(VIIB)

(VIIC)

(VIID)

(VIIE)

In some of the foregoing embodiments, the compound has structure (VIIB), in other embodiments, the compound has structure (VIIC) and in still other embodiments the compound has the structure (VIID). In other embodiments, the compound has structure (VIIE).

In some different embodiments of the foregoing, the compound has one of the following structures (VIIF), (VIIG), (VIIH) or (VIIJ):

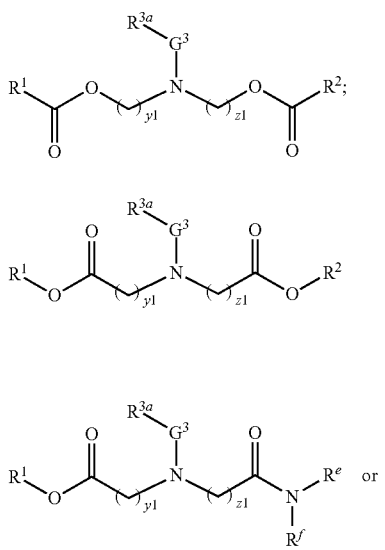

(VIIF)

(VIIG)

(VIIH)

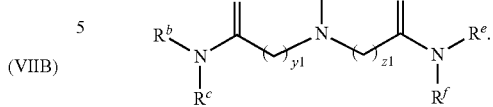

(VIIJ)

wherein y1 and z1 are each independently integers ranging from 2 to 12, for example an integer from 2 to 6, for example 4.

In some of the foregoing embodiments of structure (VII), y1 and z1 are each independently an integer ranging from 2 to 10, 2 to 8, from 4 to 10 or from 4 to 7. For example, in some embodiments of structure (VII), y1 is 4, 5, 6, 7, 8, 9, 10, 11 or 12. In some embodiments of structure (VII), z1 is 4, 5, 6, 7, 8, 9, 10, 11 or 12. In some embodiments of structure (VII), y1 and z1 are the same, while in other embodiments of structure (VII) y1 and z1 are different.

In some of the foregoing embodiments of structure (VII), $R^1$ or $R^2$, or both is branched $C_6$-$C_{24}$ alkyl. For example, in some embodiments of structure (VII), $R^1$ and $R^2$ each, independently have the following structure:

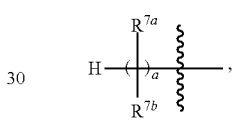

wherein:
  $R^7$ and $R^{7b}$ are, at each occurrence, independently H or $C_1$-$C_{12}$ alkyl; and
  a is an integer from 2 to 12,
wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (VII), at least one occurrence of $R^{7a}$ is H. For example, in some embodiments of structure (VII), $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of structure (VII), $R^1$ or $R^2$, or both, has one of the following structures:

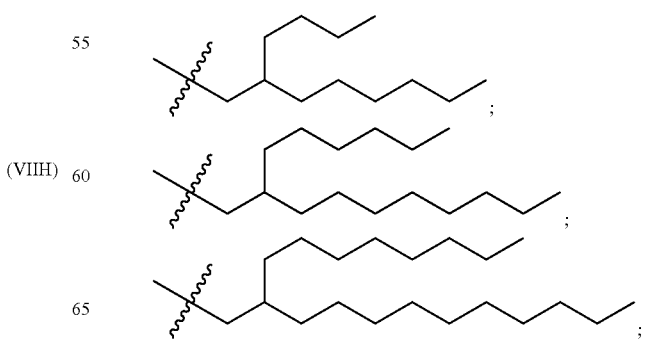

-continued

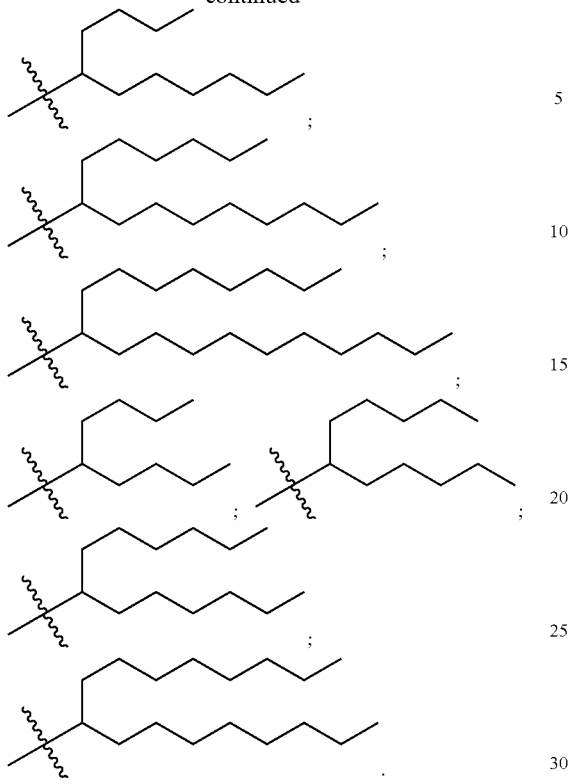

In some of the foregoing embodiments of structure (VII), $R^b$, $R^c$, $R^e$ and $R^f$ are each independently $C_3$-$C_{12}$ alkyl. For example, in some embodiments of structure (VII) $R^b$, $R^c$, $R^e$ and $R^f$ are n-hexyl and in other embodiments of structure (VII) $R^b$, $R^c$, $R^e$ and $R^f$ are n-octyl.

In some of the foregoing embodiments of structure (VII), $R^{3a}$ is —C(=O)N($R^{4a}$)$R^{5a}$. In more specific embodiments of structure (VII), $R^{4a}$ is ethyl, propyl, n-butyl, n-hexyl, n-octyl or n-nonyl. In certain embodiments of structure (VII), $R^{5a}$ is H, methyl, ethyl, propyl, n-butyl, n-hexyl or n-octyl. In some of these embodiments of structure (VII), $R^{4a}$ and/or $R^{5a}$ is optionally substituted with a substituent, for example hydroxyl.

In some embodiments of structure (VII), $R^{3a}$ is —C(=O)$OR^6$. In certain embodiments of structure (VII), $R^6$ is benzyl and in other embodiments $R^6$ is H.

In some of the foregoing embodiments of structure (VII), $R^{4a}$, $R^{5a}$ and $R^6$ are independently optionally substituted with one or more substituents selected from the group consisting of —$OR^g$, —$NR^gC(=O)R^h$, —$C(=O)NR^gR^h$, —$C(=O)R^h$, —$OC(=O)R^h$, —$C(=O)OR^h$ and —$OR^iOH$, wherein:

$R^g$ is, at each occurrence independently H or $C_1$-$C_6$ alkyl;
$R^h$ is at each occurrence independently $C_1$-$C_6$ alkyl; and
$R^i$ is, at each occurrence independently $C_1$-$C_6$ alkylene.

In certain specific embodiments of structure (VII), $R^{3a}$ has one of the following structures:

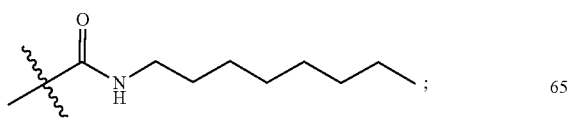

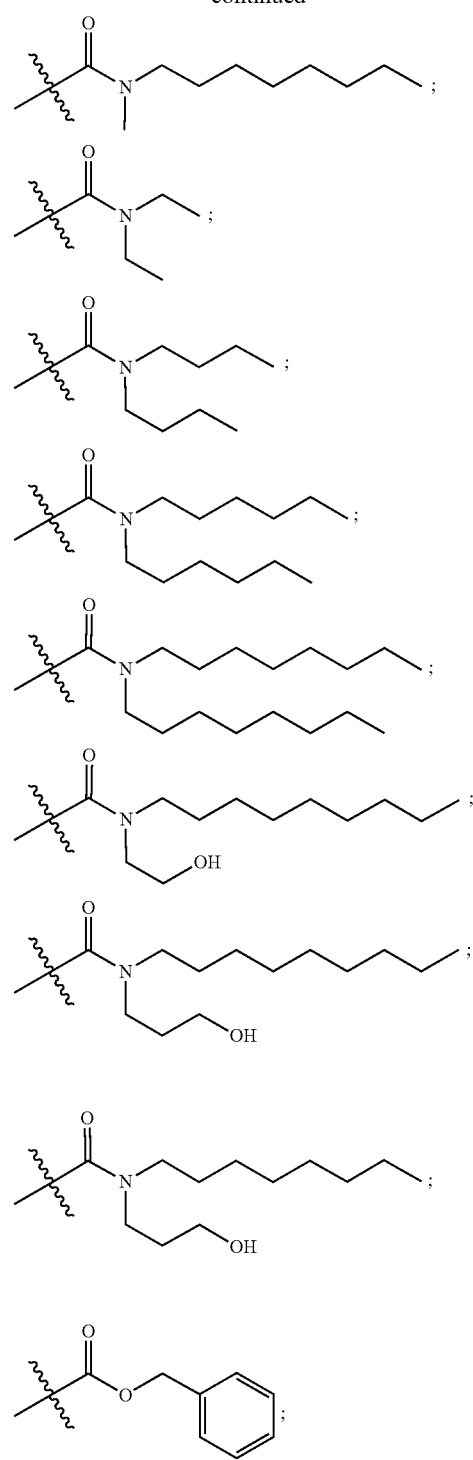

143
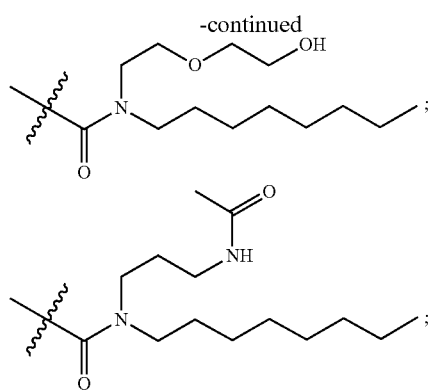
144
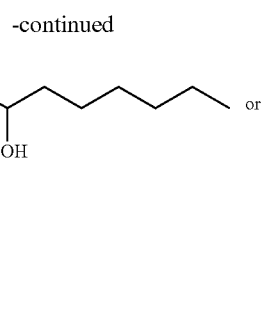
In various different embodiments, the compound has one of the structures set forth in Table 6 below.
TABLE 6
Representative Compounds of Structure (VII)
| No. | Structure |
|---|---|
| VII-1 | 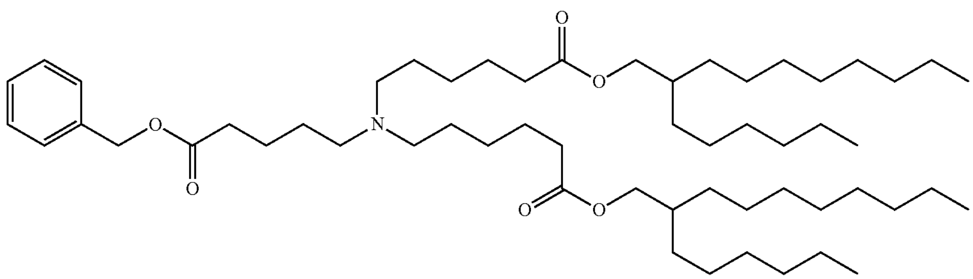 [SMILES: CCCCCCCCC(CCCCCC)COC(=O)CCCCCN(CCCCCC(=O)OCC(CCCCCC)CCCCCCCC)CCCCC(=O)OCc1ccccc1] |
| VII-2 | 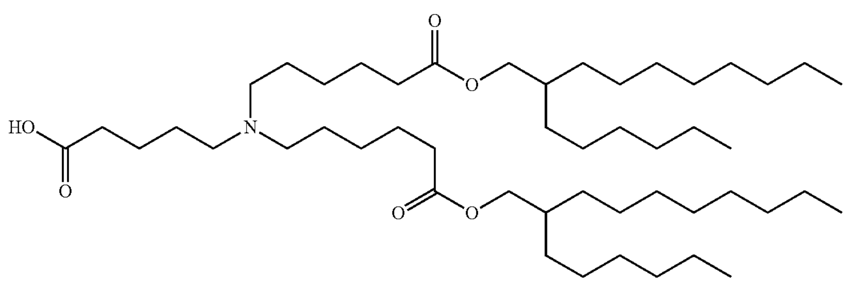 [SMILES: CCCCCCCCC(CCCCCC)COC(=O)CCCCCN(CCCCCC(=O)OCC(CCCCCC)CCCCCCCC)CCCCC(=O)O] |
| VII-3 | 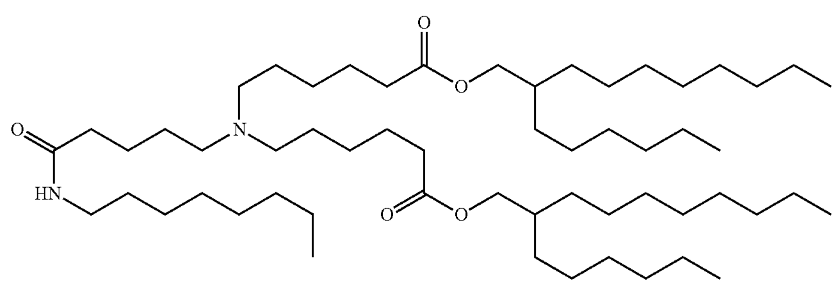 [SMILES: CCCCCCCCNC(=O)CCCCN(CCCCCC(=O)OCC(CCCCCC)CCCCCCCC)CCCCCC(=O)OCC(CCCCCC)CCCCCCCC] |
| VII-4 | 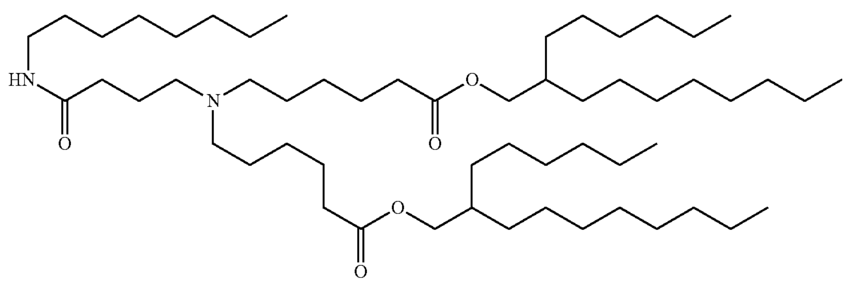 [SMILES: CCCCCCCCNC(=O)CCCN(CCCCCC(=O)OCC(CCCCCC)CCCCCCCC)CCCCCC(=O)OCC(CCCCCC)CCCCCCCC] |

TABLE 6-continued

Representative Compounds of Structure (VII)

| No. | Structure |
|---|---|
| VII-5 | 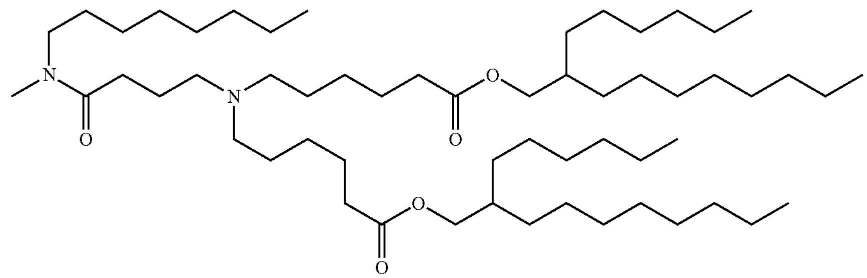 [SMILES: CCCCCCCCC(CCCCCC)COC(=O)CCCCCN(CCCCCC(=O)OCC(CCCCCC)CCCCCCCC)CCCC(=O)N(C)CCCCCCCC] |
| VII-6 | 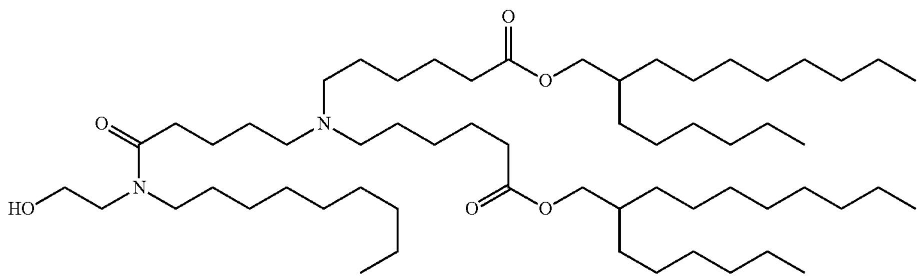 [SMILES: CCCCCCCCCN(CCO)C(=O)CCCCN(CCCCCC(=O)OCC(CCCCCC)CCCCCCCC)CCCCCC(=O)OCC(CCCCCC)CCCCCCCC] |
| VII-7 | 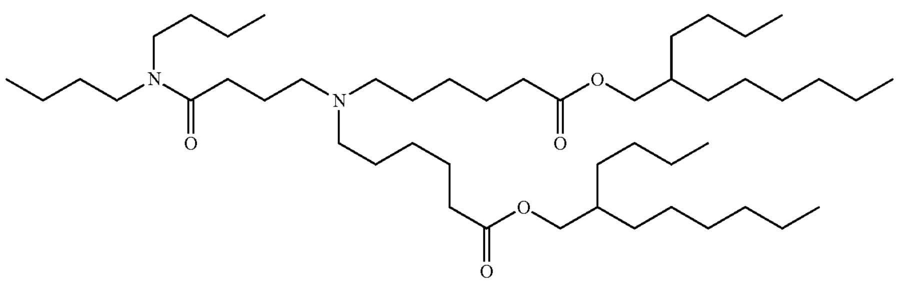 [SMILES: CCCCCCC(CCCC)COC(=O)CCCCCN(CCCCCC(=O)OCC(CCCC)CCCCCC)CCCC(=O)N(CCCC)CCCC] |
| VII-8 | 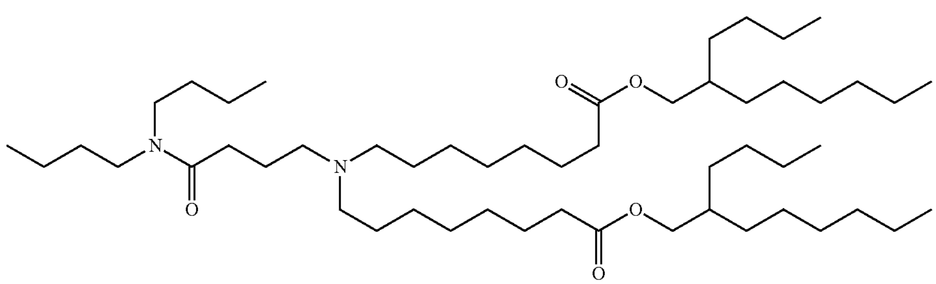 [SMILES: CCCCCCC(CCCC)COC(=O)CCCCCCCN(CCCCCCCC(=O)OCC(CCCC)CCCCCC)CCCC(=O)N(CCCC)CCCC] |
| VII-9 | 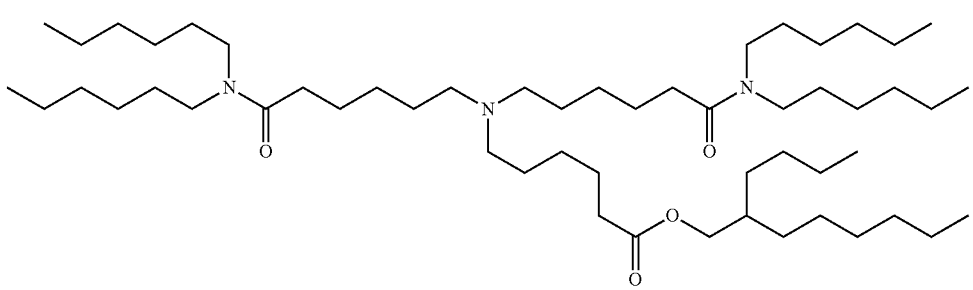 [SMILES: CCCCCCC(CCCC)COC(=O)CCCCCN(CCCCCC(=O)N(CCCCCC)CCCCCC)CCCCCC(=O)N(CCCCCC)CCCCCC] |

TABLE 6-continued

Representative Compounds of Structure (VII)

| No. | Structure |
|---|---|
| VII-10 | 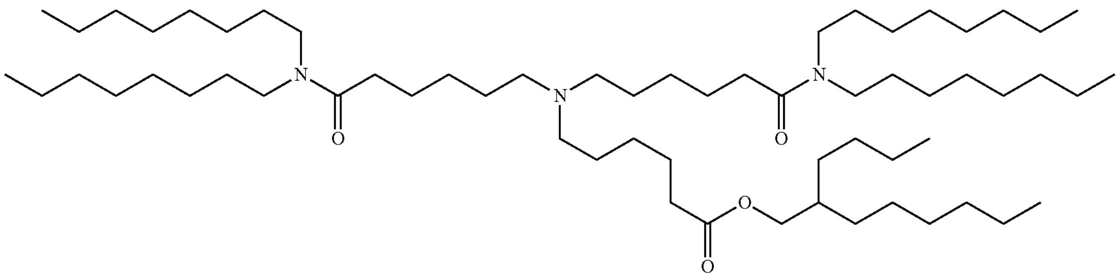 [SMILES: CCCCCCCCN(CCCCCCCC)C(=O)CCCCCN(CCCCCC(=O)OCC(CCCC)CCCCCC)CCCCCC(=O)N(CCCCCCCC)CCCCCCCC] |
| VII-11 | 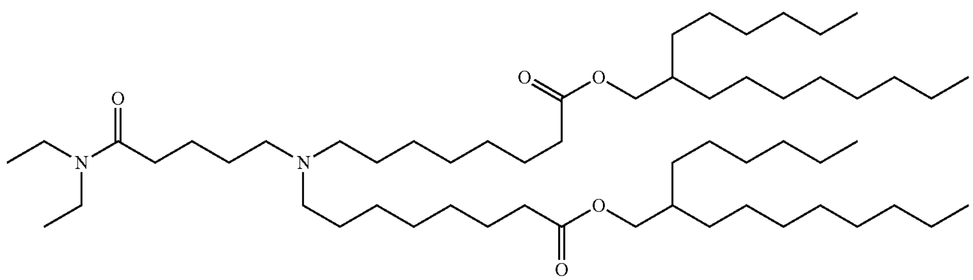 [SMILES: CCCCCCCCC(CCCCCC)COC(=O)CCCCCCCN(CCCCCCCC(=O)OCC(CCCCCC)CCCCCCCC)CCCCC(=O)N(CC)CC] |
| VII-12 | 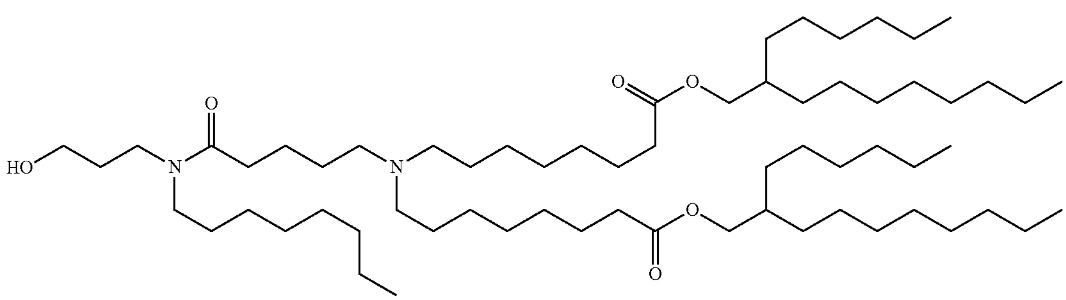 [SMILES: CCCCCCCCC(CCCCCC)COC(=O)CCCCCCCN(CCCCCCCC(=O)OCC(CCCCCC)CCCCCCCC)CCCCC(=O)N(CCCO)CCCCCCCC] |
| VII-13 | 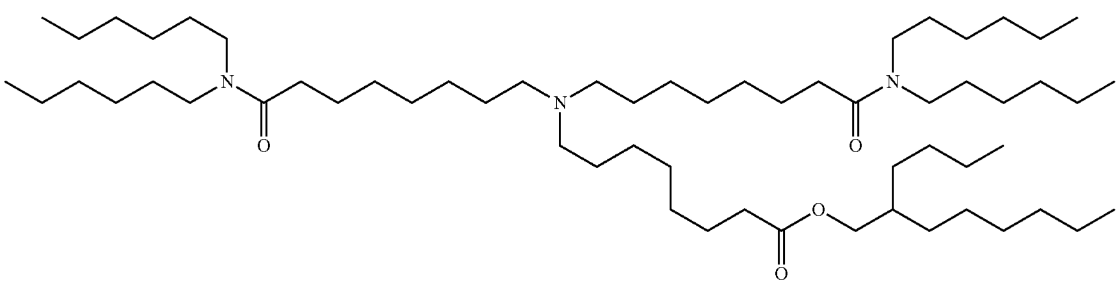 [SMILES: CCCCCCC(CCCC)COC(=O)CCCCCCCN(CCCCCCCC(=O)N(CCCCCC)CCCCCC)CCCCCCCC(=O)N(CCCCCC)CCCCCC] |
| VII-14 | 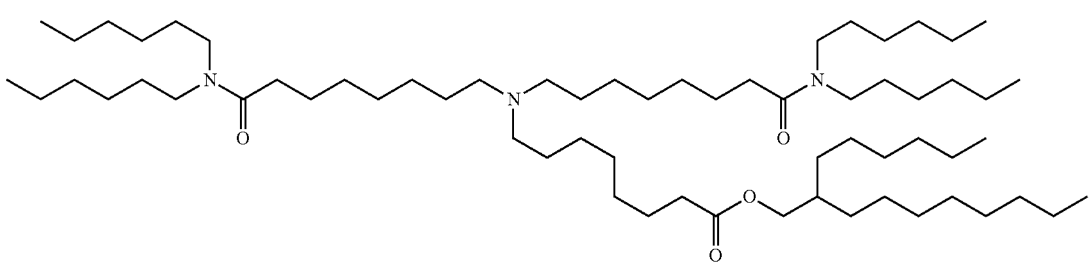 [SMILES: CCCCCCCCC(CCCCCC)COC(=O)CCCCCCCN(CCCCCCCC(=O)N(CCCCCC)CCCCCC)CCCCCCCC(=O)N(CCCCCC)CCCCCC] |

TABLE 6-continued
Representative Compounds of Structure (VII)
| No. | Structure |
|---|---|
| VII-15 | 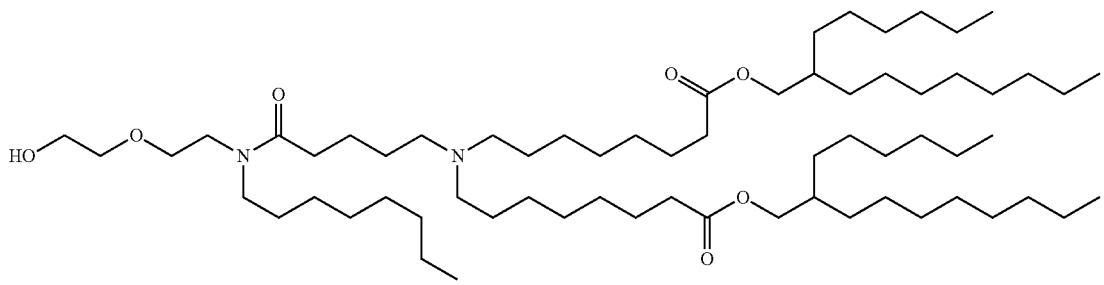 [SMILES: CCCCCCCCC(CCCCCC)COC(=O)CCCCCCCN(CCCCCCCC(=O)OCC(CCCCCC)CCCCCCCC)CCCCC(=O)N(CCCCCCCC)CCOCCO] |
| VII-16 | 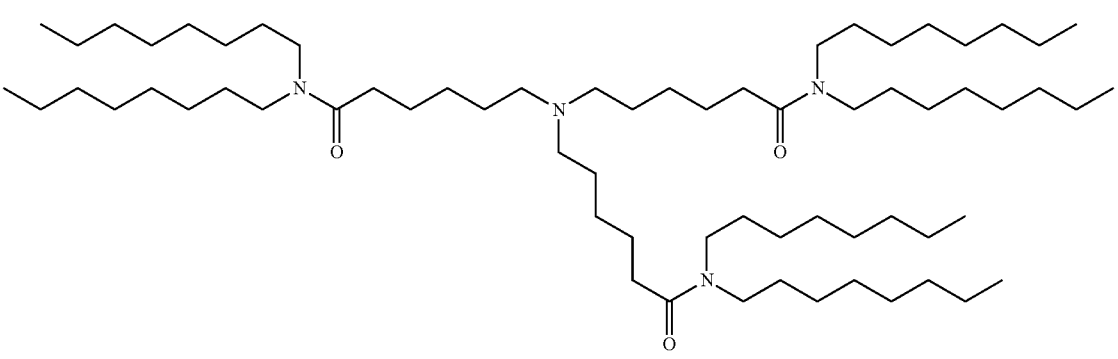 [SMILES: CCCCCCCCN(CCCCCCCC)C(=O)CCCCCN(CCCCCC(=O)N(CCCCCCCC)CCCCCCCC)CCCCCC(=O)N(CCCCCCCC)CCCCCCCC] |
| VII-17 | 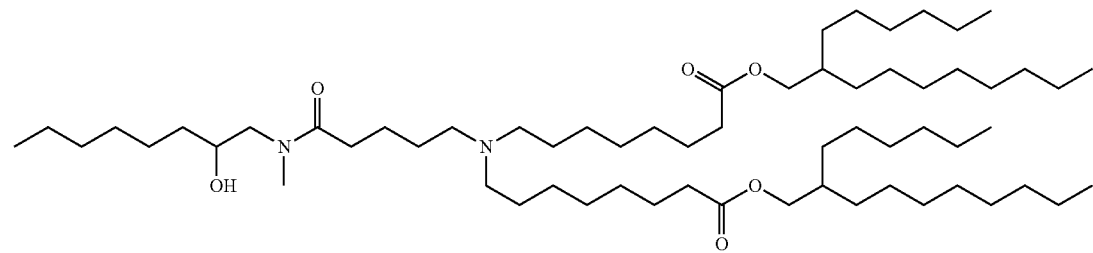 [SMILES: CCCCCCCCC(CCCCCC)COC(=O)CCCCCCCN(CCCCCCCC(=O)OCC(CCCCCC)CCCCCCCC)CCCCC(=O)N(C)CC(O)CCCCCC] |
| VII-18 | 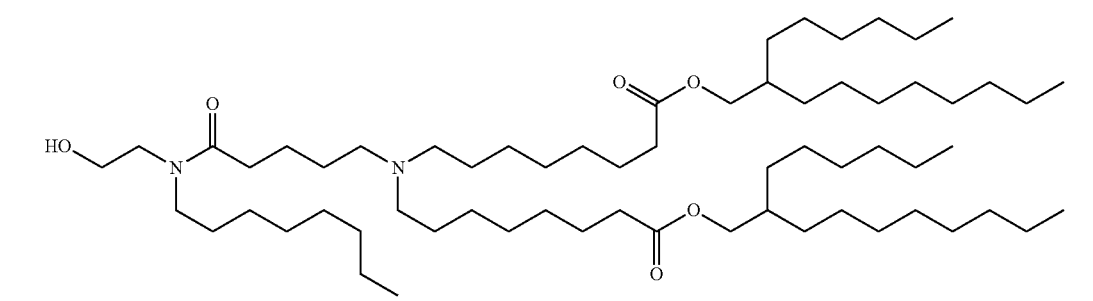 [SMILES: CCCCCCCCC(CCCCCC)COC(=O)CCCCCCCN(CCCCCCCC(=O)OCC(CCCCCC)CCCCCCCC)CCCCC(=O)N(CCO)CCCCCCCC] |
| VII-19 | 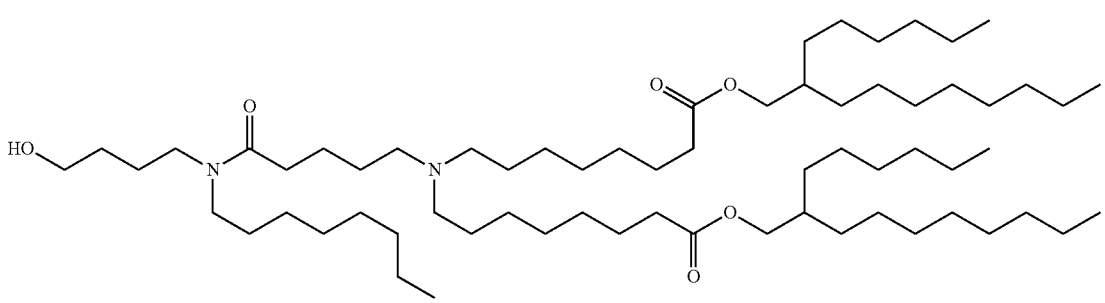 [SMILES: CCCCCCCCC(CCCCCC)COC(=O)CCCCCCCN(CCCCCCCC(=O)OCC(CCCCCC)CCCCCCCC)CCCCC(=O)N(CCCCO)CCCCCCCC] |

Compounds of Formula (VII) can be prepared and tested according to the procedures set forth in PCT Pub. No. WO 2018/200943, the full disclosure of which is incorporated by reference in its entirety.

Cationic Lipids of Formula VIII

In still different embodiments the cationic lipid has the structure of Formula (VIII):

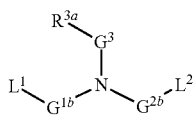

(VIII)

or a pharmaceutically acceptable salt, tautomer or stereoisomer thereof, wherein:

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$ or —N$R^a$C(=O)O$R^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^c$C(=O)N$R^e$$R^f$, —OC(=O)N$R^e$$R^f$; —N$R^d$C(=O)O$R^2$ or a direct bond;

$G^{1b}$ and $G^{2b}$ are each independently $C_1$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene, $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3b}$ is —N$R^{4b}$C(=O)$R^{5b}$;

$R^{4b}$ is H, $C_1$-$C_{12}$ alkyl or $C_2$-$C_{12}$ alkenyl;

$R^{5b}$ is $C_2$-$C_{12}$ alkyl or $C_2$-$C_{12}$ alkenyl when $R^{4b}$ is H; or $R^5$ is $C_1$-$C_{12}$ alkyl or $C_2$-$C_{12}$ alkenyl when $R^{4b}$ is $C_1$-$C_{12}$ alkyl or $C_2$-$C_{12}$ alkenyl; and x is 0, 1 or 2, and wherein each alkyl, alkenyl, alkylene, alkenylene, cycloalkylene and cycloalkenylene is independently substituted or unsubstituted.

In certain embodiments of structure (VIII), $G^3$ is unsubstituted. In more specific embodiments of structure (VIII) $G^3$ is $C_1$-$C_{12}$ alkylene, for example, $G^3$ is $C_3$-$C_5$ alkylene or $G^3$ is $C_3$-$C_{12}$ alkylene.

In some of the foregoing embodiments, the compound has the following structure (VIIIA).

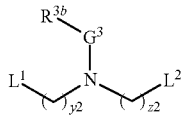

(VIIIA)

wherein y2 and z2 are each independently integers ranging from 1 to 12.

In some of the foregoing embodiments of structure (VIII), $L^1$ and $L^2$ are each independently —O(C=O)$R^1$ or —(C=O)O$R^1$.

In other embodiments of the foregoing, the compound has one of the following structures (VIIIB) or (VIIIC):

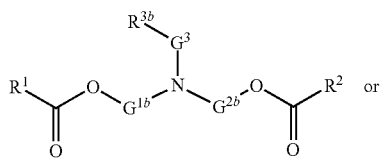

(VIIIB)

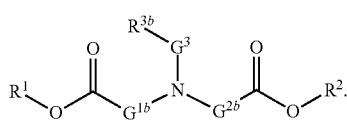

(VIIIC)

In some of the foregoing embodiments, the compound has structure (VIIIB), in other embodiments, the compound has structure (VIIIC).

In some embodiments, the compound has one of the following structures (VIIID) or (VIIIE):

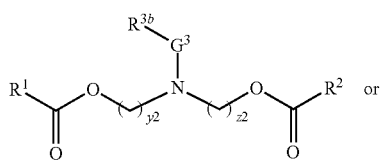

(VIIID)

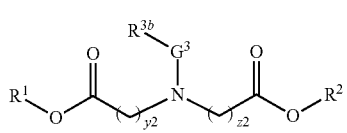

(VIIIE)

wherein y2 and z2 are each independently integers ranging from 1 to 12.

In some of the foregoing embodiments of structure (VIII), y2 and z2 are each independently an integer ranging from 2 to 12, for example from 2 to 10, from 2 to 8, from 4 to 7 or from 4 to 10. For example, in some embodiments of structure (VIII), y2 is 4, 5, 6, 7, 8, 9, 10, 11 or 12. In some embodiments of structure (VIII), z2 is 4, 5, 6, 7, 8, 9, 10, 11 or 12. In some embodiments of structure (VIII), y2 and z2 are the same, while in other embodiments of structure (VIII), y2 and z2 are different.

In some of the foregoing embodiments of structure (VIII), $R^1$ or $R^2$, or both is branched $C_6$-$C_{24}$ alkyl. For example, in some embodiments of structure (VIII), $R^1$ and $R^2$ each, independently have the following structure:

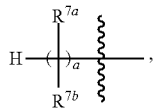

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of structure (VIII), at least one occurrence of $R^{7a}$ is H. For example, in some embodiments of structure (VIII), $R^{7a}$ is H at each occurrence. In other different embodiments of the foregoing, at least one occurrence of $R^{7b}$ is $C_1$-$C_8$ alkyl. For example, in some embodiments of structure (VIII), $C_1$-$C_8$ alkyl is methyl, ethyl, n-propyl, iso-propyl, n-butyl, iso-butyl, tert-butyl, n-hexyl or n-octyl.

In different embodiments of structure (VIII), $R^1$ or $R^2$, or both, has one of the following structures:

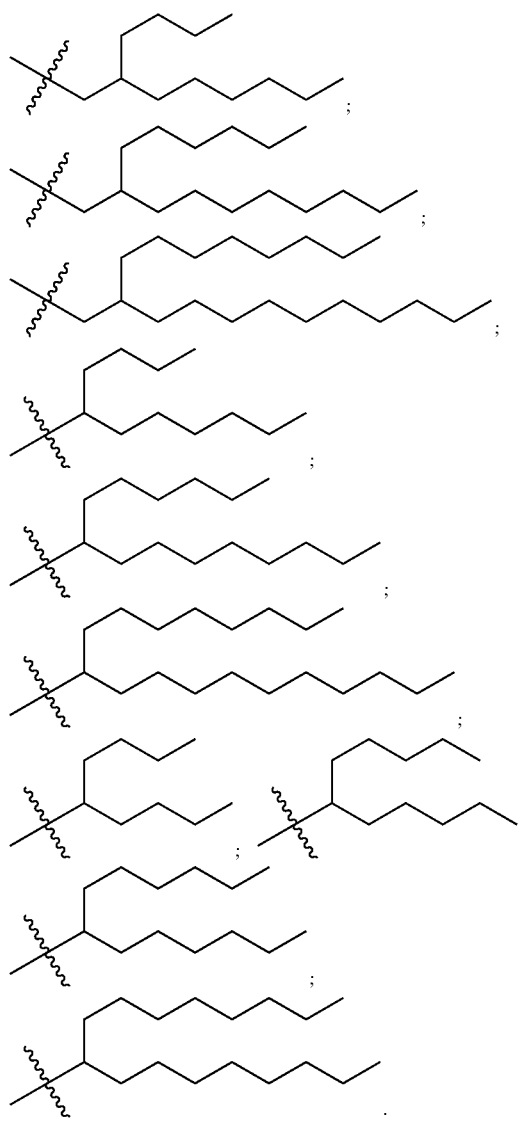

In some of the foregoing embodiments of structure (VIII), $R^{4b}$ is H, methyl, ethyl, propyl or octyl. In some embodiments of structure (VIII), $R^{5b}$ is methyl, ethyl, propyl, heptyl or octyl, for example n-heptyl or n-octyl.

In certain related embodiments of structure (VIII), $R^{4b}$ and $R^{5b}$ are independently optionally substituted with one or more substituents selected from the group consisting of —$OR^g$, —$NR^gC(=O)R^h$, —$C(=O)NR^gR^h$, —$C(=O)R^h$, —$OC(=O)R^h$, —$C(=O)OR^h$ and —$OR^hOH$, wherein:

$R^g$ is, at each occurrence independently H or $C_1$-$C_6$ alkyl;
$R^h$ is at each occurrence independently $C_1$-$C_6$ alkyl; and $R^i$ is, at each occurrence independently $C_1$-$C_6$ alkylene.

In certain specific embodiments of structure (VIII), $R^{3b}$ has one of the following structures:

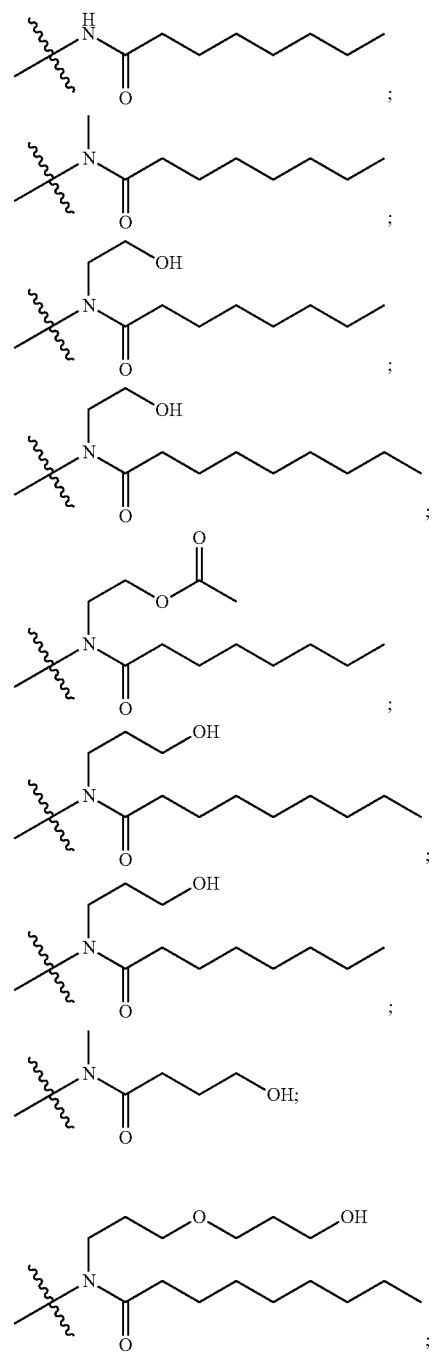

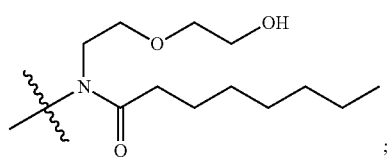

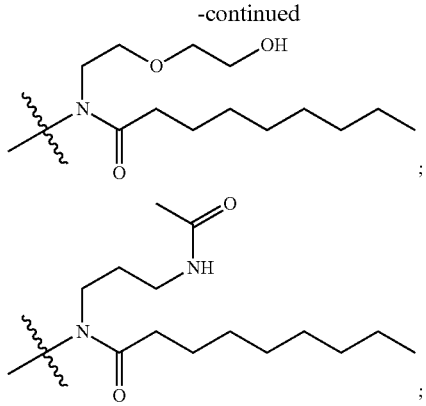
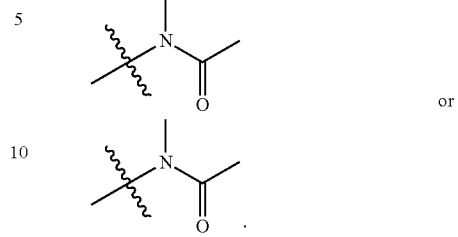
In various different embodiments, the compound of structure (VIII) has one of the structures set forth in Table 7 below.
TABLE 7
Representative Compounds of Structure (VIII)
| No. | Structure |
|---|---|
| VIII-1 | 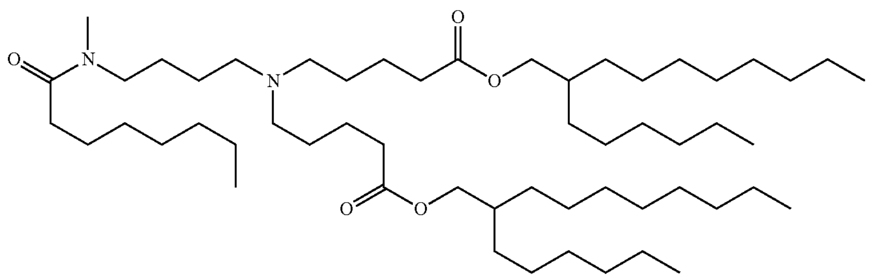 [SMILES: CCCCCCCCC(CCCCCC)COC(=O)CCCCN(CCCCC(=O)OCC(CCCCCC)CCCCCCCC)CCCCN(C)C(=O)CCCCCCC] |
| VIII-2 | 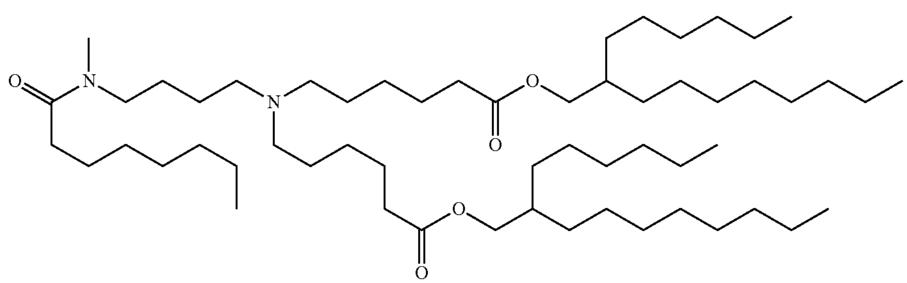 [SMILES: CCCCCCCCC(CCCCCC)COC(=O)CCCCCN(CCCCCC(=O)OCC(CCCCCC)CCCCCCCC)CCCCN(C)C(=O)CCCCCCC] |
| VIII-3 | 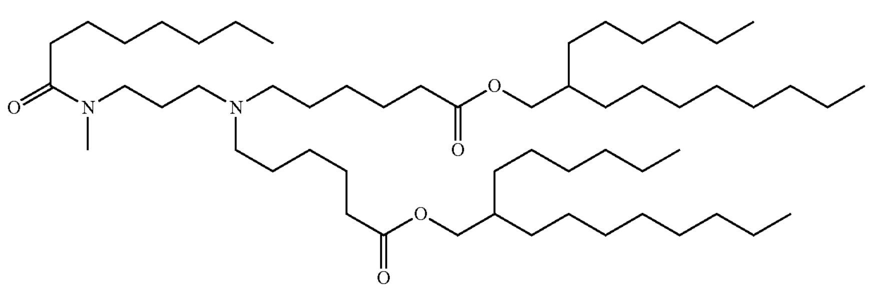 [SMILES: CCCCCCCCC(CCCCCC)COC(=O)CCCCCN(CCCCCC(=O)OCC(CCCCCC)CCCCCCCC)CCCN(C)C(=O)CCCCCCC] |

TABLE 7-continued
Representative Compounds of Structure (VIII)
| No. | Structure |
|---|---|
| VIII-4 | 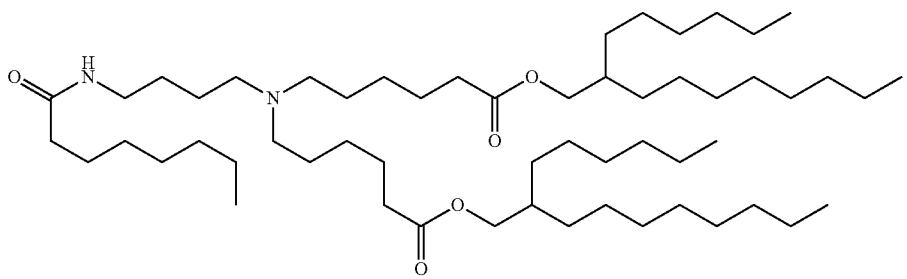 [SMILES: CCCCCCCCC(CCCCCC)COC(=O)CCCCCN(CCCCCC(=O)OCC(CCCCCC)CCCCCCCC)CCCCNC(=O)CCCCCCC] |
| VIII-5 | 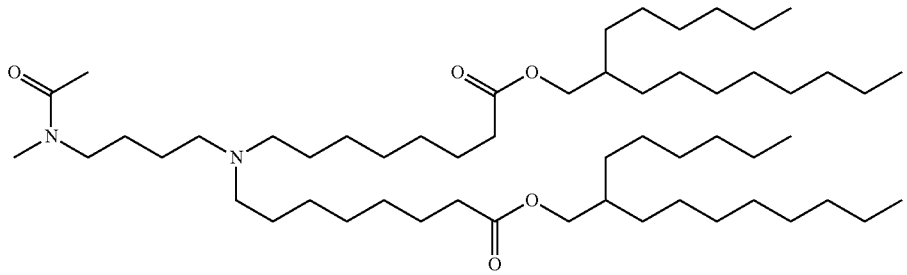 [SMILES: CCCCCCCCC(CCCCCC)COC(=O)CCCCCCCN(CCCCCCCC(=O)OCC(CCCCCC)CCCCCCCC)CCCCN(C)C(C)=O] |
| VIII-6 | 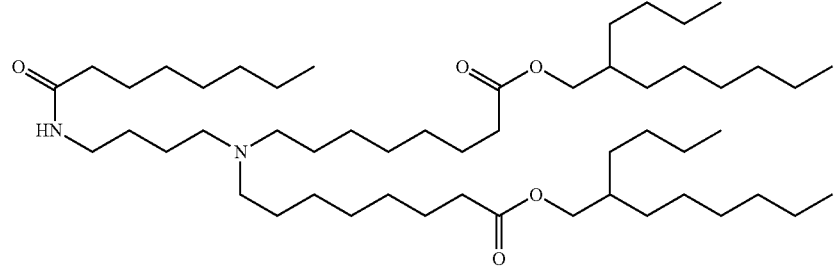 [SMILES: CCCCCCCC(=O)NCCCCN(CCCCCCCC(=O)OCC(CCCC)CCCCCC)CCCCCCCC(=O)OCC(CCCC)CCCCCC] |
| VIII-7 | 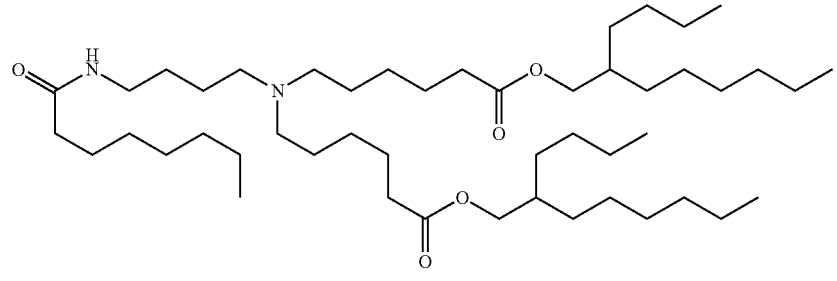 [SMILES: CCCCCCCC(=O)NCCCCN(CCCCCC(=O)OCC(CCCC)CCCCCC)CCCCCC(=O)OCC(CCCC)CCCCCC] |
| VIII-8 | 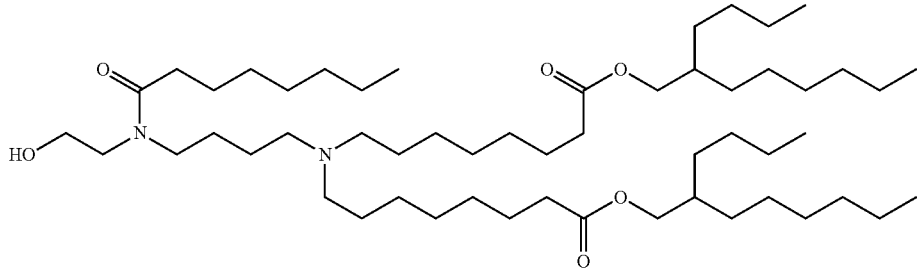 [SMILES: CCCCCCCC(=O)N(CCO)CCCCN(CCCCCCCC(=O)OCC(CCCC)CCCCCC)CCCCCCCC(=O)OCC(CCCC)CCCCCC] |

TABLE 7-continued
Representative Compounds of Structure (VIII)
| No. | Structure |
|---|---|
| VIII-9 | 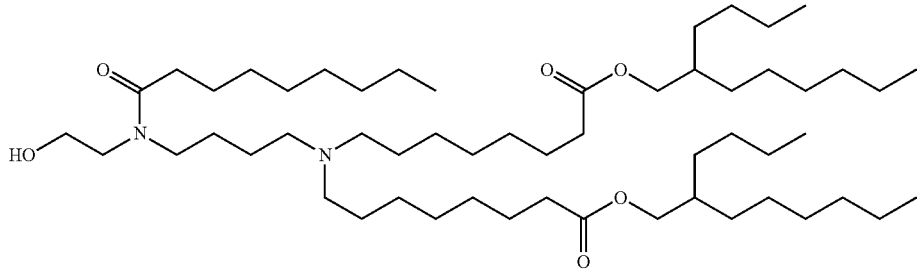 [SMILES: CCCCCCCCC(=O)N(CCO)CCCCN(CCCCCCCC(=O)OCC(CCCC)CCCCCC)CCCCCCCC(=O)OCC(CCCC)CCCCCC] |
| VIII-10 | 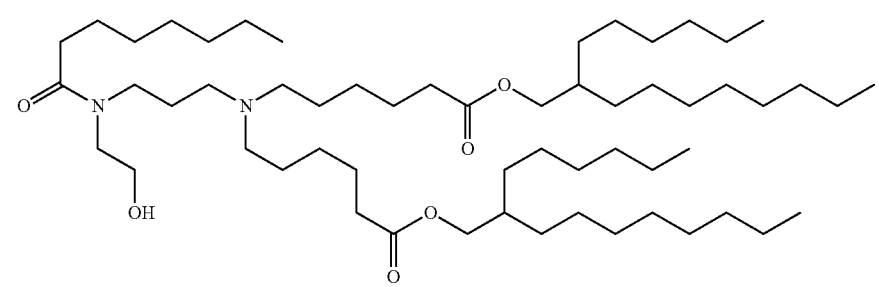 [SMILES: CCCCCCCCC(CCCCCC)COC(=O)CCCCCN(CCCCCC(=O)OCC(CCCCCC)CCCCCCCC)CCCN(CCO)C(=O)CCCCCCC] |
| VIII-11 | 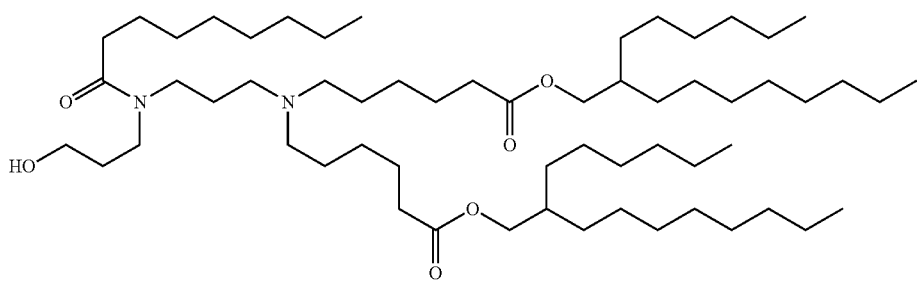 [SMILES: CCCCCCCCC(=O)N(CCCO)CCCN(CCCCCC(=O)OCC(CCCCCC)CCCCCCCC)CCCCCC(=O)OCC(CCCCCC)CCCCCCCC] |
| VIII-12 | 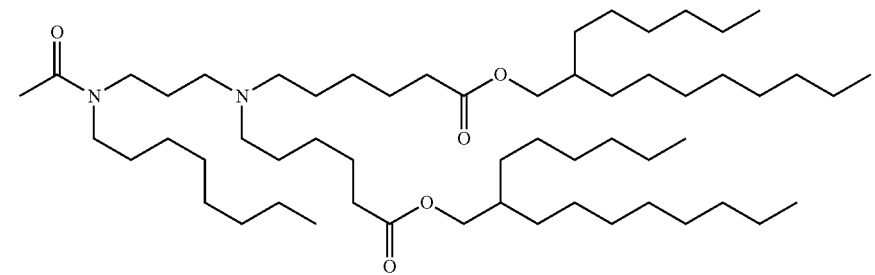 [SMILES: CCCCCCCCC(CCCCCC)COC(=O)CCCCCN(CCCCCC(=O)OCC(CCCCCC)CCCCCCCC)CCCN(CCCCCCCC)C(C)=O] |
| VIII-13 | 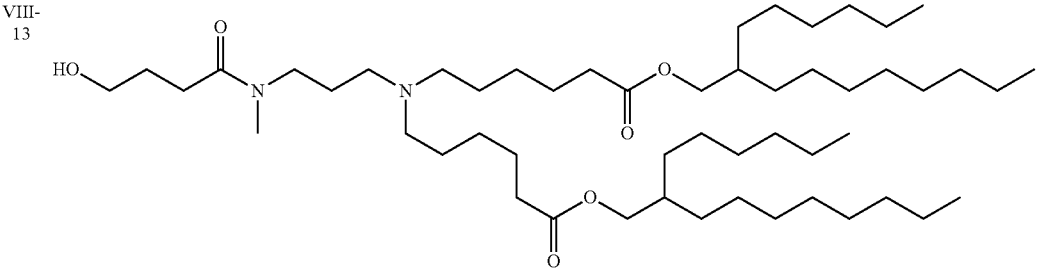 |

TABLE 7-continued

Representative Compounds of Structure (VIII)

| No. | Structure |
|---|---|
| VIII-14 | 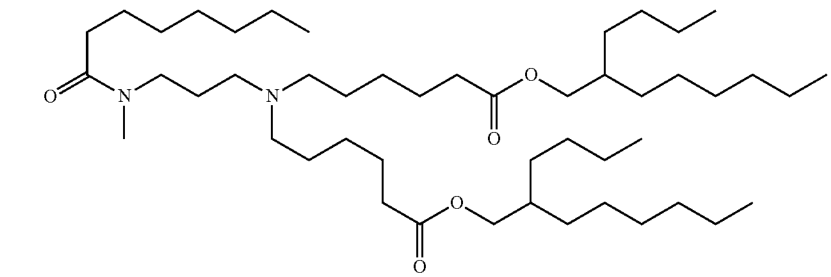 [SMILES: CCCCCCCC(=O)N(C)CCCN(CCCCCC(=O)OCC(CCCC)CCCCCC)CCCCCC(=O)OCC(CCCC)CCCCCC] |
| VIII-15 | 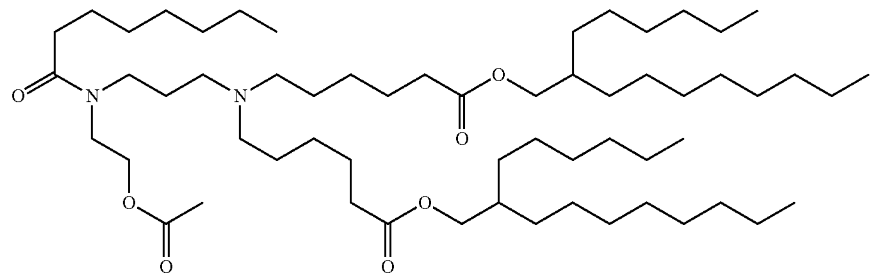 [SMILES: CCCCCCCCC(CCCCCC)COC(=O)CCCCCN(CCCCCC(=O)OCC(CCCCCC)CCCCCCCC)CCCN(CCOC(C)=O)C(=O)CCCCCCC] |
| VIII-16 | 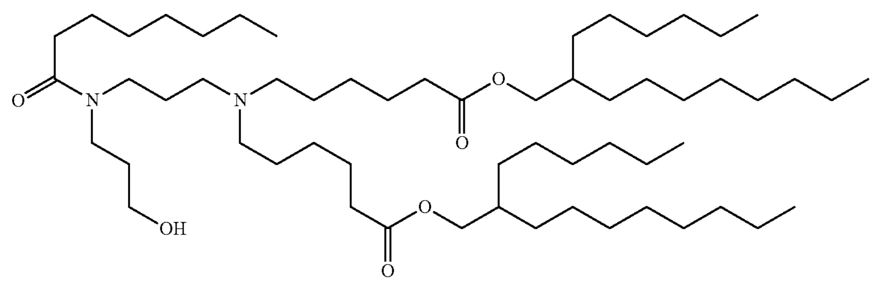 [SMILES: CCCCCCCCC(CCCCCC)COC(=O)CCCCCN(CCCCCC(=O)OCC(CCCCCC)CCCCCCCC)CCCN(CCCO)C(=O)CCCCCCC] |
| VIII-17 | 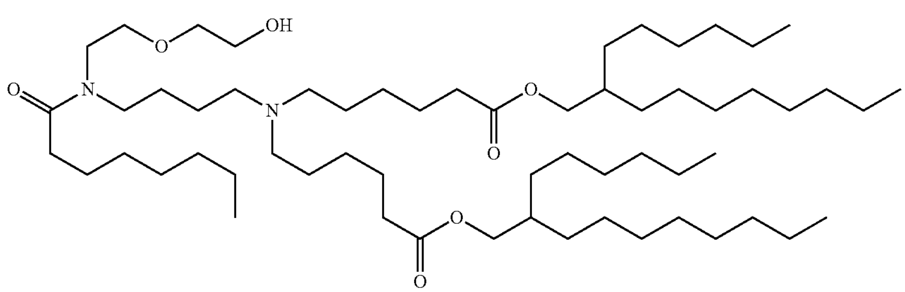 [SMILES: CCCCCCCCC(CCCCCC)COC(=O)CCCCCN(CCCCCC(=O)OCC(CCCCCC)CCCCCCCC)CCCCN(CCOCCO)C(=O)CCCCCCC] |
| VIII-18 | 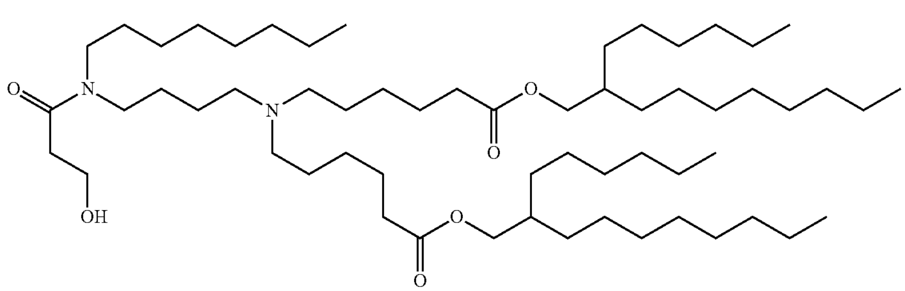 [SMILES: CCCCCCCCC(CCCCCC)COC(=O)CCCCCN(CCCCCC(=O)OCC(CCCCCC)CCCCCCCC)CCCCN(CCCCCCCC)C(=O)CCO] |

TABLE 7-continued

Representative Compounds of Structure (VIII)

VIII-19

VIII-20

Compounds of Formula (VIII) can be prepared and tested according to the procedures set forth in PCT Pub. No. WO 2018/200943, the full disclosure of which is incorporated by reference in its entirety.

Cationic Lipids of Formula IX

In still different embodiments the cationic lipid has the structure of Formula (IX):

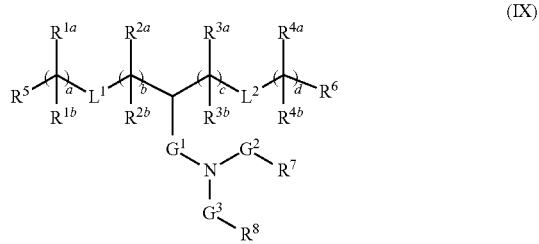

(IX)

or a pharmaceutically acceptable salt, tautomer or stereoisomer thereof, wherein:

$L^1$ and $L^2$ are each independently —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$—, —OC(=O)NR$^a$—, —NR$^a$C(=O)O— or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is H or $C_1$-$C_{20}$ alkyl;

$R^8$ is OH, —N($R^9$)(C=O)$R^{10}$, —(C=O)NR$^9$R$^{10}$, —NR$^9$R$^{10}$, —(C=O)OR$^{11}$ or —O(C=O)R$^{11}$, provided that $G^3$ is $C_4$-$C_6$ alkylene when $R^8$ is —NR$^9$R$^{10}$, $R^9$ and $R^{10}$ are each independently H or $C_1$-$C_{12}$ alkyl;

$R^{11}$ is aralkyl;

a, b, c and d are each independently an integer from 1 to 24; and x is 0, 1 or 2, wherein each alkyl, alkylene and aralkyl is optionally substituted.

In some embodiments of (IX), $L^1$ and $L^2$ are each independently —O(C=O)—,

—(C=O)O— or a direct bond. In other embodiments of (IX), $G^1$ and $G^2$ are each independently —(C=O)— or a direct bond. In some different embodiments of (IX), $L^1$ and $L^2$ are each independently —O(C=O)—, —(C=O)O— or a direct bond; and $G^1$ and $G^2$ are each independently —(C=O)— or a direct bond.

In some different embodiments of (IX), $L^1$ and $L^2$ are each independently —C(=O)—, —O—, —S(O)$_x$—, —S—S—, —C(=O)S—, —SC(=O)—, —NR$^a$—, —NR$^a$C(=O)—, —C(=O)NR$^a$—, —NR$^a$C(=O)NR$^a$—, —OC(=O)NR$^a$—, —NR$^a$C(=O)O—, —NR$^a$S(O)$_x$NR$^a$—, —NR$^a$S(O)$_x$— or —S(O)$_x$NR$^a$—.

In other of the foregoing embodiments, the compound has one of the following structures (IXA) or (IXB):

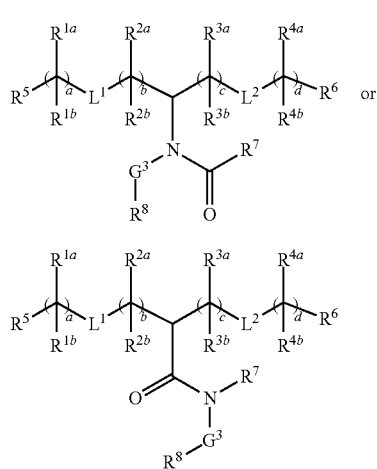

In some embodiments, the compound has structure (IXA). In other embodiments, the compound has structure (IXB).

In any of the foregoing embodiments of (IX), one of $L^1$ or $L^2$ is —O(C=O)—. For example, in some embodiments of (IX) each of $L^1$ and $L^2$ are —O(C=O)—.

In some different embodiments of any of the foregoing embodiments of (IX), one of $L^1$ or $L^2$ is —(C=O)O—. For example, in some embodiments of (IX) each of $L^1$ and $L^2$ is —(C=O)O—.

In different embodiments of (IX), one of $L^1$ or $L^2$ is a direct bond. As used herein, a "direct bond" means the group (e.g., $L^1$ or $L^2$) is absent. For example, in some embodiments of (IX) each of $L^1$ and $L^2$ is a direct bond.

In other different embodiments of (IX), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of (IX), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of (IX), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of (IX), for at least one occurrence of $R^{3a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

It is understood that "carbon-carbon" double bond refers to one of the following structures:

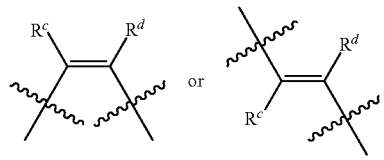

wherein $R^c$ and $R^d$ are, at each occurrence, independently H or a substituent. For example, in some embodiments of (IX) $R^c$ and $R^d$ are, at each occurrence, independently H, $C_1$-$C_{12}$ alkyl or cycloalkyl, for example H or $C_1$-$C_{12}$ alkyl.

In various other embodiments, the compound has one of the following structures (IC) or (ID):

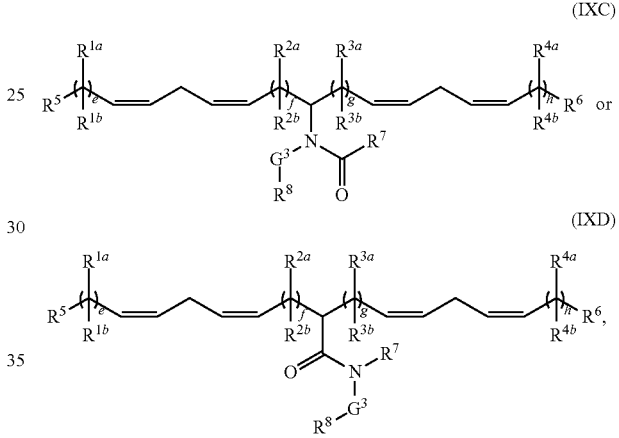

wherein e, f, g and h are each independently an integer from 1 to 12.

In some embodiments, the compound has structure (IXC). In other embodiments, the compound has structure (IXD).

In various embodiments of the compounds of structures (IXC) or (IXD), e, f, g and h are each independently an integer from 4 to 10.

In other different embodiments of (IX),

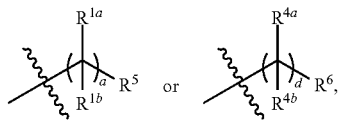

or both, independently has one of the following structures:

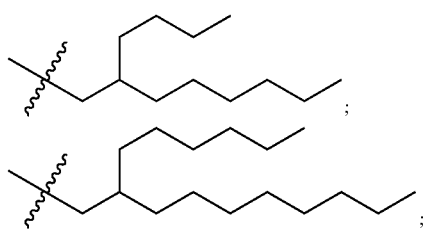

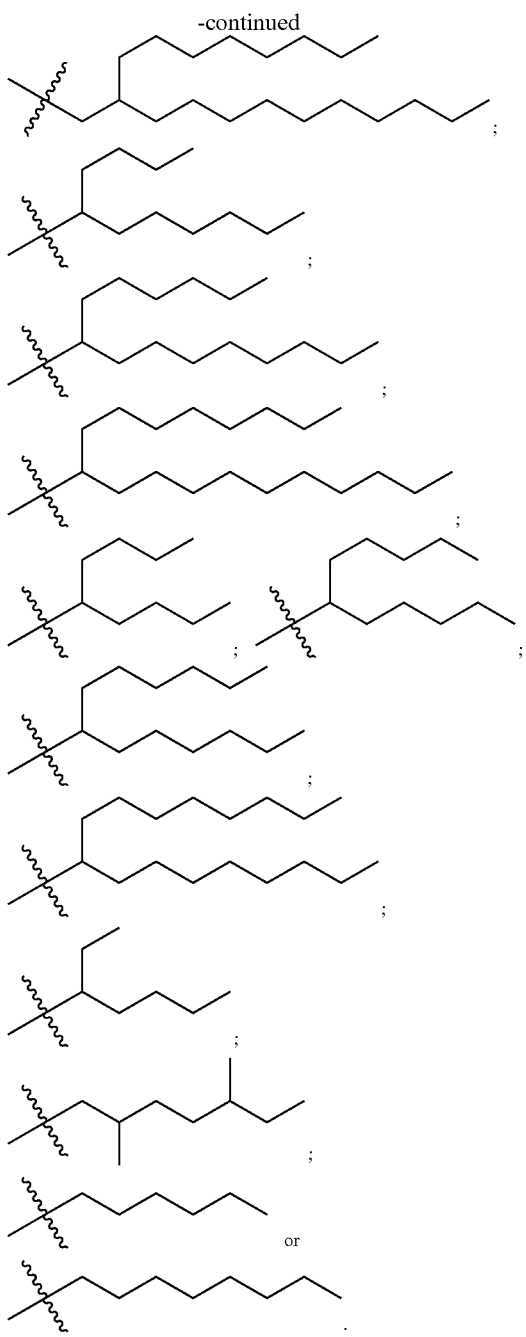

In certain embodiments of (IX), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of (IX), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of (IX), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of (IX), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of (IX), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of (IX), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of (IX), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of (IX), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of (IX), a and d are the same. In some other embodiments, b and c are the same. In some other specific embodiments a and d are the same and b and c are the same.

In one embodiment of (IX), a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a, b, c and d are selected such that the sum of a and b and the sum of c and d is 12 or greater.

The substituents at $R^{1a}$, $R^{2a}$, $R^{3a}$ and $R^{4a}$ of (IX) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of (IX), $R^{1a}$, $R^{1b}$, $R^{4a}$ and $R^{4b}$ are $C_1$-$C_{12}$ alkyl at each occurrence.

In further embodiments of (IX), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of (IX), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of (IX) are not particularly limited in the foregoing embodiments. In certain embodiments one of $R^5$ or $R^6$ is methyl. In other embodiments each of $R^5$ or $R^6$ is methyl.

The substituents at $R^7$ of (IX) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C=O)OR$^b$, —O(C=O)R$^b$, —C(=O)R$^b$, —OR$^b$, —S(O)$_x$R$^b$, —S—SR$^b$, —C(=O)SR$^b$, —SC(=O)R$^b$, —N$^a$R$^b$, —NR$^a$C(=O)R$^b$, —C(=O)NR$^a$R$^b$, —NR$^a$C(=O)NR$^a$R$^b$, —OC(=O)NR$^a$R$^b$, —NR$^a$C(=O)OR$^b$, —NR$^a$S(O)$_x$NR$^a$R$^b$, —NR$^a$S(O)$_x$R$^b$ or —S(O)$_x$NR$^a$R$^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C=O)OR$^b$ or —O(C=O)R$^b$.

In various of (IX), $R^b$ is branched $C_3$-$C_{15}$ alkyl. For example, in some embodiments $R^b$ has one of the following structures:

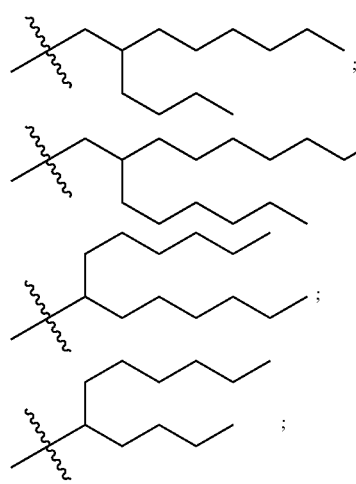

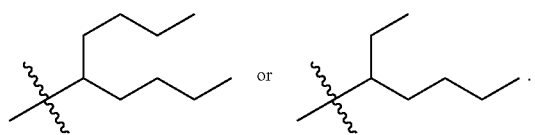

In certain embodiments of (IX), $R^8$ is OH.

In other embodiments of (IX), $R^8$ is —N(R$^9$)(C=O)R$^{10}$. In some other embodiments, $R^8$ is —(C=O)NR$^9$R$^{10}$. In still more embodiments, $R^8$ is —NR$^9$R$^{10}$. In some of the foregoing embodiments, $R^9$ and $R^{10}$ are each independently H or $C_1$-$C_8$ alkyl, for example H or $C_1$-$C_3$ alkyl. In more specific of these embodiments, the $C_1$-$C_8$ alkyl or $C_1$-$C_3$ alkyl is unsubstituted or substituted with hydroxyl. In other of these embodiments, $R^9$ and $R^{10}$ are each methyl.

In yet more embodiments of (IX), $R^8$ is —(C=O)OR$^{11}$. In some of these embodiments $R^{11}$ is benzyl.

In yet more specific embodiments of (IX), $R^8$ has one of the following structures:

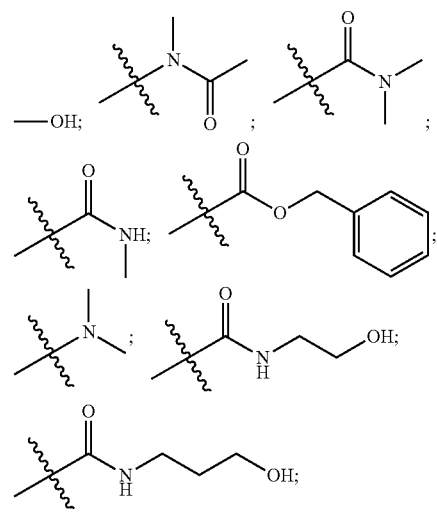

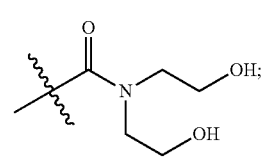

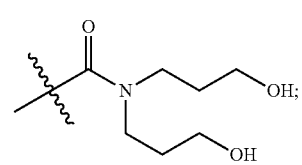

171
-continued

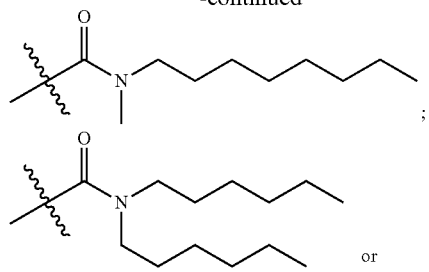

172
-continued

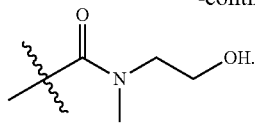

In still other embodiments of (IX), $G^3$ is $C_2$-$C_5$ alkylene, for example $C_2$-$C_4$ alkylene, $C_3$ alkylene or $C_4$ alkylene. In some of these embodiments, $R^8$ is OH. In other embodiments, $G^2$ is absent and $R^7$ is $C_1$-$C_2$ alkylene, such as methyl.

In various different embodiments, the compound has one of the structures set forth in Table 8 below.

TABLE 8

Representative Compounds of Structure (IX)

| No. | Structure |
|---|---|
| IX-1 | 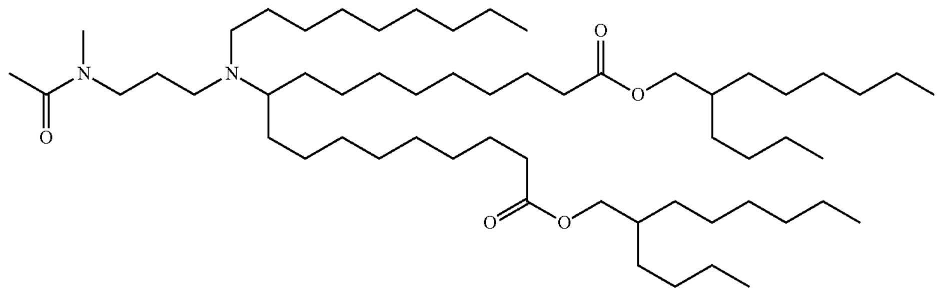 [SMILES: CCCCCCCCCN(CCCN(C)C(C)=O)C(CCCCCCCCC(=O)OCC(CCCC)CCCCCC)CCCCCCCCC(=O)OCC(CCCC)CCCCCC] |
| IX-2 | 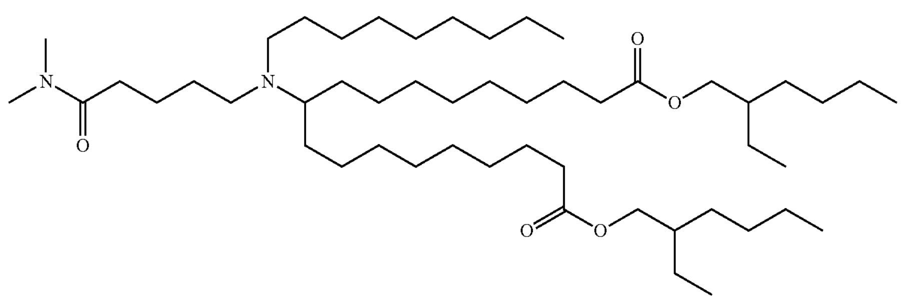 [SMILES: CCCCCCCCCN(CCCCC(=O)N(C)C)C(CCCCCCCCC(=O)OCC(CC)CCCC)CCCCCCCCC(=O)OCC(CC)CCCC] |
| IX-3 | 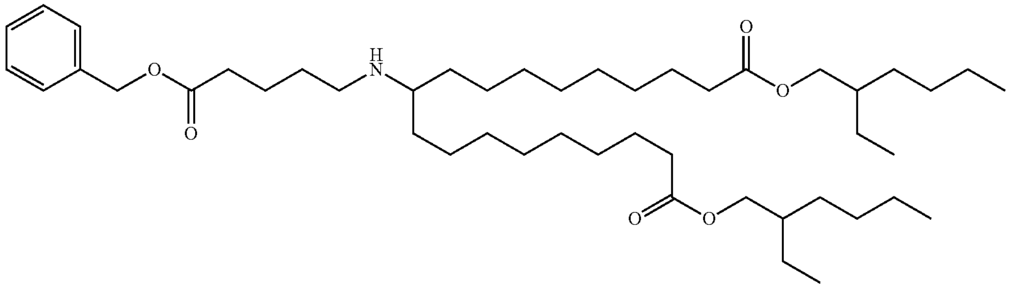 [SMILES: CCCCC(CC)COC(=O)CCCCCCCCC(CCCCCCCCC(=O)OCC(CC)CCCC)NCCCCC(=O)OCc1ccccc1] |

TABLE 8-continued
Representative Compounds of Structure (IX)
| No. | Structure |
|---|---|
| IX-4 | 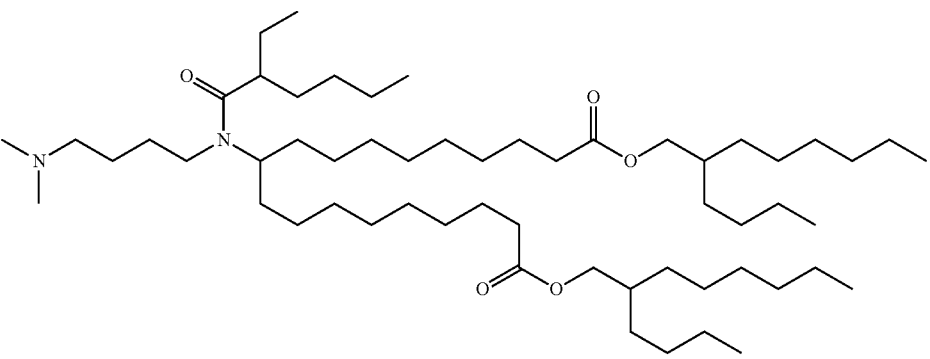 [SMILES: CCCCCCC(CCCC)COC(=O)CCCCCCCCC(CCCCCCCCC(=O)OCC(CCCC)CCCCCC)N(CCCCN(C)C)C(=O)C(CC)CCCC] |
| IX-5 | 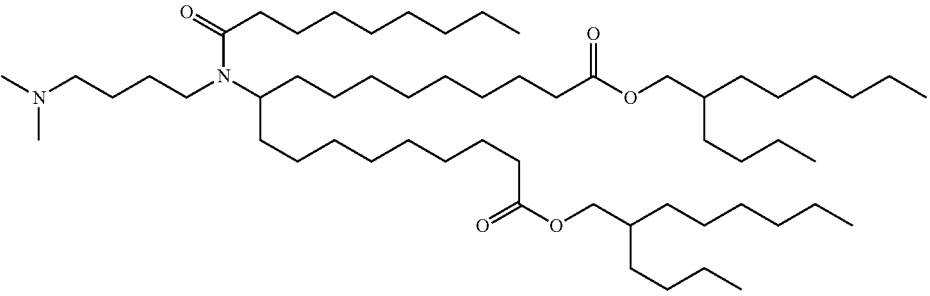 [SMILES: CCCCCCCCC(=O)N(CCCCN(C)C)C(CCCCCCCCC(=O)OCC(CCCC)CCCCCC)CCCCCCCCC(=O)OCC(CCCC)CCCCCC] |
| IX-6 | 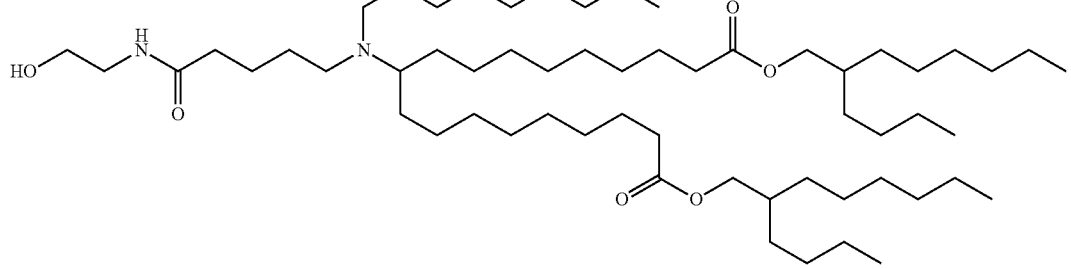 |
| IX-7 | 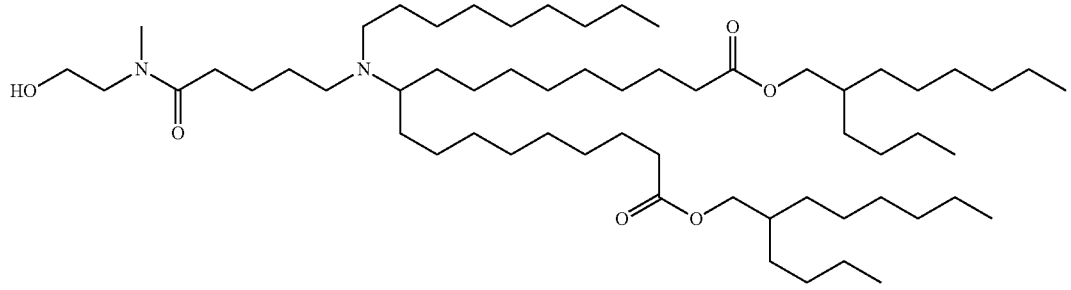 [SMILES: CCCCCCCCCN(CCCCC(=O)N(C)CCO)C(CCCCCCCCC(=O)OCC(CCCC)CCCCCC)CCCCCCCCC(=O)OCC(CCCC)CCCCCC] |
| IX-8 | 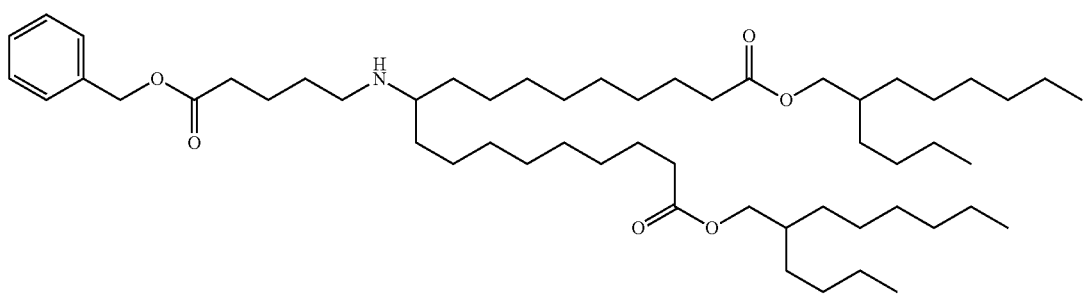 [SMILES: CCCCCCC(CCCC)COC(=O)CCCCCCCCC(CCCCCCCCC(=O)OCC(CCCC)CCCCCC)NCCCCC(=O)OCc1ccccc1] |

TABLE 8-continued

Representative Compounds of Structure (IX)

| No. | Structure |
|---|---|
| IX-9 | 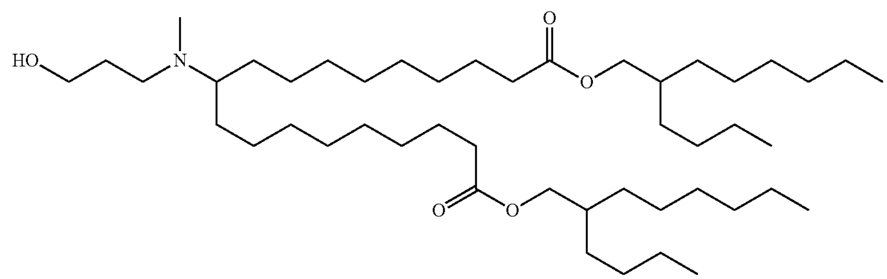 [SMILES: CCCCCCC(CCCC)COC(=O)CCCCCCCCC(CCCCCCCCC(=O)OCC(CCCC)CCCCCC)N(C)CCCO] |
| IX-10 | 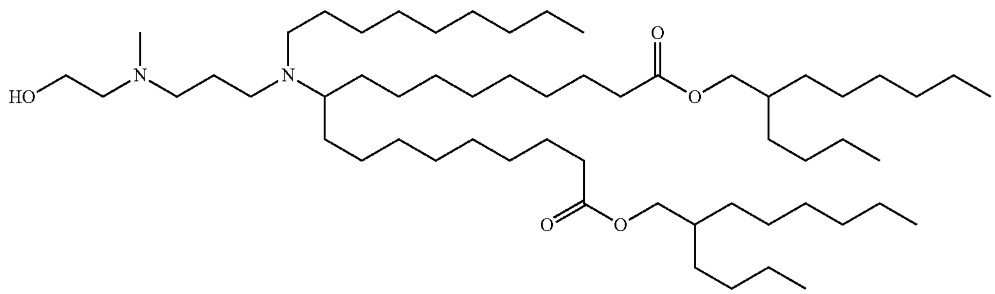 [SMILES: CCCCCCCCCN(CCCN(C)CCO)C(CCCCCCCCC(=O)OCC(CCCC)CCCCCC)CCCCCCCCC(=O)OCC(CCCC)CCCCCC] |
| IX-11 | 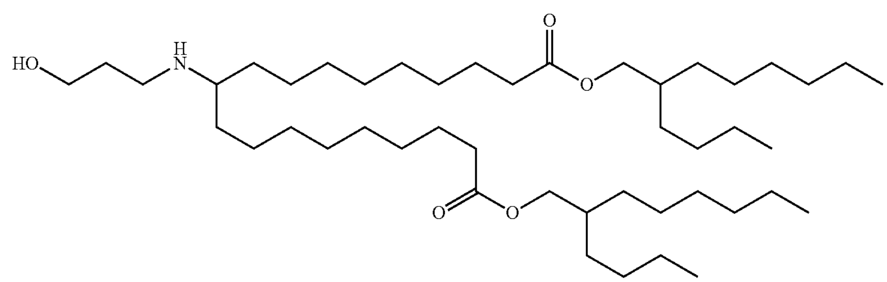 [SMILES: CCCCCCC(CCCC)COC(=O)CCCCCCCCC(CCCCCCCCC(=O)OCC(CCCC)CCCCCC)NCCCO] |
| IX-12 | 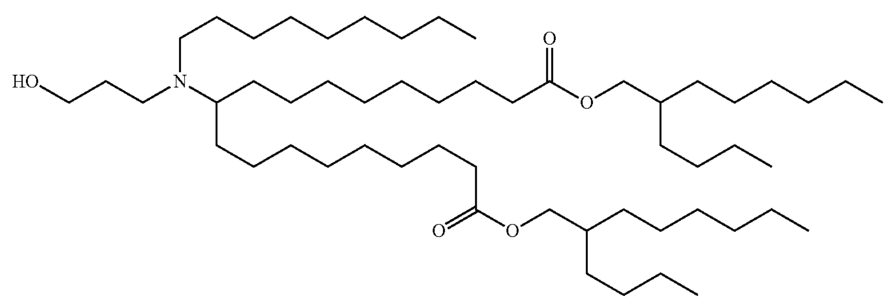 [SMILES: CCCCCCCCCN(CCCO)C(CCCCCCCCC(=O)OCC(CCCC)CCCCCC)CCCCCCCCC(=O)OCC(CCCC)CCCCCC] |
| IX-13 | 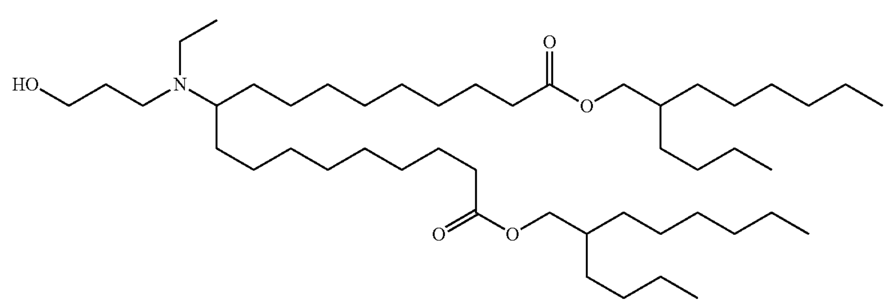 [SMILES: CCCCCCC(CCCC)COC(=O)CCCCCCCCC(CCCCCCCCC(=O)OCC(CCCC)CCCCCC)N(CC)CCCO] |

TABLE 8-continued

Representative Compounds of Structure (IX)

| No. | Structure |
|---|---|
| IX-14 | 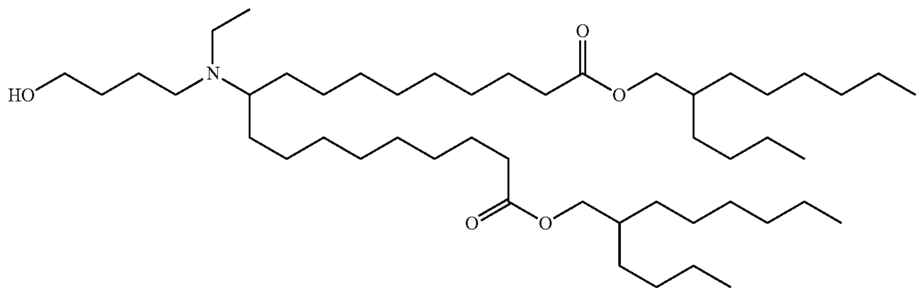 [SMILES: CCCCCCC(CCCC)COC(=O)CCCCCCCCC(CCCCCCCCC(=O)OCC(CCCC)CCCCCC)N(CC)CCCCO] |
| IX-15 | 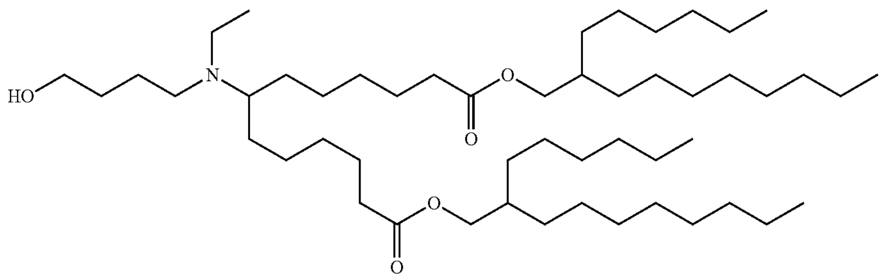 [SMILES: CCCCCCCCC(CCCCCC)COC(=O)CCCCCC(CCCCCC(=O)OCC(CCCCCC)CCCCCCCC)N(CC)CCCCO] |
| IX-16 | 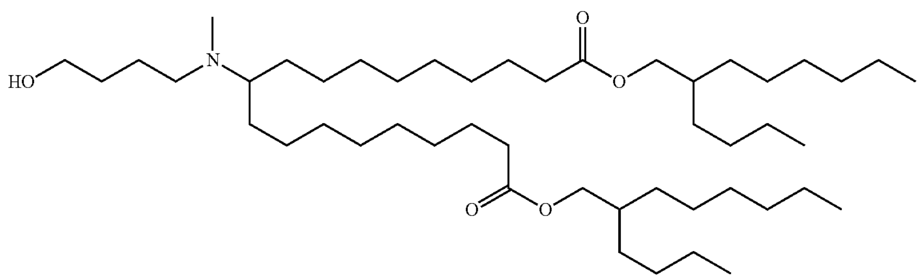 [SMILES: CCCCCCC(CCCC)COC(=O)CCCCCCCCC(CCCCCCCCC(=O)OCC(CCCC)CCCCCC)N(C)CCCCO] |
| IX-17 | 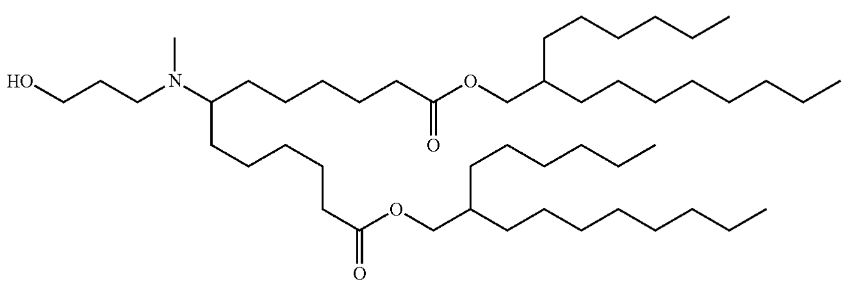 [SMILES: CCCCCCCCC(CCCCCC)COC(=O)CCCCCC(CCCCCC(=O)OCC(CCCCCC)CCCCCCCC)N(C)CCCO] |
| IX-18 | 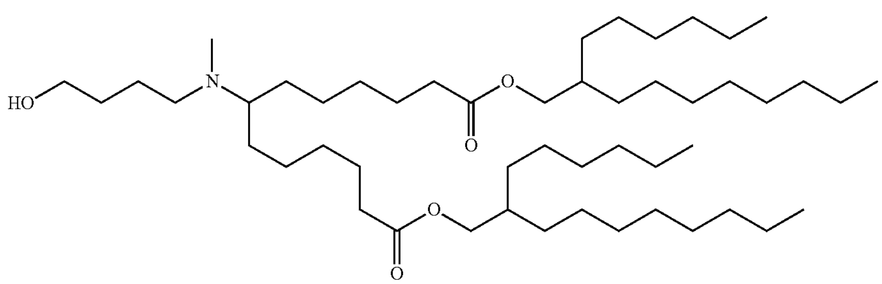 [SMILES: CCCCCCCCC(CCCCCC)COC(=O)CCCCCC(CCCCCC(=O)OCC(CCCCCC)CCCCCCCC)N(C)CCCCO] |

TABLE 8-continued

Representative Compounds of Structure (IX)

| No. | Structure |
|---|---|
| IX-19 | 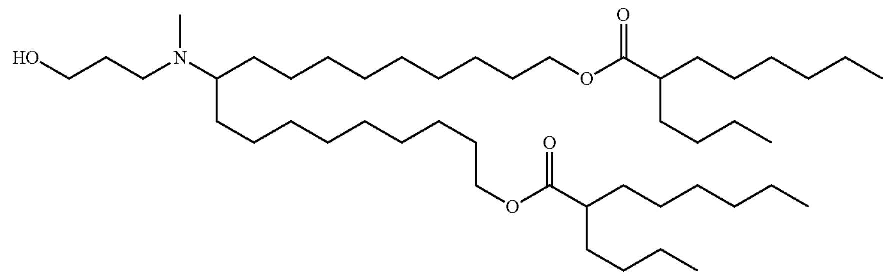 [SMILES: CCCCCCC(CCCC)C(=O)OCCCCCCCCCC(CCCCCCCCCOC(=O)C(CCCC)CCCCCC)N(C)CCCO] |
| IX-20 | 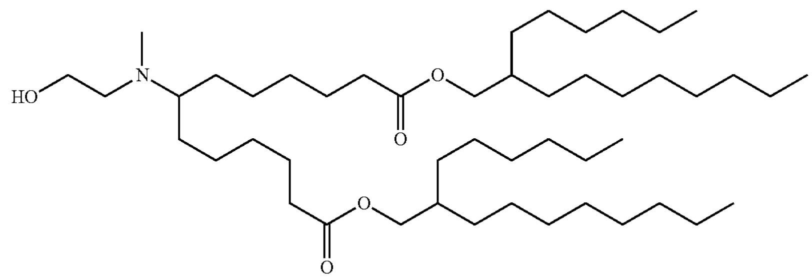 [SMILES: CCCCCCCCC(CCCCCC)COC(=O)CCCCCC(CCCCCC(=O)OCC(CCCCCC)CCCCCCCC)N(C)CCO] |
| IX-21 | 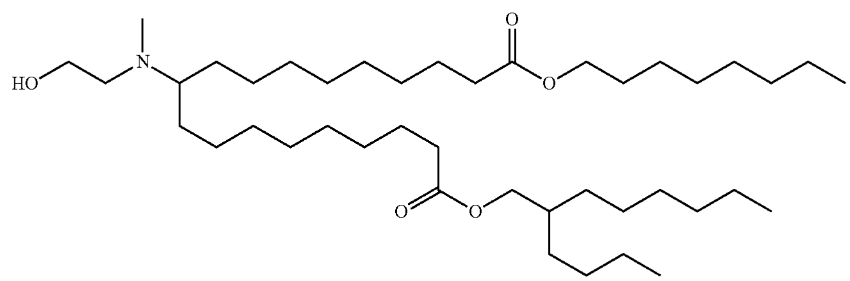 [SMILES: CCCCCCCCOC(=O)CCCCCCCCC(CCCCCCCCC(=O)OCC(CCCC)CCCCCC)N(C)CCO] |
| IX-22 | 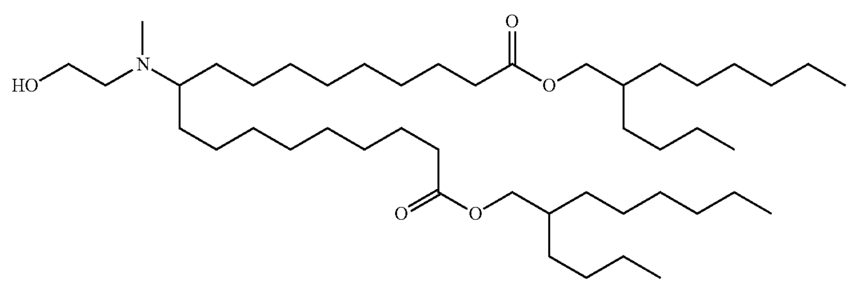 [SMILES: CCCCCCC(CCCC)COC(=O)CCCCCCCCC(CCCCCCCCC(=O)OCC(CCCC)CCCCCC)N(C)CCO] |
| IX-23 | 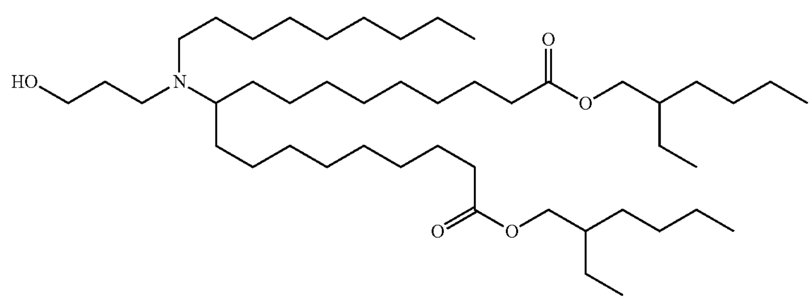 [SMILES: CCCCCCCCCN(CCCO)C(CCCCCCCCC(=O)OCC(CC)CCCC)CCCCCCCCC(=O)OCC(CC)CCCC] |

TABLE 8-continued

Representative Compounds of Structure (IX)

| No. | Structure |
|---|---|
| IX-24 | 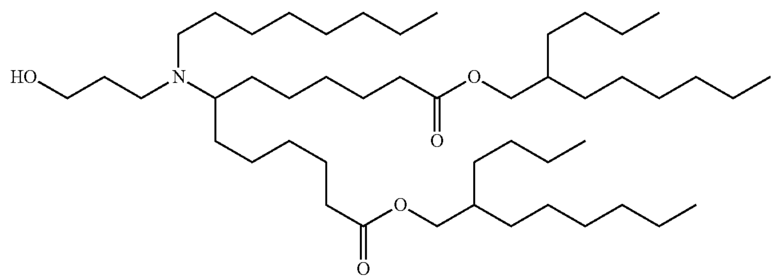 [SMILES: CCCCCCCCN(CCCO)C(CCCCCC(=O)OCC(CCCC)CCCCCC)CCCCCC(=O)OCC(CCCC)CCCCCC] |
| IX-25 | 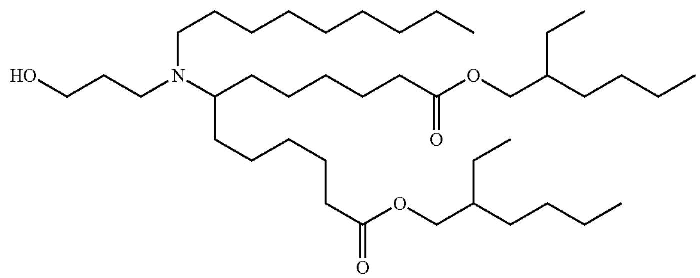 [SMILES: CCCCCCCCCN(CCCO)C(CCCCCC(=O)OCC(CC)CCCC)CCCCCC(=O)OCC(CC)CCCC] |
| IX-26 | 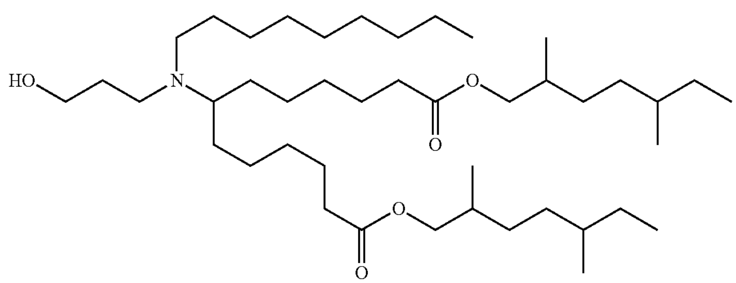 [SMILES: CCCCCCCCCN(CCCO)C(CCCCCC(=O)OCC(C)CCC(C)CC)CCCCCC(=O)OCC(C)CCC(C)CC] |
| IX-27 | 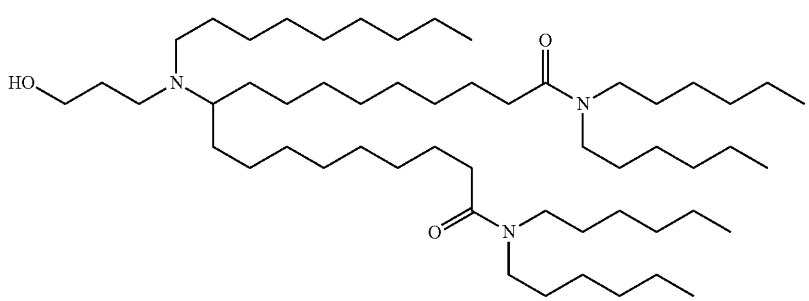 [SMILES: CCCCCCCCCN(CCCO)C(CCCCCCCCC(=O)N(CCCCCC)CCCCCC)CCCCCCCCC(=O)N(CCCCCC)CCCCCC] |
| IX-28 | 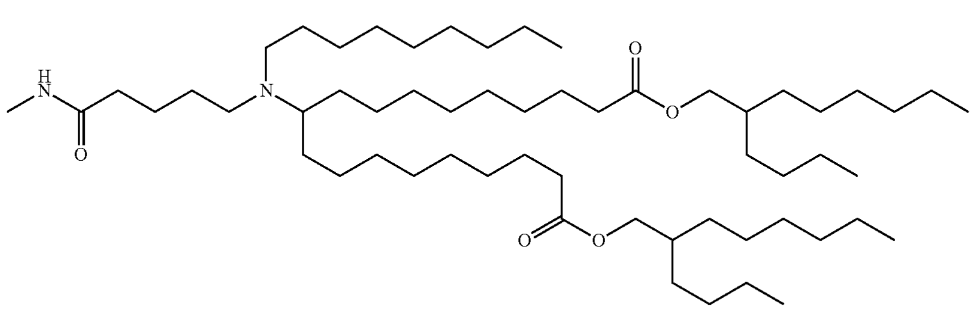 [SMILES: CCCCCCCCCN(CCCCC(=O)NC)C(CCCCCCCCC(=O)OCC(CCCC)CCCCCC)CCCCCCCCC(=O)OCC(CCCC)CCCCCC] |

TABLE 8-continued
Representative Compounds of Structure (IX)
| No. | Structure |
|---|---|
| IX-29 | 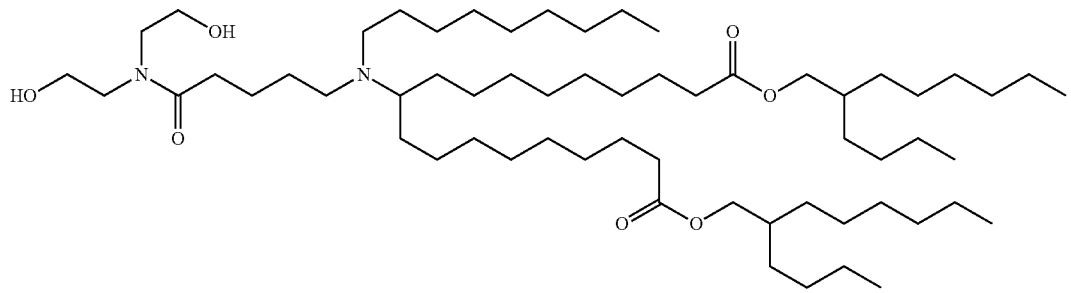 [SMILES: CCCCCCCCCN(CCCCC(=O)N(CCO)CCO)C(CCCCCCCCC(=O)OCC(CCCC)CCCCCC)CCCCCCCCC(=O)OCC(CCCC)CCCCCC] |
| IX-30 | 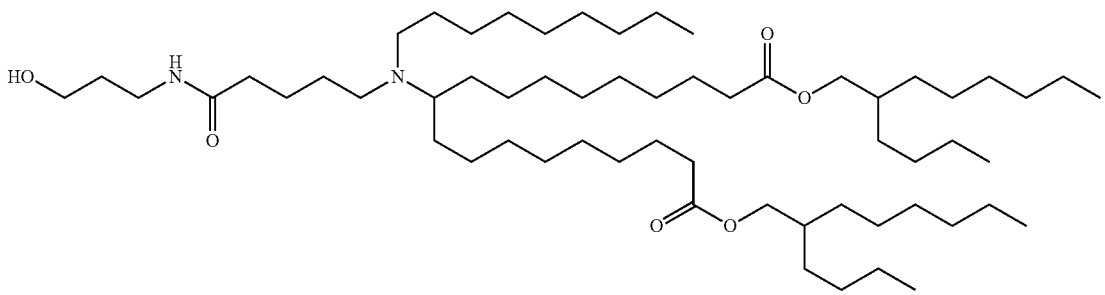 |
| IX-31 | 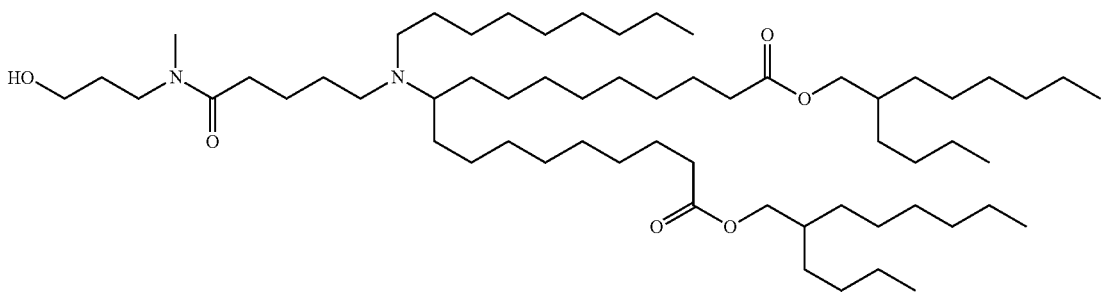 [SMILES: CCCCCCCCCN(CCCCC(=O)N(C)CCCO)C(CCCCCCCCC(=O)OCC(CCCC)CCCCCC)CCCCCCCCC(=O)OCC(CCCC)CCCCCC] |
| IX-32 | 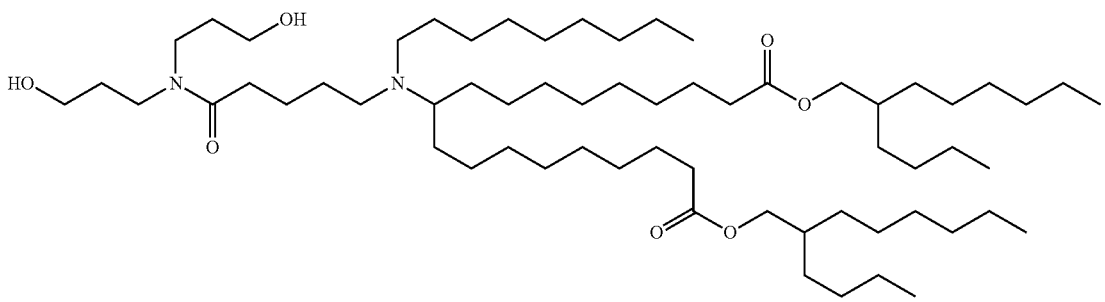 [SMILES: CCCCCCCCCN(CCCCC(=O)N(CCCO)CCCO)C(CCCCCCCCC(=O)OCC(CCCC)CCCCCC)CCCCCCCCC(=O)OCC(CCCC)CCCCCC] |
| IX-33 | 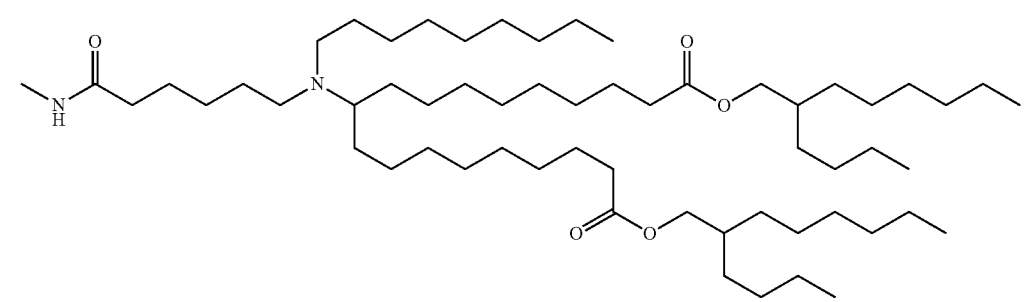 [SMILES: CCCCCCCCCN(CCCCCC(=O)NC)C(CCCCCCCCC(=O)OCC(CCCC)CCCCCC)CCCCCCCCC(=O)OCC(CCCC)CCCCCC] |

TABLE 8-continued

Representative Compounds of Structure (IX)

| No. | Structure |
|---|---|
| IX-34 | 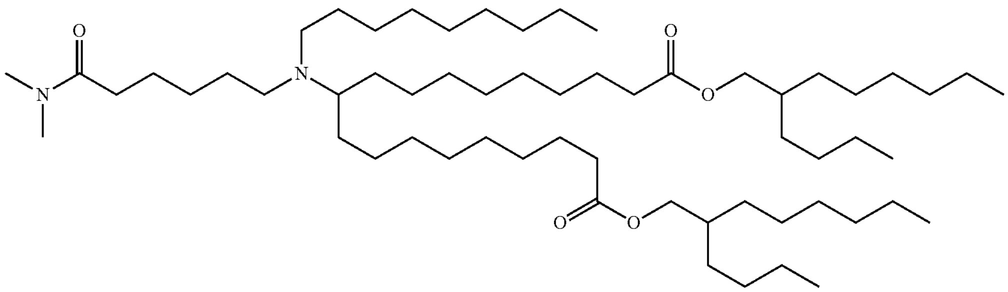 [SMILES: CCCCCCCCCN(CCCCCC(=O)N(C)C)C(CCCCCCCCC(=O)OCC(CCCC)CCCCCC)CCCCCCCCC(=O)OCC(CCCC)CCCCCC] |
| IX-35 | 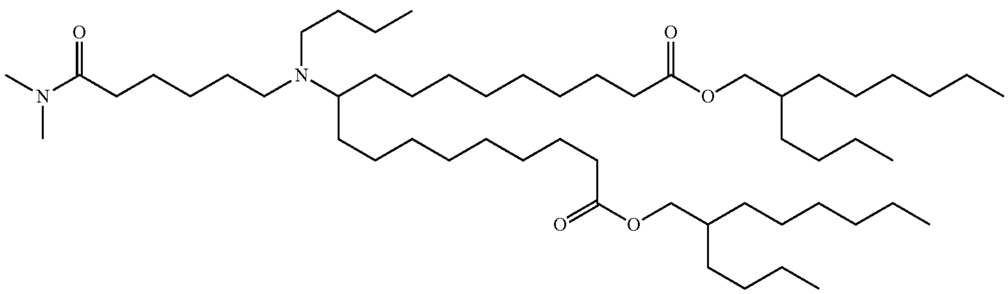 [SMILES: CCCCCCC(CCCC)COC(=O)CCCCCCCCC(CCCCCCCCC(=O)OCC(CCCC)CCCCCC)N(CCCC)CCCCCC(=O)N(C)C] |
| IX-36 | 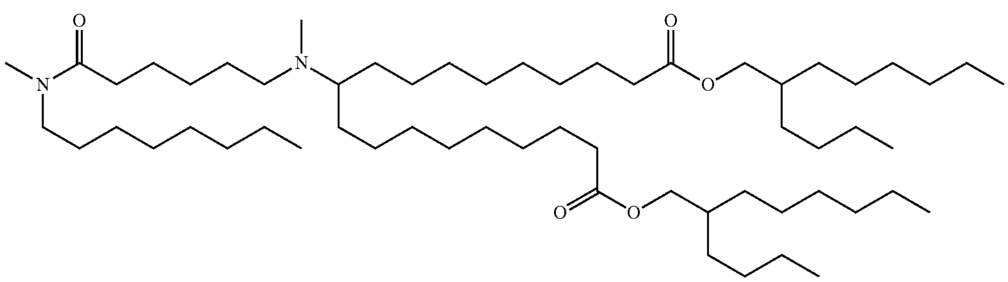 [SMILES: CCCCCCCCN(C)C(=O)CCCCCN(C)C(CCCCCCCCC(=O)OCC(CCCC)CCCCCC)CCCCCCCCC(=O)OCC(CCCC)CCCCCC] |
| IX-37 | 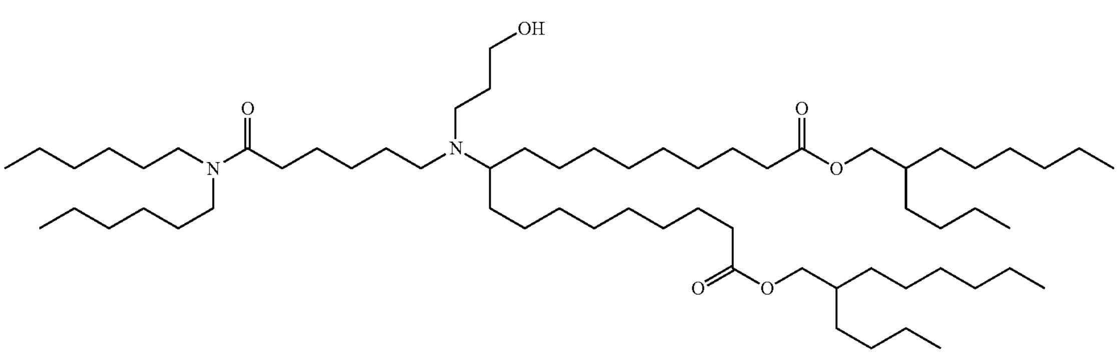 [SMILES: CCCCCCC(CCCC)COC(=O)CCCCCCCCC(CCCCCCCCC(=O)OCC(CCCC)CCCCCC)N(CCCO)CCCCCC(=O)N(CCCCCC)CCCCCC] |

Compounds of Formula (IX) can be prepared and tested according to the procedures set forth in PCT Pub. No. WO 2019/036000, the full disclosure of which is incorporated by reference in its entirety.

Cationic Lipids of Formula X

In still different embodiments the cationic lipid has the structure of Formula (X):

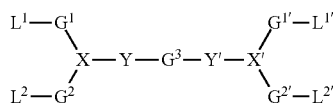
(X)

or a pharmaceutically acceptable salt or stereoisomer thereof, wherein:

X and X' are each independently N or CR;

Y and Y' are each independently absent, —O(C=O)—, —(C=O)O— or NR, provided that:
 a) Y is absent when X is N;
 b) Y' is absent when X' is N;
 c) Y is —O(C=O)—, —(C=O)O— or NR when X is CR; and
 d) Y' is —O(C=O)—, —(C=O)O— or NR when X' is CR, $L^1$ and $L^{1'}$ are each independently —O(C=O)$R^1$, —(C=O)O$R^1$, —C(=O)$R^1$, —O$R^1$, —S(O)$_z R^1$, —S—S$R^1$, —C(=O)S$R^1$, —SC(=O)$R^1$, —$NR^a$C(=O)$R^1$, —C(=O)$NR^b R^c$, —$NR^a$C(=O)$NR^b R^c$, —OC(=O)$NR^b R^c$ or —$NR^a$C(=O)O$R^1$;

$L^2$ and $L^{2'}$ are each independently —O(C=O)$R^2$, —(C=O)O$R^2$, —C(=O)$R^2$, —O$R^2$, —S(O)$_z R^2$, —S—S$R^2$, —C(=O)S$R^2$, —SC(=O)$R^2$, —$NR^d$C(=O)$R^2$, —C(=O)$NR^e R^f$, —$NR^d$C(=O)$NR^e R^f$, —OC(=O)$NR^e R^f$; —$NR^d$C(=O)O$R^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ heteroalkylene or $C_2$-$C_{24}$ heteroalkenylene;

$R^a$, $R^b$, $R^d$ and $R^e$ are, at each occurrence, independently H, $C_1$-$C_{12}$ alkyl or $C_2$-$C_{12}$ alkenyl;

$R^c$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, heteroalkylene and heteroalkenylene is independently substituted or unsubstituted unless otherwise specified.

In other different embodiments of structure (X):

X and X' are each independently N or CR;

Y and Y' are each independently absent or NR, provided that:
 a) Y is absent when X is N;
 b) Y' is absent when X' is N;
 c) Y is NR when X is CR; and
 d) Y' is NR when X' is CR, $L^1$ and $L^{1'}$ are each independently —O(C=O)$R^1$, —(C=O)O$R^1$, —C(=O)$R^1$, —O$R^1$, —S(O)$_z R^1$, —S—S$R^1$, —C(=O)S$R^1$, —SC(=O)$R^1$, —$NR^a$C(=O)$R^1$, —C(=O)$NR^b R^c$, —$NR^a$C(=O)$NR^b R^c$, —OC(=O)$NR^b R^c$ or —$NR^a$C(=O)O$R^1$;

$L^2$ and $L^{2'}$ are each independently —O(C=O)$R^2$, —(C=O)O$R^2$, —C(=O)$R^2$, —O$R^2$, —S(O)$_z R^2$, —S—S$R^2$, —C(=O)S$R^2$, —SC(=O)$R^2$, —$NR^d$C(=O)$R^2$, —C(=O)$NR^e R^f$, —$NR^d$C(=O)$NR^e R^f$, —OC(=O)$NR^e R^f$; —$NR^d$C(=O)O$R^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

$G^3$ is $C_2$-$C_{24}$ alkyleneoxide or $C_2$-$C_{24}$ alkenyleneoxide;

$R^a$, $R^b$, $R^d$ and $R^e$ are, at each occurrence, independently H, $C_1$-$C_{12}$ alkyl or $C_2$-$C_{12}$ alkenyl;

$R^c$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, alkyleneoxide and alkenyleneoxide is independently substituted or unsubstituted unless otherwise specified.

In some embodiments of (X), $G^3$ is $C_2$-$C_{24}$ alkyleneoxide or $C_2$-$C_{24}$ alkenyleneoxide. In certain embodiments, $G^3$ is unsubstituted. In other embodiments, $G^3$ is substituted, for example substituted with hydroxyl. In more specific embodiments $G^3$ is $C_2$-$C_{12}$ alkyleneoxide, for example, in some embodiments $G^3$ is $C_3$-$C_7$ alkyleneoxide or in other embodiments $G^3$ is $C_3$-$C_{12}$ alkyleneoxide.

In other embodiments of (X), $G^3$ is $C_2$-$C_{24}$ alkyleneaminyl or $C_2$-$C_{24}$ alkenyleneaminyl, for example $C_6$-$C_{12}$ alkyleneaminyl. In some of these embodiments, $G^3$ is unsubstituted. In other of these embodiments, $G^3$ is substituted with $C_1$-$C_6$ alkyl.

In some embodiments of (X), X and X' are each N, and Y and Y' are each absent. In other embodiments, X and X' are each CR, and Y and Y' are each NR. In some of these embodiments, R is H.

In certain embodiments of (X), X and X' are each CR, and Y and Y' are each independently —O(C=O)— or —(C=O)O—.

In some of the foregoing embodiments of (X), the compound has one of the following structures (XA), (XB), (XC), (XD), (XE), (XF), (XG) or (XH):

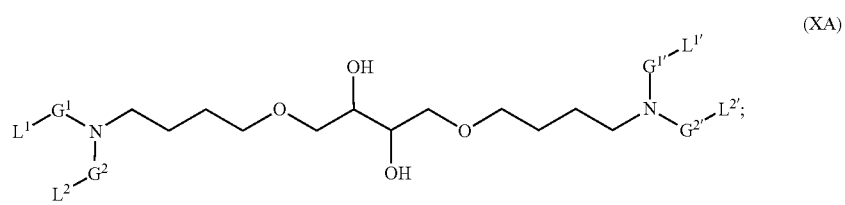
(XA)

-continued

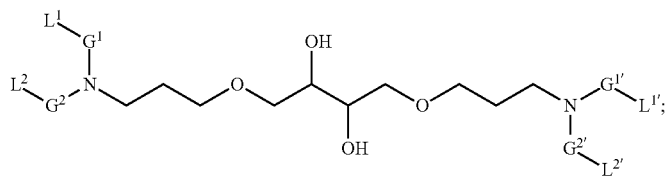
(XB)

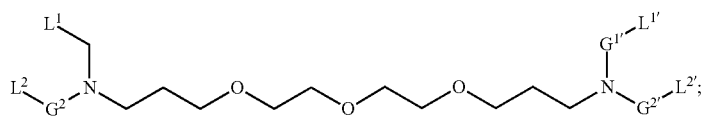
(XC)

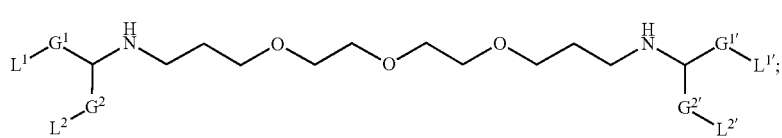
(XD)

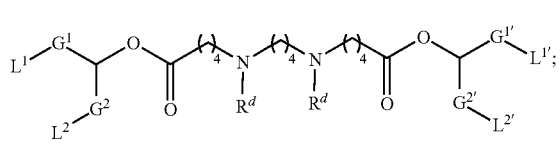
(XE)

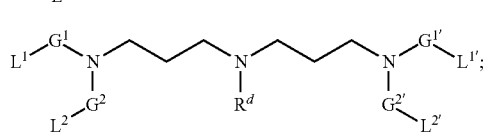
(XF)

(XG)

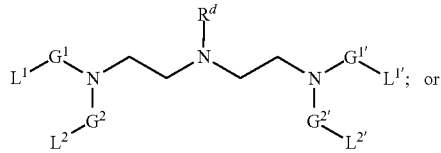
(XH)

wherein $R^d$ is, at each occurrence, independently H or optionally substituted $C_1$-$C_6$ alkyl. For example, in some embodiments $R^d$ is H. In other embodiments, $R^d$ is $C_1$-$C_6$ alkyl, such as methyl. In other embodiments, $R^d$ is substituted $C_1$-$C_6$ alkyl, such as $C_1$-$C_6$ alkyl substituted with —O(C=O)R, —(C=O)OR, —NRC(=O)R or —C(=O)N(R)$_2$, wherein R is, at each occurrence, independently H or $C_1$-$C_{12}$ alkyl.

In some of the foregoing embodiments of (X), $L^1$ and $L^{1'}$ are each independently —O(C=O)$R^1$, —(C=O)O$R^1$ or —C(=O)NR$^b$R$^c$, and $L^2$ and $L^{2'}$ are each independently —O(C=O)$R^2$, —(C=O)O$R^2$ or —C(=O)NR$^e$R$^f$. For example, in some embodiments $L^1$ and $L^{1'}$ are each —(C=O)O$R^1$, and $L^2$ and $L^{2'}$ are each —(C=O)O$R^2$. In other embodiments $L^1$ and $L^{1'}$ are each —(C=O)O$R^1$, and $L^2$ and $L^{2'}$ are each —C(=O)NR$^e$R$^f$. In other embodiments $L^1$ and $L^{1'}$ are each —C(=O)NR$^b$R$^c$, and $L^2$ and $L^{2'}$ are each —C(=O)NR$^e$R$^f$.

In some embodiments of (X), $G^1$, $G^{1'}$, $G^2$ and $G^{2'}$ are each independently $C_2$-$C_8$ alkylene, for example $C_4$-$C_8$ alkylene.

In some of the foregoing embodiments of (X), $R^1$ or $R^2$, are each, at each occurrence, independently branched $C_6$-$C_{24}$ alkyl. For example, in some embodiments, $R^1$ and $R^2$ at each occurrence, independently have the following structure:

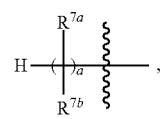

wherein:
$R^{7a}$ and $R^{7b}$ are, at each occurrence, independently H or $C_1$-$C_{12}$ alkyl; and
a is an integer from 2 to 12,
wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of (X), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of (X), $R^1$ or $R^2$, or both, at each occurrence independently has one of the following structures:

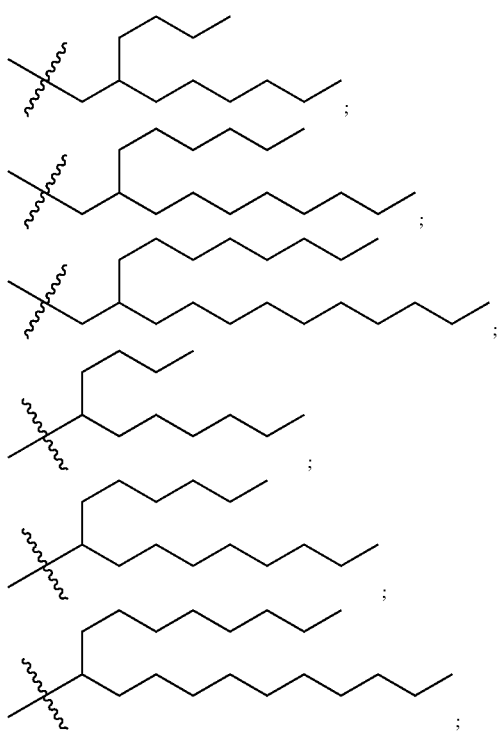

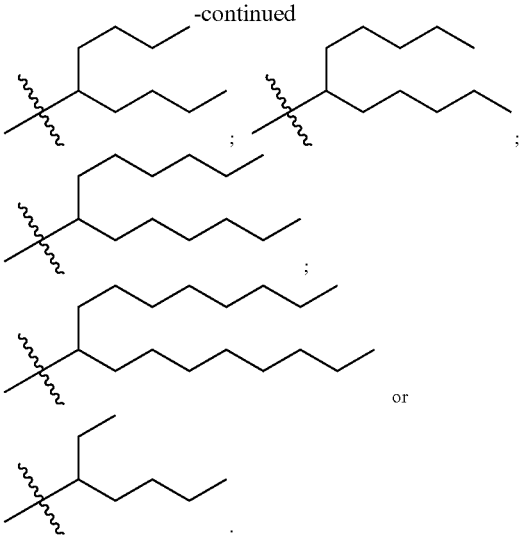

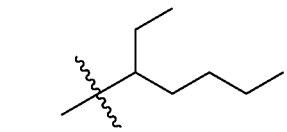

In some of the foregoing embodiments of (X), $R^b$, $R^c$, $R^e$ and $R^f$, when present, are each independently $C_3$-$C_{12}$ alkyl. For example, in some embodiments $R^b$, $R^c$, $R^e$ and $R^f$, when present, are n-hexyl and in other embodiments $R^b$, $R^c$, $R^e$ and $R^f$, when present, are n-octyl.

In various different embodiments of (X), the compound has one of the structures set forth in Table 9 below.

TABLE 9

Representative Compounds of Structure (X)

| No. | Structure |
|-----|-----------|
| X-1 | 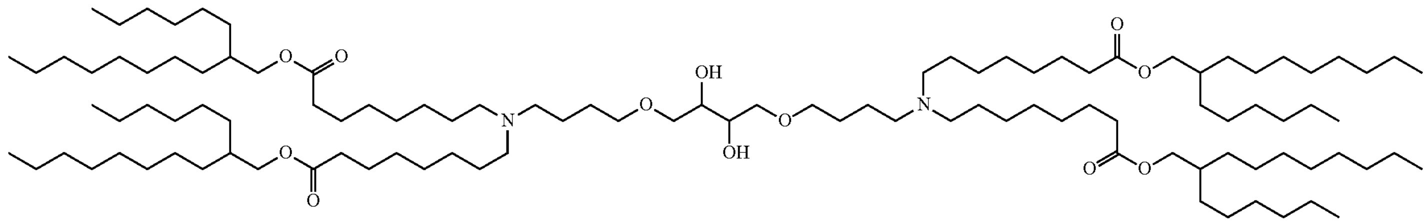 [SMILES: CCCCCCCCC(CCCCCC)COC(=O)CCCCCCCN(CCCCCCCC(=O)OCC(CCCCCC)CCCCCCCC)CCCCOCC(O)C(O)COCCCCN(CCCCCCCC(=O)OCC(CCCCCC)CCCCCCCC)CCCCCCCC(=O)OCC(CCCCCC)CCCCCCCC] |
| X-2 | 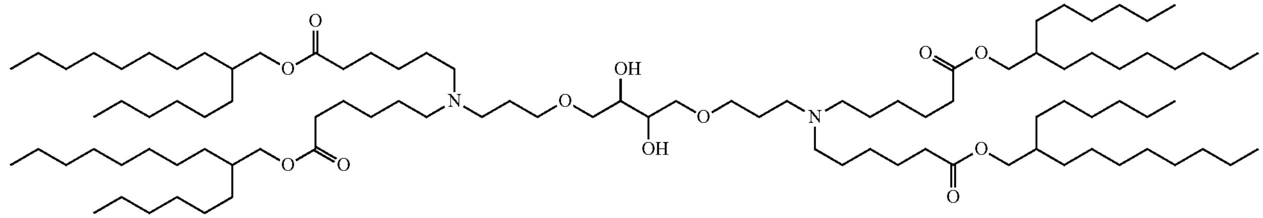 [SMILES: CCCCCCCCC(CCCCCC)COC(=O)CCCCCN(CCCCCC(=O)OCC(CCCCCC)CCCCCCCC)CCCOCC(O)C(O)COCCCN(CCCCCC(=O)OCC(CCCCCC)CCCCCCCC)CCCCCC(=O)OCC(CCCCCC)CCCCCCCC] |
| X-3 | 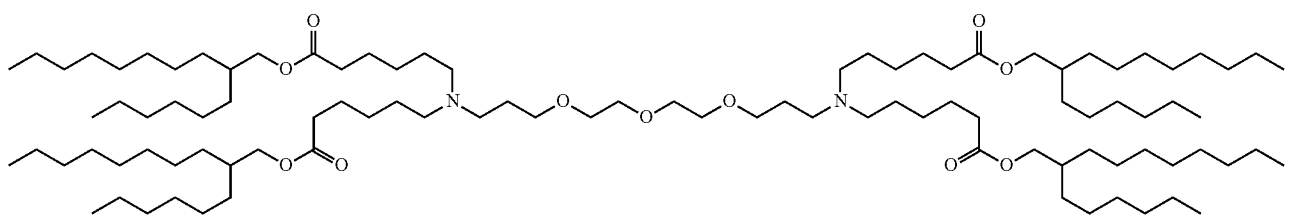 [SMILES: CCCCCCCCC(CCCCCC)COC(=O)CCCCCN(CCCCCC(=O)OCC(CCCCCC)CCCCCCCC)CCCOCCOCCOCCCN(CCCCCC(=O)OCC(CCCCCC)CCCCCCCC)CCCCCC(=O)OCC(CCCCCC)CCCCCCCC] |
| X-4 | 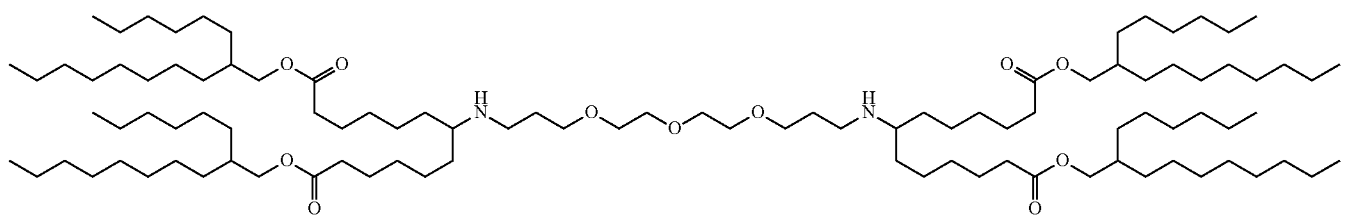 [SMILES: CCCCCCCCC(CCCCCC)COC(=O)CCCCCC(CCCCCC(=O)OCC(CCCCCC)CCCCCCCC)NCCCOCCOCCOCCCNC(CCCCCC(=O)OCC(CCCCCC)CCCCCCCC)CCCCCC(=O)OCC(CCCCCC)CCCCCCCC] |

TABLE 9-continued

Representative Compounds of Structure (X)

| No. | Structure |
|---|---|
| X-5 | 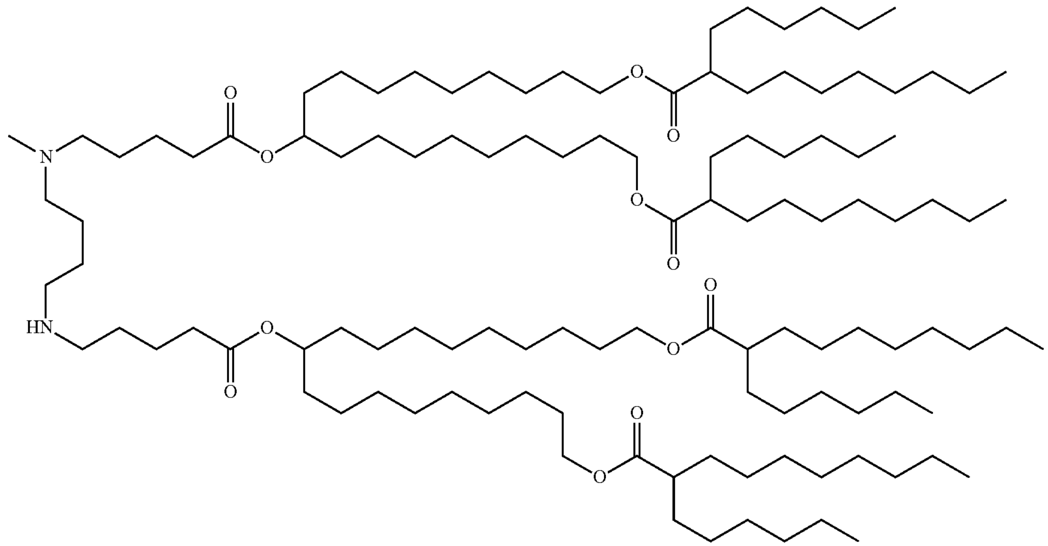 [SMILES: CCCCCCCCC(CCCCCC)C(=O)OCCCCCCCCCC(CCCCCCCCCOC(=O)C(CCCCCC)CCCCCCCC)OC(=O)CCCCNCCCCN(C)CCCCC(=O)OC(CCCCCCCCCOC(=O)C(CCCCCC)CCCCCCCC)CCCCCCCCCOC(=O)C(CCCCCC)CCCCCCCC] |
| X-6 | 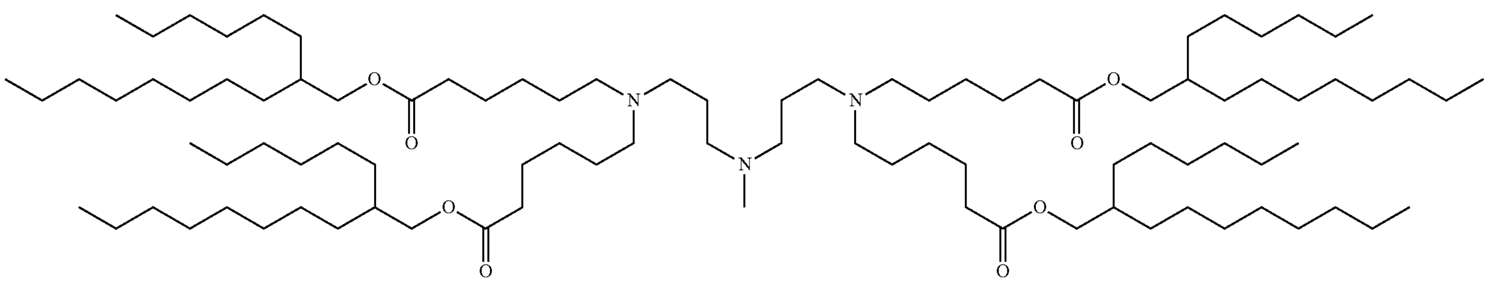 [SMILES: CCCCCCCCC(CCCCCC)COC(=O)CCCCCN(CCCCCC(=O)OCC(CCCCCC)CCCCCCCC)CCCN(C)CCCN(CCCCCC(=O)OCC(CCCCCC)CCCCCCCC)CCCCCC(=O)OCC(CCCCCC)CCCCCCCC] |

TABLE 9-continued

Representative Compounds of Structure (X)

| No. | Structure |
|---|---|
| X-7 | 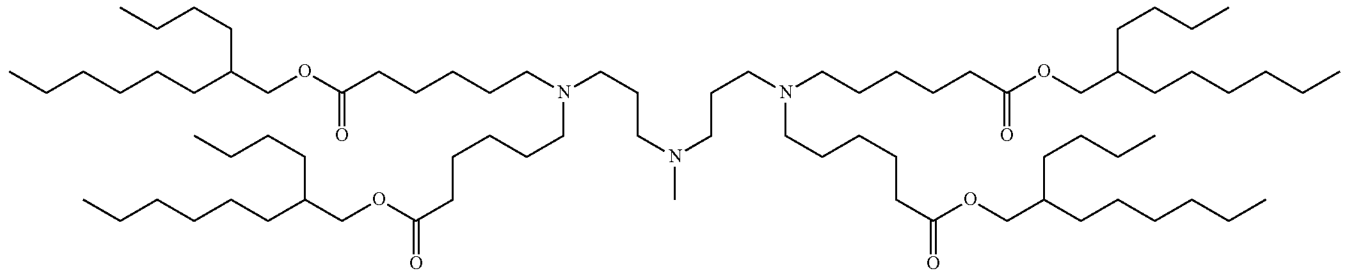 [SMILES: CCCCCCC(CCCC)COC(=O)CCCCCN(CCCCCC(=O)OCC(CCCC)CCCCCC)CCCN(C)CCCN(CCCCCC(=O)OCC(CCCC)CCCCCC)CCCCCC(=O)OCC(CCCC)CCCCCC] |
| X-8 | 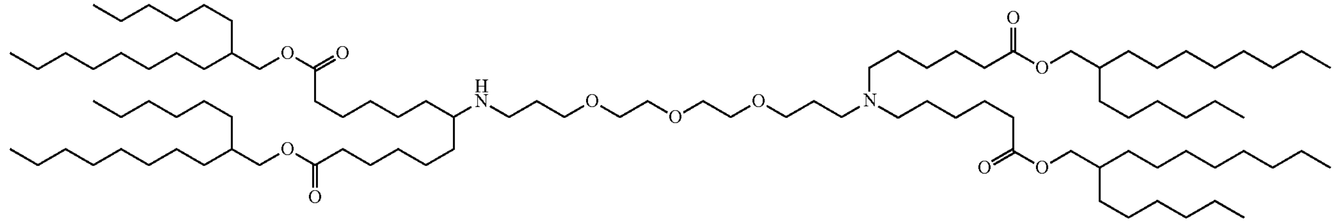 [SMILES: CCCCCCCCC(CCCCCC)COC(=O)CCCCCC(CCCCCC(=O)OCC(CCCCCC)CCCCCCCC)NCCCOCCOCCOCCCN(CCCCCC(=O)OCC(CCCCCC)CCCCCCCC)CCCCCC(=O)OCC(CCCCCC)CCCCCCCC] |
| X-9 | 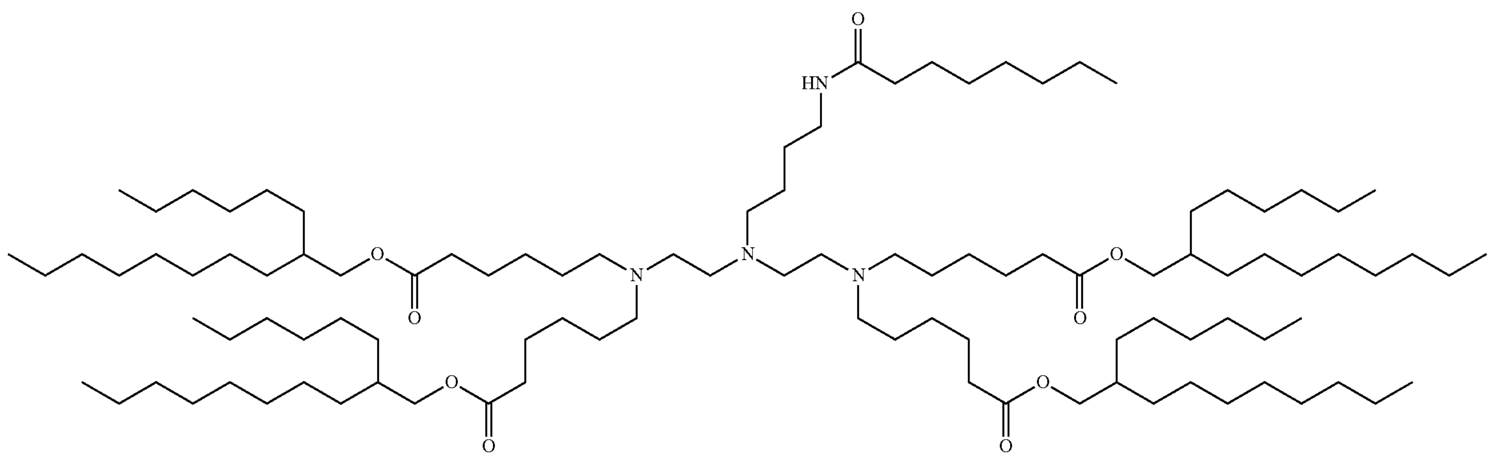 [SMILES: CCCCCCCCC(CCCCCC)COC(=O)CCCCCN(CCCCCC(=O)OCC(CCCCCC)CCCCCCCC)CCN(CCCCNC(=O)CCCCCCC)CCN(CCCCCC(=O)OCC(CCCCCC)CCCCCCCC)CCCCCC(=O)OCC(CCCCCC)CCCCCCCC] |

TABLE 9-continued

Representative Compounds of Structure (X)

| No. | Structure |
|---|---|
| X-10 | 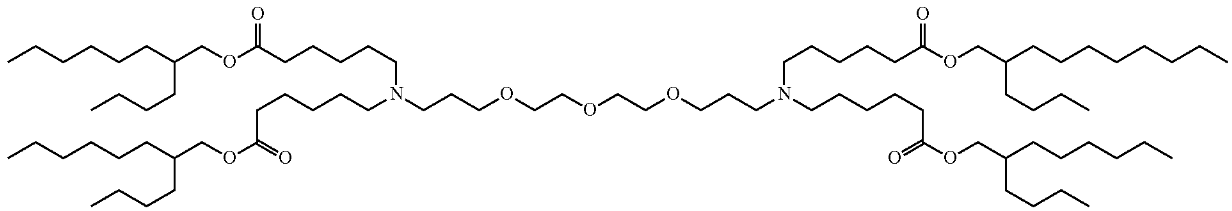 [SMILES: CCCCCCCCC(CCCC)COC(=O)CCCCCN(CCCCCC(=O)OCC(CCCC)CCCCCC)CCCOCCOCCOCCCN(CCCCCC(=O)OCC(CCCC)CCCCCC)CCCCCC(=O)OCC(CCCC)CCCCCC] |
| X-11 | 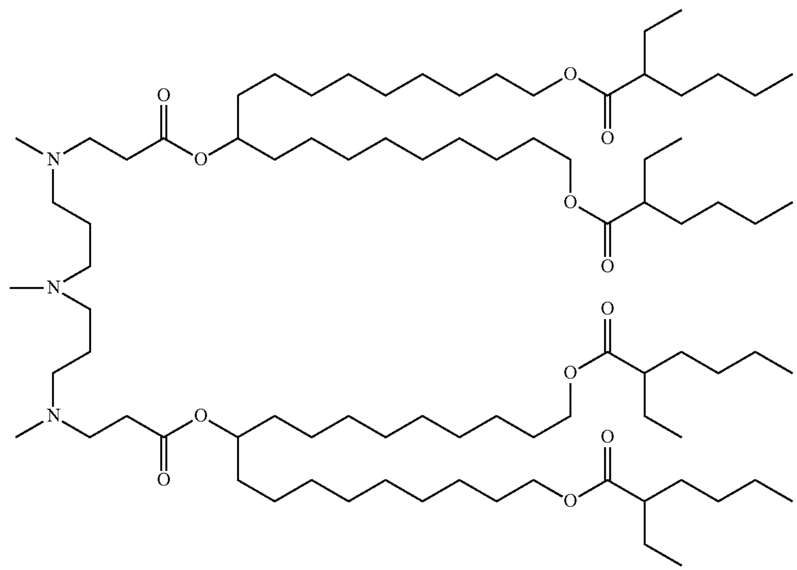 [SMILES: CCCCC(CC)C(=O)OCCCCCCCCCC(CCCCCCCCCOC(=O)C(CC)CCCC)OC(=O)CCN(C)CCCN(C)CCCN(C)CCC(=O)OC(CCCCCCCCCOC(=O)C(CC)CCCC)CCCCCCCCCOC(=O)C(CC)CCCC] |

Compounds of Formula (X) can be prepared and tested according to the procedures set forth in PCT Pub. No. WO 2019/036028, the full disclosure of which is incorporated by reference in its entirety.

Cationic Lipids of Formula XI

In still different embodiments the cationic lipid has the structure of Formula (XI):

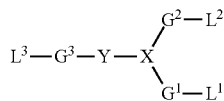

(XI)

or a pharmaceutically acceptable salt or stereoisomer thereof, wherein:

X is N, and Y is absent; or X is CR, and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$ or —N$R^a$C(=O)O$R^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$; —N$R^d$C(=O)O$R^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In more embodiments of structure (XI):

X is N, and Y is absent; or X is CR, and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^e$$R^f$, —N$R^a$C(=O)N$R^e$$R^f$, —OC(=O)N$R^b$$R^c$ or —N$R^a$C(=O)O$R^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$; —N$R^d$C(=O)O$R^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In other embodiments of structure (XI):

X is N and Y is absent, or X is CR and Y is NR;

$L^1$ is —O(C=O)$R^1$, —(C=O)O$R^1$, —C(=O)$R^1$, —O$R^1$, —S(O)$_x$$R^1$, —S—S$R^1$, —C(=O)S$R^1$, —SC(=O)$R^1$, —N$R^a$C(=O)$R^1$, —C(=O)N$R^b$$R^c$, —N$R^a$C(=O)N$R^b$$R^c$, —OC(=O)N$R^b$$R^c$ or —N$R^a$C(=O)O$R^1$;

$L^2$ is —O(C=O)$R^2$, —(C=O)O$R^2$, —C(=O)$R^2$, —O$R^2$, —S(O)$_x$$R^2$, —S—S$R^2$, —C(=O)S$R^2$, —SC(=O)$R^2$, —N$R^d$C(=O)$R^2$, —C(=O)N$R^e$$R^f$, —N$R^d$C(=O)N$R^e$$R^f$, —OC(=O)N$R^e$$R^f$; —N$R^d$C(=O)O$R^2$ or a direct bond to $R^2$;

$L^3$ is —O(C=O)$R^3$ or —(C=O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently branched $C_6$-$C_{24}$ alkyl or branched $C_6$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In certain embodiments of (XI), $G^3$ is unsubstituted. In more specific embodiments $G^3$ is $C_2$-$C_{12}$ alkylene, for example, in some embodiments $G^3$ is $C_3$-$C_7$ alkylene or in other embodiments $G^3$ is $C_3$-$C_{12}$ alkylene. In some embodiments, $G^3$ is $C_2$ or $C_3$ alkylene.

In other embodiments of (XI), $G^3$ is $C_1$-$C_{12}$ heteroalkylene, for example $C_1$-$C_{12}$ aminylalkylene.

In certain embodiments of (XI), X is N and Y is absent. In other embodiments, X is CR and Y is NR, for example in some of these embodiments R is H.

In some of the foregoing embodiments of (XI), the compound has one of the following structures (XIA), (XIB), (XIC) or (XID):

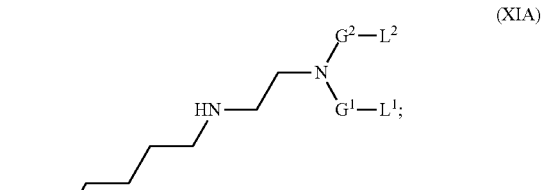

(XIA)

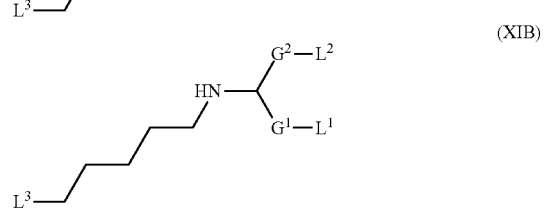

(XIB)

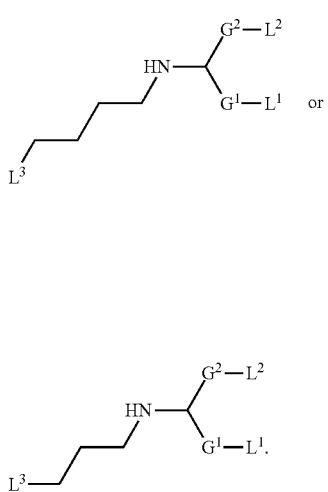

(XIC)

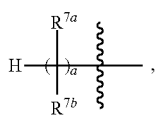

(XID)

In some of the foregoing embodiments of (XI), $L^1$ is —O(C=O)$R^1$, —(C=O)O$R^1$ or —C(=O)N$R^b R^c$, and $L^2$ is —O(C=O)$R^2$, —(C=O)O$R^2$ or —C(=O)N$R^e R^f$. In other specific embodiments of (XI), $L^1$ is —(C=O)O$R^1$ and $L^2$ is —(C=O)O$R^2$. In any of the foregoing embodiments, $L^3$ is —(C=O)O$R^3$.

In some of the foregoing embodiments of (XI), $G^1$ and $G^2$ are each independently $C_2$-$C_{12}$ alkylene, for example $C_4$-$C_{10}$ alkylene.

In some of the foregoing embodiments of (XI), $R^1$, $R^2$ and $R^3$ are each, independently branched $C_6$-$C_{24}$ alkyl. For example, in some embodiments of (XI), $R^1$, $R^2$ and $R^3$ each, independently have the following structure:

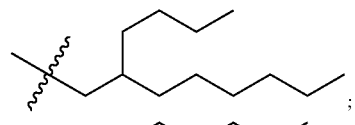

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of (XI), at least one occurrence of $R^{7a}$ is H. For example, in some embodiments, $R^{7a}$ is H at each occurrence. In other different embodiments of (XI), at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In some of the foregoing embodiments of (XI), X is CR, Y is NR and $R^3$ is $C_1$-$C_{12}$ alkyl, such as ethyl, propyl or butyl. In some of these embodiments of (XI), $R^1$ and $R^2$ are each independently branched $C_6$-$C_{24}$ alkyl.

In different embodiments of (XI), $R^1$, $R^2$ and $R^3$ each, independently have one of the following structures:

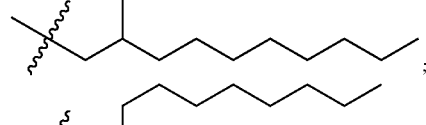

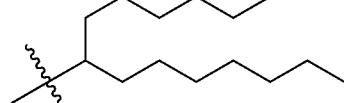

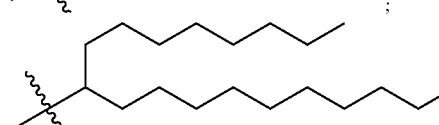

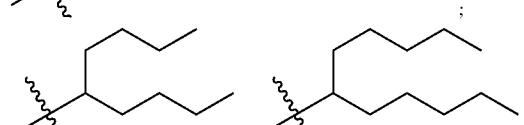

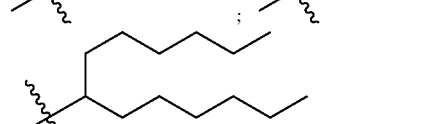

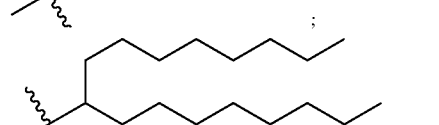

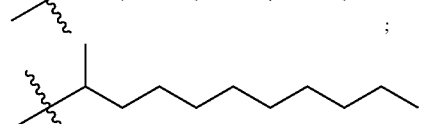

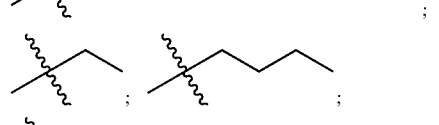

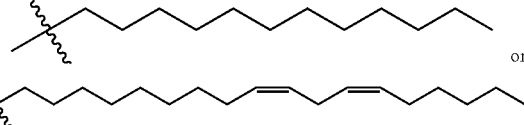

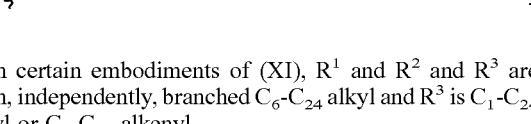

or

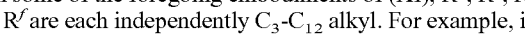

.

In certain embodiments of (XI), $R^1$ and $R^2$ and $R^3$ are each, independently, branched $C_6$-$C_{24}$ alkyl and $R^3$ is $C_1$-$C_{24}$ alkyl or $C_2$-$C_{24}$ alkenyl.

In some of the foregoing embodiments of (XI), $R^b$, $R^c$, $R^e$ and $R^f$ are each independently $C_3$-$C_{12}$ alkyl. For example, in some embodiments of (XI) $R^b$, $R^c$, $R^e$ and $R^f$ are n-hexyl and in other embodiments $R^b$, $R^c$, $R^e$ and $R^f$ are n-octyl.

In various different embodiments of (XI), the compound has one of the structures set forth in Table 10 below.

TABLE 10

Representative Compounds of Structure (XI)

| No. | Structure |
|---|---|
| XI-1 | 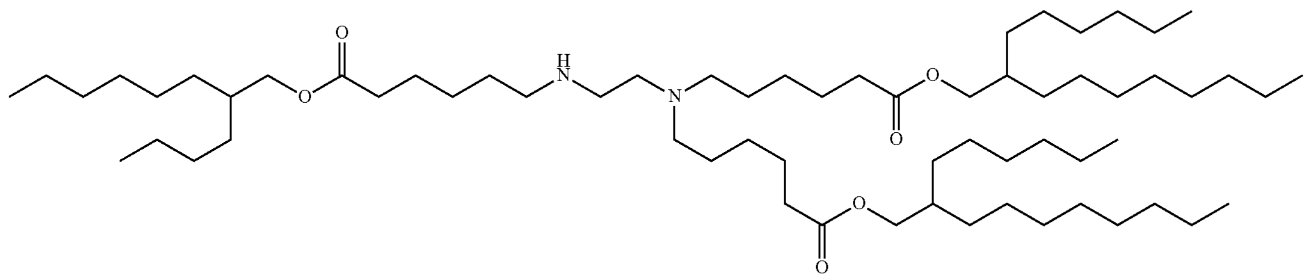 [SMILES: CCCCCCCCC(CCCCCC)COC(=O)CCCCCN(CCCCCC(=O)OCC(CCCCCC)CCCCCCCC)CCNCCCCCC(=O)OCC(CCCC)CCCCCC] |
| XI-2 | 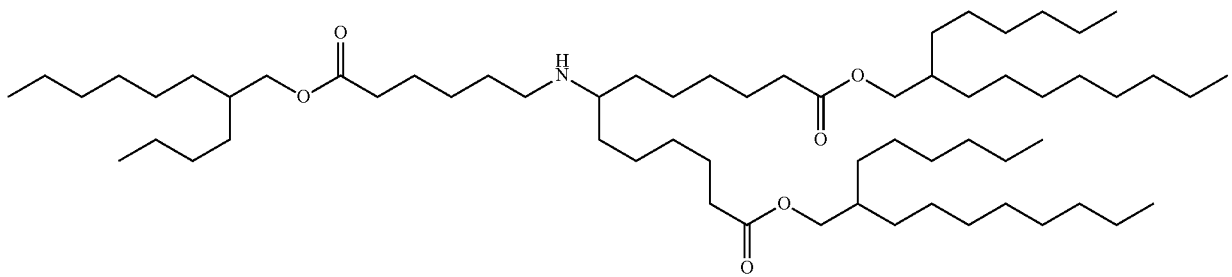 [SMILES: CCCCCCCCC(CCCCCC)COC(=O)CCCCCC(CCCCCC(=O)OCC(CCCCCC)CCCCCCCC)NCCCCCC(=O)OCC(CCCC)CCCCCC] |
| XI-3 | 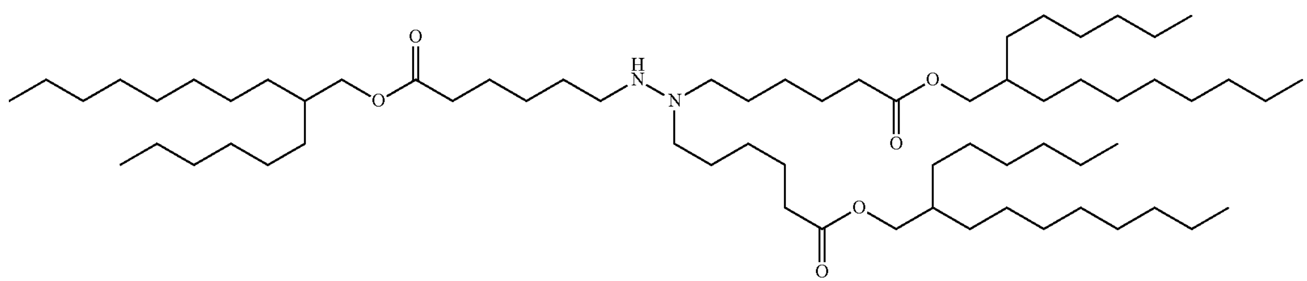 [SMILES: CCCCCCCCC(CCCCCC)COC(=O)CCCCCNN(CCCCCC(=O)OCC(CCCCCC)CCCCCCCC)CCCCCC(=O)OCC(CCCCCC)CCCCCCCC] |

TABLE 10-continued

Representative Compounds of Structure (XI)

| No. | Structure |
|---|---|
| XI-4 | 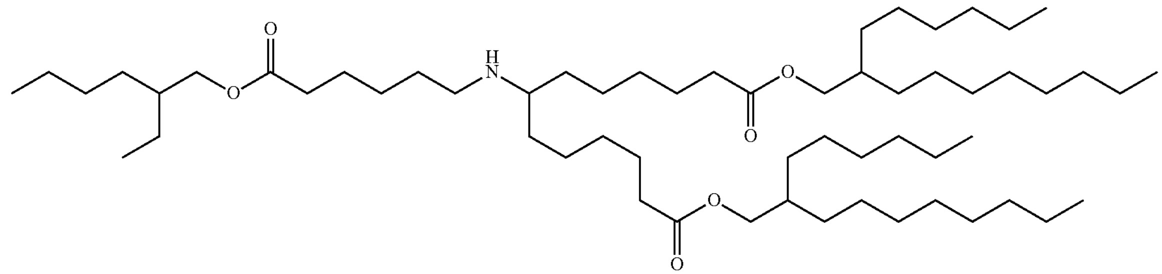 [SMILES: CCCCCCCCC(CCCCCC)COC(=O)CCCCCC(CCCCCC(=O)OCC(CCCCCC)CCCCCCCC)NCCCCCC(=O)OCC(CC)CCCC] |
| XI-5 | 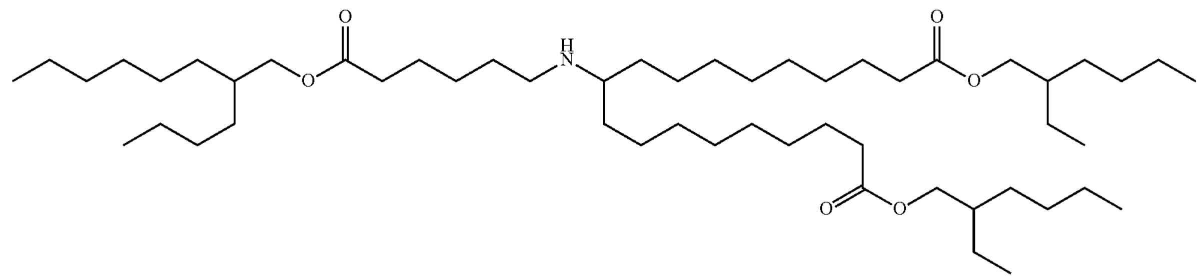 [SMILES: CCCCCCC(CCCC)COC(=O)CCCCCNC(CCCCCCCCC(=O)OCC(CC)CCCC)CCCCCCCCC(=O)OCC(CC)CCCC] |
| XI-6 | 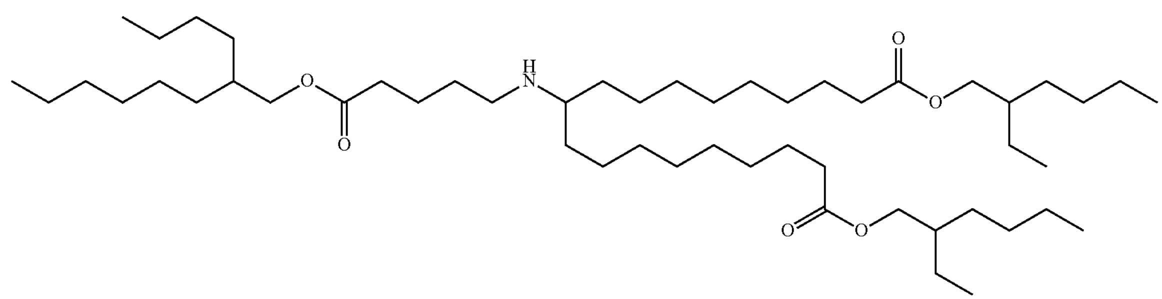 [SMILES: CCCCCCC(CCCC)COC(=O)CCCCNC(CCCCCCCCC(=O)OCC(CC)CCCC)CCCCCCCCC(=O)OCC(CC)CCCC] |

TABLE 10-continued

Representative Compounds of Structure (XI)

| No. | Structure |
|---|---|
| XI-7 | 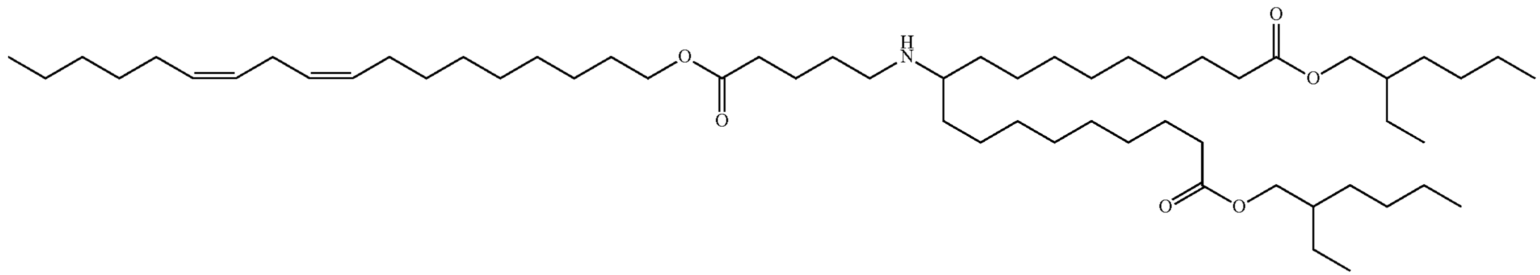 [SMILES: CCCCC/C=C\C/C=C\CCCCCCCCOC(=O)CCCCNC(CCCCCCCCC(=O)OCC(CC)CCCC)CCCCCCCCC(=O)OCC(CC)CCCC] |
| XI-8 | 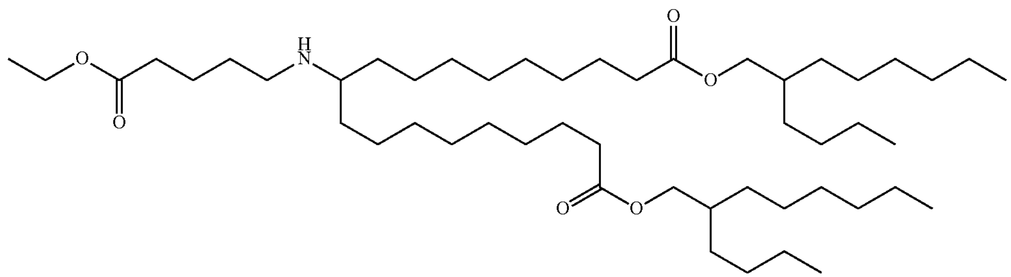 [SMILES: CCCCCCC(CCCC)COC(=O)CCCCCCCCC(CCCCCCCCC(=O)OCC(CCCC)CCCCCC)NCCCCC(=O)OCC] |
| XI-9 | 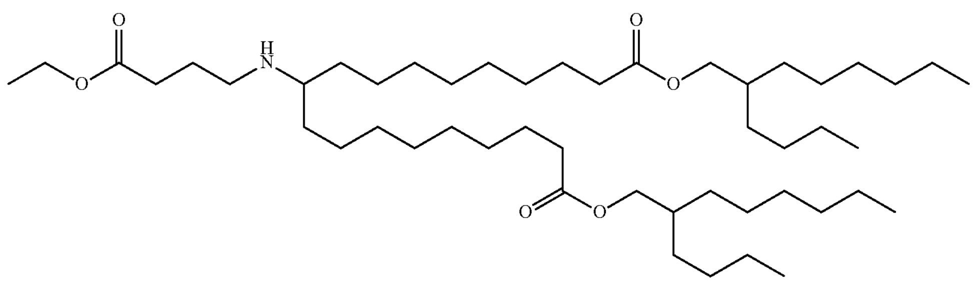 [SMILES: CCCCCCC(CCCC)COC(=O)CCCCCCCCC(CCCCCCCCC(=O)OCC(CCCC)CCCCCC)NCCCC(=O)OCC] |

TABLE 10-continued

Representative Compounds of Structure (XI)

| No. | Structure |
|-----|-----------|
| XI-10 | 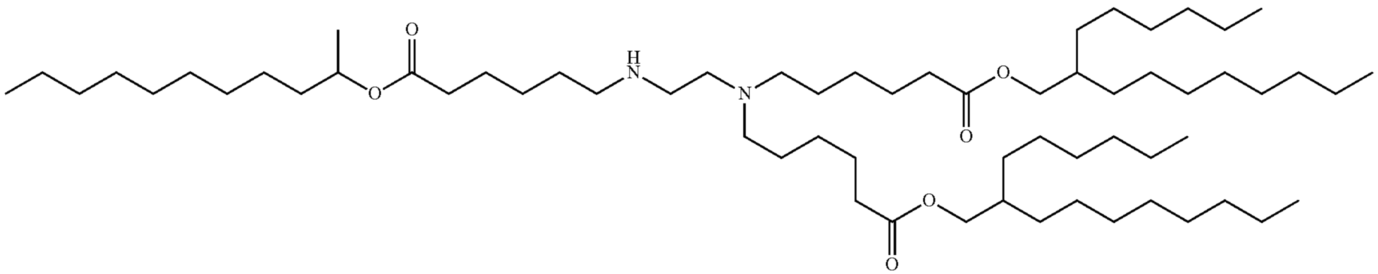 [SMILES: CCCCCCCCCC(C)OC(=O)CCCCCNCCN(CCCCCC(=O)OCC(CCCCCC)CCCCCCCC)CCCCCC(=O)OCC(CCCCCC)CCCCCCCC] |
| XI-11 | 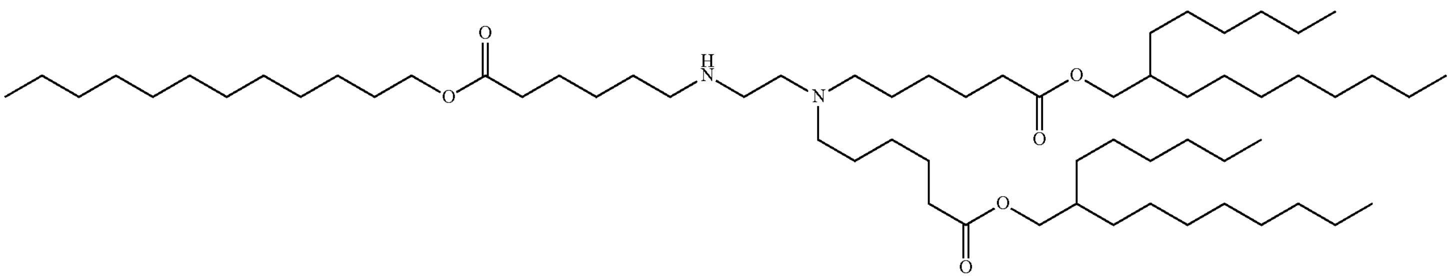 [SMILES: CCCCCCCCCCCCOC(=O)CCCCCNCCN(CCCCCC(=O)OCC(CCCCCC)CCCCCCCC)CCCCCC(=O)OCC(CCCCCC)CCCCCCCC] |
| XI-12 | 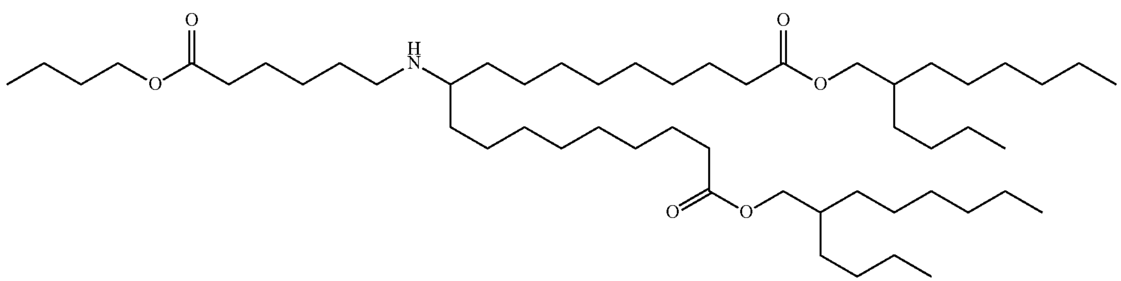 [SMILES: CCCCCCC(CCCC)COC(=O)CCCCCCCCC(CCCCCCCCC(=O)OCC(CCCC)CCCCCC)NCCCCCC(=O)OCCCC] |

Compounds of Formula (XI) can be prepared and tested according to the procedures set forth in PCT Pub. No. WO 2019/036030, the full disclosure of which is incorporated by reference in its entirety.

Cationic Lipids of Formula XII

In still different embodiments the cationic lipid has the structure of Formula (XII):

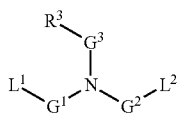
(XII)

or a pharmaceutically acceptable salt or stereoisomer thereof, wherein:

L¹ is —O(C=O)R¹, —(C=O)OR¹, —C(=O)R¹, —OR¹, —S(O)ₓR¹, —S—SR¹, —C(=O)SR¹, —SC(=O)R¹, —NRᵃC(=O)R¹, —C(=O)NRᵇRᶜ, —NRᵃC(=O)NRᵇRᶜ, —OC(=O)NRᵇRᶜ or —NRᵃC(=O)OR¹;

L² is —O(C=O)R², —(C=O)OR², —C(=O)R², —OR², —S(O)ₓR², —S—SR², —C(=O)SR², —SC(=O)R², —NRᵈC(=O)R², —C(=O)NRᵉRᶠ, —NRᵈC(=O)NRᵉRᶠ, —OC(=O)NRᵉRᶠ; —NRᵈC(=O)OR² or a direct bond to R²;

G¹ and G² are each independently C₂-C₁₂ alkylene or C₂-C₁₂ alkenylene;

G³ is C₁-C₂₄ alkylene, C₂-C₂₄ alkenylene, C₃-C₈ cycloalkylene or C₃-C₈ cycloalkenylene;

Rᵃ, Rᵇ, Rᵈ and Rᵉ are each independently H or C₁-C₁₂ alkyl or C₁-C₁₂ alkenyl;

Rᶜ and Rᶠ are each independently C₁-C₁₂ alkyl or C₂-C₁₂ alkenyl;

R¹ and R² are each independently branched C₆-C₂₄ alkyl or branched C₆-C₂₄ alkenyl;

R³ is —N(R⁴)R⁵;

R⁴ is C₁-C₁₂ alkyl;

R⁵ is substituted C₁-C₁₂ alkyl; and x is 0, 1 or 2, and wherein each alkyl, alkenyl, alkylene, alkenylene, cycloalkylene, cycloalkenylene, aryl and aralkyl is independently substituted or unsubstituted unless otherwise specified.

In certain embodiments of (XII), G³ is unsubstituted. In more specific embodiments G³ is C₂-C₁₂ alkylene, for example, in some embodiments of (XII) G³ is C₃-C₇ alkylene or in other embodiments G³ is C₃-C₁₂ alkylene. In some embodiments of (XII), G³ is C₂ or C₃ alkylene.

In some of the foregoing embodiments of (XII), the compound has the following structure (IA):

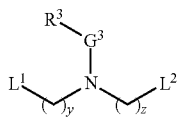
(XIIA)

wherein y and z are each independently integers ranging from 2 to 12, for example an integer from 2 to 6, from 4 to 10, or for example 4 or 5. In certain embodiments of (XII), y and z are each the same and selected from 4, 5, 6, 7, 8 and 9.

In some of the foregoing embodiments of (XII), L¹ is —O(C=O)R¹, —(C=O)OR¹ or —C(=O)NRᵇRᶜ, and L² is —O(C=O)R², —(C=O)OR² or —C(=O)NRᵉRᶠ. For example, in some embodiments of (XII) L¹ and L² are —(C=O)OR¹ and —(C=O)OR², respectively. In other embodiments L¹ is —(C=O)OR¹ and L² is —C(=O)NRᵉRᶠ. In other embodiments of (XII) L¹ is —C(=O)NRᵇRᶜ and L² is —C(=O)NRᵉRᶠ.

In other embodiments of the foregoing of (XII), the compound has one of the following structures (XIIB), (XIIC), (XIID) or (XIIE):

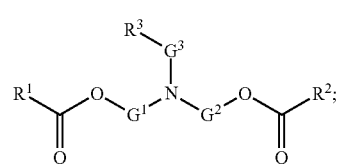
(XIIB)

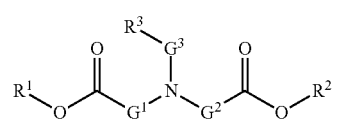
(XIIC)

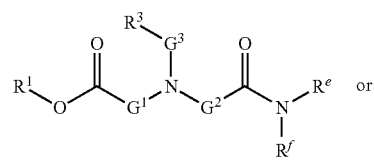
(XIID)

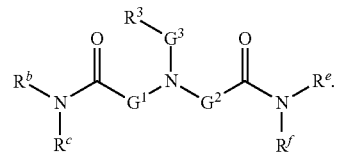
(XIIE)

In some of the foregoing embodiments, the compound has structure (XIIB), in other embodiments, the compound has structure (XIIC) and in still other embodiments the compound has the structure (XIID). In other embodiments, the compound has structure (XIIE).

In some different embodiments of the foregoing, the compound has one of the following structures (XIIF), (XIIG), (XIIH) or (XIIJ):

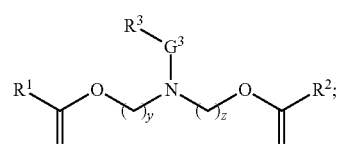
(XIIF)

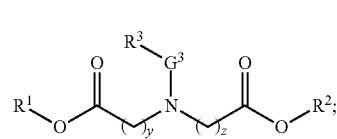
(XIIG)

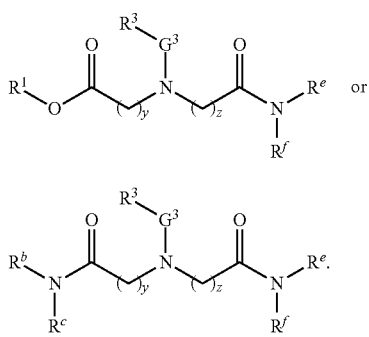

(XIIIH)

(XIIIJ)

wherein y and z are each independently integers ranging from 2 to 12, for example an integer from 2 to 6, for example 4.

In some of the foregoing embodiments of (XII), y and z are each independently an integer ranging from 2 to 10, 2 to 8, from 4 to 10 or from 4 to 7. For example, in some embodiments of (XII), y is 4, 5, 6, 7, 8, 9, 10, 11 or 12. In some embodiments of (XII), z is 4, 5, 6, 7, 8, 9, 10, 11 or 12. In some embodiments of (XII), y and z are the same, while in other embodiments y and z are different.

In some of the foregoing embodiments of (XII), $R^1$ or $R^2$, or both is branched $C_6$-$C_{24}$ alkyl. For example, in some embodiments of (XII), $R^1$ and $R^2$ each, independently have the following structure:

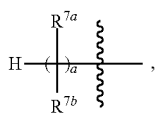

wherein:
$R^{7a}$ and $R^{7b}$ are, at each occurrence, independently H or $C_1$-$C_{12}$ alkyl; and
a is an integer from 2 to 12,
wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of (XII), at least one occurrence of $R^{7a}$ is H. For example, in some embodiments, $R^{7a}$ is H at each occurrence. In other different embodiments of (XII), at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of (XII), $R^1$ or $R^2$, or both, has one of the following structures:

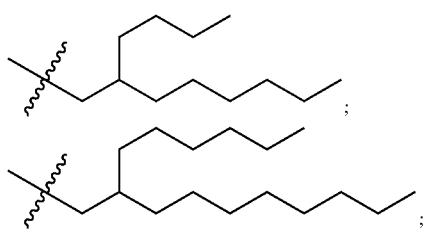

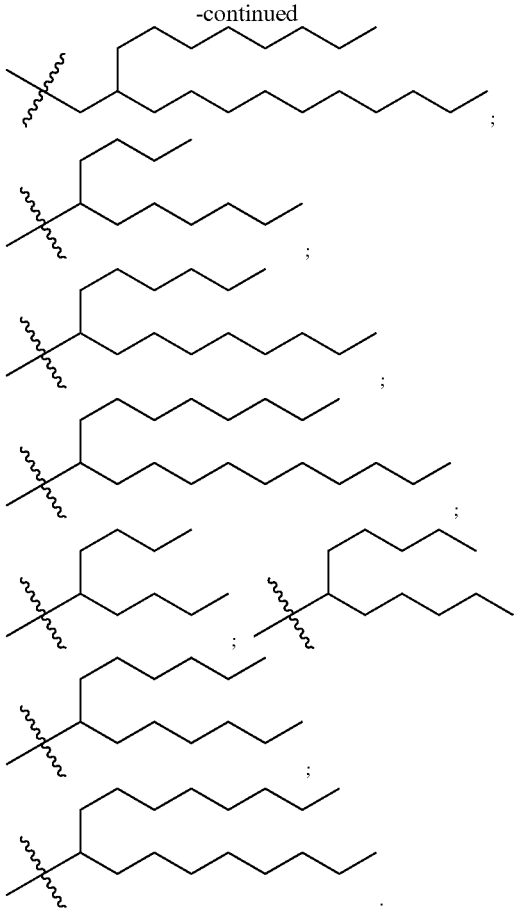

In some of the foregoing embodiments of (XII), $R^b$, $R^c$, $R^e$ and $R^f$ are each independently $C_3$-$C_{12}$ alkyl. For example, in some embodiments of (XII) $R^b$, $R^c$, $R^e$ and $R^f$ are n-hexyl and in other embodiments $R^b$, $R^c$, $R^e$ and $R^f$ are n-octyl.

In any of the foregoing embodiments of (XII), $R^4$ is substituted or unsubstituted: methyl, ethyl, propyl, n-butyl, n-hexyl, n-octyl or n-nonyl. For example, in some embodiments of (XII) $R^4$ is unsubstituted. In other embodiments of (XII) $R^4$ is substituted with one or more substituents selected from the group consisting of —$OR^g$, —$NR^gC(=O)R^h$, —$C(=O)NR^gR^h$, —$C(=O)R^h$, —$OC(=O)R^h$, —$C(=O)OR^h$ and —$OR^iOH$, wherein:
$R^g$ is, at each occurrence independently H or $C_1$-$C_6$ alkyl;
$R^h$ is at each occurrence independently $C_1$-$C_6$ alkyl; and
$R^i$ is, at each occurrence independently $C_1$-$C_6$ alkylene.

In other of the foregoing embodiments of (XII), $R^5$ is substituted: methyl, ethyl, propyl, n-butyl, n-hexyl, n-octyl or n-nonyl. In some embodiments of (XII), $R^5$ is substituted ethyl or substituted propyl. In other different embodiments of (XII), $R^5$ is substituted with hydroxyl. In still more embodiments of (XII), $R^5$ is substituted with one or more substituents selected from the group consisting of —$OR^g$, —$NR^gC(=O)R^h$, —$C(=O)NR^gR^h$, —$C(=O)R^h$, —$OC(=O)R^h$, —$C(=O)OR^h$ and —$OR^iOH$, wherein:
$R^g$ is, at each occurrence independently H or $C_1$-$C_6$ alkyl;
$R^h$ is at each occurrence independently $C_1$-$C_6$ alkyl; and
$R^i$ is, at each occurrence independently $C_1$-$C_6$ alkylene.

In other embodiments of (XII), $R^4$ is unsubstituted methyl, and $R^5$ is substituted: methyl, ethyl, propyl, n-butyl, n-hexyl, n-octyl or n-nonyl. In some of these embodiments, $R^5$ is substituted with hydroxyl.

In some other specific embodiments of (XII), $R^3$ has one of the following structures:
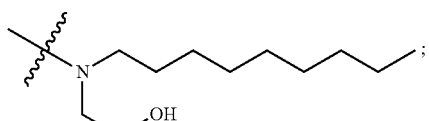
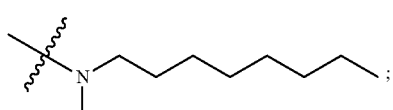
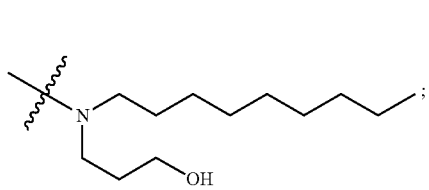
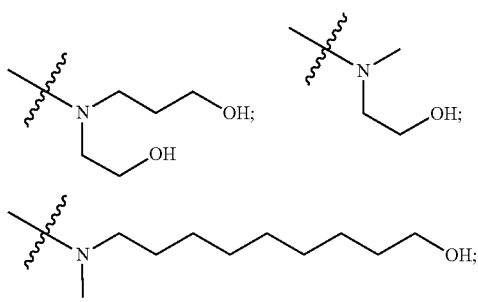
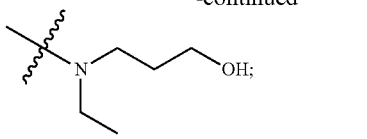
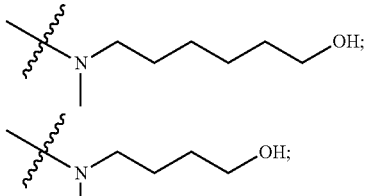
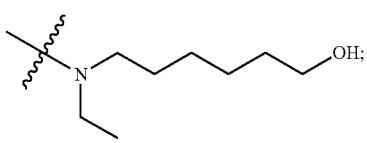
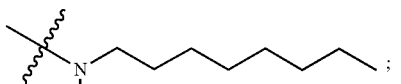
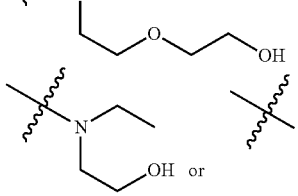
In various different embodiments, the compound has one of the structures set forth in Table 11 below.
TABLE 11
Representative Compounds of Structure (XII)
| No. | Structure |
|---|---|
| XII-1 | 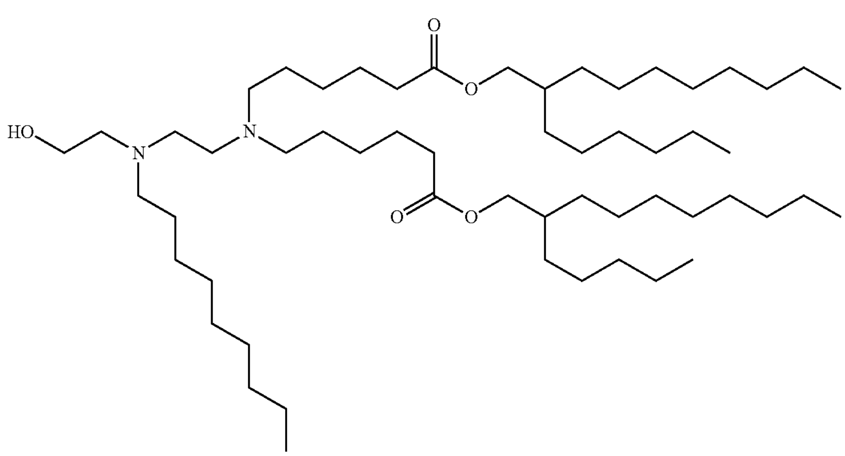 [SMILES: CCCCCCCCCN(CCO)CCN(CCCCCC(=O)OCC(CCCCC)CCCCCCCC)CCCCCC(=O)OCC(CCCCCC)CCCCCCCC] |

TABLE 11-continued

Representative Compounds of Structure (XII)

| No. | Structure |
|---|---|
| XII-2 | 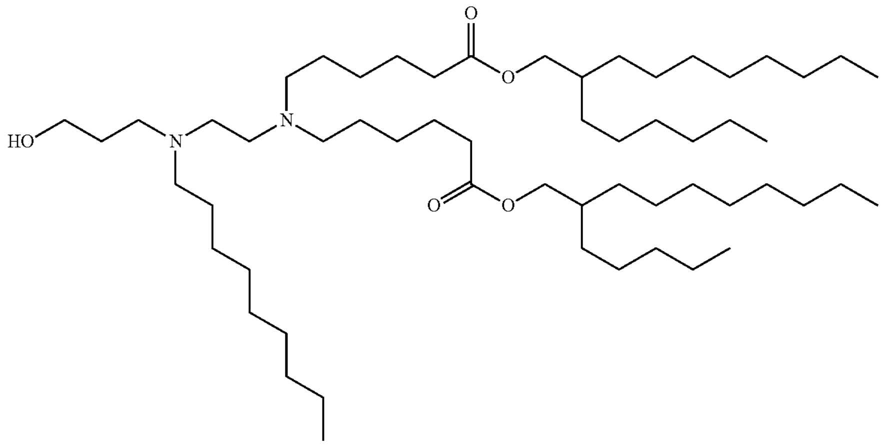 [SMILES: CCCCCCCCCN(CCCO)CCN(CCCCCC(=O)OCC(CCCCC)CCCCCCCC)CCCCCC(=O)OCC(CCCCCC)CCCCCCCC] |
| XII-3 | 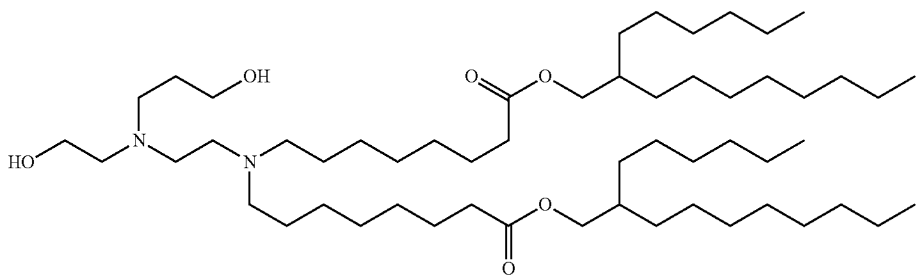 [SMILES: CCCCCCCCC(CCCCCC)COC(=O)CCCCCCCN(CCCCCCCC(=O)OCC(CCCCCC)CCCCCCCC)CCN(CCO)CCCO] |
| XII-4 | 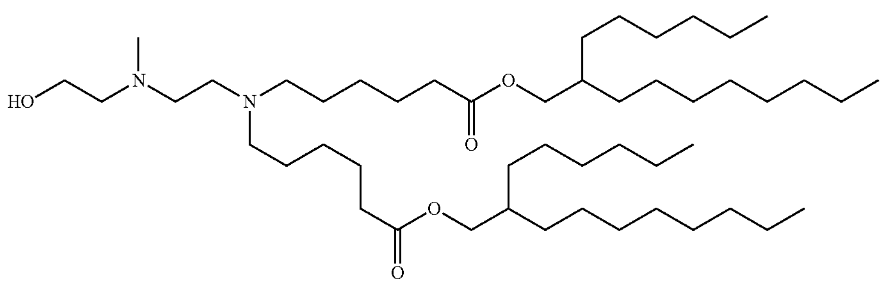 [SMILES: CCCCCCCCC(CCCCCC)COC(=O)CCCCCN(CCCCCC(=O)OCC(CCCCCC)CCCCCCCC)CCN(C)CCO] |
| XII-5 | 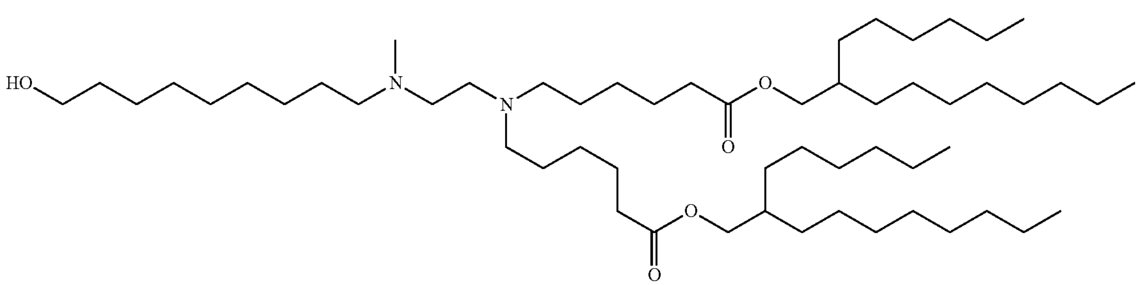 [SMILES: CCCCCCCCC(CCCCCC)COC(=O)CCCCCN(CCCCCC(=O)OCC(CCCCCC)CCCCCCCC)CCN(C)CCCCCCCCCO] |
| XII-6 | 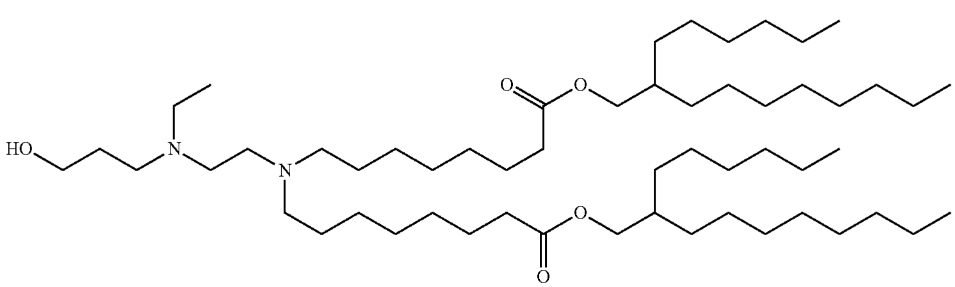 [SMILES: CCCCCCCCC(CCCCCC)COC(=O)CCCCCCCN(CCCCCCCC(=O)OCC(CCCCCC)CCCCCCCC)CCN(CC)CCCO] |

TABLE 11-continued

Representative Compounds of Structure (XII)

| No. | Structure |
|---|---|
| XII-7 | 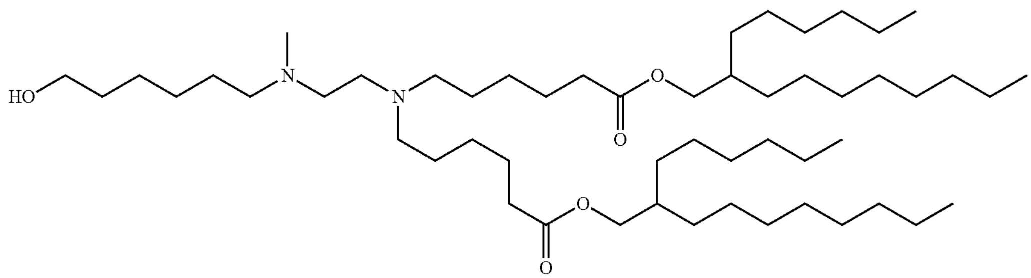 [SMILES: CCCCCCCCC(CCCCCC)COC(=O)CCCCCN(CCCCCC(=O)OCC(CCCCCC)CCCCCCCC)CCN(C)CCCCCCO] |
| XII-8 | 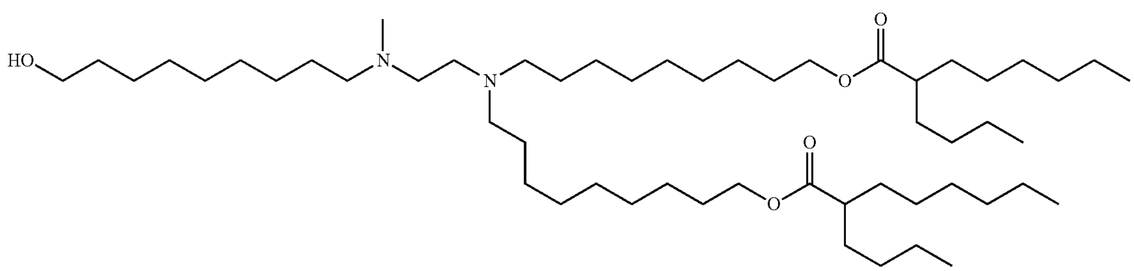 [SMILES: CCCCCCC(CCCC)C(=O)OCCCCCCCCCN(CCCCCCCCCOC(=O)C(CCCC)CCCCCC)CCN(C)CCCCCCCCCO] |
| XII-9 | 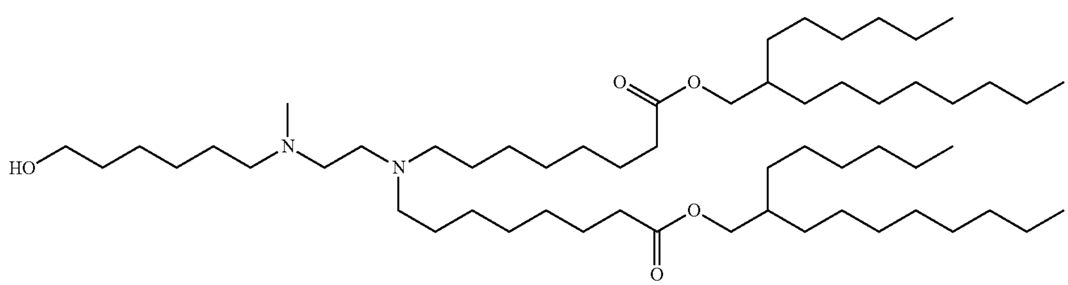 [SMILES: CCCCCCCCC(CCCCCC)COC(=O)CCCCCCCN(CCCCCCCC(=O)OCC(CCCCCC)CCCCCCCC)CCN(C)CCCCCCO] |
| XII-10 | 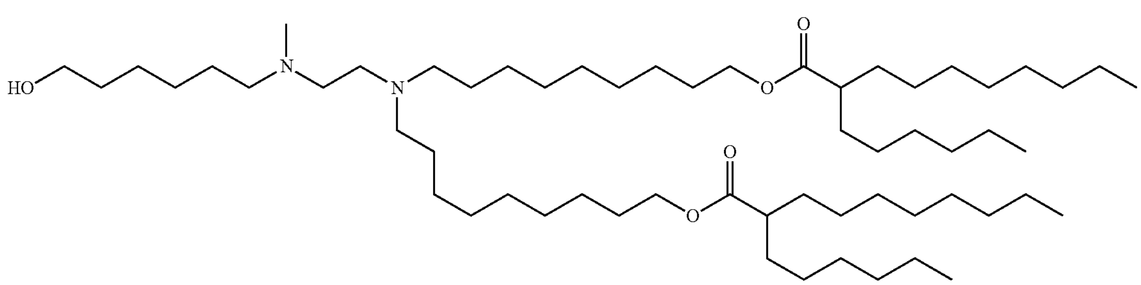 [SMILES: CCCCCCCCC(CCCCCC)C(=O)OCCCCCCCCCN(CCCCCCCCCOC(=O)C(CCCCCC)CCCCCCCC)CCN(C)CCCCCCO] |
| XII-11 | 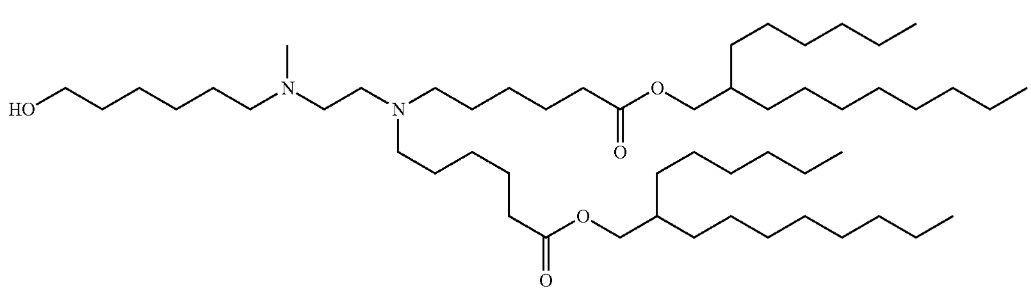 [SMILES: CCCCCCCCC(CCCCCC)COC(=O)CCCCCN(CCCCCC(=O)OCC(CCCCCC)CCCCCCCC)CCN(C)CCCCCCO] |

TABLE 11-continued
Representative Compounds of Structure (XII)
| No. | Structure |
|---|---|
| XII-12 | 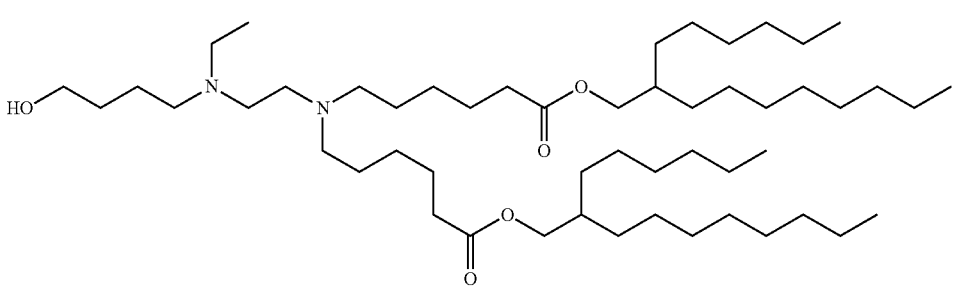 [SMILES: CCCCCCCCC(CCCCCC)COC(=O)CCCCCN(CCCCCC(=O)OCC(CCCCCC)CCCCCCCC)CCN(CC)CCCCO] |
| XII-13 | 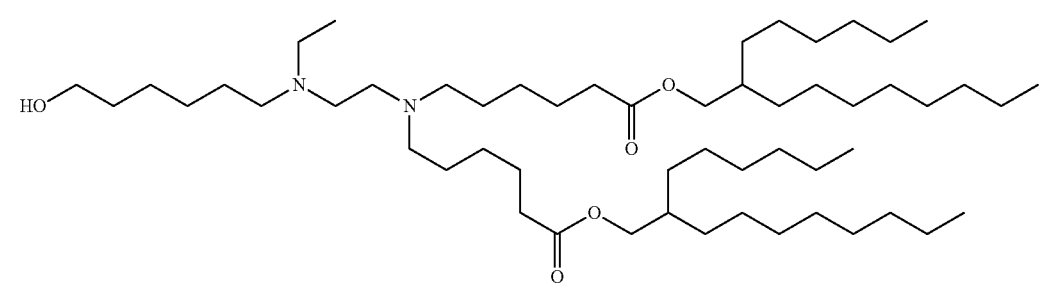 [SMILES: CCCCCCCCC(CCCCCC)COC(=O)CCCCCN(CCCCCC(=O)OCC(CCCCCC)CCCCCCCC)CCN(CC)CCCCCCO] |
| XII-14 | 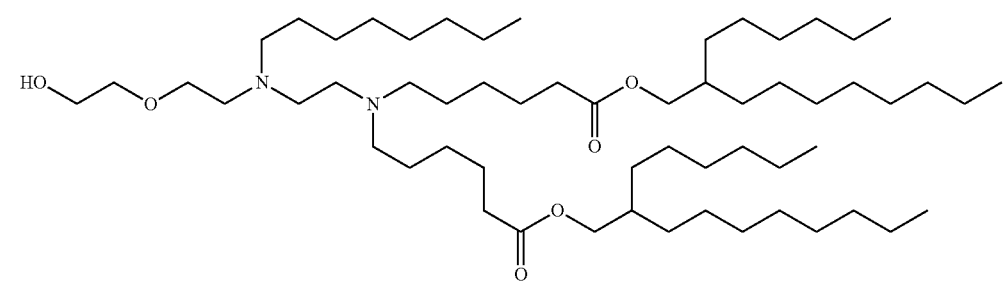 [SMILES: CCCCCCCCC(CCCCCC)COC(=O)CCCCCN(CCCCCC(=O)OCC(CCCCCC)CCCCCCCC)CCN(CCCCCCCC)CCOCCO] |
| XII-15 | 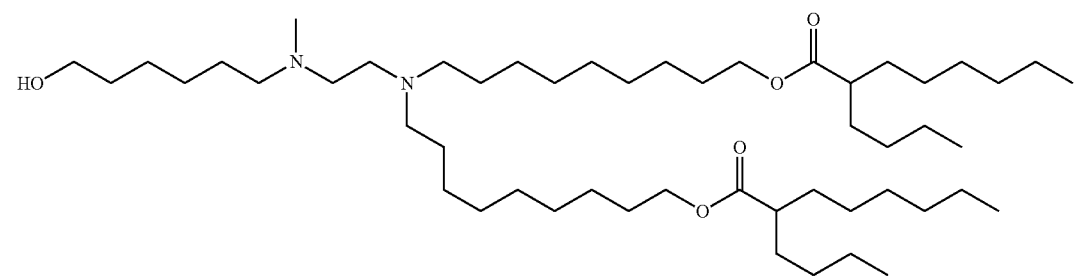 [SMILES: CCCCCCC(CCCC)C(=O)OCCCCCCCCCN(CCCCCCCCCOC(=O)C(CCCC)CCCCCC)CCN(C)CCCCCCO] |
| XII-16 | 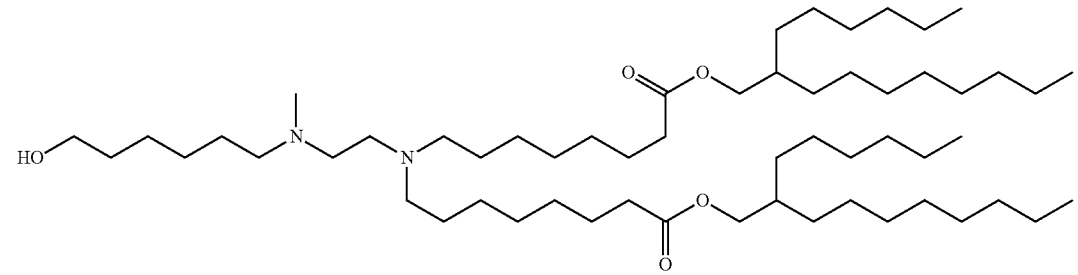 [SMILES: CCCCCCCCC(CCCCCC)COC(=O)CCCCCCCN(CCCCCCCC(=O)OCC(CCCCCC)CCCCCCCC)CCN(C)CCCCCCO] |

TABLE 11-continued

Representative Compounds of Structure (XII)

| No. | Structure |
|---|---|
| XII-17 | (chemical structure) |
| XII-18 | (chemical structure) |

Compounds of Formula (XII) can be prepared and tested according to the procedures set forth in PCT Pub. No. WO 2019/036008, the full disclosure of which is incorporated by reference in its entirety.

In any of the foregoing embodiments, the organic lipid stock solution may further comprise a neutral lipid. In various embodiments, the molar ratio of the cationic lipid to the neutral lipid ranges from about 2:1 to about 8:1. In certain embodiments, the neutral lipid is present at a concentration ranging from 5 to 10 mol percent, from 5 to 15 mol percent, 7 to 13 mol percent, or 9 to 11 mol percent relative to other components incorporated into a lipid nanoparticle. In certain specific embodiments, the neutral lipid is present in a concentration of about 9.5, 10 or 10.5 mol percent relative to other components incorporated into a lipid nanoparticle. In some embodiments, the molar ratio of cationic lipid to the neutral lipid ranges from about 4.1:1.0 to about 4.9:1.0, from about 4.5:1.0 to about 4.8:1.0, or from about 4.7:1.0 to 4.8:1.0. In some embodiments, the molar ratio of total cationic lipid to the neutral lipid ranges from about 4.1:1.0 to about 4.9:1.0, from about 4.5:1.0 to about 4.8:1.0, or from about 4.7:1.0 to 4.8:1.0.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2-dielaidoyl-sn-glycero-3-phophoethanolamine (transDOPE). In one embodiment, the neutral lipid is 1,2-distearoyl-sn-glycero-3phosphocholine (DSPC). In some embodiments, the neutral lipid is selected from DSPC, DPPC, DMPC, DOPC, POPC, DOPE and SM. In some embodiments, the neutral lipid is DSPC.

In various embodiments, the disclosed organic lipid stock solution comprises a steroid or steroid analogue. In certain embodiments, the steroid or steroid analogue is cholesterol. In some embodiments, the steroid is present in a concentration ranging from 39 to 49 molar percent, 40 to 46 molar percent, from 40 to 44 molar percent, from 40 to 42 molar percent, from 42 to 44 molar percent, or from 44 to 46 molar percent relative to other components incorporated into a lipid nanoparticle (e.g., cationic lipids, neutral lipids, polymer conjugated lipids, etc.). In certain specific embodiments, the steroid is present in a concentration of 40, 41, 42, 43, 44, 45, or 46 molar percent relative to other components incorporated into a lipid nanoparticle.

In certain embodiments, the molar ratio of cationic lipid to the steroid ranges from 1.0:0.9 to 1.0:1.2, or from 1.0:1.0 to 1.0:1.2. In some of these embodiments, the molar ratio of cationic lipid to cholesterol ranges from about 5:1 to 1:1. In certain embodiments, the steroid is present in a concentration ranging from 32 to 40 mol percent of the steroid relative to other components incorporated into a lipid nanoparticle.

In certain embodiments, the molar ratio of total cationic to the steroid ranges from 1.0:0.9 to 1.0:1.2, or from 1.0:1.0 to 1.0:1.2. In some of these embodiments, the molar ratio of total cationic lipid to cholesterol ranges from about 5:1 to 1:1. In certain embodiments, the steroid is present in a concentration ranging from 32 to 40 mol percent of the steroid relative to other components incorporated into a lipid nanoparticle.

In some embodiments, the organic lipid stock solution comprises a polymer conjugated lipid. In various other embodiments, the polymer conjugated lipid is a pegylated lipid. For example, some embodiments include a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl)carbamate.

In various embodiments, the polymer conjugated lipid is present in a concentration ranging from 1.0 to 3.5 or 1.0 to 2.5 molar percent relative to other components incorporated into a lipid nanoparticle. In certain specific embodiments, the polymer conjugated lipid is present in a concentration of about 1.7 molar percent relative to other components incorporated into a lipid nanoparticle. In some embodiments, the polymer conjugated lipid is present in a concentration of about 1.5 molar percent relative to other components incorporated into a lipid nanoparticle.

In certain embodiments, the molar ratio of cationic lipid to the polymer conjugated lipid ranges from about 35:1 to about 25:1. In some embodiments, the molar ratio of cationic lipid to polymer conjugated lipid ranges from about 100:1 to about 20:1.

In certain embodiments, the molar ratio of cationic lipid to the polymer conjugated lipid ranges from about 35:1 to about 25:1. In some embodiments, the molar ratio of cationic lipid to polymer conjugated lipid ranges from about 100:1 to about 20:1.

In some embodiments, the pegylated lipid, has the following Formula (XIII):

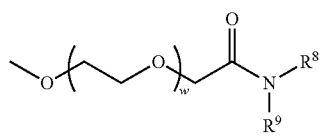

(XIII)

or a pharmaceutically acceptable salt, tautomer or stereoisomer thereof, wherein:
R$^{12}$ and R$^{13}$ are each independently a straight or branched, saturated or unsaturated alkyl chain containing from 10 to 30 carbon atoms, wherein the alkyl chain is optionally interrupted by one or more ester bonds; and
w has a mean value ranging from 30 to 60.

In some embodiments, R$^{12}$ and R$^{13}$ are each independently straight, saturated alkyl chains containing from 12 to 16 carbon atoms. In other embodiments, the average w ranges from 42 to 55, for example, the average w is 42, 43, 44, 45, 46, 47, 48, 49, 50, 51, 52, 53, 54 or 55. In some specific embodiments, the average w is about 49.

In some embodiments, the pegylated lipid has the following Formula (XIIIa):

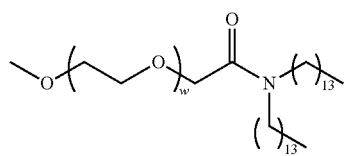

(XIIIa)

wherein the average w is about 49.

Compounds of Formula (XIII) can be prepared and tested according to the procedures set forth in PCT Pub. No. WO 2015/199952, the full disclosure of which is incorporated by reference in its entirety.

In some embodiments, the aqueous nucleic acid stock solution comprises a nucleic acid selected from antisense and messenger RNA. For example, messenger RNA may be used to formulate LNP that can be used induce an immune response (e.g., as a vaccine), for example by translation of immunogenic proteins.

In other embodiments, the nucleic acid is mRNA and the mRNA to lipid ratio in the LNP produced by embodiments of methods of the present disclosure (i.e., N/P, were N represents the moles of cationic lipid and P represents the moles of phosphate present as part of the nucleic acid backbone) range from 2:1 to 30:1, for example 3:1 to 22:1. In other embodiments, N/P ranges from 6:1 to 20:1 or 2:1 to 12:1. Exemplary N/P ranges include about 3:1. About 6:1, about 12:1 and about 22:1.

In some embodiments, the method produces a plurality of the lipid nanoparticles having a polydispersity of less than 0.12, less than 0.10, less than 0.09, less than 0.085, less than 0.080, less than 0.075, less than 0.070, less than 0.065 less than 0.060, less than 0.055, less than 0.05 or even less than 0.045. In some embodiments, the method produces a lipid nanoparticle having a mean diameter ranging from 50 nm to 100 nm, 60 nm to 100 nm, 60 nm to 80 nm, or from 60 nm to 85 nm.

In some embodiments, the first mixture comprises a plurality of the lipid nanoparticles having a polydispersity of less than 0.12, less than 0.10, less than 0.09, less than 0.085, less than 0.080, less than 0.075, less than 0.070, less than 0.065 less than 0.060, less than 0.055, less than 0.05 or even less than 0.045. In some embodiments, the first mixture comprises a plurality of lipid nanoparticles having a mean diameter ranging from 50 nm to 100 nm, 60 nm to 100 nm, 60 nm to 80 nm, or from 60 nm to 85 nm.

In some embodiments, the first mixture and diluent together comprise a plurality of the lipid nanoparticles having a polydispersity of less than 0.12, less than 0.10, less than 0.09, less than 0.085, less than 0.080, less than 0.075, less than 0.070, less than 0.065 less than 0.060, less than 0.055, less than 0.05 or even less than 0.045.

In some embodiments, the first mixture and diluent together comprise lipid nanoparticle has a mean diameter ranging from 50 nm to 100 nm, 60 nm to 100 nm, 60 nm to 80 nm, or from 60 nm to 85 nm.

Additionally, the organic lipid stock solution may utilize any suitable solvent for dissolving desired components (e.g., cationic lipids, neutral lipids, steroids, and/or polymer conjugated lipids). Accordingly, in some embodiments, the organic lipid stock solution comprises an organic solvent such as a $C_1$-$C_6$ alkanol (e.g., methanol, ethanol, propanol, butanol, pentanol, hexanal, and isomers thereof). In some embodiments, the organic lipid stock solution comprises ethanol, for example neat ethanol. In other embodiments, the solvent comprises ethanol and a cosolvent (e.g., another alcohol), with ethanol being present in about 50-90% v/v, about 60-90% v/v, about 70-90% v/v, about 80-90% v/v, about 50-80% v/v, about 50-70% v/v, about 50-60% v/v, about 40-90% v/v, about 30-90% v/v, or about 20-90% v/v.

In one aspect, the lipids occupy a volume of about 1 mL/g to about 5 mL/g, 2 mL/g to about 5 mL/g, 2.5 mL/g to about 5 mL/g, 3 mL/g to about 5 mL/g, 3.5 mL/g to about 5 mL/g, 4 mL/g to about 5 mL/g, 4.5 mL/g to about 5 mL/g, 1 mL/g to about 4.5 mL/g, 1 mL/g to about 4.0 mL/g, 1 mL/g to about 3.5 mL/g, 1 mL/g to about 3.0 mL/g, or 1 mL/g to about 2.5 mL/g.

The organic lipid stock solution may prepared and used in any suitable concentration of lipid. In certain embodiments, the total concentration of lipid (i.e., concentration of all lipids, including any cationic lipid, neutral lipid and cholesterol, in the organic lipid stock solution ranges from about 1 mg/ml to 30 mg/ml, for example from 5 mg/ml to 25 mg/ml, from 10 mg/ml to 20 mg/ml or from about 12 mg/ml to 18 mg/ml. In certain embodiments, the total concentration of all lipids in the organic lipid stock solution is about 10 mg/ml, 11 mg/ml, 12 mg/ml, 13 mg/ml, 14 mg/ml, 15 mg/ml, 16 mg/ml, 17 mg/ml, 18 mg/ml, 19 mg/ml or 20 mg/ml.

Aqueous Nucleic Acid Stock Solution and Lipid Nanoparticles

The nucleic acid as provided herein, can be any nucleic acid known in the art, such as, but not limited to: interfering RNA (such as a siRNA), a messenger RNA (mRNA), an antisense oligonucleotide, a DNAi oligonucleotide, a ribozyme, an aptamer, a plasmid, or any combination of any of the foregoing. For example, the nucleic acid can be encoded with a product of interest including, but not limited to, RNA, antisense oligonucleotide, an antagomir, a DNA, a plasmid, a ribosomal RNA (rRNA), a micro RNA (miRNA) (e.g., a miRNA which is single stranded and 17-25 nucleotides in length), transfer RNA (tRNA), a small interfering RNA (siRNA), small nuclear RNA (snRNA), antigens, fragments thereof, proteins, peptides, and vaccines or mixtures thereof. In one embodiment, the nucleic acid is an oligonucleotide (e.g., 15-50 nucleotides in length (or 15-30 or 20-30 nucleotides in length)). An siRNA can have, for instance, a duplex region that is 16-30 nucleotides long (e.g., 17-21 or 19-21 nucleotides long). In another embodiment, the nucleic acid is an immunostimulatory oligonucleotide, decoy oligonucleotide, supermir, miRNA mimic, or miRNA inhibitor. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. miRNA mimics represent a class of molecules that can be used to imitate the gene silencing ability of one or more miRNAs. The term "microRNA mimic" refers to synthetic non-coding RNAs (i.e., the miRNA is not obtained by purification from a source of the endogenous miRNA) that are capable of entering the RNAi pathway and regulating gene expression.

The nucleic acid that is present in the aqueous stock solution can be in any form. The nucleic acid can, for example, be single-stranded DNA or RNA, or double-stranded DNA or RNA, or DNA-RNA hybrids. Non-limiting examples of double-stranded RNA include siRNA. Single-stranded nucleic acids include, e.g., antisense oligonucleotides, ribozymes, microRNA, and triplex-forming oligonucleotides. The nucleic acid can be conjugated to one or more ligands.

In further embodiments, the nucleic acid is selected from mRNA, an interfering RNA, an antisense oligonucleotide, a DNAi oligonucleotide, a ribozyme, an aptamer, a plasmid, and any combination of any of the foregoing. In one embodiment, the RNA is selected from mRNA, siRNA, aiRNA, miRNA, Dicer-substrate dsRNA, shRNA, ssRNAi oligonucleotides, and any combination of any of the foregoing. In another embodiment, the nucleic acid is mRNA.

The aqueous nucleic acid stock solution may be a buffered solution in which the buffer has a pH less than the pKa of a protonated lipid in the lipid mixture. Examples of suitable buffers include MES, citrate, phosphate, and acetate. A particularly preferred buffer is citrate buffer. In some embodiments, buffers will be in the concentration range of 1-1000 mM of the anion, 1-750 mM of the anion, 1-500 mM of the anion, 1-400 mM of the anion, 1-300 mM of the anion, 1-200 mM of the anion, 1-100 mM of the anion, 100-1000 mM of the anion, 200-1000 mM of the anion, 300-1000 mM of the anion, 400-1000 mM of the anion, 500-1000 mM of the anion, 750-1000 mM of the anion or 900-1000 mM of the anion depending on the chemistry of the nucleic acid being encapsulated, and optimization of buffer concentration may be significant to achieving high loading levels.

It may be suitable to add additional additives, salts (e.g., NaCl) a cryo-protectant and/or a non-ionic solute, which will balance the osmotic potential across the particle membrane, e.g., when the particles are dialyzed to remove ethanol, increase the pH, or mixed with a pharmaceutically acceptable carrier or diluent.

In some embodiments, the amount of nucleic acid in buffer (i.e., the aqueous nucleic acid stock solution) is from about 0.05 to 0.5 mg/mL, 0.08 to 0.8 mg/mL, 0.09 to 0.9 mg/mL, 0.08 to 0.75 mg/mL, 0.10 to 0.8 mg/mL, 0.2 to 0.8 mg/mL, 0.3 to 0.8 mg/mL, 0.4 to 0.8 mg/mL, 0.5 to 0.8 mg/mL, 0.6 to 0.8 mg/mL, 0.7 to 0.8 mg/mL, 0.08 to 0.7 mg/mL, 0.08 to 0.6 mg/mL, 0.08 to 0.5 mg/mL, 0.08 to 0.4 mg/mL, 0.08 to 0.3 mg/mL, 0.08 to 0.2 mg/mL, or 0.08 to 0.3 mg/mL. In some specific embodiments, the amount of nucleic acid in buffer is from about 0.06 to 0.25 mg/mL. In some embodiments, the amount of nucleic acid in buffer is up to 0.8 mg/mL. For example, in some embodiments, the amount of nucleic acid in the nucleic acid stock solution is about 0.05 mg/mL, 0.1 mg/mL, 0.15 mg/mL, 0.2 mg/mL, 0.25 mg/mL, 0.3 mg/mL, 0.35 mg/mL or 0.40 mg/mL.

In certain embodiments, the temperature of the aqueous solution is 15 to 45° C., about 20 to 45° C., about 30 to 45° C., about 35 to 45° C., about 40 to 45° C., about 15 to 40° C., about 15 to 35° C. about 15 to 30° C., about 15 to 25° C., or about 15 to 20° C. The stock solutions may be heated or cooled to a temperature outside these ranges as necessary (e.g., if a single stranded nucleic acid is used).

In certain embodiments, the aqueous nucleic acid stock solution is prepared by dissolution of lyophilized or solid material (e.g., nucleic acid) in water that is buffered at pH 3.5-4.5 (e.g., with 50 mM citrate), or from pH 4-6. In some embodiments, the aqueous nucleic acid stock solution has a pH ranging from about 1.0 to about 7.0, from about 2.0 to about 7.0, from about 3.0 to about 7.0, from about 4.0 to about 7.0, from about 5.0 to about 7.0, from about 6.0 to about 7.0, from about 3.0 to about 5.0, from about 3.5 to about 5.0, from about 4.0 to about 5.0, from about 4.5 to about 5.0, from about 3.0 to about 4.5, from about 3.5 to about 4.5, from about 3.7 to about 4.2, or from about 3.2 to about 3.7. It should be appreciated that the aqueous nucleic acid stock solution need not be acidic when methods of the present disclosure, e.g., the pH of the buffer solution can be 7.0 or higher, for example, from about 7.0 to about 7.5, from about 7.0 to about 8.0, from about 7.5 to about 8.5, from about 8.0 to about 8.5, from about 8.0 to about 9.0, or from about 7.0 to about 9.5.

The following examples are provided for purpose of illustration and not limitation.

EXAMPLES

Example 1

Preparation of Lipid Nanoparticle Compositions (Preparation A)

A scale-up process was used wherein piston pumps were employed that provided unlimited continuous output. The characterization of lipid nanoparticles (LNP) generated by the scale-up process including the use of the piston pumps, concentration/buffer exchange by tangential flow filtration (TFF), and filling operation using a peristaltic pump, all of which comprise aspects of clinical phase manufacturing processes (either current or expected). Small samples were taken during each formulation step (i.e., mixing, concentration/diafiltration, and filling) to measure nanoparticle size and polydispersity. It was found that LNP size was consistent throughout and stayed within the size range typical for Compound III-3 and polyC (~60-75 nm) with low polydispersity (<0.1) during the entire formulation process. Size and polydispersity were determined by dynamic light scattering with a Malvern zetasizer for this and the following examples. Encapsulation was determined using a fluorescent intercalating dye based assay (Ribogreen) for this and the following examples.

Process and Results

Cationic Lipid: Compound III-3

Nucleic acid: polyC (surrogate nucleic acid)

Mixing Apparatus:
    Knauer Azura 2.1—250 mL/min pump (Organic)
    Knauer Azura 2.1—500 mL/min pump (Aqueous)
    Valco Vici Cheminert 8 port valve—(Valco Vici H-C22-6188EUH)
    PEEK tee mixing assembly—0.02" through-hole
      Organic input: 0.01" PEEK tube
      Aqueous input: 0.02" PEEK tube
      Output: 0.04" PEEK tube TFF Apparatus
    Spectrum KrosFlo Research IIi system
    Scout Pro SP4001 balance
    Spectrum cartridge D02-E500-05-N, 500 KDa MWCO, 115 cm$^2$
    Pt cured masterflex 96410-16, 3.1 mm id Filling Apparatus
    Watson Marlow 313 S/D pump
    Pt cured silicone tubing, 0.8 mm id
    ID Oneshot filler needle, 1/32"

Prior to mixing, 25 mg of polyC was hydrated in water for injection ("WFI") and diluted in 50 mM citrate at pH 4 to provide an exemplary aqueous 0.2 mg/mL nucleic acid stock solution. An exemplary organic lipid stock solution comprising cationic lipid/DSPC/cholesterol/polymer conjugated lipid (Formula XIIIa) in molar ratios of 47.5/10/40.7/1.8 prepared in anhydrous ethanol at a total lipid concentration of ~15 mg/mL. The aqueous nucleic acid stock solution and organic lipid stock solution were loaded into separate polyethylene terephthalate co-polyester (PETG) reservoirs and loaded onto the 500 mL and 250 mL Knauer pumps, respectively. The Cheminert valve was initially set to "recirculation mode" where the input from each pump back is directed back to the respective reservoir. The system was kept in recirculation mode at target flow rates (aqueous: 30 mL/min, organic: 10 mL/min) to prime the system and remove any air bubbles in the line. Polypropylene collection tubes were set up to capture different output fractions during the mixing process. After recirculating for a few minutes, the Cheminert Valve was changed to "mixing mode" where the outputs from the valve are directed to the inputs of the PEEK tee mixing chamber. The first fraction of the output from the PEEK tee mixing chamber was collected in ~0.5 mL to assess particle size upon immediate mixing. Subsequent fractions were collected in ~10 mL aliquots until the stock solutions were consumed and the air from the pump input tubing was judged to have reached the pump heads. The process was allowed to continue and the last two fraction volumes being ~0.5 mL (Table 12) were used to verify the expected impact on the mixing process.

Particle sizes were generally consistent among Fractions 1-14 with acceptable polydispersity index values (PDI values). As expected, the introduction of air to the pump heads disrupted volume delivery of the aqueous nucleic acid stock solution and organic lipid stock solutions, with the result that Fractions 15-16 increased dramatically in size. Fractions 1-14 were pooled and prepared for tangential flow filtration.

TABLE 12

Nanoparticle size post-in-line mixing

| Fraction | Z-Average (nm) | Intensity (nm) | PDI |
|---|---|---|---|
| 1 | 71 | 71 | 0.086 |
| 2 | 61 | 62 | 0.094 |
| 3 | 64 | 65 | 0.060 |
| 4 | 61 | 62 | 0.061 |
| 5 | 61 | 63 | 0.061 |
| 6 | 63 | 64 | 0.046 |
| 7 | 63 | 65 | 0.063 |
| 8 | 62 | 63 | 0.055 |
| 9 | 63 | 65 | 0.051 |
| 10 | 63 | 65 | 0.044 |
| 11 | 63 | 65 | 0.059 |
| 12 | 62 | 65 | 0.049 |
| 13 | 62 | 64 | 0.048 |
| 14 | 62 | 64 | 0.046 |
| 15* | 70 | 112 | 0.132 |
| 16* | 398 | 384 | 0.362 |

*air in pumps leading to uncontrolled aqueous/ethanol ratios

During the tangential flow filtration (TFF) process, the sample was first concentrated. Care was taken to ensure that the transmembrane pressure (TMP) remained <20 psi with a shear rate~8000/s. The volume was reduced ~13× thereby achieving a concentration of ~2 mg/mL polyC. An aliquot was taken for size analysis. Following concentration, the sample was buffer exchanged with 10× volumes of phosphate-buffered saline (PBS). Again, an aliquot was taken to determine particle size. In comparison to the post-in-line (PIL) samples, particle size increased by ~10 nm, which can be attributed to the presence of ethanol during the concentration phase (see Table 13). The TFF system was then emptied and a backflush was performed by running the pump in reverse. Two rinses with PBS were performed and a sample collected for each to measure size and polyC content. These samples were collected to evaluate the feasibility of such processes to recover material from the TFF process vs. the risk of collecting agglomerated material. The samples were stored in the fridge overnight at 5° C.

TABLE 13

Sample size during concentration/diafiltration via TFF

| Sample | Z-Average (nm) | Intensity (nm) | PDI |
|---|---|---|---|
| Post concentration | 71 | 71 | 0.076 |
| Post diafiltration | 71 | 71 | 0.084 |
| Backflush | 73 | 75 | 0.088 |
| Rinse 1 | 78 | 81 | 0.136 |
| Rinse 2 | 85 | 126 | 0.18 |

The following day, sample sizes were re-measured to monitor any size drift. The bulk polyC sample remained similar in size as they day before (see Table 14). Routine analyses were then performed to determine lipid content, polyC concentration and percent encapsulation.

TABLE 14

LNP size check after 18 hour storage at 5° C.

| Sample | Z-Average (nm) | Intensity (nm) | PDI |
|---|---|---|---|
| Main | 73 | 76 | 0.064 |
| Backflush | 74 | 75 | 0.078 |
| Rinse 1 | 80 | 78 | 0.157 |
| Rinse 2 | 87 | 77 | 0.206 |

After measuring the polyC concentration, the sample was diluted with a combination of PBS and 1.2 M sucrose to achieve final concentrations of 1 mg/mL encapsulated polyC and 300 mM sucrose. The sample was passed through a single 0.2 μm polyethersulfone (PES) syringe filter to achieve product sterilization. Small aliquots were taken in each case to determine particle size. The data indicates the sucrose addition and filtration steps did not significantly affect the lipid nanoparticle size and thus samples were then prepared for storage (see Table 15).

TABLE 15

Effect of sucrose and filtration on LNP size

| Sample | Z-Average (nm) | Intensity (nm) | PDI |
|---|---|---|---|
| Post sucrose | 73 | 74 | 0.076 |
| Post 0.2 μm filtration | 73 | 73 | 0.093 |

Following addition of sucrose and sterile filtration into a separate container, LNPs were then syringe-loaded into a 50 mL bioprocess container (BPC) for vial filling. Using a peristaltic pump coupled to the BPC bag, ~0.5 mL aliquots were filled into 38 glass vials. Following transfer to the glass vials, nanoparticle sizes were periodically sampled. Again, little change was observed in terms of particle size. No visible particulates were observed in any of the filled vials (Table 16).

TABLE 16

Nanoparticle size following filling

| Vial | Z-Average (nm) | Intensity (nm) | PDI |
|---|---|---|---|
| 1 | 74 | 76 | 0.080 |
| 2 | 73 | 76 | 0.043 |
| 3 | 73 | 75 | 0.035 |
| 4 | 71 | 73 | 0.071 |
| 5 | 73 | 76 | 0.039 |
| 6 | 72 | 72 | 0.076 |
| 7 | 73 | 75 | 0.055 |
| 8 | 73 | 74 | 0.073 |
| 9 | 72 | 73 | 0.060 |
| 10 | 73 | 75 | 0.038 |
| 19 | 73 | 75 | 0.056 |
| 29 | 72 | 74 | 0.049 |
| 35 | 73 | 75 | 0.049 |
| 36 | 74 | 76 | 0.065 |
| 37 | 75 | 76 | 0.057 |
| 38* | 76 | 76 | 0.091 |

*less than 0.5 mL aliquoted, bubbles created by pumping air

Overall, 18.9 mg of encapsulated polyC was recovered, equating to a 76% yield. Particle size remained within a range of about 72-76 nm, PDI was <0.1, and polyC encapsulation was 92%. The mRNA:lipid ratio was determined to be 0.31. All parameters are within acceptable ranges (see Table 17).

TABLE 17

Summary of scale-up procedure

| Sample | Total Recovered (mg) | Encapsulation (%) | Amount Encapsulated (mg) | Yield (%) | mRNA/lipid | Size Intensity (nm) | PDI |
|---|---|---|---|---|---|---|---|
| Pooled PolyC | 20.5 | 92 | 18.9 | 76 | 0.31 | ~72-76 | 0.035-0.091 |

Example 2

High Flow Rate Preparation of Lipid Nanoparticle Compositions with Quaternary Diaphragm Pumps Empty LNP's at a scale equivalent to 20 mg mRNA were generated using Quattroflow quaternary diaphragm pumps for inputs using 50 mM pH 4 citrate buffer and an exemplary organic lipid stock solution comprising cationic lipid (Formula I-6)/DSPC/cholesterol/polymer conjugated lipid (Formula XIIIa) in molar ratios of 47.5/10/40.7/1.8 prepared in anhydrous ethanol at ~8 mg/mL total lipid. Two different total flow rates were evaluated:

A) 30 mL/min aqueous+10 mL min organic for a total of 40 mL/min total output; and B) 120 mL/min aqueous+40 mL/min organic for a total of 160 mL/min total output.

The aqueous buffer stock solution and organic lipid stock solution were loaded into separate polyethylene terephthalate co-polyester (PETG) reservoirs with dip tubes connected to the 500 mL and 250 mL Knauer pumps, respectively. The system was kept in recirculation mode at target flow rates (aqueous: 30 mL/min, organic: 10 mL/min, or aqueous: 120 mL/min, organic: 40 mL/min, respectively) to prime the system and remove any air bubbles in the lines. After recirculating for a few minutes, the Cheminert Valve was changed to mixing mode as described in Example 1. Fractions of the output were collected to evaluate size throughout the mixing process. The first fraction was collected in ~0.5 mL to assess particle size upon immediate mixing. Subsequent fractions were collected in ~10 mL aliquots until the stock solutions were consumed and the air from the pump input tubing was judged to have reached the pump heads. Fractions were then pooled and split for further processing by either membrane dialysis or tangential flow filtration to achieve buffer exchange and organic solvent removal. Size analysis was performed at various points to monitor process suitability. The data is summarized in the table below and shows excellent results for size and polydispersity of individual fractions at higher flow rates. The data also shows excellent results post processing by dialysis or TFF after filtration (see Table 18).

TABLE 18

LNP physical characteristics with high flow rate preparation

| | A (40 mL/min) | | | B (160 mL/min) | | | |
|---|---|---|---|---|---|---|---|
| Sample | Z-Ave (nm) | Int (nm) | PDI | Z-Ave (nm) | Int (nm) | PDI | Remarks |
| Fraction 1 | 77 | 113 | 0.229 | 69 | 71 | 0.098 | |
| Fraction 2 | 79 | 93 | 0.131 | 84 | 94 | 0.107 | |
| Fraction 3 | 78 | 158 | 0.144 | 58 | 59 | 0.059 | |
| Fraction 4 | 71 | 150 | 0.145 | 59 | 60 | 0.068 | |
| Fraction 5 | 79 | 108 | 0.14 | 61 | 63 | 0.036 | |
| Fraction 6 | 79 | 99 | 0.13 | 62 | 63 | 0.053 | |
| Fraction 7 | 83 | 88 | 0.107 | 64 | 66 | 0.056 | |
| Fraction 8 | 81 | 92 | 0.137 | 69 | 71 | 0.036 | |
| Fraction 9 | 79 | 91 | 0.154 | 66 | 69 | 0.049 | |
| Fraction 10 | 82 | 102 | 0.129 | 66 | 68 | 0.054 | |
| Dial/Filt | 75 | 76 | 0.097 | 60 | 62 | 0.033 | 35 mL of pooled sample dialyzed O/N and filtered 0.22 μm filtered |
| Dial/Filt/conc | 76 | 78 | 0.101 | 64 | 65 | 0.051 | Filtered sample then concentrated via amicon |
| PIL O/N | 84 | 92 | 0.078 | 111 | 55 | 0.204 | Bulk pooled sample in ethanol stored 5° C. O/N |
| Post TFF | 79 | 78 | 0.119 | 69 | 69 | 0.137 | Samples post concentration/ diafiltration |
| Post TFF/Filt | 79 | 80 | 0.084 | 66 | 69 | 0.041 | Samples post conc./diafiltration then 0.22 μm filtered |

Example 3

High Flow Rate Preparation of Lipid Nanoparticle Compositions with Piston Pumps

Empty LNP at a scale equivalent to 10 mg mRNA were generated using Knauer Azura piston pumps for inputs to deliver 50 mM pH 4 citrate buffer and an exemplary organic lipid stock solution comprising cationic lipid (Formula III-45)/DSPC/cholesterol/polymer conjugated lipid (Formula XIIIa) in molar ratios of 47.5/10/40.7/1.8 prepared in anhydrous ethanol at ~7.5 mg/mL total lipid. The pumps were set at 120 mL/min aqueous+40 mL/min organic for a total of 160 mL/min total output. The aqueous buffer stock solution and organic lipid stock solution were loaded into separate polyethylene terephthalate co-polyester (PETG) reservoirs with dip tubes connected to the 500 mL and 250 mL Knauer pumps, respectively. The system was kept in recirculation mode at target flow rates (aqueous: 120 mL/min, organic: 40 mL/min, respectively) to prime the system and remove any air bubbles in the lines. After recirculating for a few minutes, the Cheminert Valve was changed to mixing mode as described in Example 1. An initial 1 mL fraction was collected for comparison to the subsequently collected bulk product. All product was pooled for further processing by tangential flow filtration to achieve buffer exchange and organic solvent removal. Size analysis was performed at various points to monitor process suitability. The data is summarized in Table 19 below and shows the process incorporating the valve system immediately produces LNP that are indistinguishable from the subsequent bulk product. Furthermore, the size and polydispersity characteristics of these LNP are stable upon processing by TFF.

TABLE 19

| Sample | Intensity Mean Size (nm) | PDI |
|---|---|---|
| Initial Fraction (1 mL) | 62 | 0.033 |
| Subsequent bulk product (~120 mL) | 64 | 0.005 |
| TFF concentrated 10-15x | 68 | 0.045 |
| TFF diafiltered 10 wash volumes | 62 | 0.096 |
| Post-TFF, sterile filtered | 62 | 0.033 |

Example 4

High Flow Rate Preparation of Loaded Lipid Nanoparticle Compositions with Piston Pumps Loaded LNP at 50 mg nucleic acid scale were generated using Knauer Azura piston pumps for inputs to deliver an exemplary nucleic acid stock solution comprising 0.1 mg/mL PolyA (Millipore Sigma catalogue #10108626001) in 25 mM pH 4 acetate buffer and an exemplary organic lipid stock solution comprising cationic lipid (Formula III-45)/DSPC/cholesterol/polymer conjugated lipid (Formula XIIIa) in molar ratios of 47.5/10/40.7/1.8 prepared in anhydrous ethanol at ~7.5 mg/mL total lipid. A corresponding batch was made at the same scale with the same components where the concentration of the nucleic acid stock was 0.2 mg/mL PolyA and the associated lipid stock was ~15 mg/mL total lipid. For both batches, the pumps were set at 120 mL/min aqueous+40 mL/min organic for a total of 160 mL/min total output. The aqueous buffer stock solution and organic lipid stock solution were loaded into separate polyethylene bioprocess bags (St. Gobain Biopharm) connected to the 500 mL and 250 mL Knauer pumps, respectively. The pump outputs were connected to an 8-port stainless steel switching valve (Valco Vici EUDA-L8UW) such that in the initial recirculation mode valve position, the pump flows were directed back to their respective bioprocess bag reservoirs. The system was kept in recirculation mode at target flow rates (aqueous: 120 mL/min, organic: 40 mL/min, respectively) to prime the system and remove any air bubbles in the lines. After recirculating for a few minutes, the switching valve was changed to mixing mode as described in Example 1. All product was collected for processing by tangential flow filtration to achieve buffer exchange and organic solvent removal. Size analysis was performed at various points to monitor process suitability. The data is summarized in Table 20. An increase in size is observed upon completion of the buffer exchange process for these particles that encapsulate PolyA which is larger and more polydisperse than a typical therapeutic nucleic acid such as an mRNA. The encapsulation efficiencies are high (>95%) and size characteristics are within acceptable ranges for the processes across this range of input stock concentrations.

processed by TFF to exchange the buffer and concentrate to the final target of 1 mg/mL in terms of nucleic acid content. For the 400 mg PolyA batch, the product was processed immediately after completion of the mixing step. Size analysis was performed at various points to monitor process suitability. The data is summarized in Table 21 which shows high encapsulation efficiency for the final product and good particle size characteristics from initial formation through to completion of buffer exchange and solvent removal. This demonstrates utility of the process for nucleic acid LNP therapeutics approaching gram scales with respect to the nucleic acid.

TABLE 20

| | Input concentrations | | | | | | |
|---|---|---|---|---|---|---|---|
| | 0.1 mg/mL PolyA - 7.5 mg/mL Lipid | | | 0.2 mg/mL PolyA - 15 mg/mL Lipid | | | |
| Process Step | Intensity Mean d · nm | Z-Ave d · nm | PdI | Encaps % | Intensity Mean d · nm | Z-Ave d · nm | PdI | Encaps % |
| Post mixing | 62.1 | 59.2 | 0.045 | | 58.7 | 57.3 | 0.055 | |
| Post TFF process | 75.0 | 76.3 | 0.121 | 95.5 | 70.0 | 70.3 | 0.113 | 95.6 |
| Final product | 79.6 | 79.6 | 0.088 | 95.2 | 70.1 | 69.5 | 0.096 | 97.7 |

Example 5

Larger Scale Preparations of Loaded Lipid Nanoparticle Compositions

Loaded LNP at 200 mg and 400 mg nucleic acid scales were generated using Knauer Azura piston pumps for inputs to deliver an exemplary nucleic acid stock solution comprising 0.2 mg/mL PolyA (Millipore Sigma catalogue #10108626001) in 25 mM pH 4 acetate buffer and an exemplary organic lipid stock solution comprising cationic lipid (Formula III-45)/DSPC/cholesterol/polymer conjugated lipid (Formula XIIIa) in molar ratios of 47.5/10/40.7/1.8 prepared in anhydrous ethanol at ~15 mg/mL total lipid. The pumps were set at 120 mL/min aqueous+40 mL/min organic for a total of 160 mL/min total output. The aqueous buffer stock solution and organic lipid stock solution were loaded into separate polyethylene bioprocess bags (St. Gobain Biopharm) connected to the 500 mL and 250 mL Knauer pumps, respectively. The pump outputs were connected to an 8-port stainless steel switching valve (Valco Vici EUDA-L8UW) such that in the initial recirculation mode valve position, the pump flows were directed back to their respective bioprocess bag reservoirs. The system was kept in recirculation mode at target flow rates (aqueous: 120 mL/min, organic: 40 mL/min, respectively) to prime the system and remove any air bubbles in the lines. An additional peristaltic pump was arranged to deliver aqueous stock buffer (25 mM pH 4 acetate buffer) to the product receptacle at a flow rate of 80 mL/min. After recirculating for a few minutes, the switching valve was changed to mixing mode as described in Example 1 and the peristaltic pump for delivery of additional aqueous buffer was initiated simultaneously.

For the 200 mg PolyA batch, the product was collected in approximately 8.5 minutes after which the valve was returned to recirculation mode and the peristaltic pump delivering buffer was halted. The product was held at ambient temperature for an additional 45 minutes to emulate process time to complete mixing of a batch corresponding to greater than 1 g of nucleic acid. The product was then

TABLE 21

| | Scale (mg) | | | | | |
|---|---|---|---|---|---|---|
| | 200 | | | 400 | | |
| Process Step | Intensity Mean d · nm | Z-Ave d · nm | PdI | Intensity Mean d · nm | Z-Ave d · nm | PdI | Encaps % |
| Post mixing | 64.5 | 62.9 | 0.030 | 62.59 | 60.72 | 0.062 | |
| Post mixing + 45 minutes | 62.5 | 61.1 | 0.045 | — | — | — | |
| Post processing | 69.2 | 69.4 | 0.099 | 71.31 | 71.91 | 0.108 | 96.5 |

Example 6

100 mg Scale mRNA-LNP Batch with Luciferase mRNA

Loaded LNP at 100 mg nucleic acid scale was generated using Knauer Azura piston pumps for inputs to deliver an exemplary nucleic acid stock solution comprising 0.2 mg/mL Luciferase encoding mRNA in 50 mM pH 4 citrate buffer and an exemplary organic lipid stock solution comprising cationic lipid (Formula II-15)/DSPC/cholesterol/polymer conjugated lipid (Formula XIIIa) in molar ratios of 47.5/10/40.7/1.8 prepared in anhydrous ethanol at ~15 mg/mL total lipid. The pumps were set at 120 mL/min aqueous+40 mL/min organic for a total of 160 mL/min total output. The aqueous buffer stock solution and organic lipid stock solution were loaded into separate polyethylene bioprocess bags (St. Gobain Biopharm) connected to the 500 mL and 250 mL Knauer pumps, respectively. The pump outputs were connected to an 8-port stainless steel switching valve (Valco Vici EUDA-L8UW) such that in the initial recirculation mode valve position, the pump flows were directed back to their respective bioprocess bag reservoirs. The system was kept in recirculation mode at target flow rates (aqueous: 120 mL/min, organic: 40 mL/min, respectively) to prime the system and remove any air bubbles in the lines. An additional peristaltic pump was arranged to deliver aqueous stock buffer (50 mM pH 4 citrate buffer) to the product receptacle at a flow rate of 80 mL/min. After recirculating for a few minutes, the switching valve was changed to mixing mode as described in Example 1 and the peristaltic pump for delivery of additional aqueous buffer was initiated simultaneously. All product was collected for processing by tangential flow filtration to achieve buffer exchange and organic solvent removal. The size and encapsulation results are summarized in Table 22 which demonstrate excellent size, polydispersity and encapsulation efficiency for this process using a representative messenger RNA with physical characteristics typical of an mRNA-LNP therapeutic product candidate.

TABLE 22

| Process Step | Z-Average Diameter (nm) | Intensity Wt. Diameter (nm) | Poly-dispersity | Encapsulation Efficiency (%) |
| --- | --- | --- | --- | --- |
| Final Product | 74 | 76 | 0.032 | 96.8 |

Example 7

Very High Flow Rate Preparation of Loaded Lipid Nanoparticle Composition

Loaded LNP at 100 mg nucleic acid scale was generated using Knauer Azura piston pumps for inputs to deliver an exemplary nucleic acid stock solution comprising 0.2 mg/mL PolyA (Millipore Sigma catalogue #10108626001) in 25 mM acetate buffer and an exemplary organic lipid stock solution comprising cationic lipid (Formula III-45)/DSPC/cholesterol/polymer conjugated lipid (Formula II-15)/DSPC/cholesterol/polymer conjugated lipid (Formula XIIIa) in molar ratios of 47.5/10/40.7/1.8 prepared in anhydrous ethanol at ~15 mg/mL total lipid. The pumps were set at 360 mL/min aqueous+120 mL/min organic for a total of 480 mL/min total output. The aqueous buffer stock solution and organic lipid stock solution were loaded into separate polyethylene bioprocess bags (St. Gobain Biopharm) connected to the 500 mL and 250 mL Knauer pumps, respectively. The pump outputs were connected to an 8-port stainless steel switching valve (Valco Vici EUDA-L8UW) such that in the initial recirculation mode valve position, the pump flows were directed back to their respective bioprocess bag reservoirs. The system was kept in recirculation mode at target flow rates (aqueous: 360 mL/min, organic: 120 mL/min, respectively) to prime the system and remove any air bubbles in the lines. An additional peristaltic pump was arranged to deliver aqueous stock buffer (25 mM acetate buffer) to the product receptacle at a flow rate of 240 mL/min. After recirculating for a few minutes, the switching valve was changed to mixing mode as described in Example 1 and the peristaltic pump for delivery of additional aqueous buffer was initiated simultaneously. The first fraction of the output from the tee mixing chamber was collected in ~25 mL to assess particle size upon immediate mixing. Subsequent fractions were collected in ~100 mL aliquots until the stock solutions were consumed and the air from the pump input tubing was judged to have reached the pump heads. The size and encapsulation results are summarized in Table 23 which demonstrate excellent size, polydispersity and encapsulation efficiency for the initial fraction and all subsequent fractions. This demonstrates the utility of the process under conditions that enable production of mRNA-LNP at multi gram (greater than 10 g) scales with respect to the mRNA within timeframes that can reasonably be achieved in a practical manufacturing setting.

TABLE 23

| FM-0990 Process Step | Z-Average Diameter (nm) | Intensity Wt. Diameter (nm) | Poly-dispersity | Encapsulation Efficiency (%) |
| --- | --- | --- | --- | --- |
| Fraction 1* | 60.02 | 60.14 | 0.096 | 99.5 |
| Fraction 2 | 60.36 | 60.51 | 0.109 | 99.5 |
| Fraction 3 | 60.56 | 60.78 | 0.127 | 99.3 |
| Fraction 4 | 59.84 | 59.69 | 0.116 | 99.3 |
| Fraction 5 | 60.79 | 61.94 | 0.091 | 98.9 |
| Fraction 6 | 61.01 | 61.13 | 0.09 | 99.1 |
| Fraction 7 | 61.47 | 60.83 | 0.121 | 98.9 |
| Fraction 8 | 61.94 | 62.63 | 0.093 | 99.1 |
| Fraction 9 | 60.07 | 59.00 | 0.105 | 99.0 |
| Fraction 10 | 60.96 | 61.16 | 0.104 | 99.1 |
| Fraction 11 ** | 60.09 | 61.13 | 0.100 | 99.2 |
| Fractions 2-10 Combined | 60.63 | 59.58 | 0.106 | 99.0 |

*25 mL lead fraction
** partial fraction at end of run

Example 8

Large Scale Preparation of Loaded Lipid Nanoparticle Compositions

An mRNA-LNP batch comprising 20 g mRNA is prepared in the following manner using piston pumps with a tee mixing assembly connected through a switching valve.
Mixing Apparatus:
  Knauer Azura 2.1—250 mL/min pump (Organic)
  Knauer Azura 2.1—500 mL/min pump (Aqueous)
  Valco Vici Stainless Steel 8 port valve—(Valco Vici EUDA-L8UW)
  Stainless steel tee mixing assembly—0.02" through-hole
    Organic input: 0.01" PEEK tube
    Aqueous input: 0.02" PEEK tube
    Output: 0.04" PEEK tube
TFF Apparatus
  Spectrum KrosFlo® KMPi TFF System
  Spectrum cartridge X-06-E100-05N, 12.8 m²

Prior to mixing, 20 g of mRNA is diluted in 25 mM acetate buffer at pH 4 to provide an aqueous 0.2 mg/mL mRNA acid stock solution. An organic lipid stock solution comprising cationic lipid/DSPC/cholesterol/polymer conjugated lipid in molar ratios of 47.5/10/40.7/1.8 is prepared in anhydrous ethanol at a total lipid concentration of ~15 mg/mL. The aqueous nucleic acid stock solution and organic lipid stock solution are loaded into separate polyethylene bioprocess bags (St. Gobain Biopharm) and connected to the inlets of the 500 mL and 250 mL Knauer pumps, respectively. The pump outputs are connected to an 8-port 2-position stainless steel switching valve (Valco Vici EUDA-L8UW) as depicted in FIG. 5 such that in the initial recirculation mode valve position shown in FIG. 6A, the pump flows are directed through the valve and back to their respective bioprocess bag reservoirs. The pumps are initiated at 360 mL/min aqueous+120 mL/min organic for a total of 480 mL/min total output and the system is kept in recirculation mode at target flow rates to prime the system and remove any air bubbles in the line. An additional peristaltic pump is arranged to deliver aqueous stock buffer (25 mM acetate buffer) to the product receptacle at a flow rate of 240 mL/min. After recirculating for a few minutes, the switching valve position is changed to mixing mode as depicted in FIG. 6B and the peristaltic pump for delivery of additional aqueous buffer is initiated simultaneously. The output is collected in a bioprocess bag (St. Gobain) until the stock solutions are consumed. Prior to air being judged to have reached the inlet of any of the piston pump heads, the switching valve is returned to recirculation mode and all the pump flows are promptly stopped.

The bulk product is concentrated and the external buffer exchanged on the TFF system at shear rates below 10,000 $s^{-1}$. The final concentration of the bulk intermediate product is 0.5-5 mg/mL. The bulk intermediate product is filtered through a 0.2 um polyethersulfone (PES) filter to a new bioprocess bag and samples taken for determination of drug content. The intermediate bulk may be stored for short periods in this format. Based on the results of the content determination, the intermediate is diluted to label claim and sterile filtered with redundant 0.2 um PES filters followed by aseptic filling to the final container closure system.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/734,837, filed Sep. 21, 2018, are incorporated herein by reference, in their entirety.

Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
a first reservoir, the first reservoir containing an organic lipid stock solution;
a first pump having a first pump inlet and a first pump outlet, the first pump inlet fluidically coupled to the first reservoir;
a second reservoir, the second reservoir containing an aqueous nucleic acid stock solution;
a second pump having a second pump inlet and a second pump outlet, the second pump inlet fluidically coupled to the second reservoir;
a valve having a first valve inlet port fluidically coupled to the first pump outlet, a second valve inlet port fluidically coupled to the second pump outlet, a first valve outlet port, a second valve outlet port, a third valve outlet port, and a fourth valve outlet port; and
a mixing assembly having a first mixing assembly inlet fluidically coupled to the first valve outlet port, a second mixing assembly inlet fluidically coupled to the second valve outlet port, and a mixing assembly outlet, wherein the first mixing assembly inlet is fluidically coupled to the mixing assembly outlet and the second mixing assembly inlet is fluidically coupled to the mixing assembly outlet;
wherein the valve has a first operating position in which the first valve inlet port is fluidically coupled to the first valve outlet port and the second valve inlet port is fluidically coupled to the second valve outlet port and a second operating position in which the first valve inlet port is not fluidically coupled to the first valve outlet port and the second valve inlet port is not fluidically coupled to the second valve outlet port,
wherein the third valve outlet port is fluidically coupled to the first reservoir in both of the first and second operating positions, and
wherein the fourth valve outlet port is fluidically coupled to the second fluid reservoir in both of the first and second operating positions.

2. The system of claim 1, wherein when the valve is in the second operating position, the first valve inlet port is fluidically coupled to the third valve outlet port and the second valve inlet port is fluidically coupled to the fourth valve outlet port.

3. The system of claim 1, wherein the valve is a six-port, two-position valve.

4. The system of claim 1, wherein when the valve is in the first operating position, the third valve outlet port is fluidically coupled to the fourth valve outlet port.

5. The system of claim 1, wherein when the valve is in the second operating position, the first valve outlet port is fluidically coupled to the second valve outlet port.

6. The system of claim 1, wherein the organic lipid stock solution comprises a cationic lipid or mixtures thereof.

7. The system of claim 1, wherein the first mixing assembly inlet has a first inside diameter and the second mixing assembly inlet has a second inside diameter that is different than the first inside diameter.

8. The system of claim 7, wherein the first inside diameter is half the second inside diameter.

9. The system of claim 8, wherein the first inside diameter is 0.01 inches, the second inside diameter is 0.02 inches, and the first mixing assembly outlet has a third inside diameter of 0.04 inches.

10. The system of claim 8, wherein the first inside diameter is 0.02 inches and the second inside diameter is 0.04 inches.

11. The system of claim 1, wherein the valve is an eight-port, two-position valve and has a first open port and a second open port.

12. The system of claim 11, wherein when the valve is in the first operating position, the first open port is fluidically coupled to the third valve outlet port and the second open port is fluidically coupled to the fourth valve outlet port.

13. The system of claim 11, wherein when the valve is in the second operating position, the first open port is fluidically coupled to the first valve outlet port and the second open port is fluidically coupled to the second valve outlet port.

14. The system of claim 11, wherein the first open port is fluidically coupled to air and the second open port is fluidically coupled to air.

15. The system of claim 1, further comprising:
a third reservoir, the third reservoir containing a diluent; and
a third pump having a third pump inlet and a third pump outlet, the third pump inlet fluidically coupled to the third reservoir;
wherein the valve has a third valve inlet port fluidically coupled to the third pump outlet and a fifth valve outlet port;
wherein the mixing assembly has a third mixing assembly inlet fluidically coupled to the fifth valve outlet port, wherein the third mixing assembly inlet is fluidically coupled to the mixing assembly outlet;
wherein when the valve is in the first operating position, the third valve inlet port is fluidically coupled to the fifth valve outlet port and when the valve is in the second operating position, the third valve inlet port is not fluidically coupled to the fifth valve outlet port.

16. The system of claim 15, wherein the mixing assembly includes a single mixing chamber and the first mixing assembly inlet, the second mixing assembly inlet, the third mixing assembly inlet, and the mixing assembly outlet are each directly fluidically coupled to the single mixing chamber.

17. The system of claim 15, wherein the mixing assembly includes a first mixing chamber and a second mixing chamber, the first mixing assembly inlet and the second mixing assembly inlet are each directly fluidically coupled to the first mixing chamber, and the first mixing chamber, the third mixing assembly inlet, and the mixing assembly outlet are each directly fluidically coupled to the second mixing chamber.

18. A method of manufacturing lipid nanoparticles, comprising:
providing the system of claim 1;
pumping the organic lipid stock solution from the first reservoir to the first valve inlet port of the valve;
pumping the aqueous nucleic acid stock solution from the second reservoir to the second valve inlet port of the valve;
flowing the organic lipid stock solution and the aqueous nucleic acid stock through the valve and operating the valve in the second operating position in which the first valve inlet port is not fluidically connected to the first mixing assembly inlet of the mixing assembly and the second valve inlet port is not fluidically connected to the second mixing assembly inlet of the mixing assembly in the second operating position; and
switching the valve to the first operating position and flowing the organic lipid stock solution through the valve to the first mixing assembly inlet of the mixing assembly and flowing the aqueous nucleic acid stock solution through the valve to the second mixing assembly inlet of the mixing assembly thereby mixing the organic lipid stock solution and the aqueous nucleic acid stock solution within the mixing assembly to create a first mixture and flowing the first mixture out of the mixing assembly through the mixing assembly outlet.

19. A method of manufacturing lipid nanoparticles, comprising:
providing an organic lipid stock solution within a first reservoir, the first reservoir fluidically coupled to a first valve outlet port of a valve in both a first operating position of the valve and a second operating position of the valve;
providing an aqueous nucleic acid stock solution within a second reservoir, the second reservoir fluidically coupled to a second valve outlet port of the valve in both the first operating position of the valve and the second operating position of the valve;
pumping the organic lipid stock solution from the first reservoir to a first valve inlet port of the valve;
pumping the aqueous nucleic acid stock solution from the second reservoir to a second valve inlet port of the valve;
flowing the organic lipid stock solution and the aqueous nucleic acid stock through the valve and operating the valve in the second operating position in which the first valve inlet port is not fluidically connected to a first mixing assembly inlet of a mixing assembly and the second valve inlet port is not fluidically connected to a second mixing assembly inlet of the mixing assembly in the second operating position; and
switching the valve to the first operating position and flowing the organic lipid stock solution through the valve to the first mixing assembly inlet of a mixing assembly and flowing the aqueous nucleic acid stock solution through the valve to the second mixing assembly inlet of the mixing assembly thereby mixing the organic lipid stock solution and the aqueous nucleic acid stock solution within the mixing assembly to create a first mixture and flowing the first mixture out of the mixing assembly through a mixing assembly outlet.

20. The method of claim 19, the method further comprising flowing the organic lipid stock solution through the valve to the first reservoir and flowing the aqueous nucleic acid stock solution through the valve to the second reservoir.

21. The method of claim 19, wherein less than 5 ml of an initial 10 ml of the first mixture flowing out of the mixing assembly through the mixing assembly outlet, is discarded as not meeting a predefined particle generation specification.

22. The method of claim 19, wherein less than 5% by mass of the first mixture flowing out of the mixing assembly through the mixing assembly outlet, is discarded as not meeting a predefined particle generation specification.

23. The method of claim 19, wherein the method further comprises:
providing a diluent within a third reservoir; and
pumping the diluent from the third reservoir to a third valve inlet port of the valve,
wherein switching the valve to the first operating position further comprises flowing the diluent through the valve to a third mixing assembly inlet of the mixing assembly thereby mixing the diluent with the first mixture within the mixing assembly and flowing the diluent and first mixture out of the mixing assembly through the mixing assembly outlet.

24. The method of claim 23, wherein operating the valve in the second operating position further comprises preventing the diluent from flowing through the valve to the third mixing assembly inlet of the mixing assembly.

\* \* \* \* \*